United States Patent
Boggs et al.

(10) Patent No.: US 7,495,004 B2
(45) Date of Patent: Feb. 24, 2009

(54) PURINE DERIVATIVES AS LIVER X RECEPTOR AGONISTS

(75) Inventors: Sharon Davis Boggs, Durham, NC (US); Jon Loren Collins, Durham, NC (US); Adam Fivush, Fishers, IN (US); Eugene Lee Stewart, Durham, NC (US); Timothy Mark Willson, Durham, NC (US)

(73) Assignee: Glaxo Group Limited, Greenford, Middlesex (GB)

( * ) Notice: Subject to any disclaimer, the term of this patent is extended or adjusted under 35 U.S.C. 154(b) by 551 days.

(21) Appl. No.: 10/516,168

(22) PCT Filed: May 20, 2003

(86) PCT No.: PCT/US03/16016

§ 371 (c)(1), (2), (4) Date: Jun. 23, 2005

(87) PCT Pub. No.: WO2004/009091

PCT Pub. Date: Jan. 29, 2004

(65) Prior Publication Data

US 2006/0094733 A1    May 4, 2006

Related U.S. Application Data

(60) Provisional application No. 60/389,689, filed on Jun. 17, 2002.

(51) Int. Cl.
```
C07D 473/04       (2006.01)
C07D 473/06       (2006.01)
C07D 473/08       (2006.01)
A61K 31/522       (2006.01)
A61P 9/10         (2006.01)
A61P 3/06         (2006.01)
A61P 29/00        (2006.01)
```
(52) U.S. Cl. .................. 514/263.21; 514/263.22; 514/263.23; 514/263.34; 514/263.35; 514/263.3; 544/267; 544/269; 544/272

(58) Field of Classification Search ............ 544/267, 544/269, 272; 514/263.21, 263.22, 263.23, 514/263.34, 263.35, 263.3
See application file for complete search history.

(56) References Cited

U.S. PATENT DOCUMENTS

| | | | |
|---|---|---|---|
| 2,928,833 A | 3/1960 | Leake et al. | |
| 4,883,801 A | 11/1989 | Nathanson | |
| 4,968,672 A | 11/1990 | Jacobson et al. | |
| 5,102,880 A | 4/1992 | Chakravarty et al. | |
| 5,157,026 A | 10/1992 | Chakravarty et al. | |
| 5,177,074 A | 1/1993 | Allen et al. | |
| 5,332,744 A | 7/1994 | Chakravarty et al. | |
| 5,374,638 A | 12/1994 | Dhanoa et al. | |
| 5,409,934 A | 4/1995 | Smith et al. | |
| 5,412,097 A | 5/1995 | Chakravarty et al. | |
| 5,461,059 A | 10/1995 | Bonnet et al. | |
| 5,470,579 A | 11/1995 | Bonte et al. | |
| 5,641,784 A | 6/1997 | Kufner-Muhl et al. | |
| 5,714,494 A | 2/1998 | Connell et al. | |
| 5,719,279 A | 2/1998 | Kufner-Muhl et al. | |
| 6,187,780 B1 | 2/2001 | Blech et al. | |
| 6,316,503 B1 | 11/2001 | Hasegawa et al. | |
| 6,821,978 B2 * | 11/2004 | Chackalamannil et al. | 514/262.1 |
| 7,074,923 B2 * | 7/2006 | Dahanukar et al. | 544/267 |
| 7,192,952 B2 * | 3/2007 | Kanstrup et al. | 514/217.06 |
| 2006/0205711 A1 * | 9/2006 | Himmelsbach et al. | 514/217.06 |

FOREIGN PATENT DOCUMENTS

| | | |
|---|---|---|
| CA | 2062558 | 3/1992 |
| DE | 4325254 | 2/1994 |

(Continued)

OTHER PUBLICATIONS

Samura et al., Pharmaceutical Chemistry Journal vol. 20, No. 1 Jan. 1986 pp. 37-40.*

(Continued)

*Primary Examiner*—Mark L Berch
(74) *Attorney, Agent, or Firm*—J. Scott Young

(57) ABSTRACT

The invention relates to methods for the treatment or prevention of an LXR mediated disease or condition, including cardiovascular disease and atherosclerosis, novel compounds of formula (I) for use in such methods and pharmaceutical compositions comprising compounds for use in such methods.

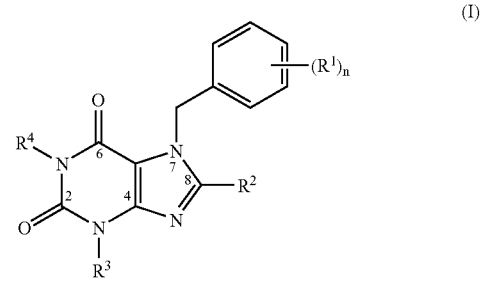

19 Claims, 122 Drawing Sheets

FOREIGN PATENT DOCUMENTS

| | | |
|---|---|---|
| EP | 400974 | 12/1990 |
| EP | 430300 | 6/1991 |
| WO | WO 92/05175 | 4/1992 |
| WO | WO 92/05176 | 4/1992 |
| WO | WO 92/11260 | 7/1992 |
| WO | WO 93/23401 | 11/1993 |
| WO | WO 94/03456 | 2/1994 |
| WO | WO 94/20460 | 9/1994 |
| WO | WO 99/36073 | 7/1999 |
| WO | WO 00/09507 | 2/2000 |
| WO | WO 00/54759 | 9/2000 |
| WO | WO 01/34610 | 5/2001 |
| WO | WO 01/60824 | 8/2001 |
| WO | WO 01/68600 | 9/2001 |
| WO | WO 02/02560 | 1/2002 |
| WO | WO 02/24632 | 3/2002 |
| WO | 02/24698 | 3/2002 |
| WO | 02/067942 | 9/2002 |
| WO | 02/068420 | 9/2002 |
| WO | 03/004496 | 1/2003 |

OTHER PUBLICATIONS

Collins, J.L., et al. "Identification of a Nonsteroidal Liver X Receptor Agonist Through Parallel Array Synthesis of Tertiary Amines." Journal of Medicinal Chemistry, American Chemical Society. Vo. 45, 2002, pp. 1963-1966.

Chlon, G et al.; Synthesis, 5-HT1A and 5-HT2A Receptor Activity of New 1-Phenylpiperazinylpropyl Derivatives with Arylakyl Substituents in Position 7 of Purine-2,6-Dione; Pol J Pharm: 2001; 53/4; 359-368; Polish Academy of Sciences, Institute of Pharmacology.

Pozharskii, AF, et al.; N-Anions of Heteroarymatic Amines,; Khlm Geterotslkt Soedln (Russian); 1971; 7/9; 1230-1237, abstract only.

Priimenko, BA et al.; Synthesis and Physicochemical Properties of 7,8-Disubstituted 3-Methylxanthine and 2,6,7,8-tetrasubstituted Purine; Izvestiya Vysshikh Uchebnykh Zavedenii, Khimiya i Khimicheskaya Tekhnologiya; 1986; 29/2; 35-38; (Russian), Abstract only.

Romanenko, NI, et al.; Reactions of 7-Substituted 8-bromo-3-methylxanthine with some Electrophilic and Nucleophilic Reagents; Ukr. Khim. Zh. (Russian); 1987; 53/9; 983-986, Abstract only.

Romanenko, NI, et al.; Synthesis and Antibacterial and Antifungal Activity of Some 3-methyl-8-nitroxanthine Derivatives; Khimiko-Farmatsevticheskii Zhurnal; 1997; 31/4; 28-29, Abstract only.

Bolte, M. "Nearly Centrosymmetric (S)-7-(2,6-dichlorobenzyl)-8-(3-oxocyclopentyl)-1,3-dipropyl-7H-purine-2,6-dione." Acta Cryst, Sect. C, 1996, C52(8), pp. 1985-1987.

Drabczynska, A., et al. "Structure and Activity Studies of Glycine Receptor Ligands. Part 4. N-[(7-arylalkyl,7-aryloxyalkyl)-8-theophyllyl]-glycines." Pol. J. chem.., 1999, 73(5), pp. 783-792.

Drabczynska, A., et al. "Synthesis and preliminary Pharmacological Screening of Some 8-Substituted Methylxanthines." Pol. J. Pharmacol. Pharm., 1989, 41(4), pp. 385-394.

Jarymowicz, B. "Pochodne 1,3-Dimetylo-8-Formylo-7-Podstawione Ksantyny W Syntezie Hantzscha." ACTA Polon. Pharm. XXXVIII, No. 2, 1981, pp. 201-205.

Mosselhi, M.A.N., et al. "Synthesis and Properties of 8-nitro-7-alkylated Theophylline Derivatives." Bull. Pol. Acad. Sci., Chem., 1994, 41(30, pp. 179-185.

Mosselhi, M.A.N., et al. "Synthesis and Properties of 8-nitro-7-alkylated Theophylline Derivatives." J. Serb. Chem.. Soc., 1993, 58(7-8), pp. 499-505.

Van Muijlwijk-Koezen, J.E., et al. "synthesis and use of FSCPX, an Irreversible Adenosine A1 Antagonists, As a 'Receptor Knock-Down' Tool." Bioorganic & Medicinal Chemistry Letters, 2001, 11, pp. 815-818.

ChemCats Database, Accession No. 2001:1002466.
ChemCats Database, Accession No. 2001:954502.
ChemCats Database, Accession No. 2001:950360.
ChemCats Database, Accession No. 2001:403692.
ChemCats Database, Accession No. 2001:115710.
ChemCats Database, Accession No. 2001:700909.
ChemCats Database, Accession No. 2001:481318.
ChemCats Database, Accession No. 2001:480523.
ChemCats Database, Accession No. 2001:477895.
ChemCats Database, Accession No. 2001:473970.
ChemCats Database, Accession No. 2001:403815.
ChemCats Database, Accession No. 2001:403693.
ChemCats Database, Accession No. 2001:403688.
ChemCats Database, Accession No. 2001:403681.
ChemCats Database, Accession No. 2001:294351.
ChemCats Database, Accession No. 2001:294343.
ChemCats Database, Accession No. 2001:294124.
ChemCats Database, Accession No. 2001:115711.
ChemCats Database, Accession No. 2001:1022442.
ChemCats Database, Accession No. 2001:1021391.
HCAPLUS Database, Accession No. 1998:100946.
HCAPLUS Database, Accession No. 1990:604407.
HCAPLUS Database, Accession No. 1987:50153.
HCAPLUS Database, Accession No. 2002:38476.
Registry Database, Registry No. 354133-04-3.
Registry Database, Registry No. 354132-96-0.
Registry Database, Registry No. 354132-95-9.
Registry Database, Registry No. 327098-61-3.
Registry Database, Registry No. 327097-83-6.
Registry Database, Registry No. 304878-88-4.
Registry Database, Registry No. 5429-50-5.
CAPLUS Database, Accession No. 1988:186421 (abstract only).
CAPLUS Database, Accession No. 1981:620045 (abstract only).
CAPLUS Database, Accession No. 1972:25126 (abstract only).

* cited by examiner

| Ex # | Structure | MH+ | HPLC purity |
|---|---|---|---|
| 145 | 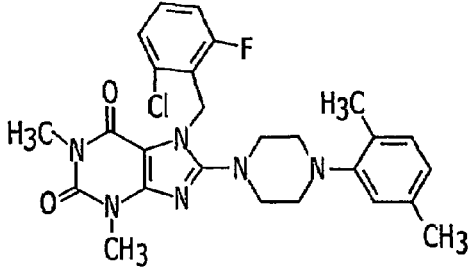 | 511 | 95 |
| 146 | 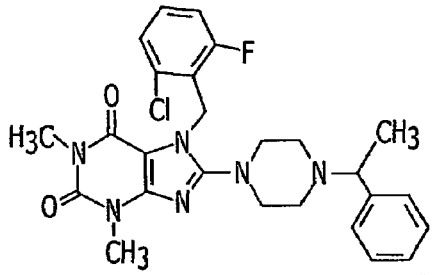 | 511 | 100 |
| 147 | 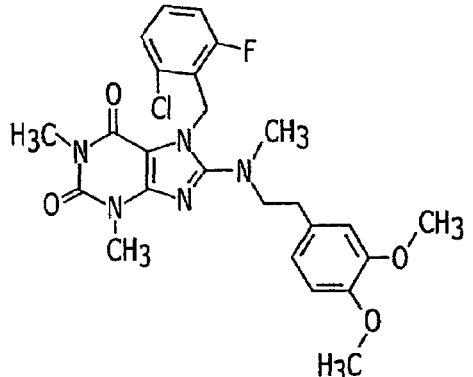 | 516 | 100 |
| 148 | 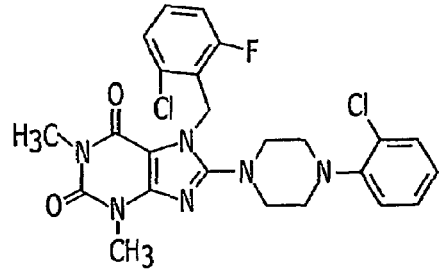 | 517 | 87 |
FIGURE 1A   TO FIGURE 1B FROM FIGURE 1A
| 149 | 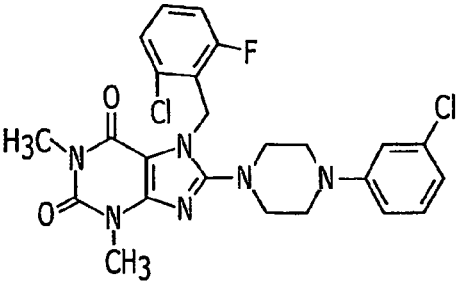 | 517 | 100 |
| 150 | 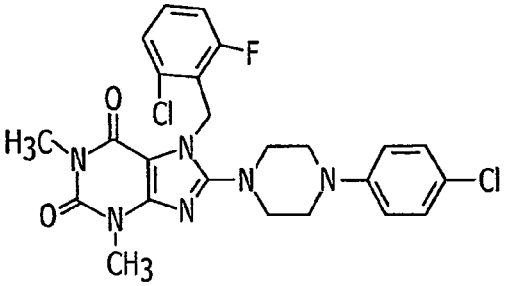 | 517 | 95 |
| 151 | 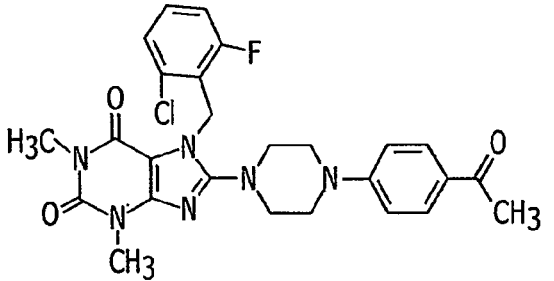 | 525 | 85 |
| 152 | 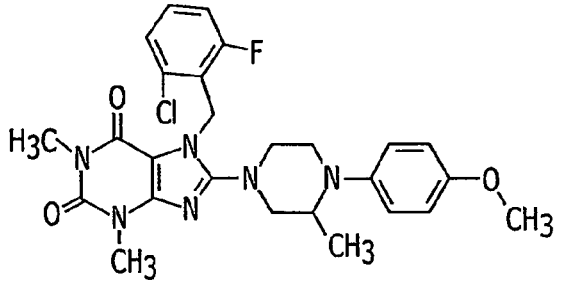 | 527 | 100 |
| 153 | 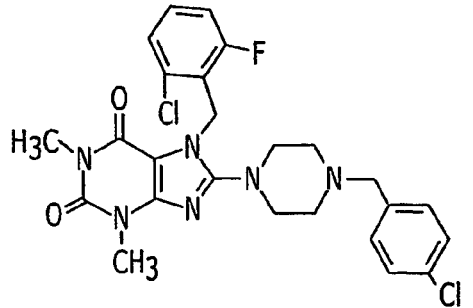 | 531 | 100 |
FIGURE 1B    TO FIGURE 1C

| 154 | 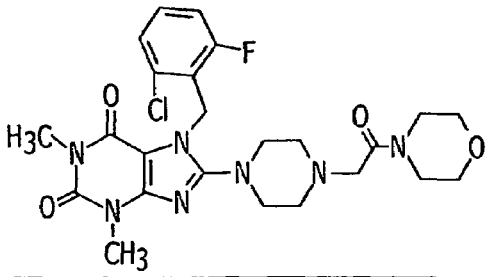 | 534 | 100 |
| 155 | 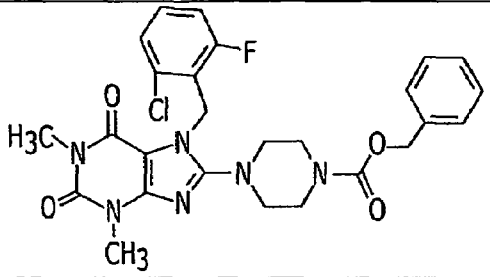 | 541 | 95 |
| 156 | 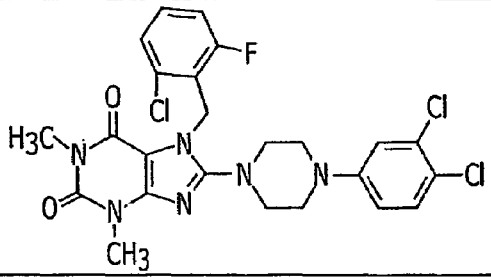 | 552 | 95 |
| 157 | 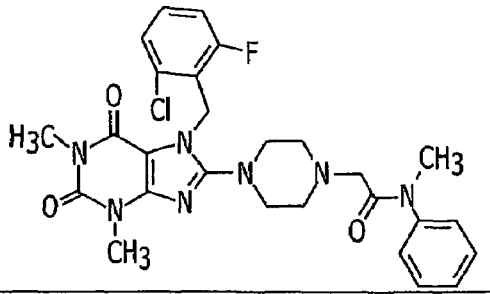 | 554 | 100 |
| 158 | 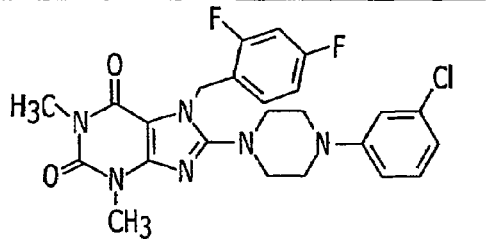 | 501 | 94 |
FIGURE 1C FROM FIGURE 1C
| 159 | 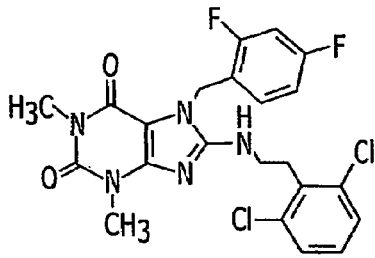 | 494 | 95 |
| 160 | 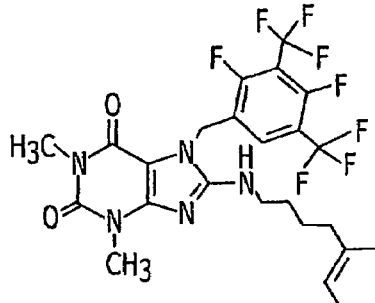 | 554 | 95 |
| 161 | 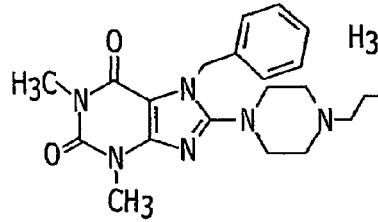 | 458 | 93 |
| 162 | 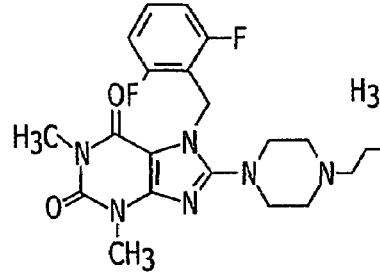 | 476 | 95 |
| 163 | 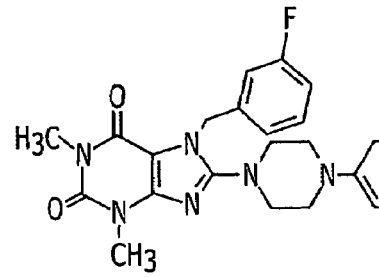 | 479 | 93 |
FIGURE 1D    TO FIGURE 1E FROM FIGURE 1D
| 164 | 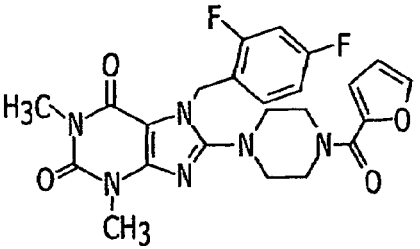 | 466 | 93 |
| 165 | 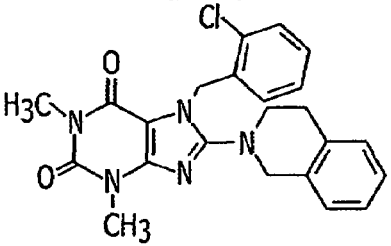 | 436 | 95 |
| 166 | 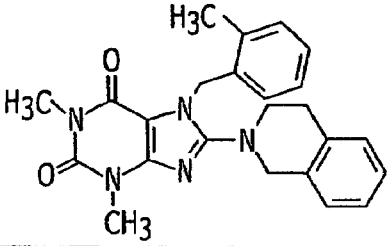 | 415 | 95 |
| 167 | 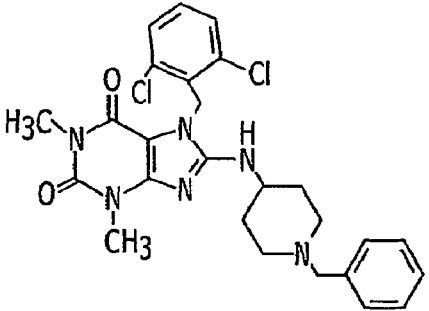 | 527 | 94 |
| 168 | 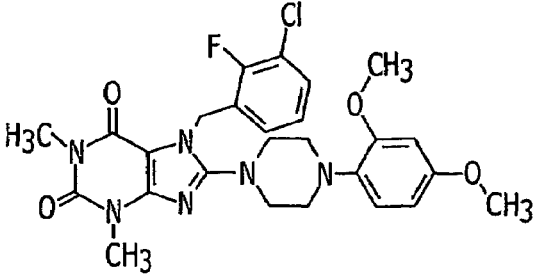 | 543 | 93 |
|     |                      |     |    |
FIGURE 1E    TO FIGURE 1F FROM FIGURE 1E
| 169 | 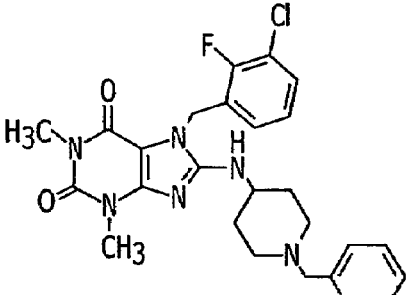 | 511 | 79 |
| 170 | 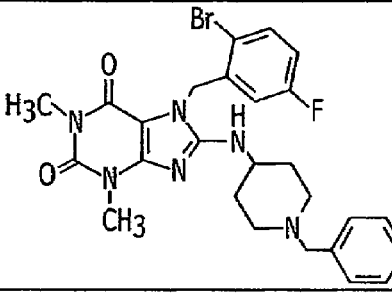 | 555 | 94 |
| 171 | 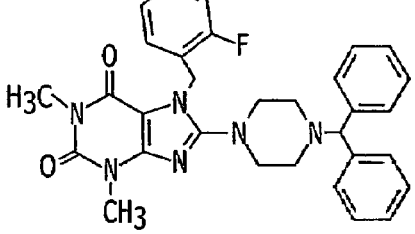 | 573 | 80 |
| 172 | 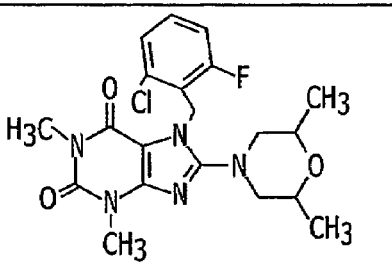 | 436 | 100 |
| 173 | 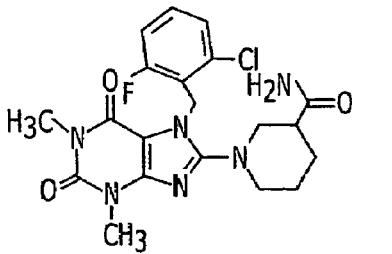 | 449 | 100 |
FIGURE 1F    TO FIGURE 1G

| | | FROM FIGURE 1F | | |
|---|---|---|---|---|
| 174 | 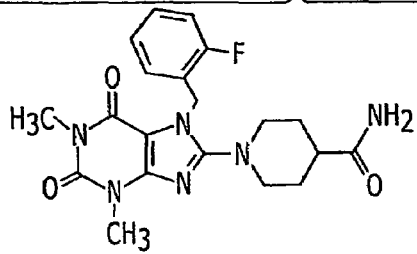 | 449 | 82 |
| 175 | 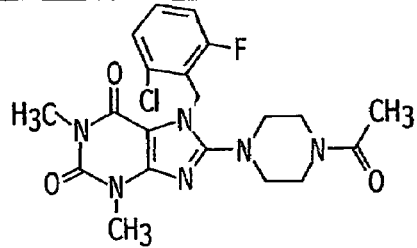 | 449 | 100 |
| 176 | 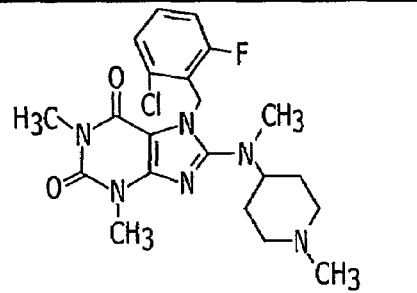 | 449 | 69 |
| 177 | 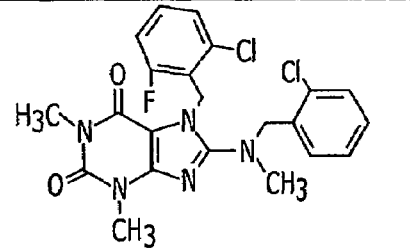 | 476 | 89 |
| 178 | 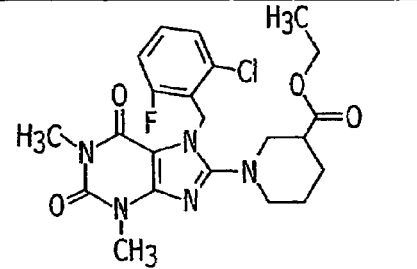 | 478 | 100 |
FIGURE 1G    TO FIGURE 1H FROM FIGURE 1G
| 179 |  | 479 | 100 |
| --- | --- | --- | --- |
| 180 |  | 505 | 100 |
| 181 |  | 456 | 100 |
| 182 | 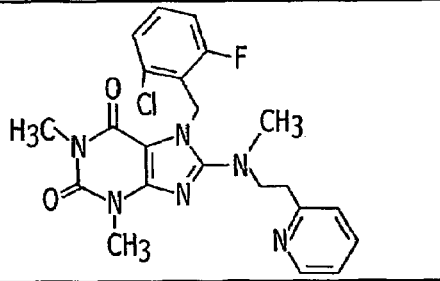 | 457 | 100 |
| 183 | 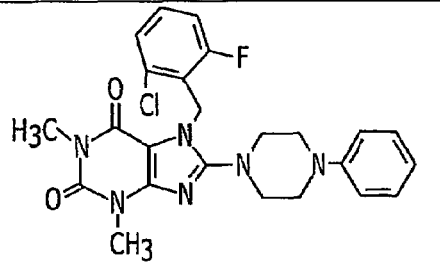 | 483 | 100 |
FIGURE 1H        TO FIGURE 1I FROM FIGURE 1H
| 184 | 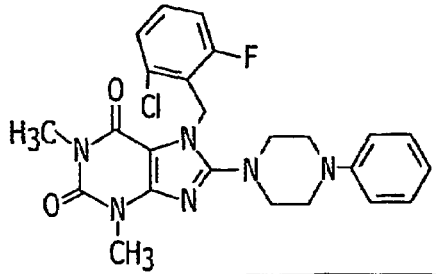 | 527 | 61 |
| 185 | 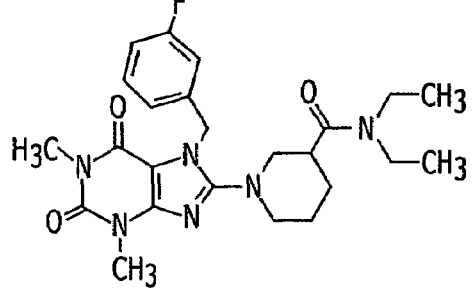 | 471 | 94 |
| 186 | 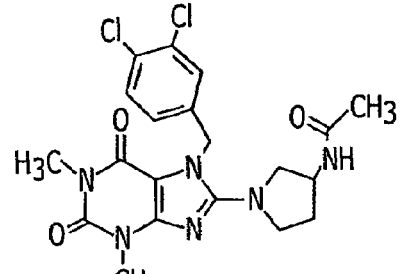 | 465 | 94 |
| 187 | 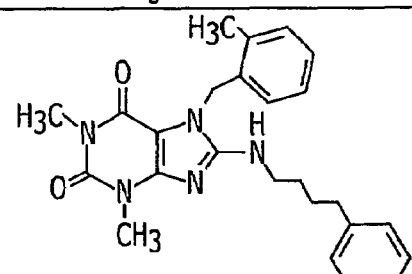 | 432 | 93 |
| 188 | 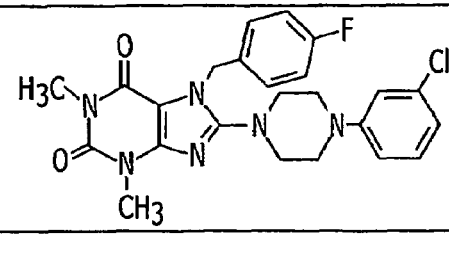 | 483 | 94 |
FIGURE 1I     TO FIGURE 1J FROM FIGURE 1I
| 189 |  | 463 | 93 |
| 190 | 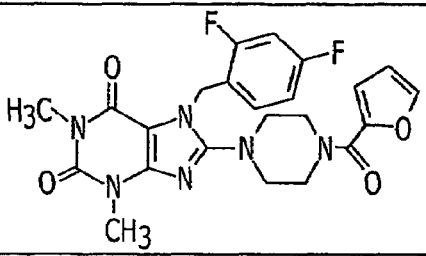 | 484 | 93 |
| 191 | 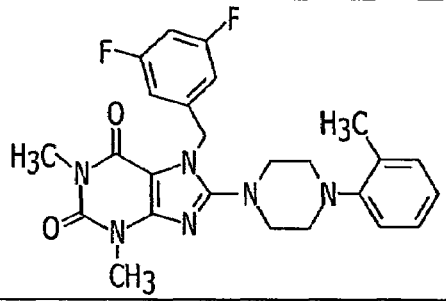 | 481 | 86 |
| 192 | 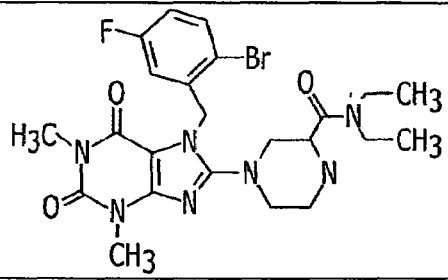 | 549 | 82 |
| 193 | 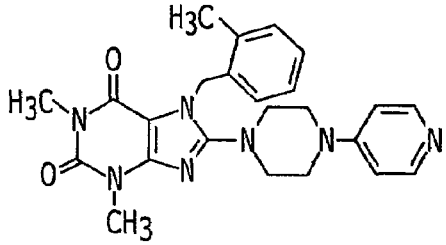 | 446 | 94 |
FIGURE 1J            TO FIGURE 1K

FROM FIGURE 1J

| 194 | [structure] | 518 | 94 |
| 195 | [structure] | 420 | 58 |
| 196 | [structure] | 493 | 94 |
| 197 | [structure] | 485 | 100 |
| 198 | [structure] | 489 | 100 |

FIGURE 1K     TO FIGURE 1L

FROM FIGURE 1K
| 199 | 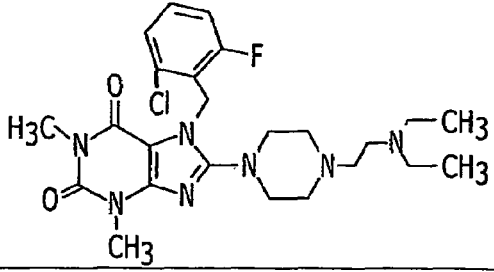 | 506 | 100 |
| 200 | 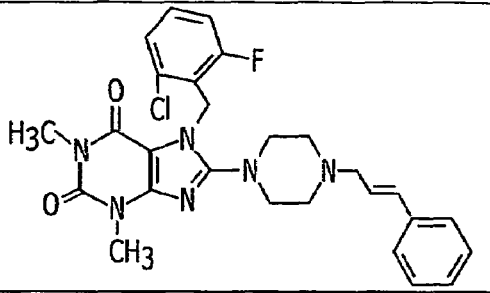 | 523 | 100 |
| 201 | 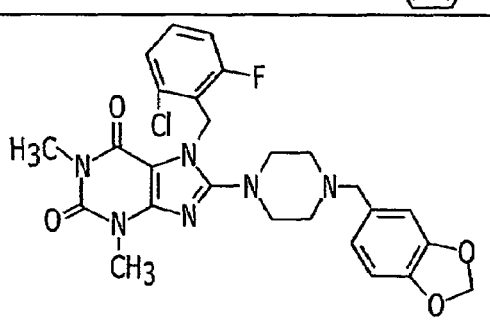 | 541 | 98 |
| 202 | 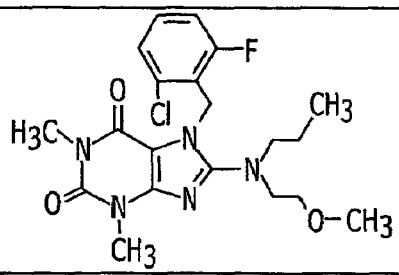 | 438 | 87 |
| 203 | 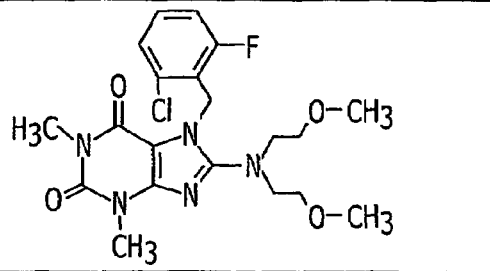 | 454 | 90 |
FIGURE 1L    TO FIGURE 1M FROM FIGURE 1L
| 204 | 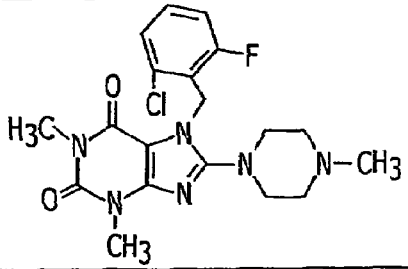 | 421 | 100 |
| 205 | 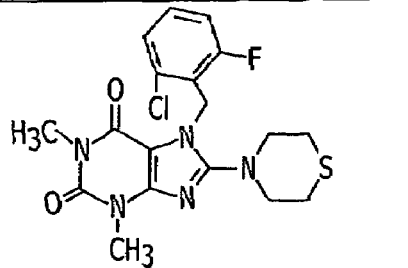 | 424 | 100 |
| 206 | 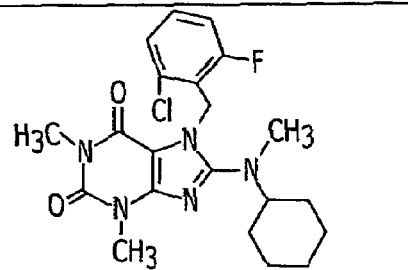 | 434 | 85 |
| 207 | 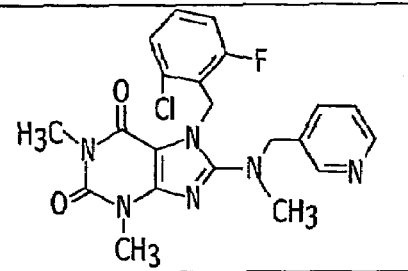 | 443 | 100 |
| 208 | 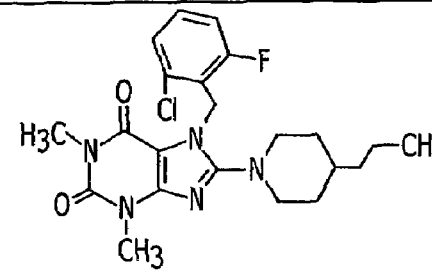 | 448 | 100 |
|     |     |     |     |
FIGURE 1M    TO FIGURE 1N FROM FIGURE 1M
| 209 | 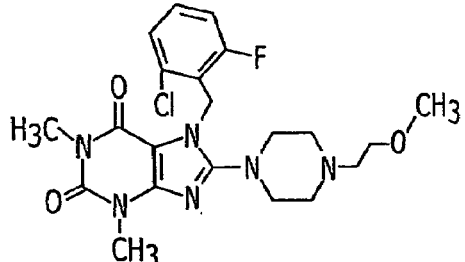 | 465 | 100 |
| 210 | 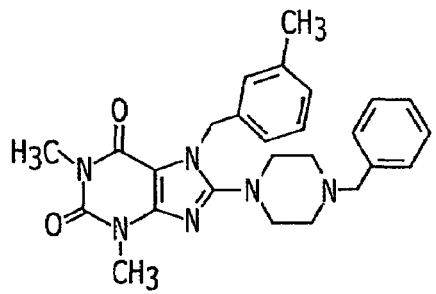 | 459 | 94 |
| 211 | 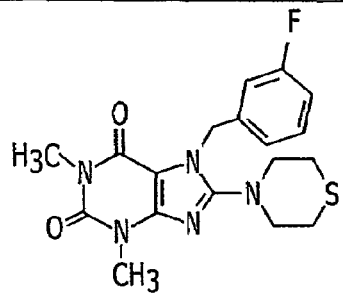 | 389 | 94 |
| 212 | 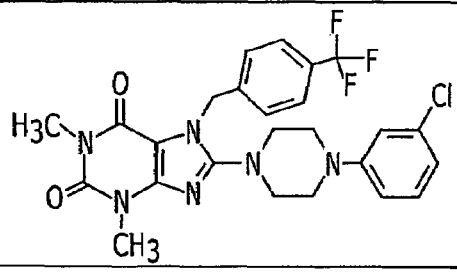 | 533 | 94 |
| 213 | 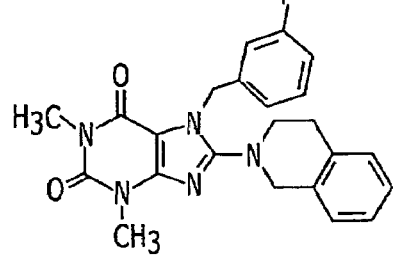 | 419 | 94 |
FIGURE 1N   TO FIGURE 1O FROM FIGURE 1N
| 214 | 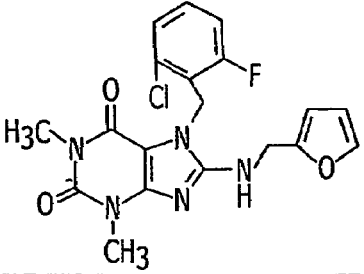 | 418 | 80 |
| --- | --- | --- | --- |
| 215 | 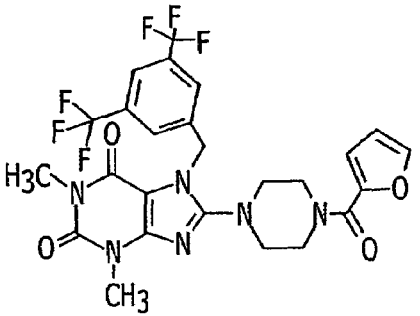 | 584 | 93 |
| 216 | 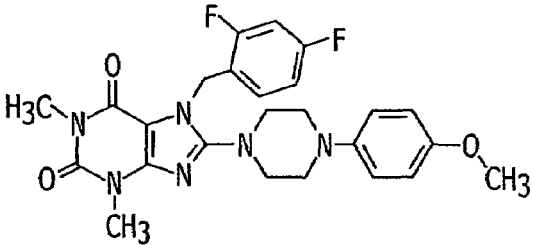 | 497 | 93 |
| 217 | 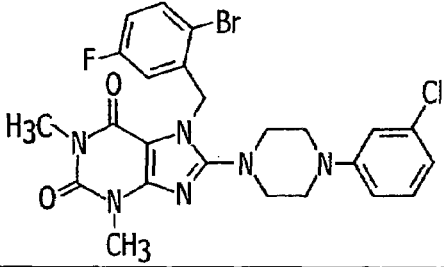 | 562 | 94 |
| 218 | 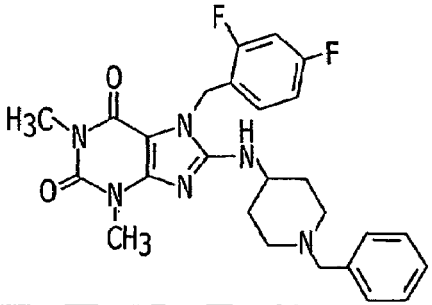 | 495 | 94 |
FIGURE 1O     TO FIGURE 1P FROM FIGURE 1O
| 219 | 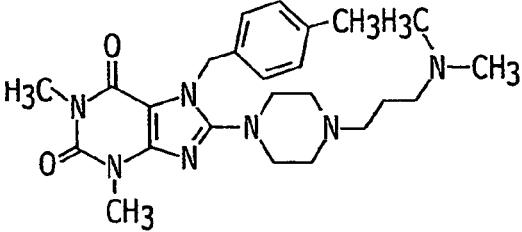 | 454 | 93 |
| 220 | 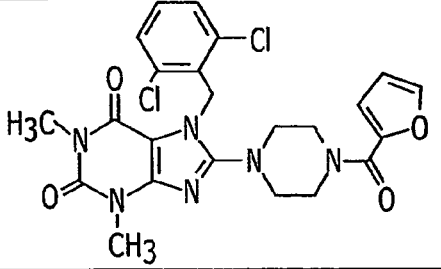 | 517 | 94 |
| 221 | 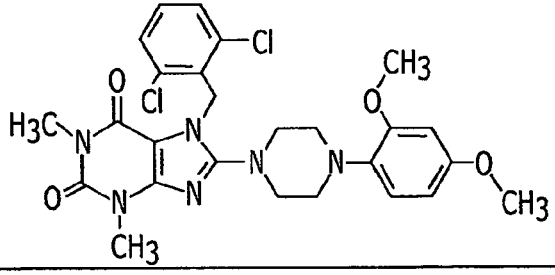 | 559 | 94 |
| 222 | 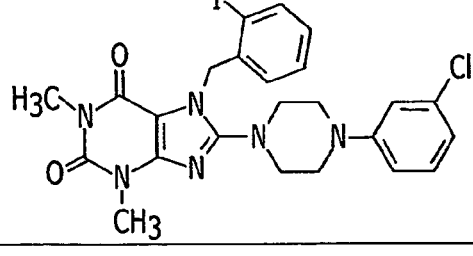 | 591 | 94 |
| 223 | 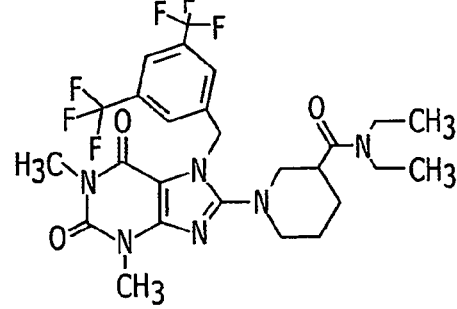 | 589 | 91 |
|     |                      |     |    |
FIGURE 1P     TO FIGURE 1Q FROM FIGURE 1P
| 224 | 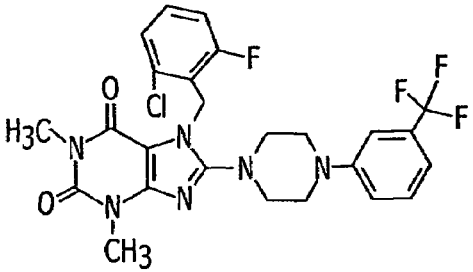 | 551 | 88 |
| --- | --- | --- | --- |
| 225 | 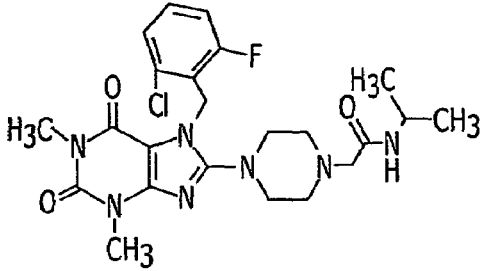 | 506 | 97 |
| 226 | 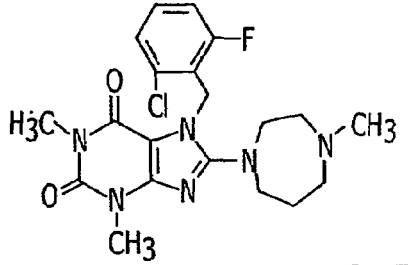 | 435 | 100 |
| 227 | 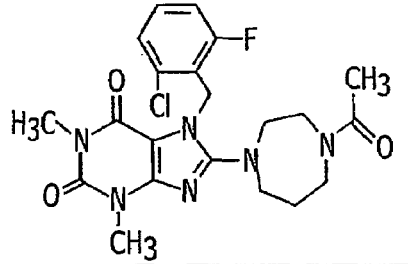 | 463 | 100 |
| 228 | 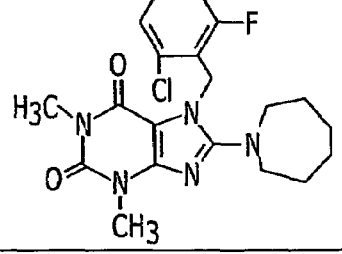 | 420 | 100 |
FIGURE 1Q    TO FIGURE 1R FROM FIGURE 1Q
| 229 | 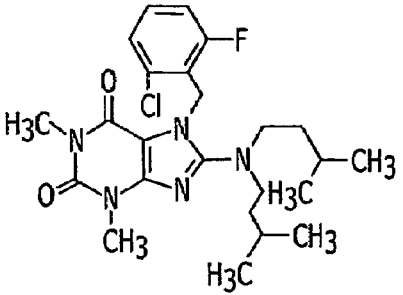 | 478 | 62 |
| 230 | 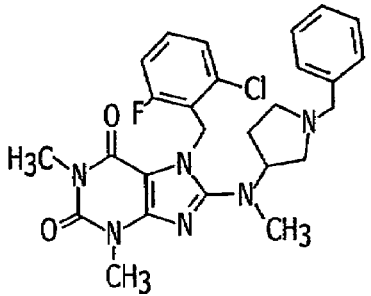 | 511 | 89 |
| 231 | 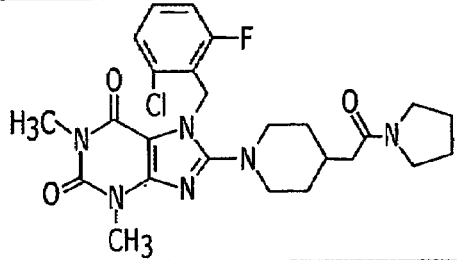 | 518 | 100 |
| 232 | 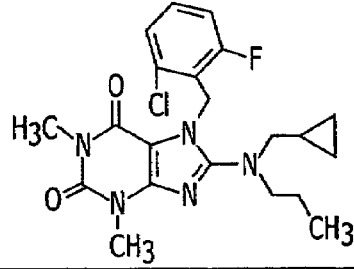 | 434 | 75 |
| 233 | 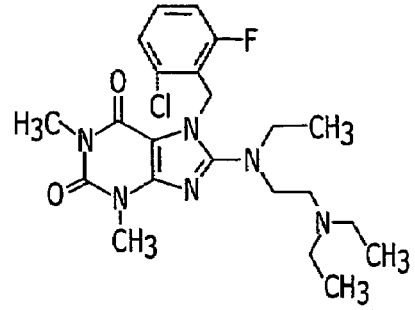 | 465 | 82 |
FIGURE 1R    TO FIGURE 1S FROM FIGURE 1R
| 234 |  | 475 | 98 |
| --- | --- | --- | --- |
| 235 |  | 475 | 100 |
| 236 | 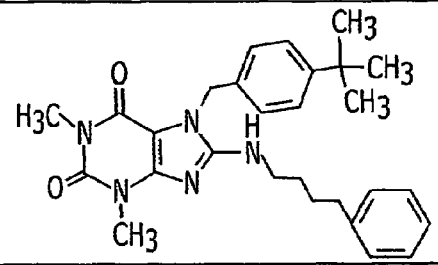 | 474 | 93 |
| 237 | 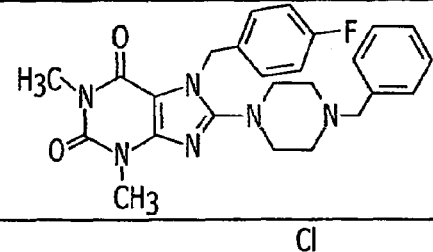 | 463 | 93 |
| 238 | 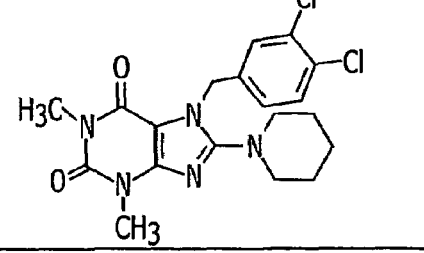 | 422 | 94 |
| | | | |
FIGURE 1S    TO FIGURE 1T FROM FIGURE 1S
| 239 | 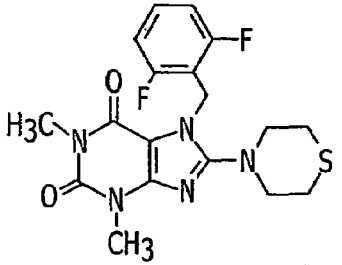 | 407 | 94 |
| 240 | 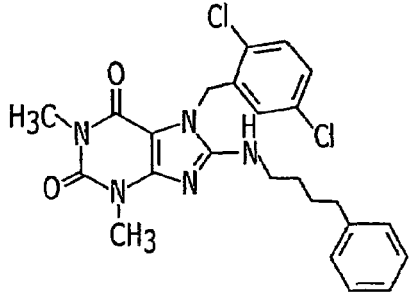 | 486 | 94 |
| 241 | 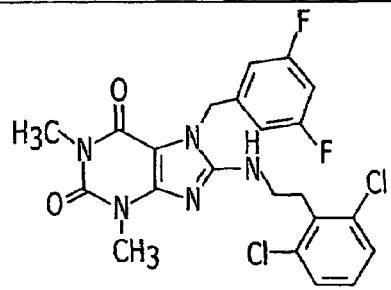 | 494 | 94 |
| 242 | 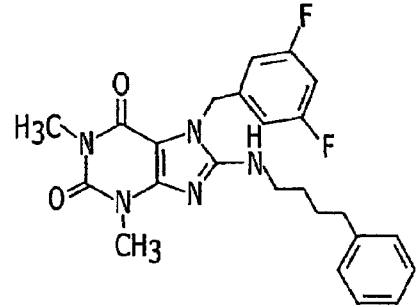 | 432 | 93 |
| 243 | 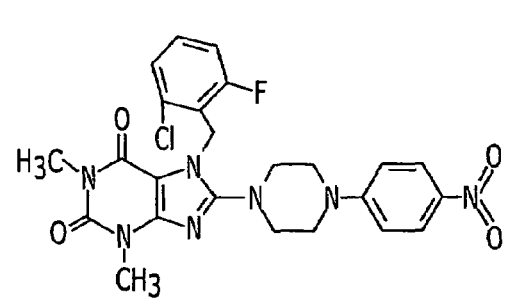 | 528 | 61 |
FIGURE 1T   TO FIGURE 1U FROM FIGURE 1T
| 246 | 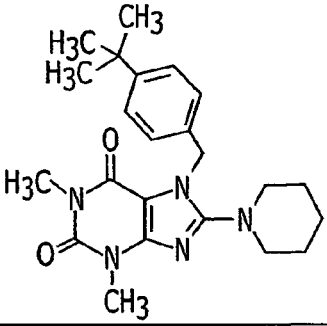 | 410 | 93 |
| 247 | 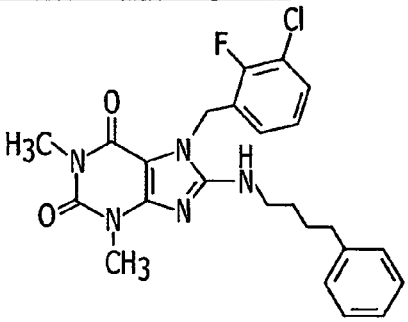 | 470 | 94 |
| 248 | 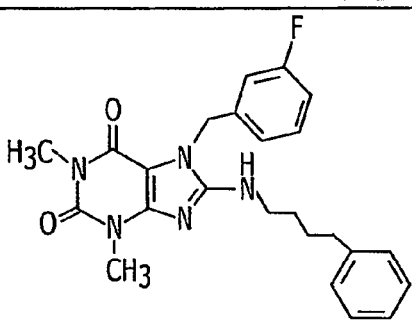 | 436 | 94 |
| 249 | 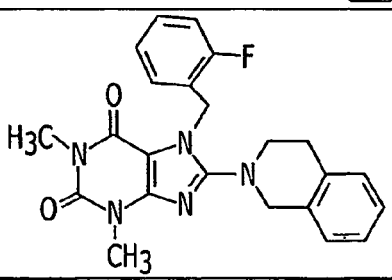 | 454 | 100 |
| | | | |
FIGURE 1U    TO FIGURE 1V FROM FIGURE 1U
| 250 | 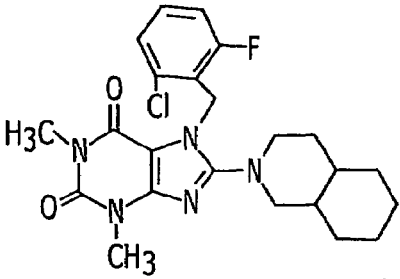 | 460 | 100 |
| 251 | 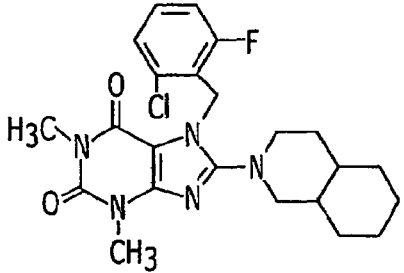 | 394 | 100 |
| 252 | 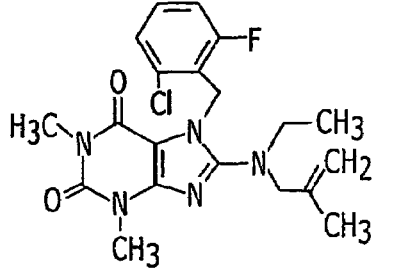 | 420 | 51 |
| 253 | 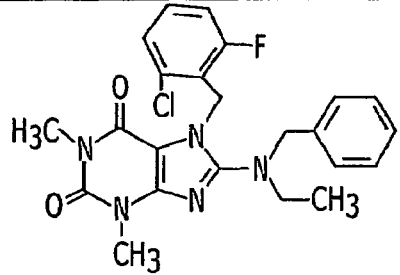 | 456 | 58 |
| 254 | 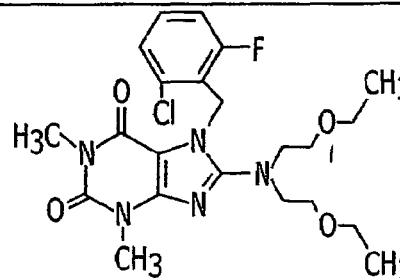 | 482 | 53 |
| | | | |
FIGURE 1V    TO FIGURE 1W FROM FIGURE 1V
| 255 | 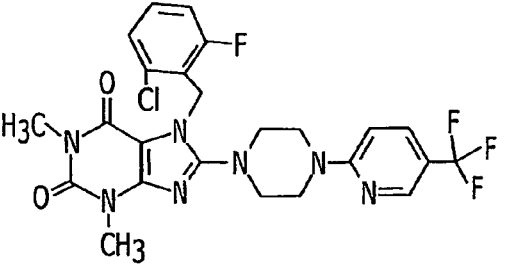 | 552 | 80 |
| --- | --- | --- | --- |
| 256 | 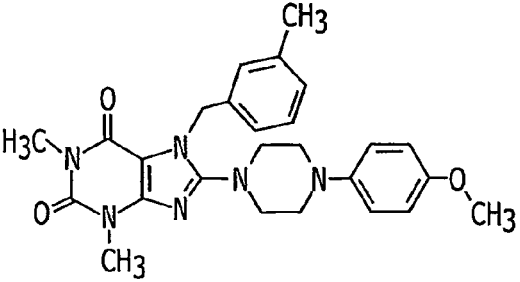 | 475 | 99 |
| 257 | 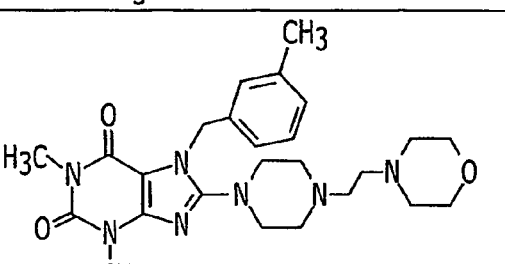 | 482 | 97 |
| 258 | 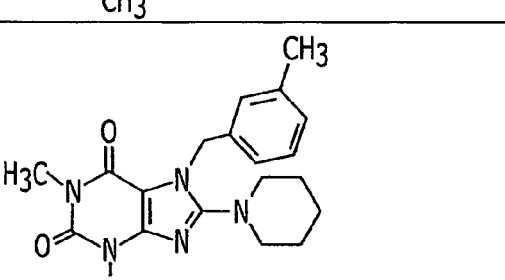 | 367 | 97 |
| 259 | 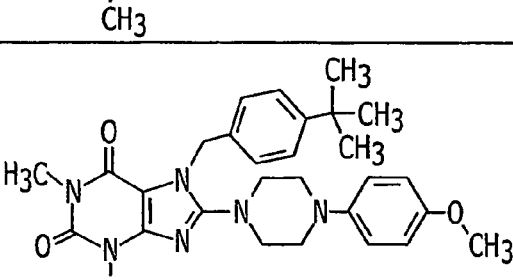 | 517 | 96 |
FIGURE 1W    TO FIGURE 1X FROM FIGURE 1W
| 260 | 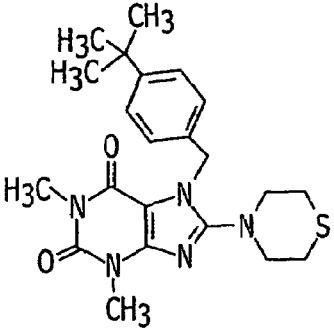 | 428 | 95 |
| 261 | 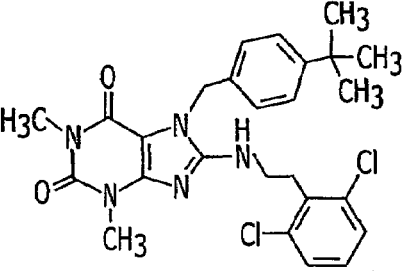 | 514 | 97 |
| 262 | 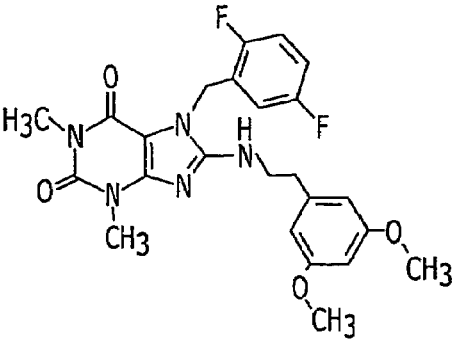 | 485 | 94 |
| 263 | 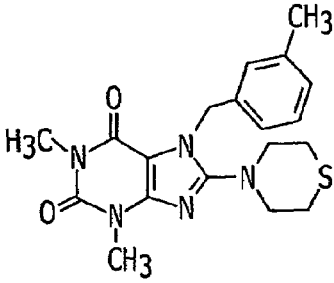 | 385 | 94 |
|     |                      |     |    |
FIGURE 1X    TO FIGURE 1Y

FROM FIGURE 1X

| | | | |
|---|---|---|---|
| 264 | (structure) | 495 | 94 |
| 265 | (structure) | 551 | 64 |
| 266 | (structure) | 405 | 66 |
| 267 | (structure) | 440 | 93 |
| 268 | (structure) | 498 | 77 |

FIGURE 1Y          TO FIGURE 1Z

FROM FIGURE 1Y

| # | Structure | | |
|---|---|---|---|
| 269 | (structure) | 547 | 89 |
| 270 | (structure) | 527 | 81 |
| 271 | (structure) | 543 | 82 |
| 272 | (structure) | 468 | 72 |

FIGURE 1Z    TO FIGURE 1A-1

FROM FIGURE 1Z
| 273 | 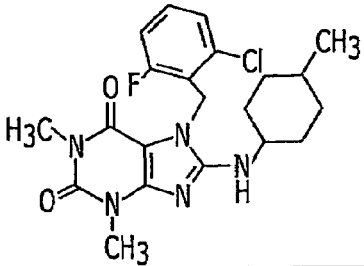 | 434 | 81 |
| 274 | 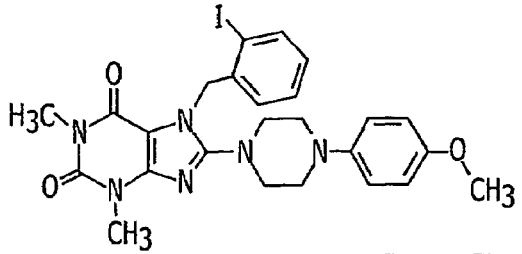 | 586 | 84 |
| 275 | 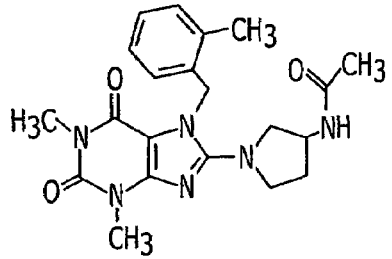 | 410 | 95 |
| 276 | 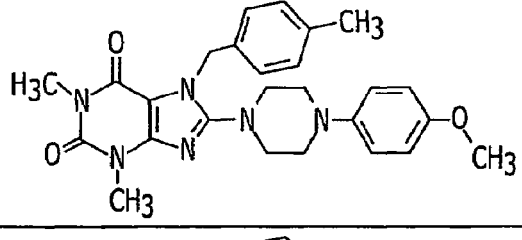 | 475 | 95 |
| 277 | 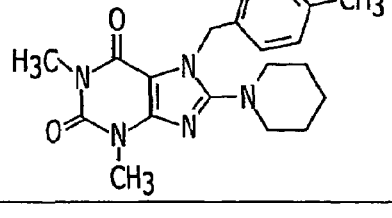 | 367 | 96 |
FIGURE 1A-1    TO FIGURE 1B-1

FROM FIGURE 1A-1
| 278 | 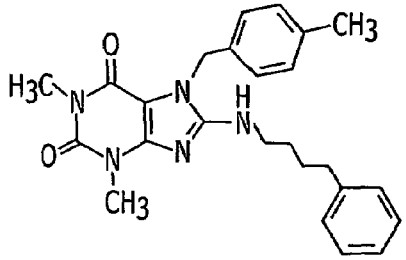 | 432 | 96 |
| 279 | 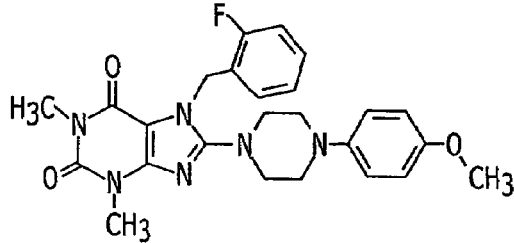 | 479 | 98 |
| 280 | 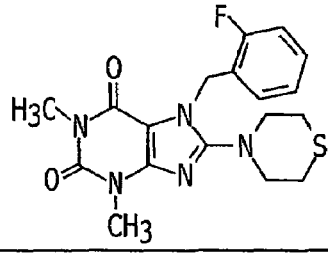 | 389 | 96 |
| 281 | 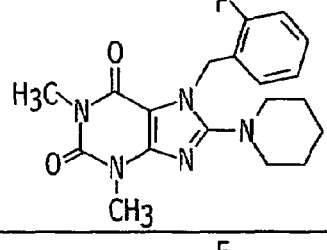 | 371 | 98 |
| 282 | 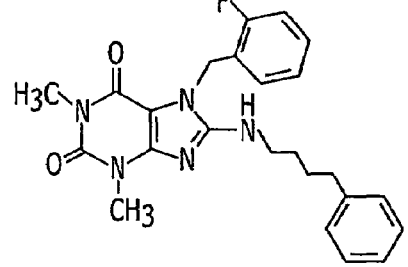 | 436 | 96 |
FIGURE 1B-1      TO FIGURE 1C-1

FROM FIGURE 1B-1
| 283 | 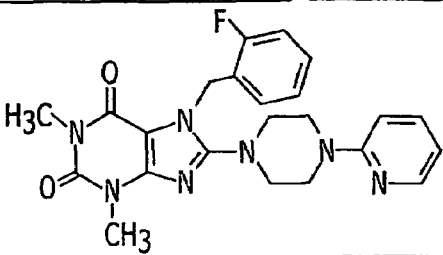 | 446 | 98 |
| 284 | 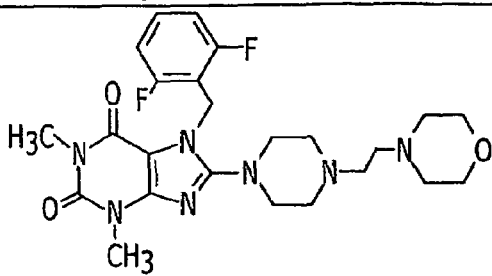 | 504 | 96 |
| 285 | 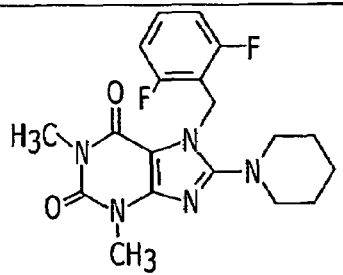 | 389 | 98 |
| 286 | 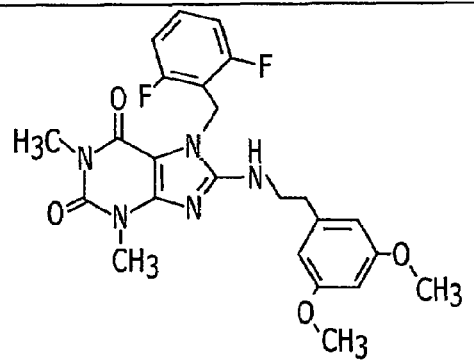 | 485 | 97 |
| 287 | 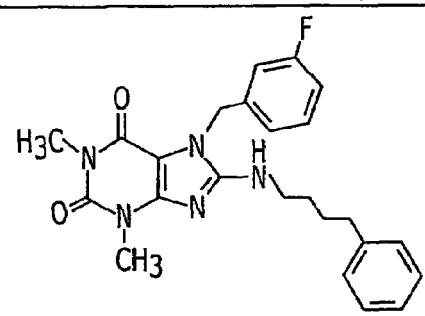 | 436 | 100 |
FIGURE 1C-1   TO FIGURE 1D-1

FROM FIGURE 1C-1
| 288 | 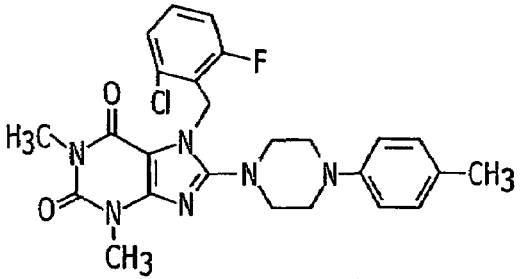 | 497 | 82 |
| --- | --- | --- | --- |
| 289 | 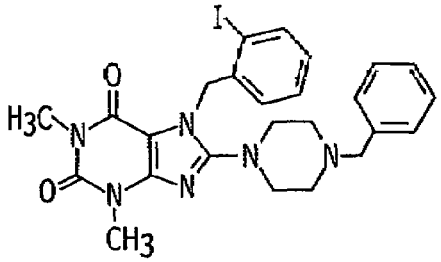 | 570 | 65 |
| 290 | 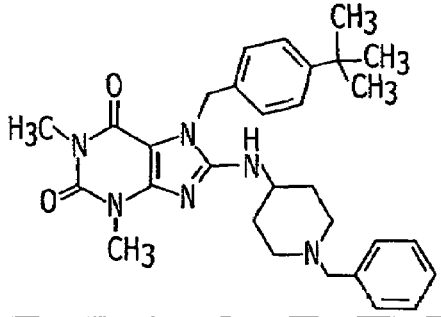 | 515 | 80 |
| 291 | 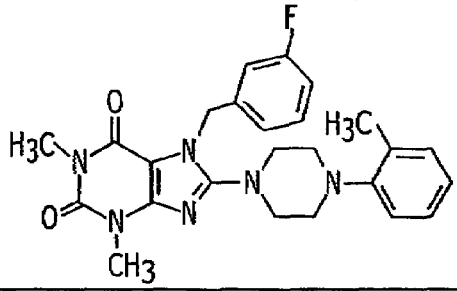 | 463 | 79 |
| 292 | 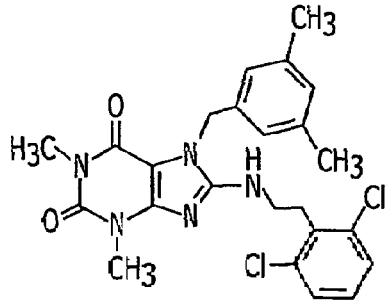 | 486 | 87 |
FIGURE 1D-1      TO FIGURE 1E-1

| 293 | 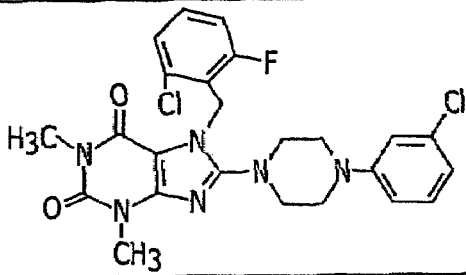 | 517 | 66 |
| 294 | 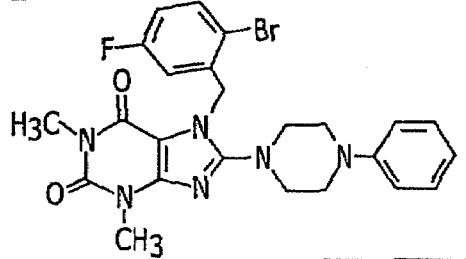 | 528 | 87 |
| 295 | 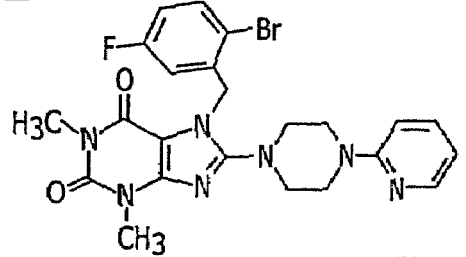 | 528 | 77 |
| 296 | 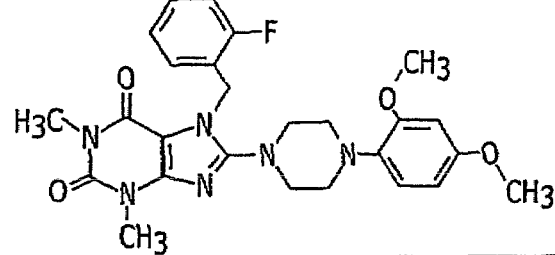 | 527 | 87 |
| 297 | 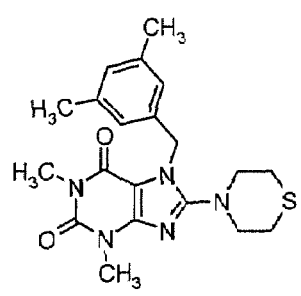 | 400 | 78 |
FIGURE 1E-1

FROM FIGURE 1E-1
| 298 | 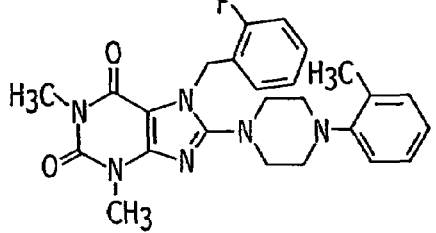 | 463 | 88 |
| 299 | 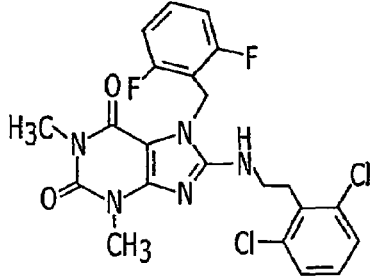 | 494 | 85 |
| 300 | 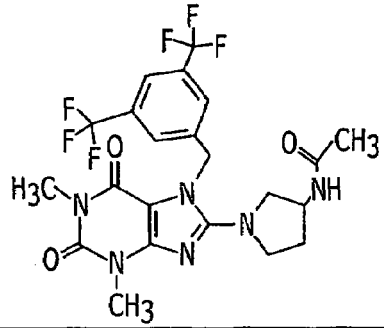 | 532 | 93 |
| 301 | 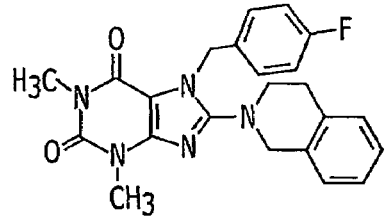 | 419 | 95 |
| 302 | 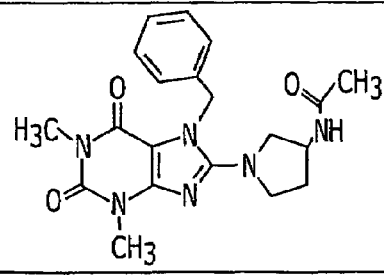 | 414 | 98 |
FIGURE 1F-1       TO FIGURE 1G-1

FROM FIGURE 1F-1
| 303 | 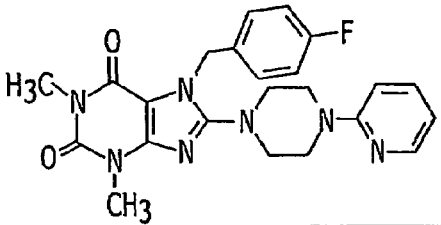 | 449 | 98 |
| --- | --- | --- | --- |
| 304 | 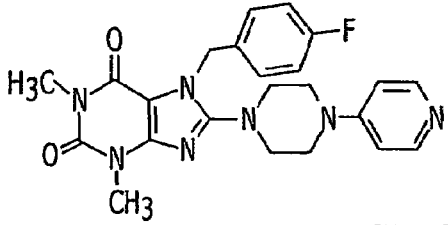 | 449 | 96 |
| 305 | 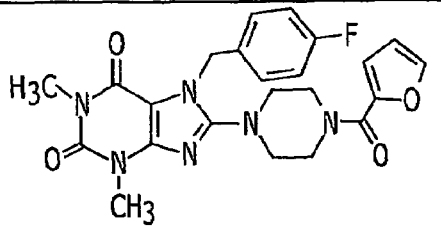 | 466 | 98 |
| 306 | 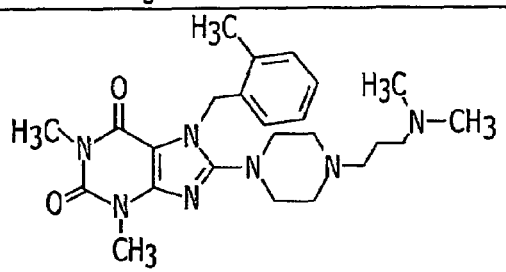 | 754 | 99 |
| 306 | 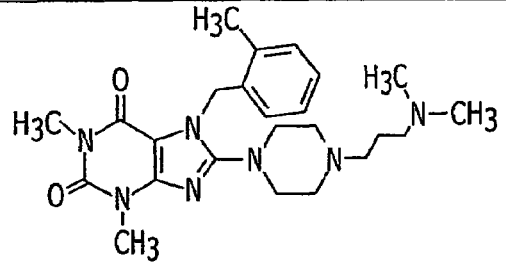 | 754 | 99 |
| 307 | 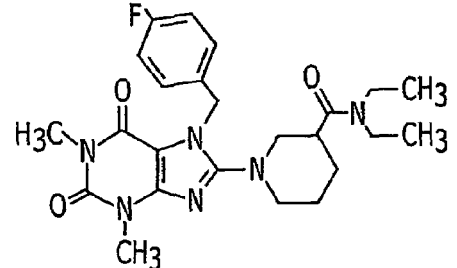 | 471 | 97 |
FIGURE 1G-1          TO FIGURE 1H-1

FROM FIGURE 1G-1
| 308 | 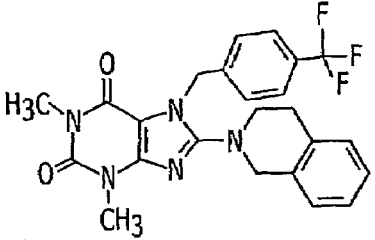 | 469 | 95 |
| 309 | 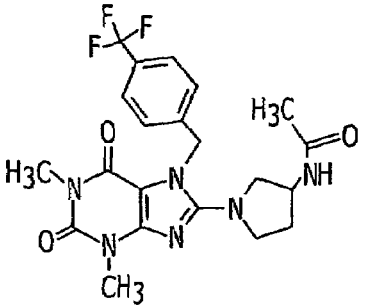 | 464 | 100 |
| 310 | 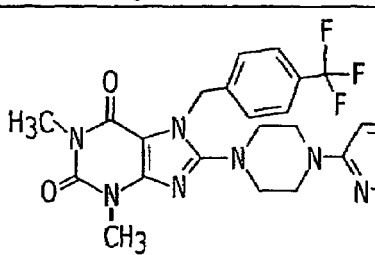 | 499 | 100 |
| 311 | 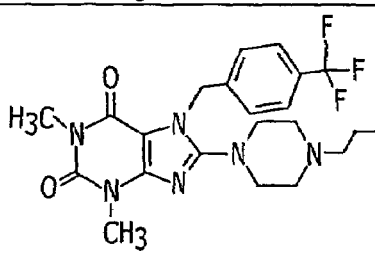 | 508 | 97 |
| 312 | 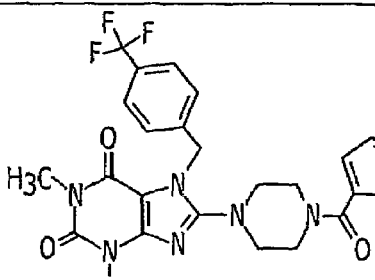 | 516 | 97 |
FIGURE 1H-1     TO FIGURE 1I-1

FROM FIGURE 1H-1
| 313 | 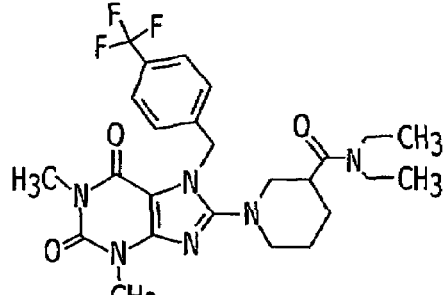 | 521 | 95 |
| 314 | 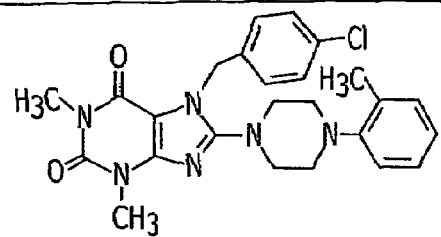 | 479 | 61 |
| 315 | 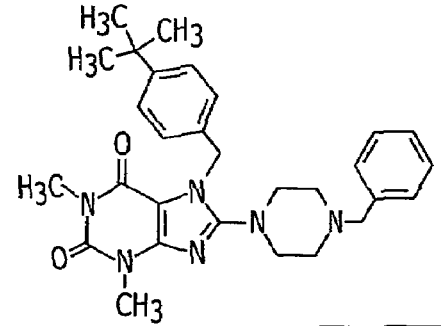 | 501 | 88 |
| 316 | 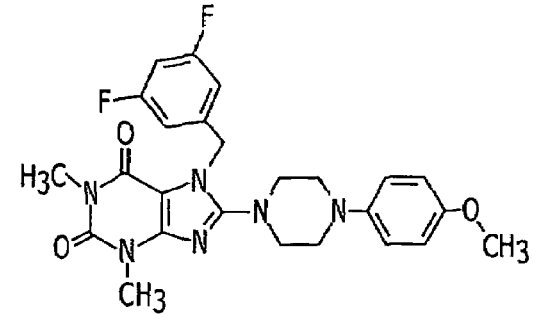 | 497 | 87 |
| 317 | 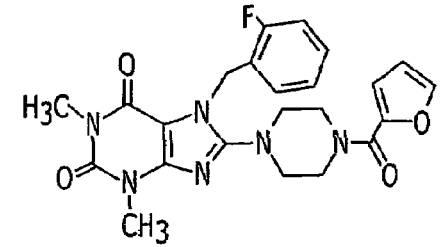 | 466 | 75 |
FIGURE 1I-1    TO FIGURE 1J-1

FROM FIGURE 1I-1
| 318 | 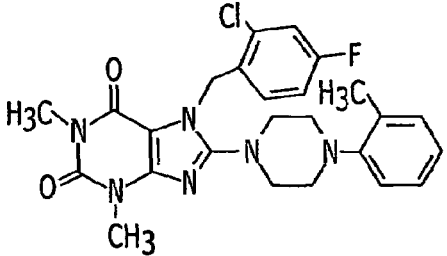 | 497 | 86 |
| 319 | 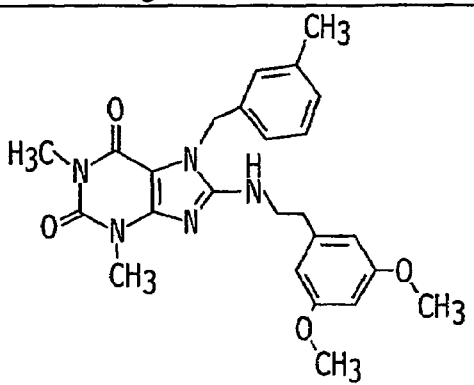 | 464 | 90 |
| 320 | 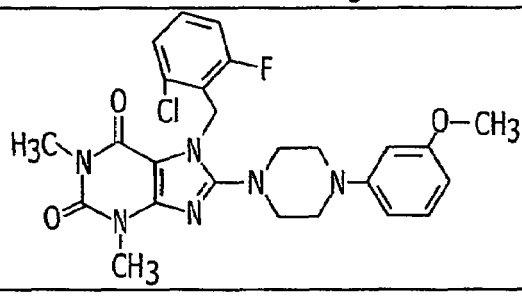 | 513 | 83 |
| 321 | 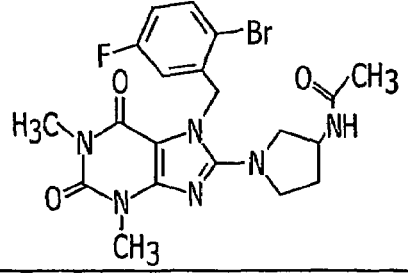 | 493 | 62 |
| 322 | 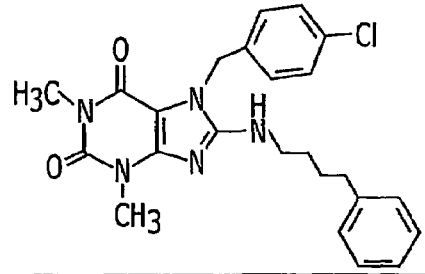 | 452 | 93 |
FIGURE 1J-1    TO FIGURE 1K-1

| | FROM FIGURE 1J-1 | | |
|---|---|---|---|
| 323 | 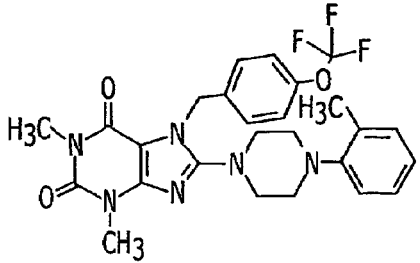 | 529 | 90 |
| 324 | 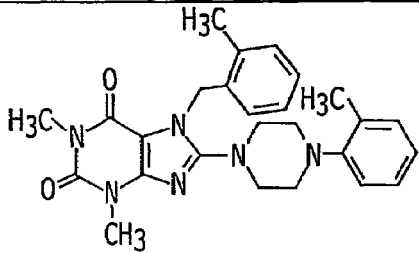 | 459 | 84 |
| 325 | 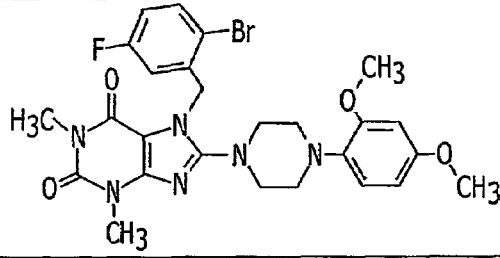 | 587 | 82 |
| 326 | 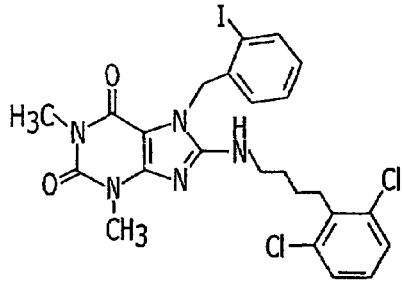 | 584 | 85 |
| 327 | 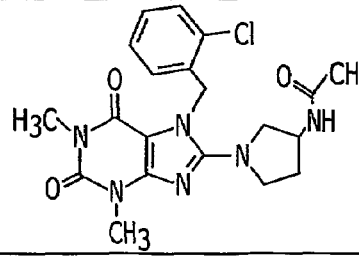 | 431 | 97 |
| | | | |
FIGURE 1K-1  TO FIGURE 1L-1

FROM FIGURE 1K-1

| # | Structure | | |
|---|---|---|---|
| 328 | (7-(2-chlorobenzyl)-1,3-dimethyl-8-(4-(pyridin-2-yl)piperazin-1-yl)xanthine) | 466 | 100 |
| 329 | (7-(2-chlorobenzyl)-8-(4-(furan-2-carbonyl)piperazin-1-yl)-1,3-dimethylxanthine) | 483 | 98 |
| 330 | (8-(4-(furan-2-carbonyl)piperazin-1-yl)-1,3-dimethyl-7-(2-methylbenzyl)xanthine) | 463 | 96 |
| 331 | (7-(2-chlorobenzyl)-N,N-diethyl-1-(1,3-dimethylxanthin-8-yl)piperidine-3-carboxamide) | 487 | 97 |
| 332 | (7-(2,6-dichlorobenzyl)-8-(3,4-dihydroisoquinolin-2(1H)-yl)-1,3-dimethylxanthine) | 470 | 98 |
|  |  |  |  |

FIGURE 1L-1    TO FIGURE 1M-1

FROM FIGURE 1L-1

| # | Structure | | |
|---|---|---|---|
| 333 | (2,6-dichlorobenzyl; 3-acetamidopyrrolidin-1-yl) | 465 | 97 |
| 334 | (2,6-dichlorobenzyl; 4-(pyridin-2-yl)piperazin-1-yl) | 500 | 98 |
| 335 | (2-chloro-6-fluorobenzyl; 4-hydroxypiperidin-1-yl) | 442 | 83 |
| 336 | (2-methylbenzyl; 3-(N,N-dimethylcarbamoyl)piperidin-1-yl) | 467 | 97 |
| 337 | (2-chlorobenzyl; 3-(N,N-dimethylcarbamoyl)piperidin-1-yl) | 521 | 95 |

FIGURE 1M-1     TO FIGURE 1N-1

FROM FIGURE 1M-1
| 338 | 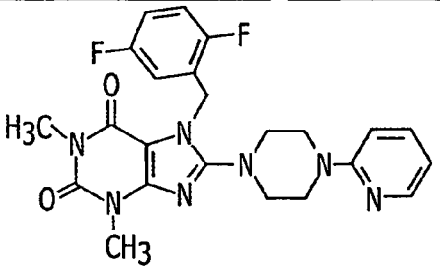 | 467 | 99 |
| 339 | 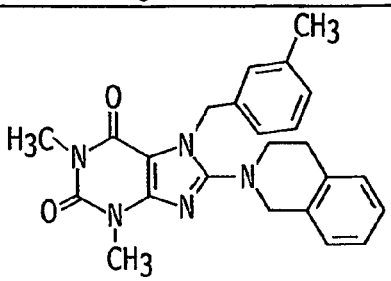 | 415 | 96 |
| 340 | 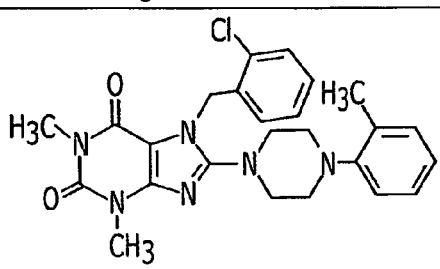 | 479 | 82 |
| 341 | 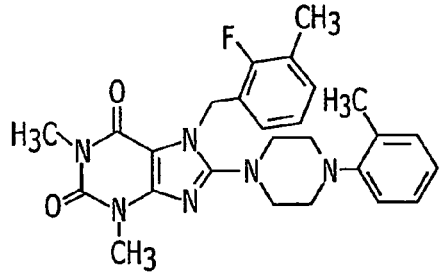 | 477 | 86 |
| 342 | 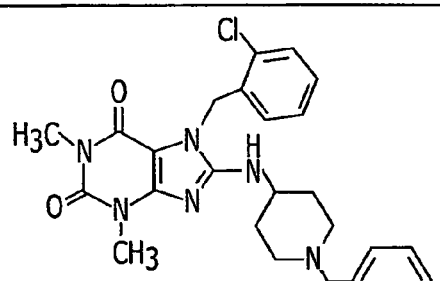 | 493 | 86 |
FIGURE 1N-1       TO FIGURE 10-1

FROM FIGURE 1N-1
| 343 | 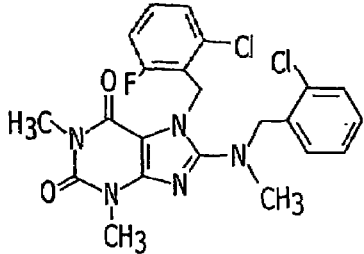 | 476 | 66 |
| --- | --- | --- | --- |
| 344 | 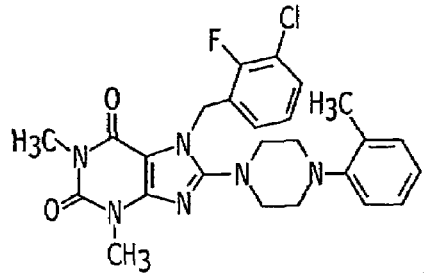 | 497 | 85 |
| 345 | 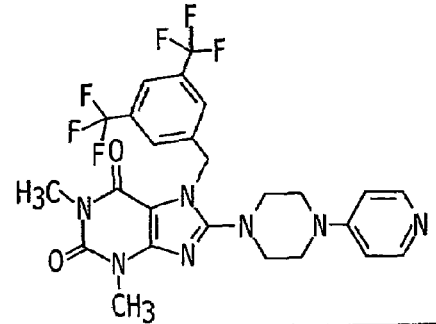 | 567 | 88 |
| 346 | 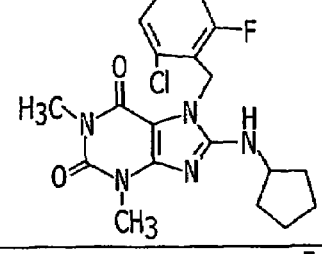 | 406 | 67 |
| 347 | 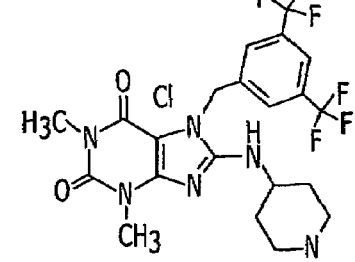 | 595 | 90 |
FIGURE 1O-1  TO FIGURE 1P-1

FROM FIGURE 1O-1
| 348 | 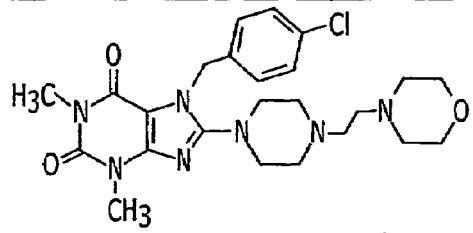 | 502 | 91 |
| 349 | 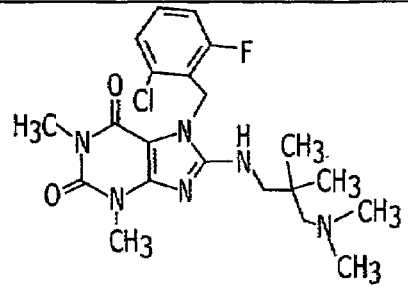 | 451 | 85 |
| 350 | 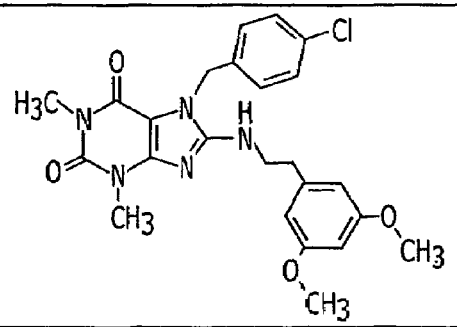 | 484 | 60 |
| 351 | 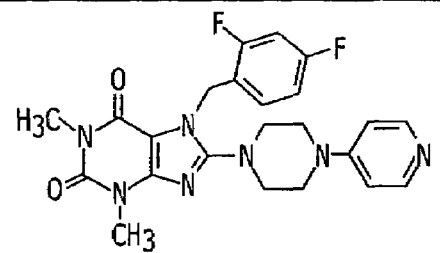 | 467 | 90 |
| 352 | 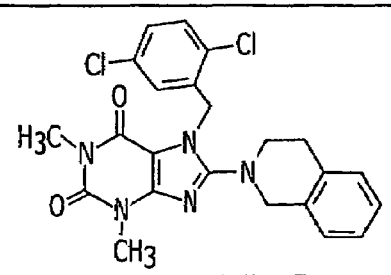 | 470 | 78 |
| | | | |
FIGURE 1P-1   TO FIGURE 1Q-1

FROM FIGURE 1Q-1
| 353 | 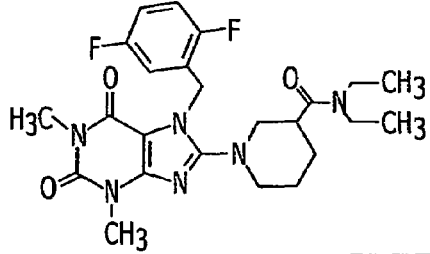 | 489 | 95 |
| 354 | 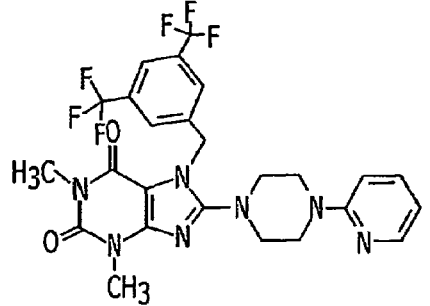 | 567 | 95 |
| 355 | 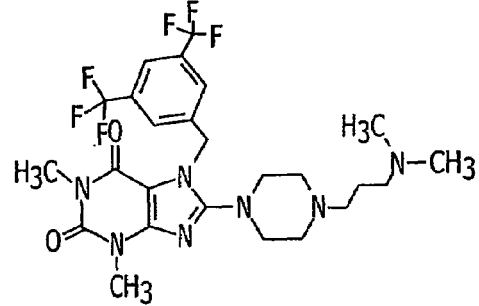 | 576 | 96 |
| 356 | 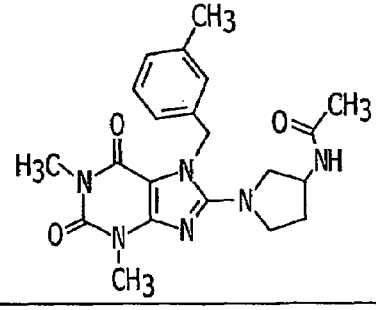 | 410 | 97 |
|     |                      |     |    |
FIGURE 1R-1      TO FIGURE 1S-1

FROM FIGURE 1R-1

| # | Structure | | |
|---|---|---|---|
| 357 | (3,5-difluorobenzyl xanthine with 3-acetamidopyrrolidinyl) | 432 | 98 |
| 358 | (3,5-difluorobenzyl xanthine with 3-acetamidopyrrolidinyl) | 432 | 96 |
| 359 | (2,4-difluorobenzyl xanthine with 4-(2-pyridyl)piperazinyl) | 467 | 97 |
| 360 | (2,4-difluorobenzyl xanthine with 4-(2-(dimethylamino)ethyl)piperazinyl) | 476 | 97 |
| 361 | (3-methylbenzyl xanthine with 4-(2-pyridyl)piperazinyl) | 446 | 100 |

FIGURE 1S-1    TO FIGURE 1T-1

FROM FIGURE 1S-1
| 362 | 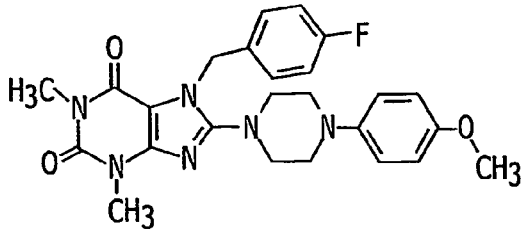 | 479 | 97 |
| 363 | 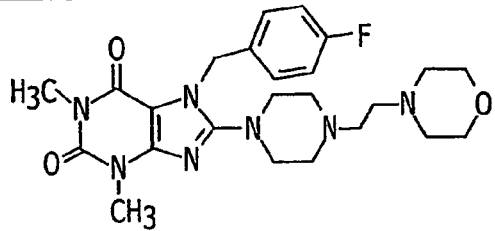 | 486 | 100 |
| 364 | 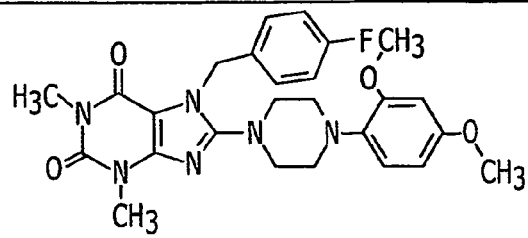 | 509 | 98 |
| 365 | 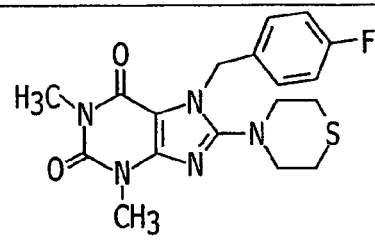 | 389 | 100 |
| 366 | 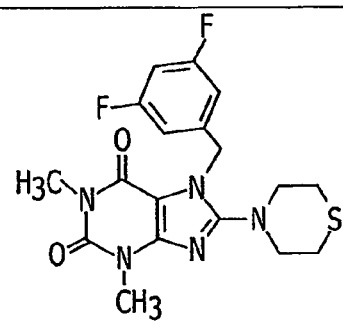 | 407 | 53 |
|     |                      |     |    |
FIGURE 1T-1      TO FIGURE 1U-1

FROM FIGURE 1T-1
| 367 | 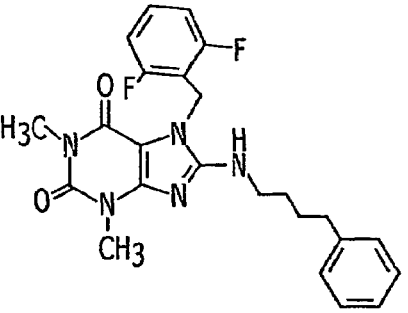 | 453 | 56 |
| 368 | 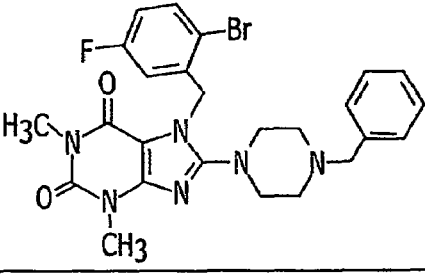 | 541 | 77 |
| 369 | 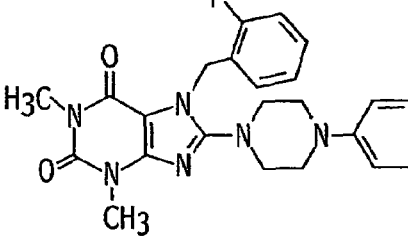 | 483 | 86 |
| 370 | 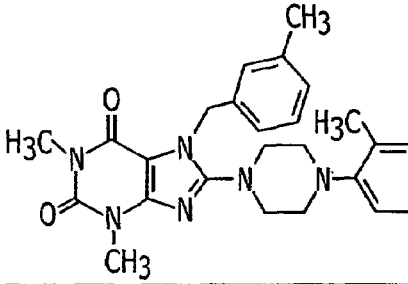 | 459 | 86 |
| 371 | 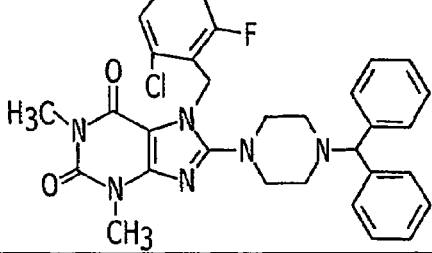 | 573 | 69 |
FIGURE 1U-1    TO FIGURE 1V-1

| 372 | 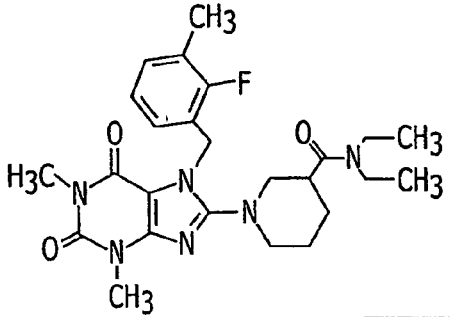 | 485 | 83 |
| 373 | 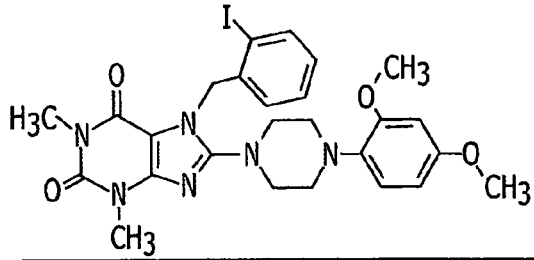 | 616 | 83 |
| 374 | 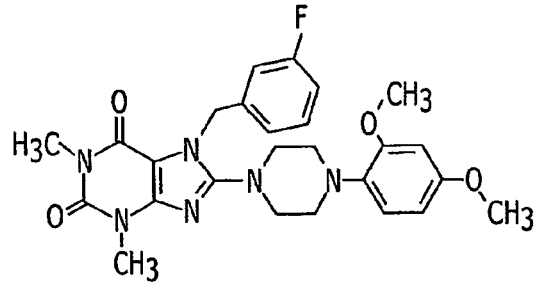 | 459 | 93 |
| 375 | 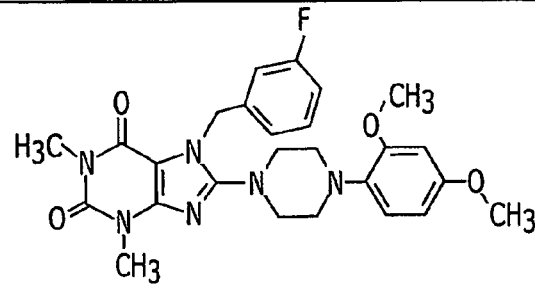 | 509 | 85 |
| 376 | 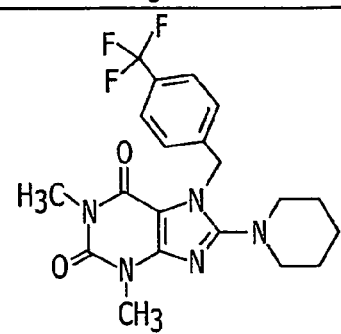 | 421 | 93 |
FIGURE 1V-1

FROM FIGURE 1V-1
| 377 | 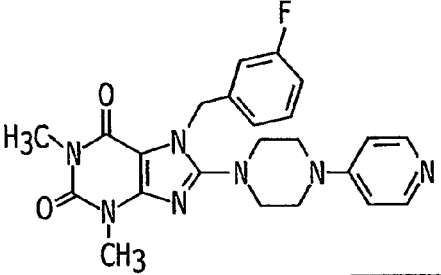 | 449 | 86 |
| --- | --- | --- | --- |
| 378 | 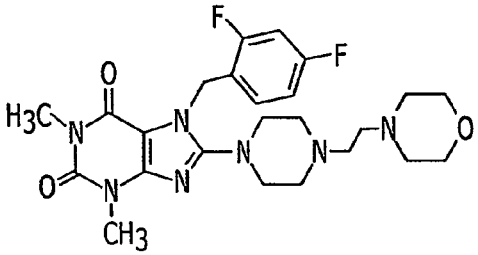 | 504 | 93 |
| 379 | 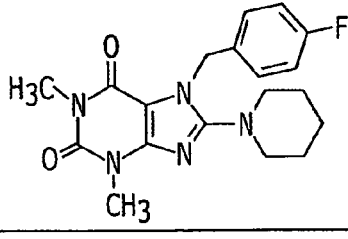 | 371 | 100 |
| 380 | 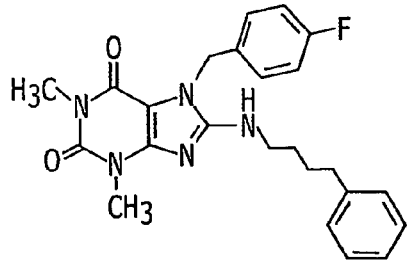 | 436 | 100 |
| 381 | 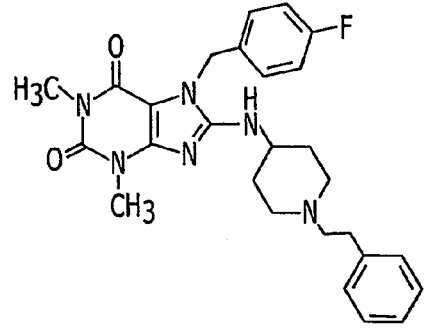 | 477 | 96 |
FIGURE 1W-1     TO FIGURE 1X-1

FROM FIGURE 1W-1
| 382 | 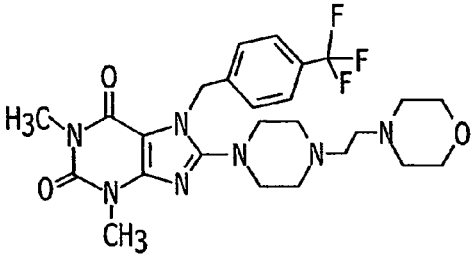 | 536 | 99 |
| 383 | 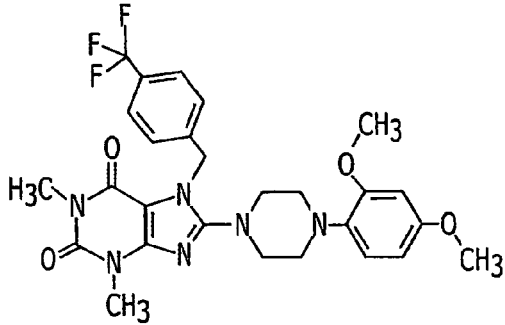 | 559 | 95 |
| 384 | 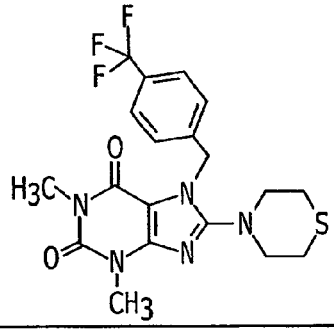 | 439 | 99 |
| 385 | 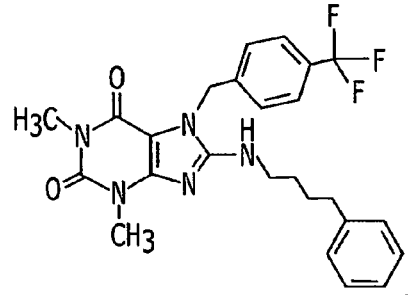 | 486 | 100 |
|     |                      |     |    |
FIGURE 1X-1    TO FIGURE 1Y-1

| | | | |
|---|---|---|---|
| 386 | 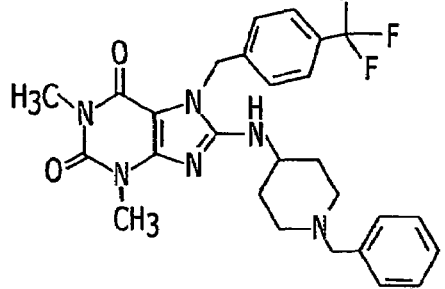 | 527 | 95 |
| 387 | 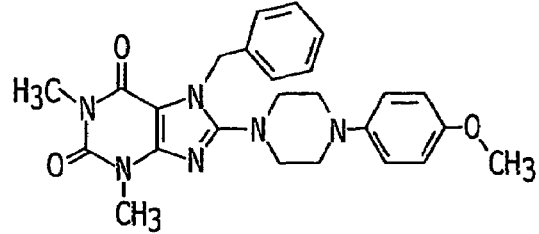 | 495 | 98 |
| 388 | 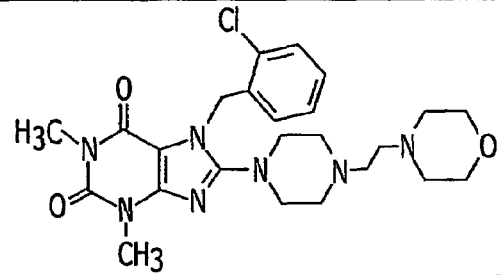 | 502 | 96 |
| 389 | 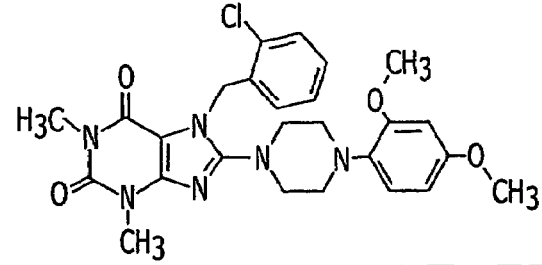 | 525 | 96 |
| 390 | 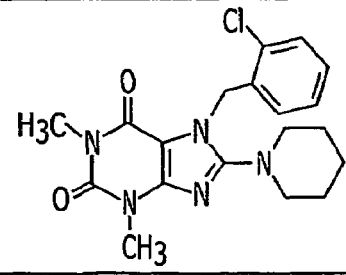 | 388 | 100 |
FIGURE 1Y-1

FROM FIGURE 1Y-1

| 391 |  | 452 | 98 |
| 392 |  | 536 | 93 |
| 393 |  | 627 | 92 |
| 394 |  | 513 | 76 |
| | | | |

FROM FIGURE 1Z-1
| 395 | 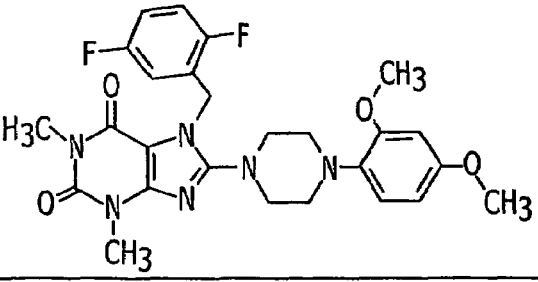 | 527 | 90 |
| 396 | 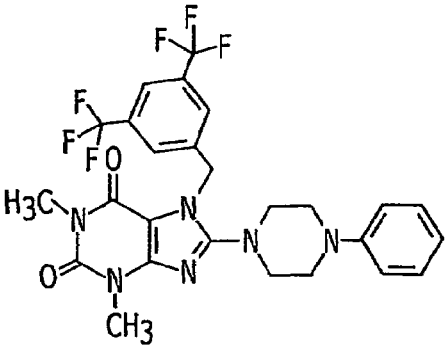 | 601 | 54 |
| 397 | 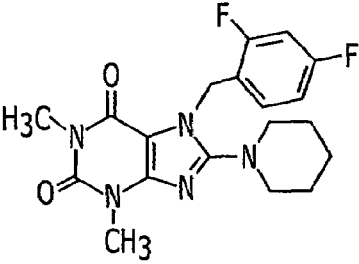 | 389 | 90 |
| 398 | 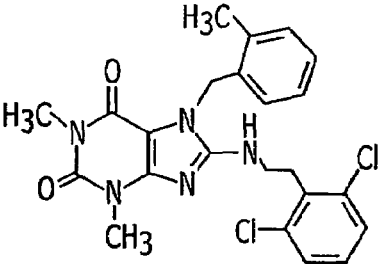 | 472 | 92 |
| 399 | 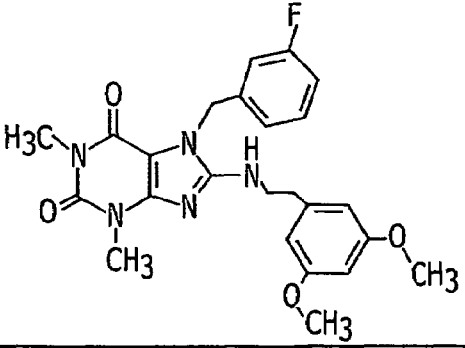 | 468 | 65 |
FIGURE 1A-2  TO FIGURE 1B-2

FROM FIGURE 1A-2

| # | Structure | | |
|---|---|---|---|
| 400 | (structure) | 482 | 87 |
| 401 | (structure) | 467 | 74 |
| 402 | (structure) | 529 | 77 |
| 403 | (structure) | 473 | 85 |
| 404 | (structure) | 584 | 87 |

FIGURE 1B-2    TO FIGURE 1C-2

FROM FIGURE 1B-2
| 405 | 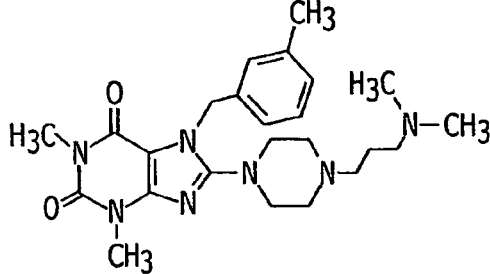 | 454 | 96 |
| 406 | 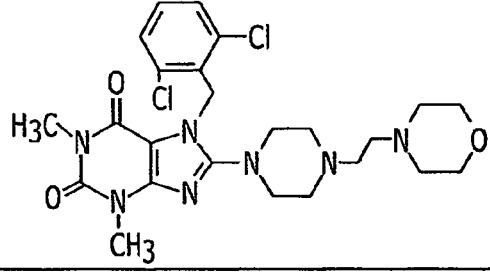 | 536 | 98 |
| 407 | 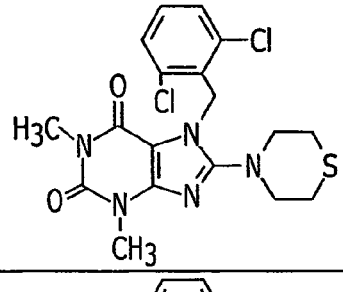 | 440 | 98 |
| 408 | 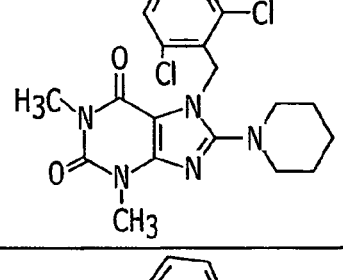 | 422 | 100 |
| 409 | 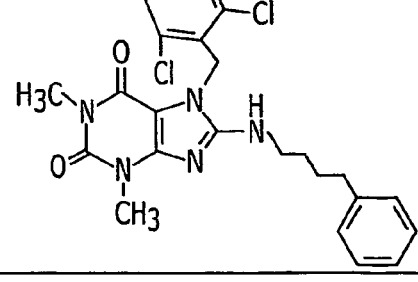 | 486 | 96 |
FIGURE 1C-2    TO FIGURE 1D-2

FROM FIGURE 1C-2
| 410 | 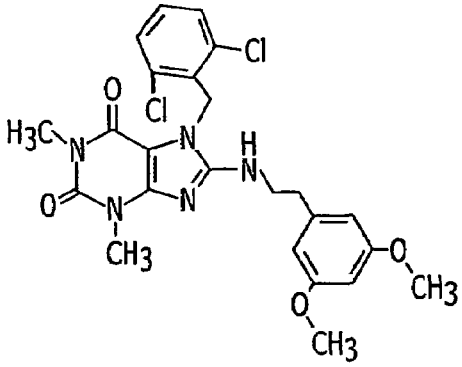 | 518 | 100 |
| 411 | 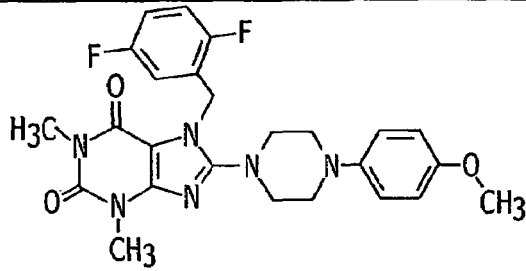 | 497 | 96 |
| 412 | 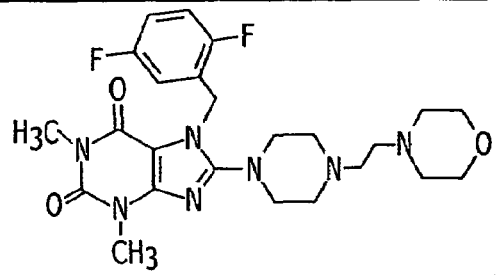 | 504 | 97 |
| 413 | 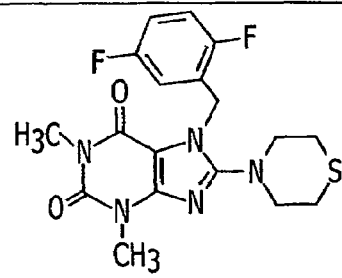 | 407 | 100 |
| 414 | 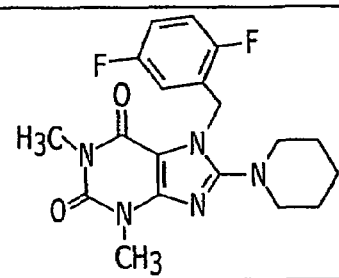 | 389 | 97 |
FIGURE 1D-2        TO FIGURE 1E-2

FROM FIGURE 1D-2
| 415 | 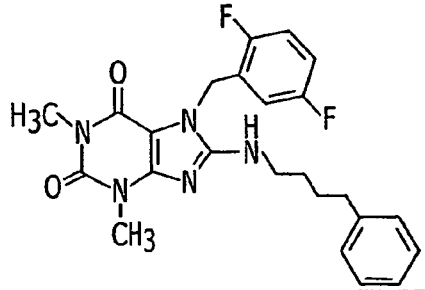 | 453 | 97 |
| 416 | 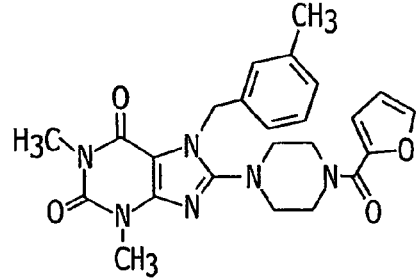 | 463 | 95 |
| 417 | 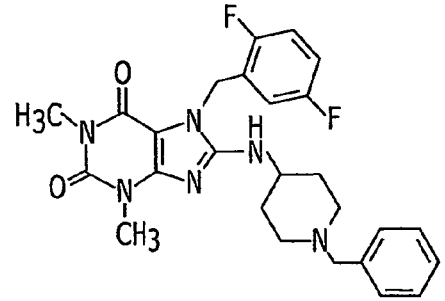 | 495 | 95 |
| 418 | 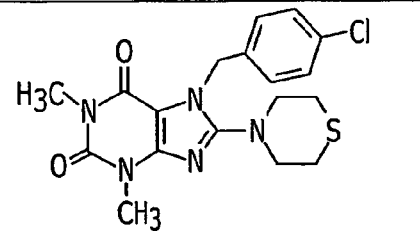 | 406 | 69 |
| 419 | 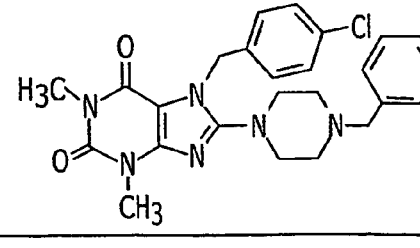 | 479 | 87 |
|     |                      |     |    |
FIGURE 1E-2        TO FIGURE 1F-2

FROM FIGURE 1E-2
| 420 | 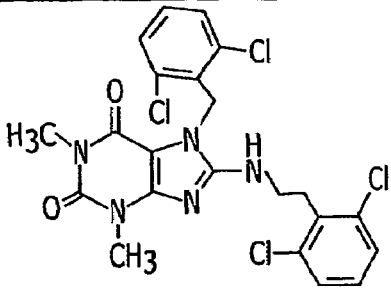 | 527 | 87 |
| 421 | 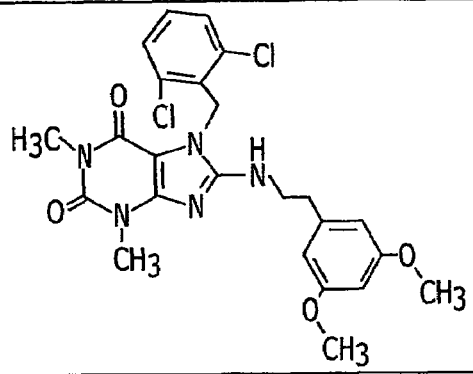 | 518 | 92 |
| 422 | 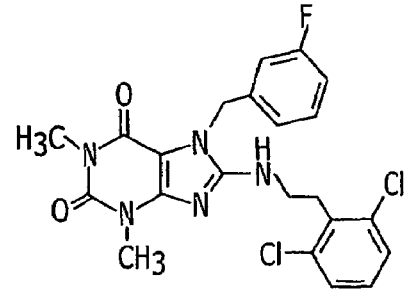 | 476 | 76 |
| 423 | 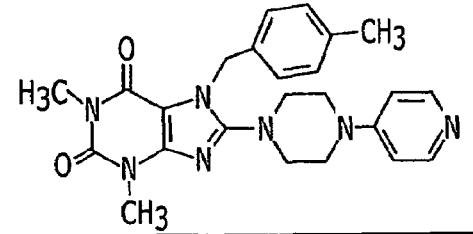 | 446 | 92 |
| 424 | 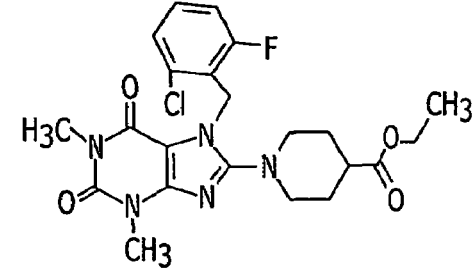 | 479 | 70 |
FIGURE 1F-2    TO FIGURE 1G-2

FROM FIGURE 1F-2
| 425 | 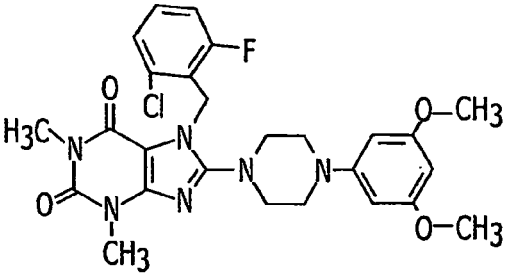 | 543 | 86 |
| --- | --- | --- | --- |
| 426 | 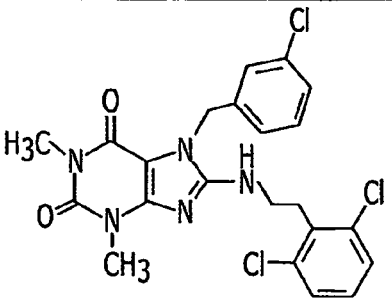 | 472 | 92 |
| 427 | 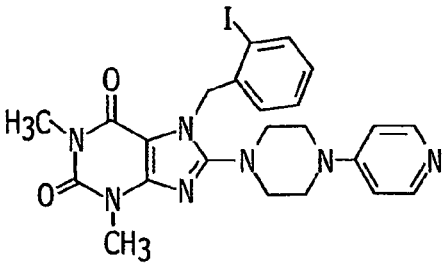 | 557 | 85 |
| 428 | 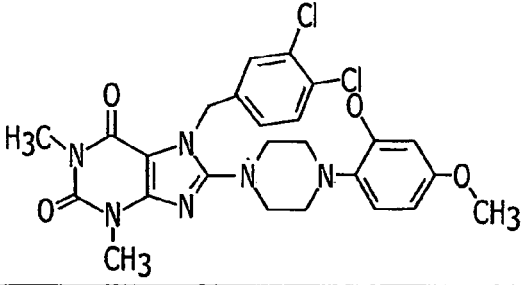 | 559 | 84 |
| 429 | 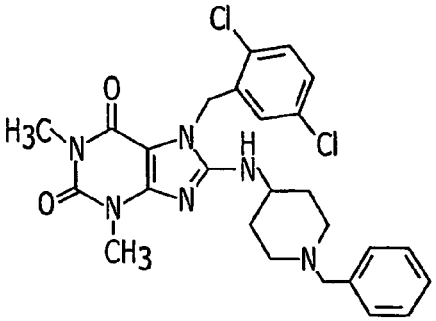 | 527 | 59 |
FIGURE 1G-2     TO FIGURE 1H-2

FROM FIGURE 1G-2

| # | Structure | | |
|---|---|---|---|
| 430 | (structure) | 422 | 87 |
| 431 | (structure) | 597 | 96 |
| 432 | (structure) | 604 | 98 |
| 433 | (structure) | 507 | 97 |

FIGURE 1H-2      TO FIGURE 1I-2

FROM FIGURE 1H-2

| 434 |  | 489 | 98 |
| 435 |  | 467 | 98 |
| 436 |  | 407 | 96 |
| 437 |  | 453 | 95 |
|     |                      |     |    |

FROM FIGURE 1I-2
| 438 | 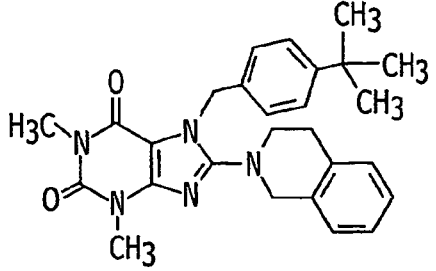 | 458 | 95 |
| 439 | 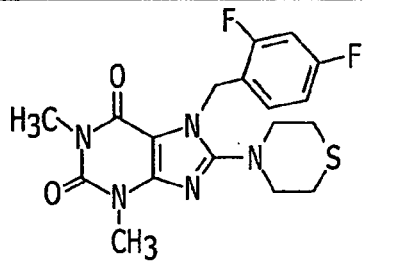 | 407 | 96 |
| 440 | 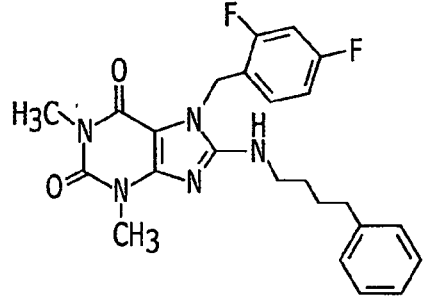 | 453 | 96 |
| 441 | 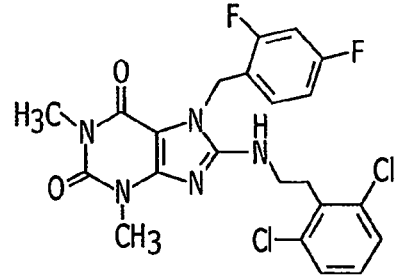 | 494 | 95 |
| 442 | 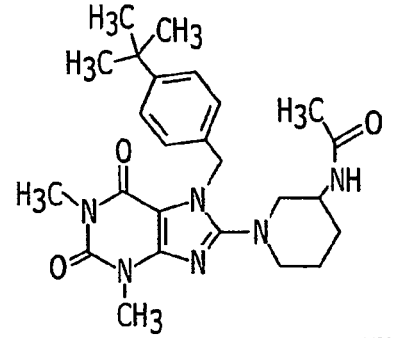 | 453 | 97 |
FIGURE 1J-2    TO FIGURE 1K-2

FROM FIGURE 1J-2
| | | | |
|---|---|---|---|
| 443 | 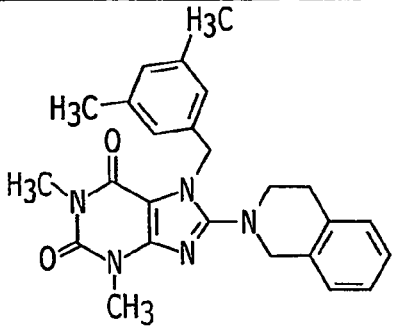 | 430 | 98 |
| 444 | 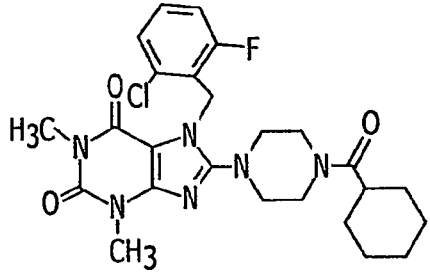 | 517 | 71 |
| 445 | 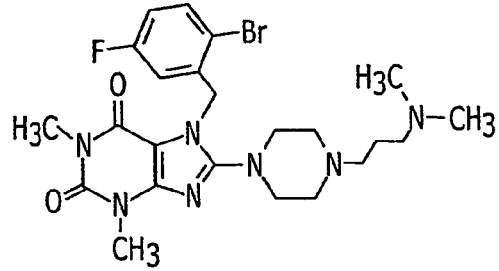 | 536 | 87 |
| 446 | 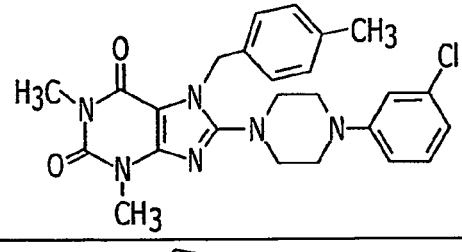 | 479 | 83 |
| 447 | 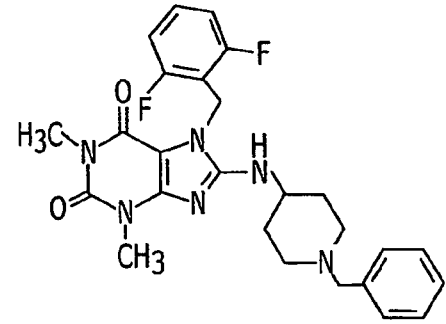 | 495 | 88 |
FIGURE 1K-2        TO FIGURE 1L-2

FROM FIGURE 1K-2
| 448 | 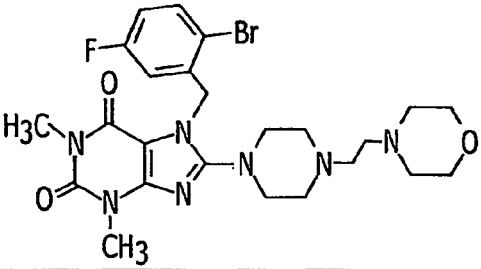 | 564 | 86 |
| 449 | 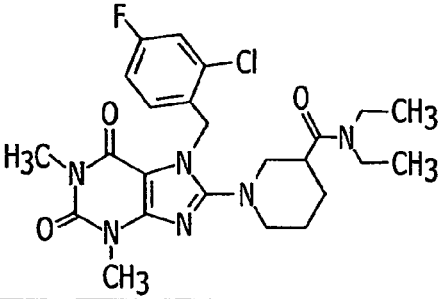 | 505 | 67 |
| 450 | 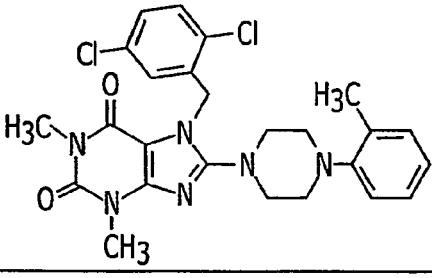 | 513 | 54 |
| 451 | 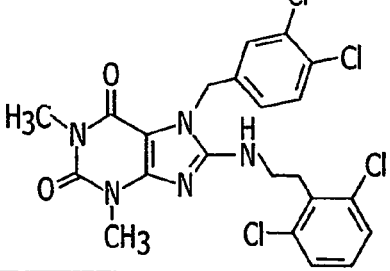 | 527 | 66 |
| 452 | 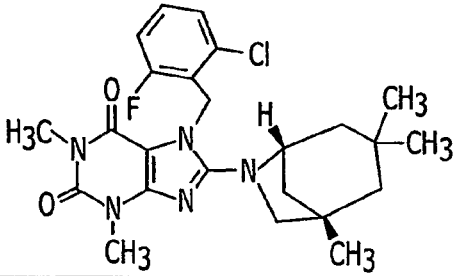 | 474 | 88 |
FIGURE 1L-2        TO FIGURE 1M-2

FROM FIGURE 1L-2

| 453 |  | 575 | 78 |
| 454 |  | 493 | 54 |
| 455 |  | 484 | 83 |
| 456 |  | 464 | 88 |
|     |                      |     |    |

FROM FIGURE 1M-2

| 457 |  | 425 | 98 |
| 458 |  | 460 | 98 |
| 459 |  | 477 | 99 |
| 460 |  | 404 | 88 |

FROM FIGURE 1N-2
| 461 | 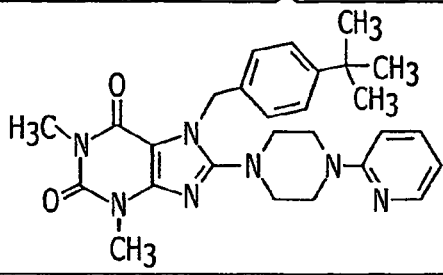 | 488 | 99 |
| 462 | 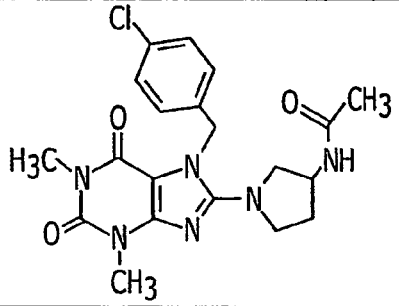 | 431 | 100 |
| 463 | 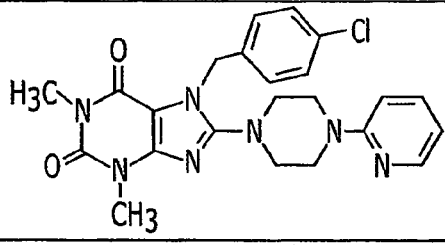 | 466 | 100 |
| 464 | 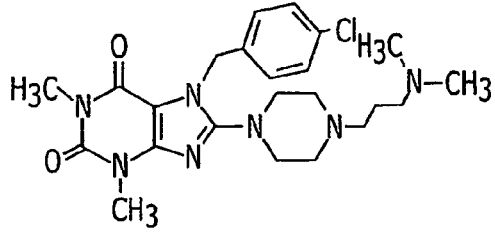 | 474 | 99 |
| 465 | 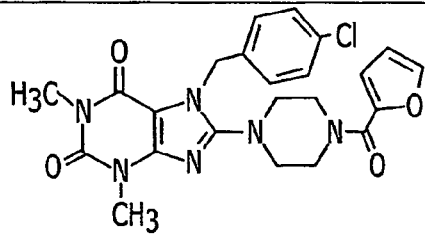 | 483 | 96 |
FIGURE 1O-2   TO FIGURE 1P-2

FROM FIGURE 1O-2
| 466 | 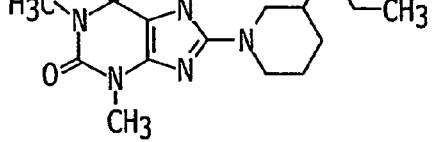 | 487 | 95 |
| 467 | 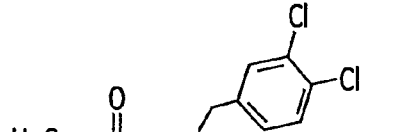 | 470 | 100 |
| 468 | 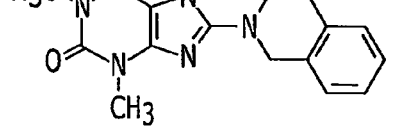 | 500 | 100 |
| 469 | 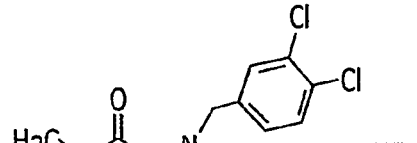 | 534 | 95 |
| 470 | 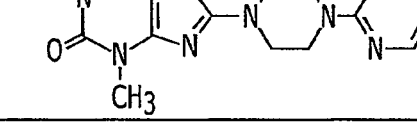 | 481 | 87 |
FIGURE 1P-2     TO FIGURE 1Q-2

FROM FIGURE 1P-2
| 471 | 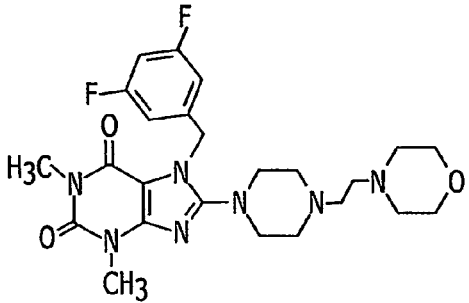 | 504 | 88 |
| 472 | 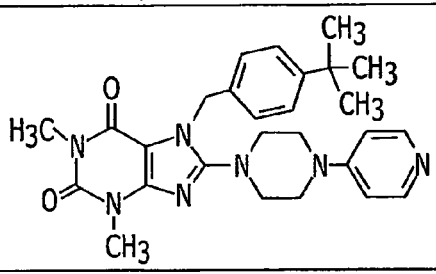 | 488 | 90 |
| 473 | 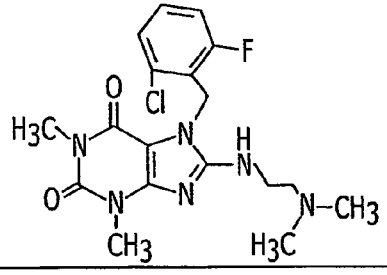 | 409 | 71 |
| 474 | 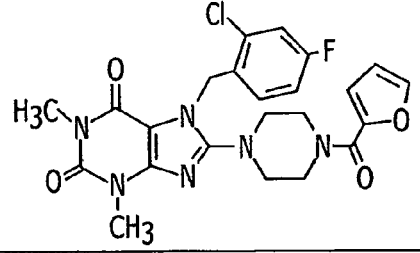 | 501 | 89 |
| 475 | 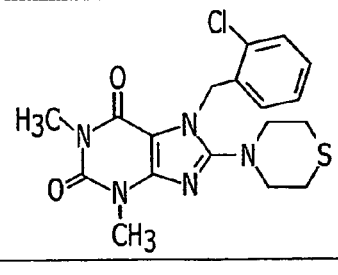 | 406 | 92 |
|  |  |  |  |
FIGURE 1Q-2     TO FIGURE 1R-2

FROM FIGURE 1Q-2
| | | | |
|---|---|---|---|
| 476 | 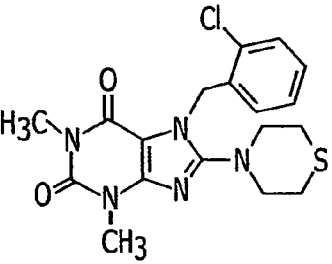 | 523 | 90 |
| 477 | 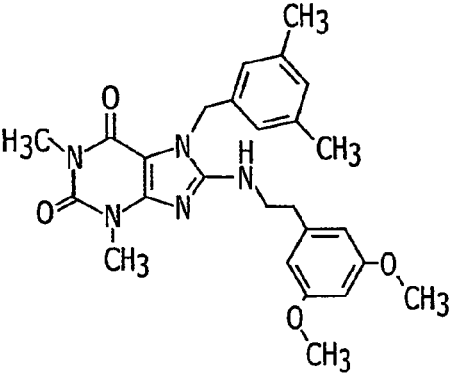 | 478 | 90 |
| 478 | 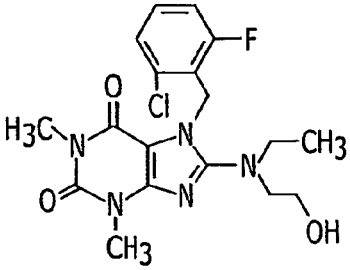 | 410 | 71 |
| 479 | 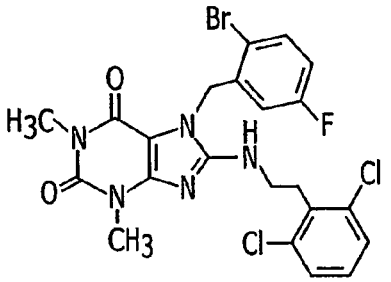 | 555 | 63 |
| 480 | 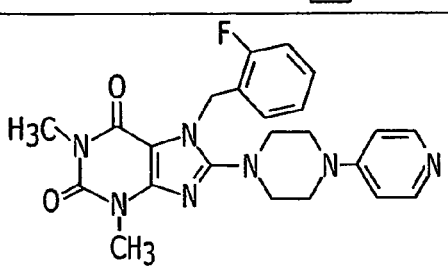 | 449 | 92 |
FIGURE 1R-2    TO FIGURE 1S-2

FROM FIGURE 1R-2
| 481 | 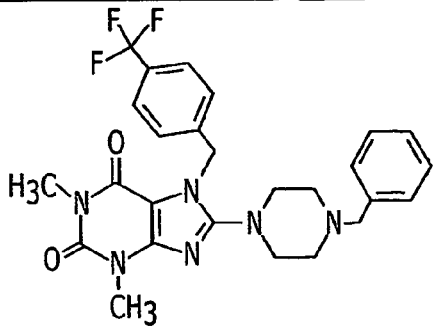 | 513 | 90 |
| 482 | 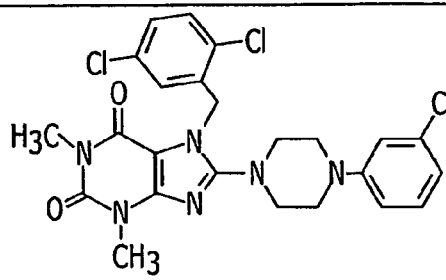 | 534 | 54 |
| 483 | 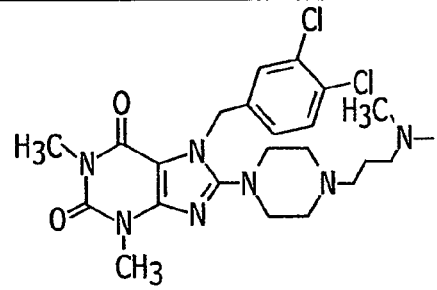 | 508 | 99 |
| 484 | 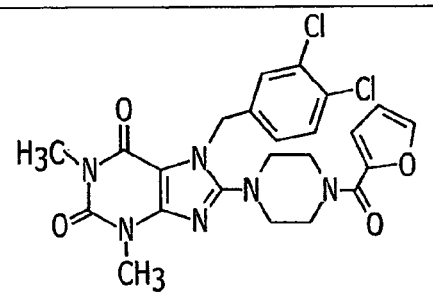 | 517 | 98 |
| 485 | 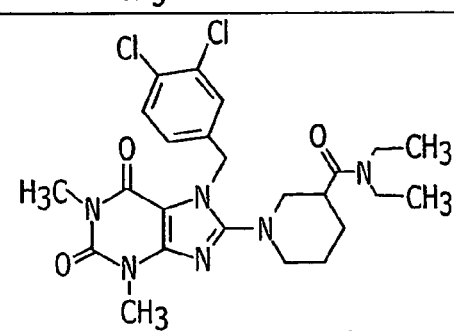 | 521 | 97 |
FIGURE 1S-2   TO FIGURE 1T-2

FROM FIGURE 1S-2
| 486 | 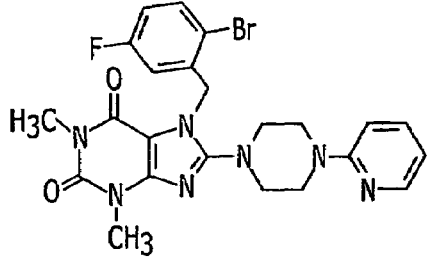 | 528 | 95 |
| 487 | 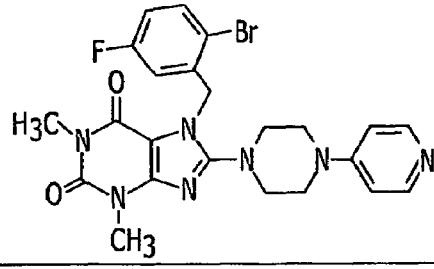 | 528 | 96 |
| 488 | 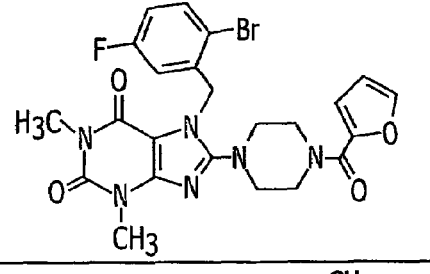 | 545 | 99 |
| 489 | 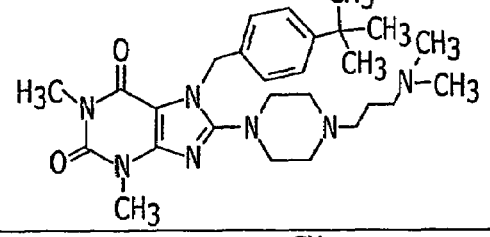 | 496 | 95 |
| 490 | 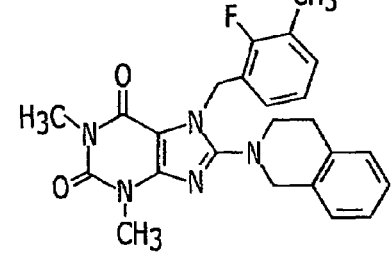 | 433 | 98 |
|     |                      |     |    |
FIGURE 1T-2     TO FIGURE 1U-2

FROM FIGURE 1T-2
| 491 | 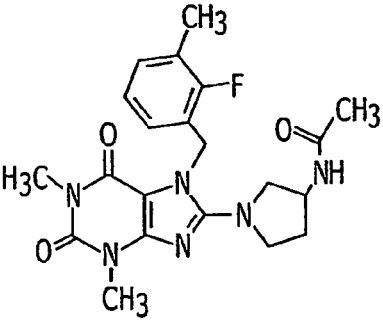 | 428 | 100 |
| 492 | 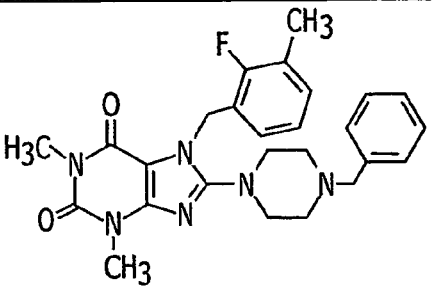 | 477 | 96 |
| 493 | 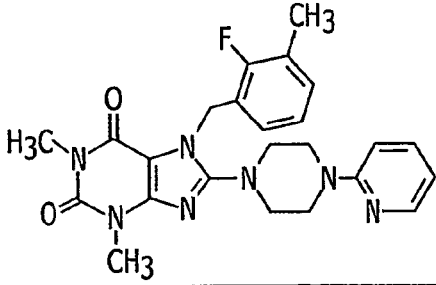 | 464 | 100 |
| 494 | 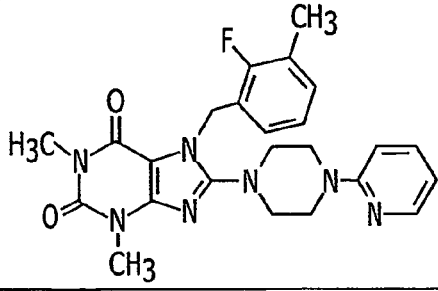 | 464 | 100 |
| 495 | 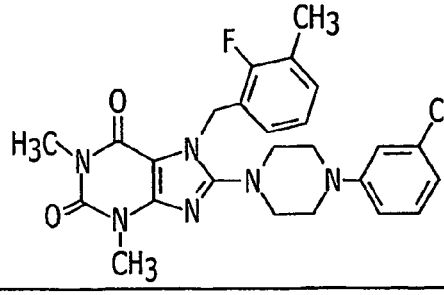 | 497 | 97 |
FIGURE 1U-2     TO FIGURE 1V-2

FROM FIGURE 1U-2
| 496 | 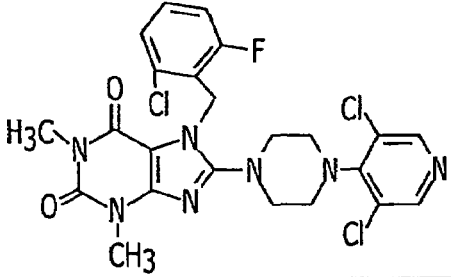 | 553 | 88 |
| 497 | 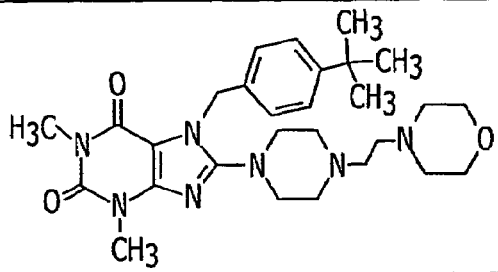 | 524 | 88 |
| 498 | 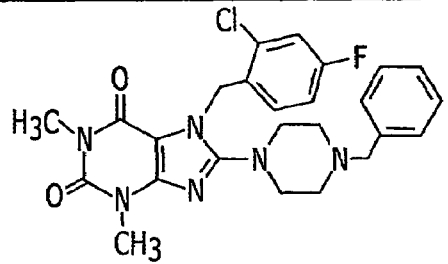 | 497 | 81 |
| 499 | 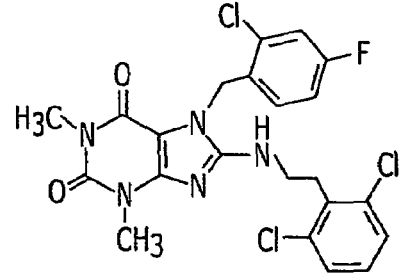 | 511 | 59 |
| 500 | 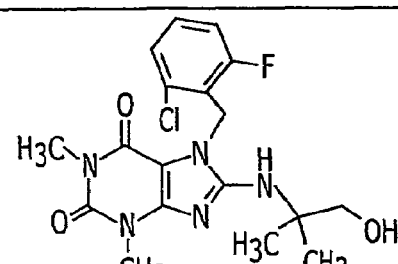 | 410 | 71 |
FIGURE 1V-2     TO FIGURE 1W-2

FROM FIGURE 1V-2
| | | | |
|---|---|---|---|
| 501 | 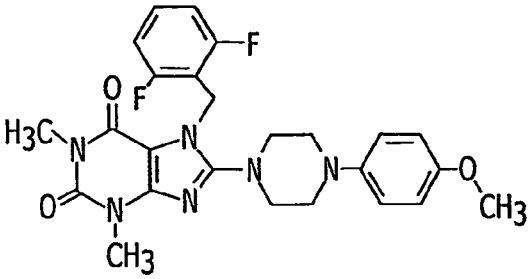 | 497 | 90 |
| 502 | 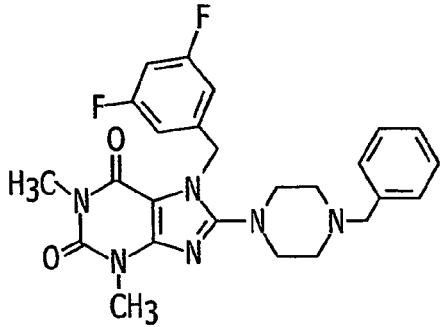 | 481 | 55 |
| 503 | 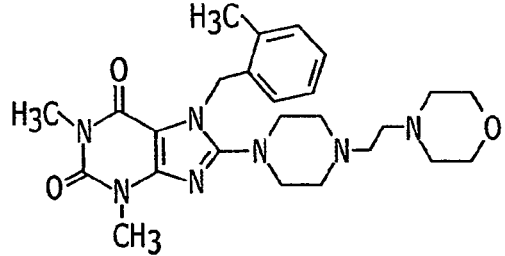 | 482 | 98 |
| 504 | 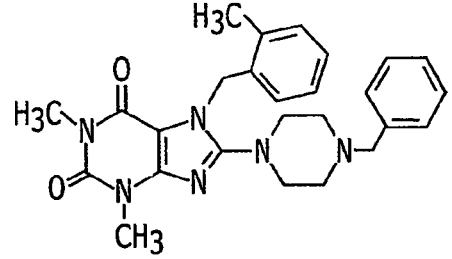 | 459 | 92 |
| 505 | 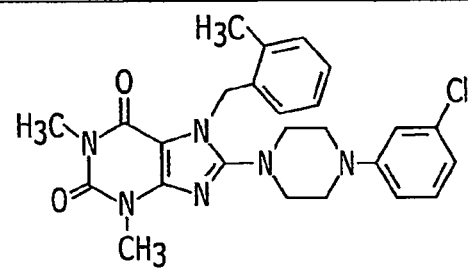 | 483 | 71 |
FIGURE 1W-2     TO FIGURE 1X-2

FROM FIGURE 1W-2
| 506 | 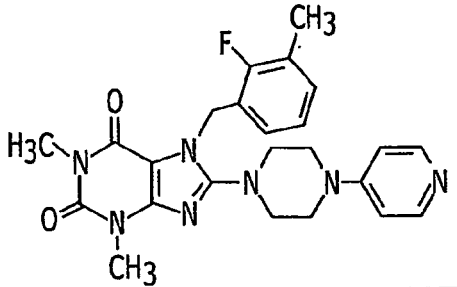 | 464 | 92 |
| 507 | 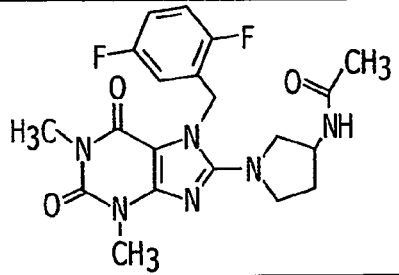 | 432 | 92 |
| 508 | 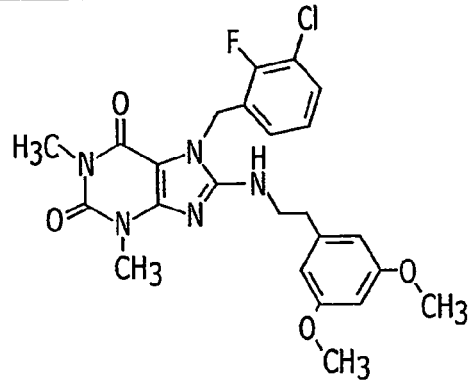 | 502 | 82 |
| 509 | 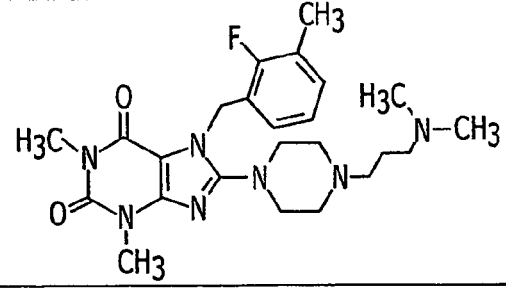 | 472 | 100 |
| 510 | 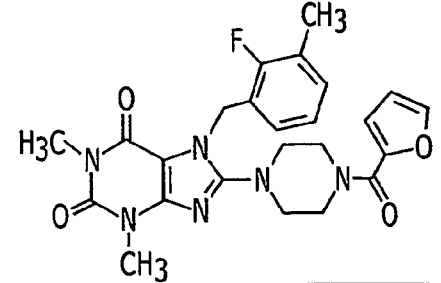 | 481 | 100 |
FIGURE 1X-2        TO FIGURE 1Y-2

FROM FIGURE 1X-2

| 511 |  | 485 | 100 |
| 512 |  | 454 | 96 |
| 513 |  | 454 | 96 |
| 514 |  | 449 | 100 |
|     |                      |     |     |

FROM FIGURE 1Y-2

| | | | |
|---|---|---|---|
| 515 | (structure) | 497 | 99 |
| 516 | (structure) | 484 | 100 |
| 517 | (structure) | 517 | 97 |
| 518 | (structure) | 492 | 100 |
| 519 | (structure) | 501 | 97 |

FIGURE 1Z-2   TO FIGURE 1A-3

FROM FIGURE 1Z-2

| | | | |
|---|---|---|---|
| 520 |  | 505 | 97 |
| 521 |  | 505 | 100 |
| 522 |  | 481 | 92 |
| 523 |  | 484 | 92 |
| 524 |  | 481 | 92 |

FROM FIGURE 1A-3

| 525 |  | 484 | 89 |
| 526 |  | 513 | 76 |
| 527 |  | 458 | 92 |
| 528 |  | 521 | 89 |
| 529 |  | 527 | 92 |
| | | | |

FROM FIGURE 1B-3

| # | Structure | | |
|---|---|---|---|
| 530 | 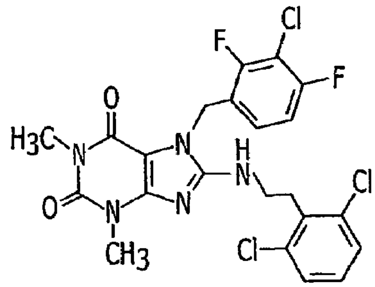 | 511 | 85 |
| 531 | 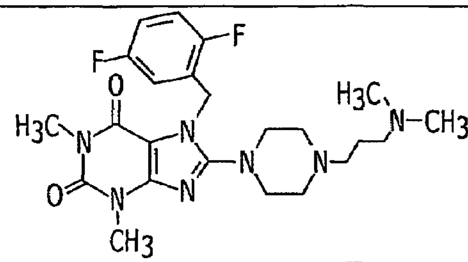 | 476 | 92 |
| 532 | 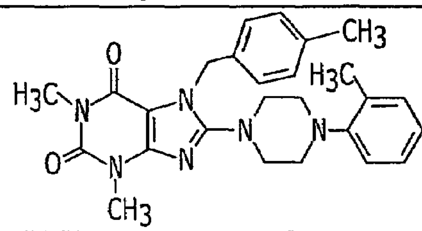 | 459 | 85 |
| 533 | 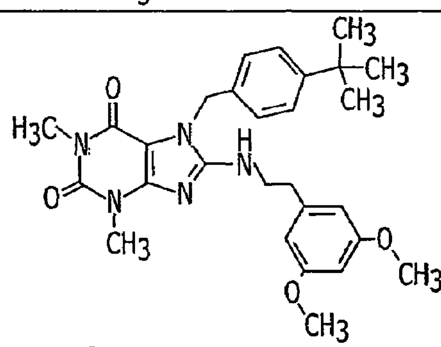 | 506 | 83 |
| 534 | 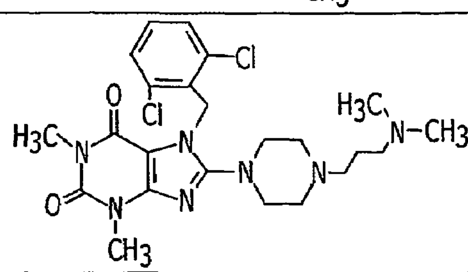 | 508 | 77 |

FROM FIGURE 1C-3
| 535 | 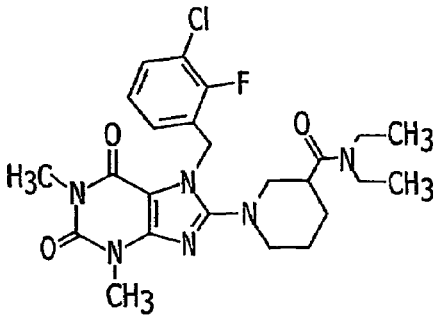 | 505 | 100 |
| 536 | 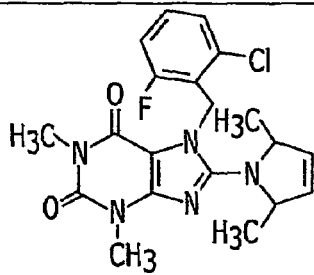 | 418 | 73 |
| 537 | 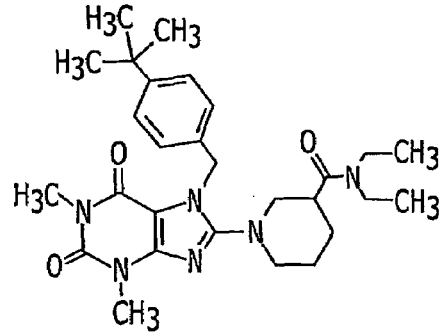 | 509 | 100 |
| 538 | 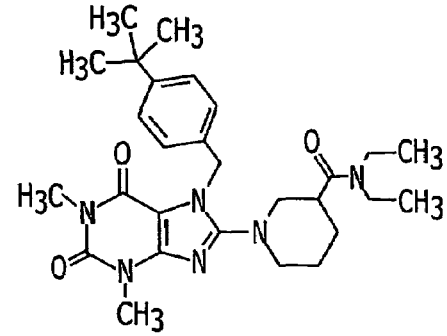 | 509 | 95 |
FIGURE 1D-3    TO FIGURE 1E-3

FROM FIGURE 1D-3
| 539 | 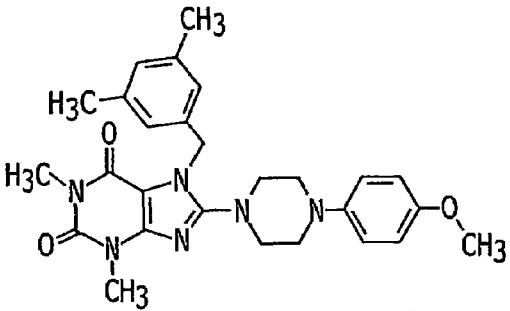 | 489 | 99 |
| 540 | 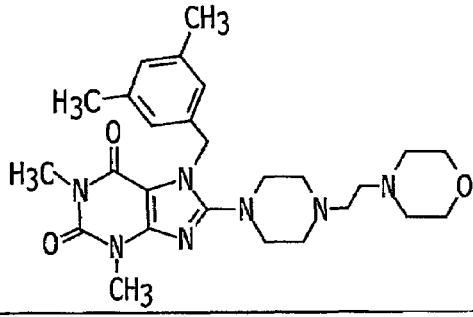 | 496 | 96 |
| 541 | 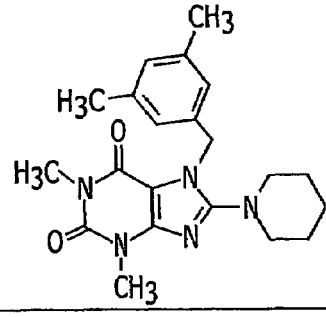 | 381 | 96 |
| 542 | 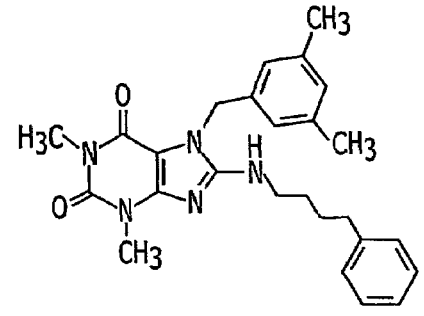 | 446 | 95 |
|  |  |  |  |
FIGURE 1E-3    TO FIGURE 1F-3

FROM FIGURE 1E-3

| 543 |  | 446 | 95 |
| 544 |  | 415 | 97 |
| 545 |  | 410 | 97 |
| 546 |  | 388 | 99 |
| 547 |  | 529 | 96 |

FROM FIGURE 1F-3

| 548 |  | 481 | 92 |
| 549 |  | 467 | 90 |
| 550 |  | 576 | 92 |
| 551 |  | 458 | 55 |
| 552 |  | 371 | 89 |

FROM FIGURE 1G-3
| 553 | 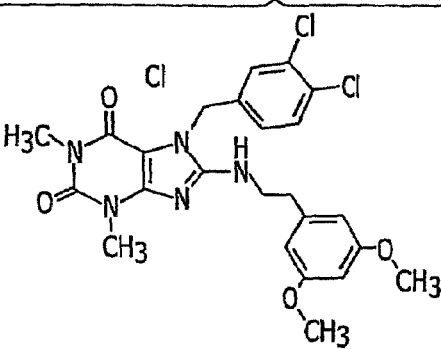 | 518 | 76 |
| 554 | 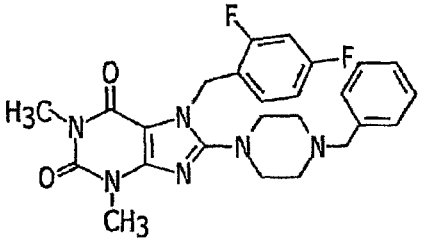 | 481 | 77 |
| 555 | 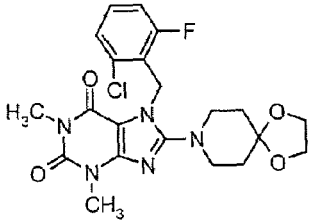 | 464 | 90 |
| 556 | 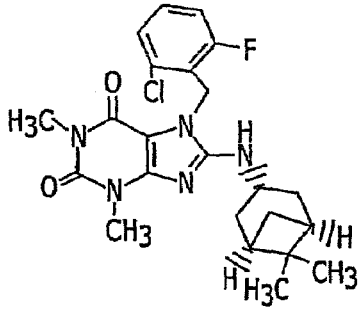 | 474 | 74 |
|  |  |  |  |
FIGURE 1H-3    TO FIGURE 1I-3

FROM FIGURE 1H-3

| 557 |  | 497 | 91 |
| 558 |  | 513 | 74 |
| 559 |  | 486 | 89 |
| 560 |  | 451 | 93 |
| 561 |  | 446 | 99 |
|     |                      |     |    |

FROM FIGURE 1I-3

| 562 | *(structure: 1,3-dimethyl-7-(2-bromo-4-fluorobenzyl)-8-thiomorpholinyl xanthine)* | 468 | 95 |
|---|---|---|---|
| 563 | *(structure: 1,3-dimethyl-7-(2-bromo-4-fluorobenzyl)-8-piperidinyl xanthine)* | 450 | 99 |
| 564 | *(structure: 1,3-dimethyl-7-(2-bromo-5-fluorobenzyl)-8-(3-phenylpropylamino) xanthine)* | 514 | 98 |
| 565 | *(structure: 1,3-dimethyl-7-(2-fluoro-3-methylbenzyl)-8-[4-(2-morpholinoethyl)piperazin-1-yl] xanthine)* | 500 | 96 |
| 566 | *(structure: 1,3-dimethyl-7-(2-fluoro-3-methylbenzyl)-8-thiomorpholinyl xanthine)* | 403 | 97 |

FIGURE 1J-3    TO FIGURE 1K-3

FROM FIGURE 1J-3
| 567 | 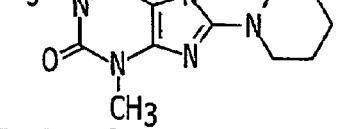 | 385 | 97 |
| 568 | 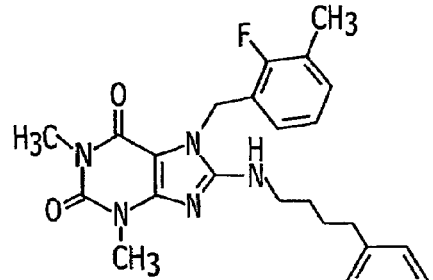 | 450 | 96 |
| 569 | 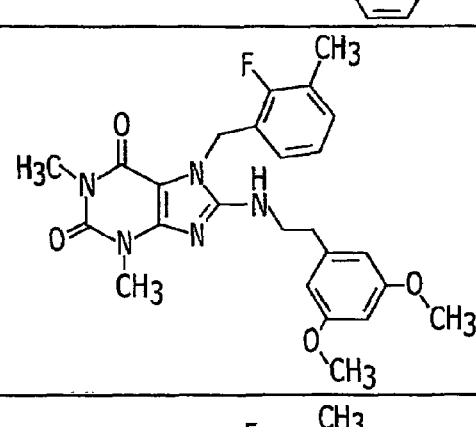 | 482 | 95 |
| 570 | 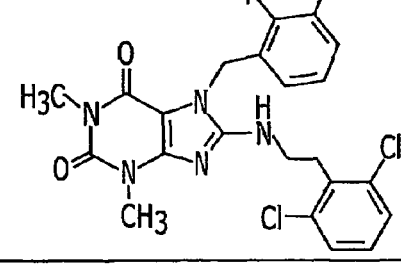 | 490 | 97 |
FIGURE 1K-3     TO FIGURE 1L-3

FROM FIGURE 1K-3

| 571 |  | 513 | 98 |
| 572 |  | 520 | 96 |
| 573 |  | 424 | 98 |
| 574 |  | 474 | 90 |
| 575 |  | 498 | 78 |

FROM FIGURE 1L-3

| 576 |  | 408 | 93 |
| 577 |  | 500 | 79 |
| 578 |  | 459 | 70 |
| 579 |  | 581 | 83 |
| 580 |  | 481 | 85 |

FROM FIGURE 1M-3
| 581 | 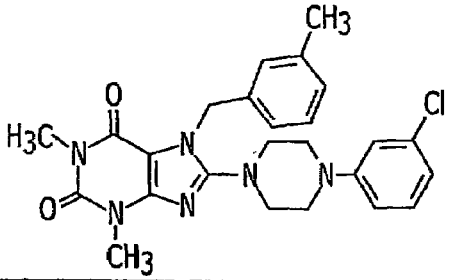 | 479 | 88 |
| 582 | 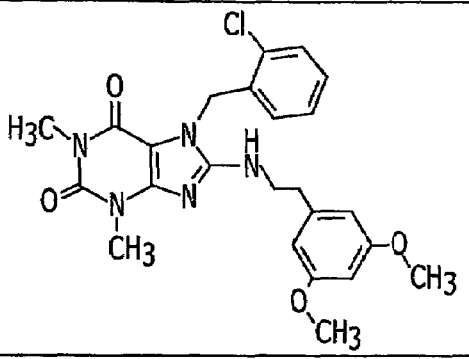 | 484 | 61 |
| 583 | 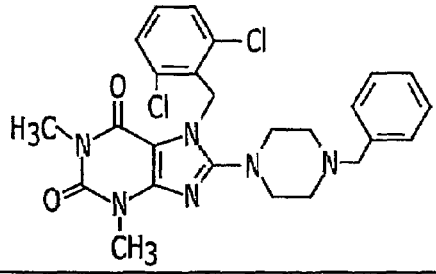 | 513 | 83 |
| 584 | 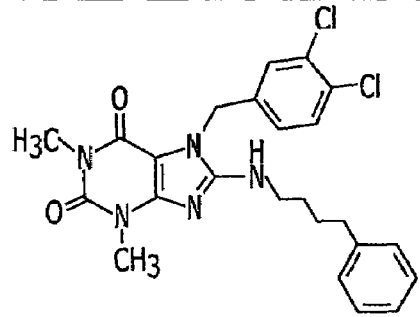 | 486 | 88 |
|     |                      |     |    |
FIGURE 1N-3    TO FIGURE 1O-3

FROM FIGURE 1N-3
| 585 | 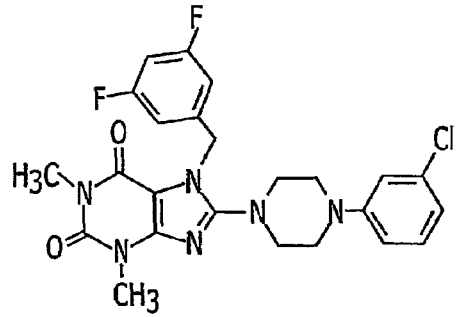 | 501 | 69 |
| 586 | 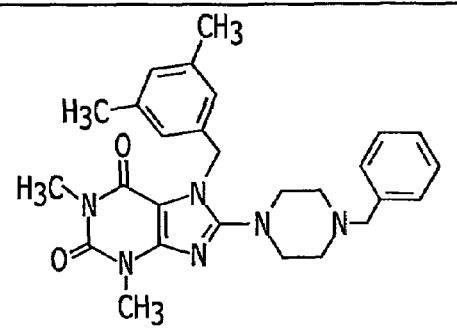 | 473 | 89 |
| 587 | 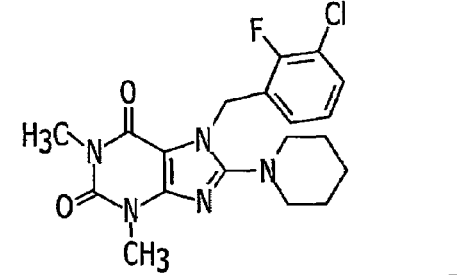 | 406 | 98 |
| 588 | 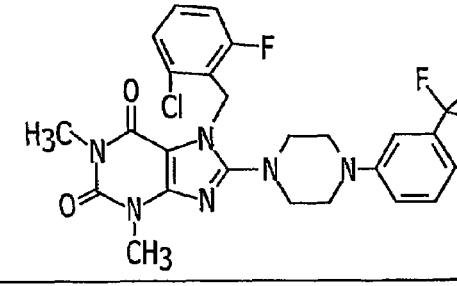 | 585 | 76 |
|  |  |  |  |
FIGURE 1O-3  TO FIGURE 1P-3

FROM FIGURE 1O-3

| 589 |  | 463 | 98 |
| 590 |  | 438 | 76 |
| 591 |  | 434 | 78 |
| 592 |  | 551 | 78 |
| 593 |  | 446 | 79 |
|     |                      |     |    |

FROM FIGURE 1P-3

| | | | |
|---|---|---|---|
| 594 |  | 497 | 79 |
| 595 |  | 466 | 88 |
| 596 |  | 468 | 85 |
| 597 |  | 567 | 96 |
| 598 |  | 481 | 86 |

FROM FIGURE 1Q-3

| 599 |  | 492 | 83 |
| 600 |  | 495 | 87 |
| 601 |  | 494 | 52 |
| 602 |  | 501 | 87 |
| 603 |  | 581 | 86 |

| | | | |
|---|---|---|---|
| 604 | 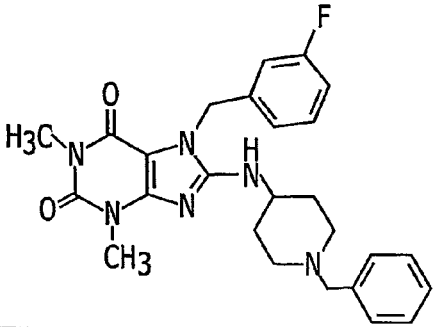 | 477 | 85 |
| 605 | 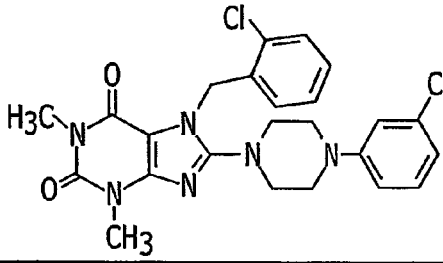 | 499 | 92 |
| 606 | 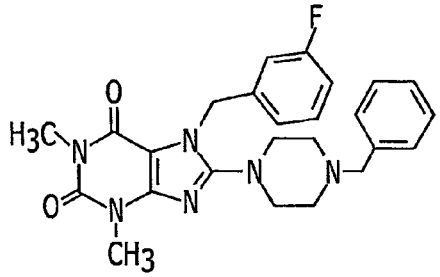 | 463 | 92 |
| 607 | 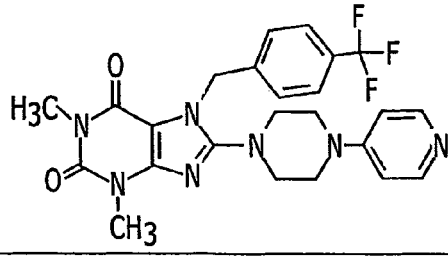 | 499 | 89 |
| 608 | 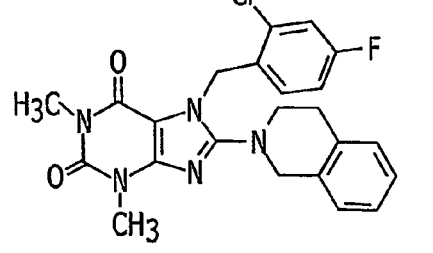 | 454 | 80 |
FIGURE 1S-3

FROM FIGURE 1S-3

| 609 |  | 446 | 90 |
| 610 |  | 476 | 70 |
| 611 |  | 460 | 69 |
| 612 |  | 473 | 90 |
| 613 |  | 475 | 98 |

FROM FIGURE 1T-3

| 614 |  | 449 | 97 |
| 615 |  | 419 | 96 |
| 616 |  | 414 | 97 |
| 617 |  | 662 | 53 |
| 618 |  | 537 | 87 |

FROM FIGURE 1U-3

| 619 |  | 484 | 98 |
| --- | --- | --- | --- |
| 620 |  | 467 | 99 |
| 621 |  | 543 | 100 |
| 622 |  | 479 | 97 |
| 623 |  | 497 | 95 |
|  |  |  |  |

FROM FIGURE 1V-3

| 624 |  | 414 | 98 |
| 626 |  | 473 | 87 |
| 627 |  | 473 | 91 |
| 628 |  | 467 | 79 |
| 629 |  | 489 | 95 |

FROM FIGURE 1W-3

| 630 |  | 472 | 69 |
| 631 |  | 570 | 81 |
| 632 |  | 501 | 98 |
| 633 |  | 546 | 89 |
| 634 |  | 486 | 91 |

FROM FIGURE 1X-3

| 635 |  | 436 | 87 |
| 636 |  | 513 | 91 |
| 637 |  | 484 | 88 |
| 638 |  | 449 | 58 |
| 639 |  | 454 | 96 |
|     |                      |     |    |

FROM FIGURE 1Y-3
| 640 | 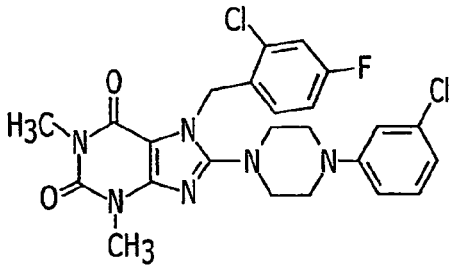 | 517 | 97 |
| 641 | 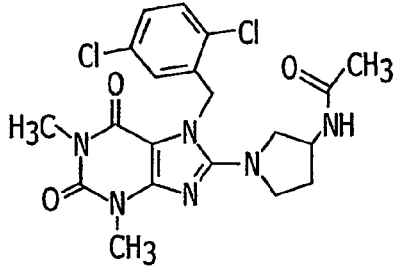 | 465 | 100 |
| 642 | 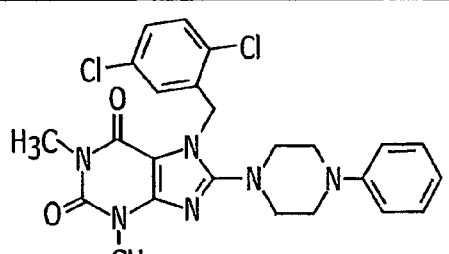 | 500 | 99 |
| 643 | 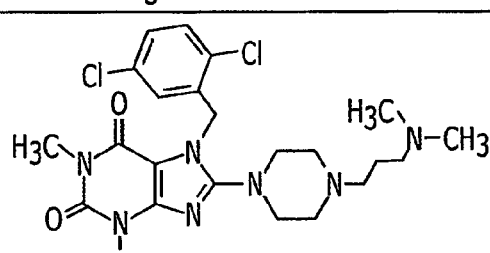 | 508 | 96 |
| 644 | 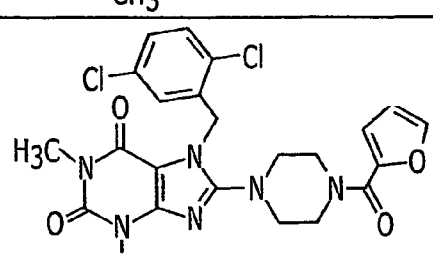 | 517 | 100 |
FIGURE 1Z-3     TO FIGURE 1A-4

FROM FIGURE 1Z-3

| 645 | [structure] | 449 | 100 |
| --- | --- | --- | --- |
| 646 | [structure] | 521 | 96 |
| 647 | [structure] | 519 | 91 |
| 648 | [structure] | 479 | 91 |
| 649 | [structure] | 479 | 87 |

FIGURE 1A-4   TO FIGURE 1B-4

FROM FIGURE 1A-4
| 649 | 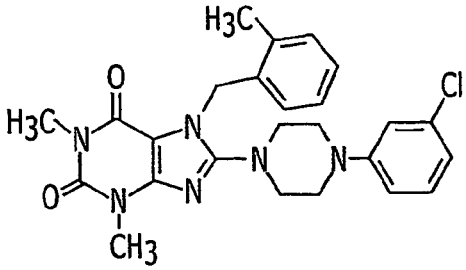 | 479 | 87 |
| --- | --- | --- | --- |
| 650 | 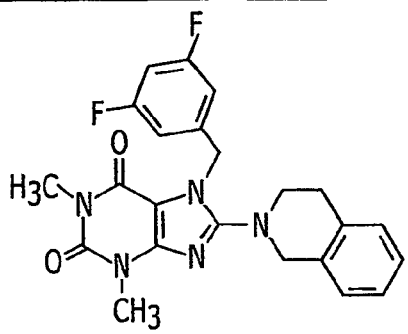 | 437 | 60 |
| 651 | 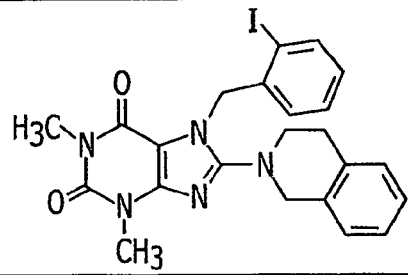 | 527 | 96 |
| 652 | 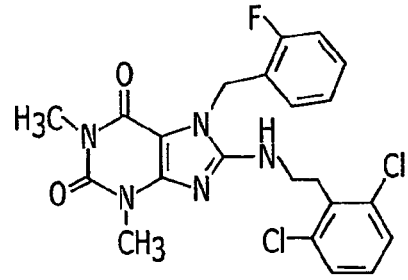 | 476 | 89 |
| 653 | 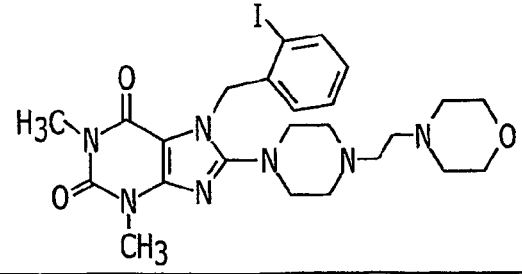 | 593 | 98 |
|     |                      |     |    |
FIGURE 1B-4    TO FIGURE 1C-4

FROM FIGURE 1B-4

| # | Structure | | |
|---|---|---|---|
| 654 | (structure) | 501 | 91 |
| 655 | (structure) | 536 | 90 |
| 656 | (structure) | 557 | 78 |
| 657 | (structure) | 501 | 91 |
| 658 | (structure) | 513 | 91 |

FIGURE 1C-4    TO FIGURE 1D-4

FROM FIGURE 1C-4
| 659 | 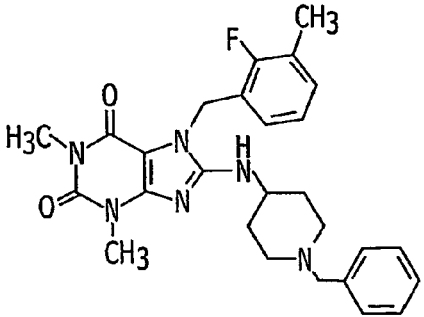 | 491 | 78 |
| 660 | 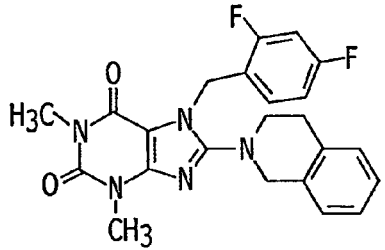 | 437 | 81 |
| 661 | 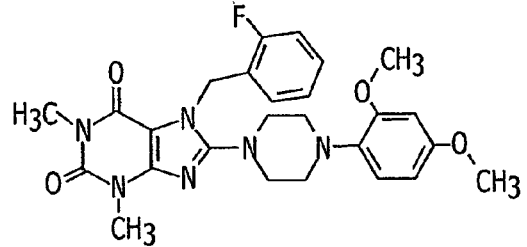 | 509 | 91 |
| 662 | 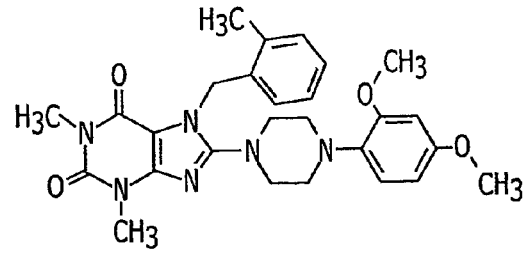 | 505 | 98 |
| 663 | 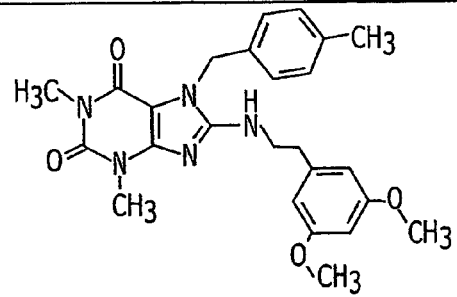 | 464 | 91 |
FIGURE 1D-4  TO FIGURE 1E-4

FROM FIGURE 1D-4
| 664 | 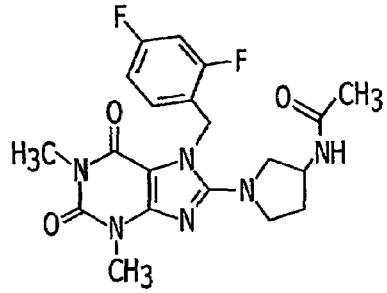 | 432 | 75 |
| 665 | 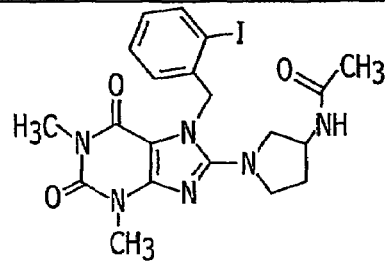 | 522 | 99 |
| 666 | 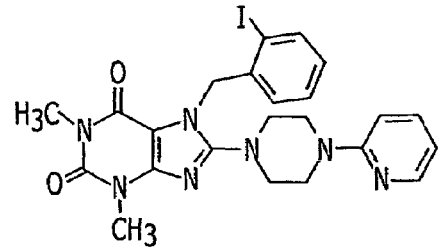 | 557 | 97 |
| 667 | 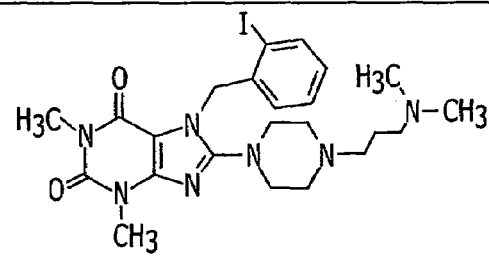 | 565 | 97 |
| 668 | 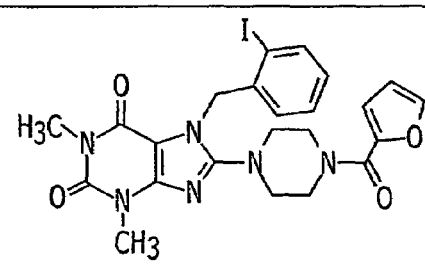 | 574 | 100 |
| | | | |
FIGURE 1E-4    TO FIGURE 1F-4

FROM FIGURE 1E-4
| 669 | 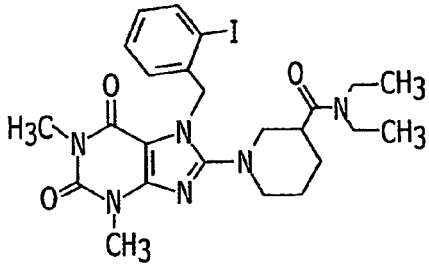 | 578 | 98 |
| 670 | 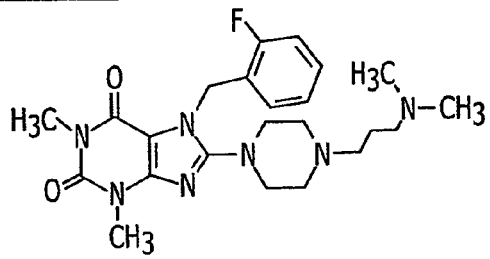 | 458 | 97 |
| 671 | 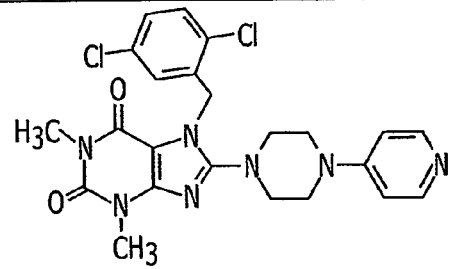 | 500 | 83 |
| 672 | 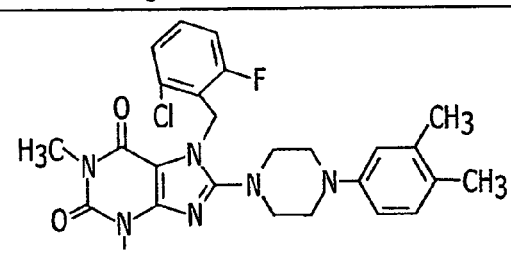 | 511 | 94 |
| 673 | 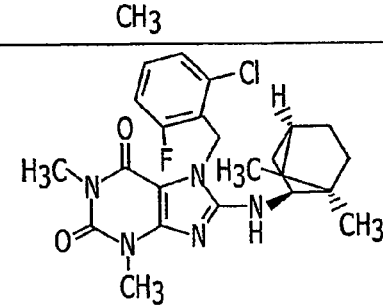 | 474 | 94 |
FIGURE 1F-4     TO FIGURE 1G-4

FROM FIGURE 1F-4
| 674 | 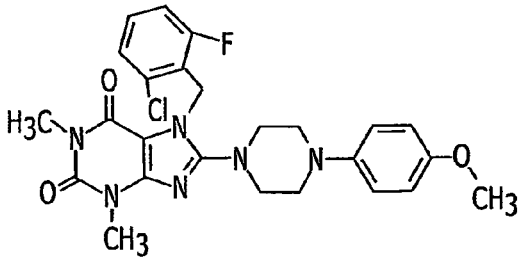 | 513 | 96 |
| 675 | 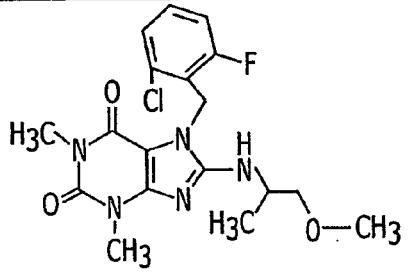 | 410 | 97 |
| 676 | 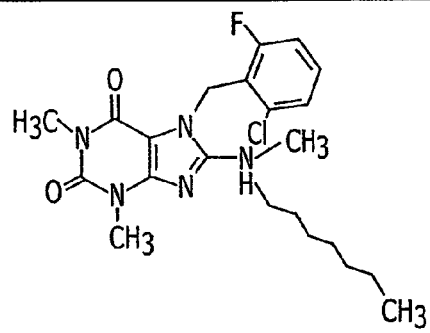 | 450 | 97 |
| 677 | 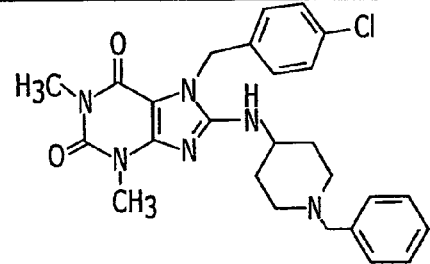 | 493 | 84 |
| 678 | 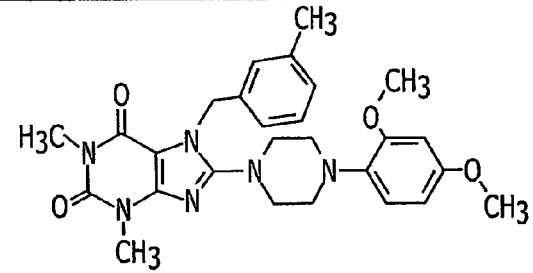 | 505 | 89 |
FIGURE 1G-4        TO FIGURE 1H-4

FROM FIGURE 1G-4
| 679 | 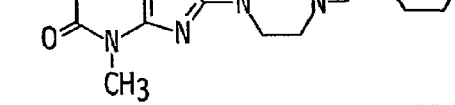 | 520 | 82 |
| 680 | 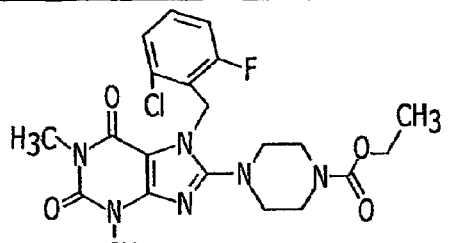 | 478 | 100 |
| 681 | 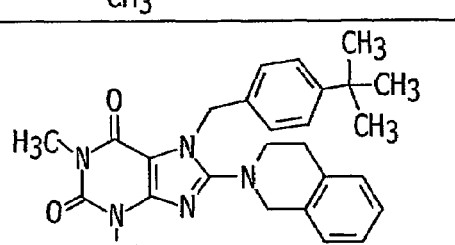 | 458 | 91 |
| 682 | 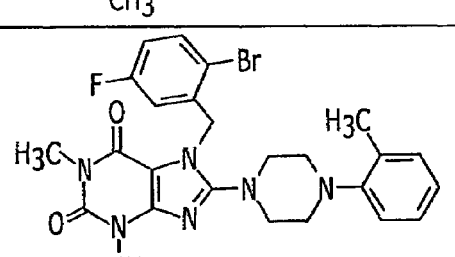 | 541 | 87 |
|     |                      |     |    |
FIGURE 1H-4    TO FIGURE 1I-4

FROM FIGURE 1H-4
| 698 | 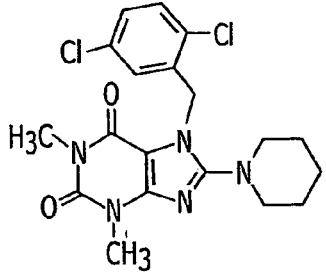 | 422 | 100 |
| 699 | 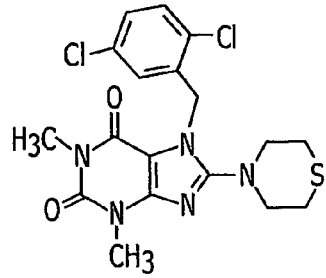 | 440 | 100 |
| 700 | 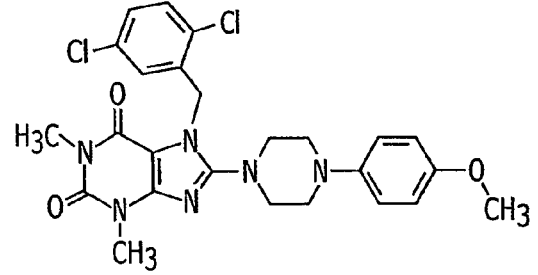 | 529 | 99 |
| 701 | 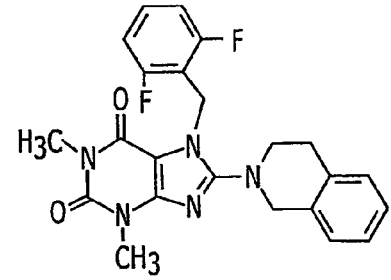 | 437 | 97 |
| 702 | 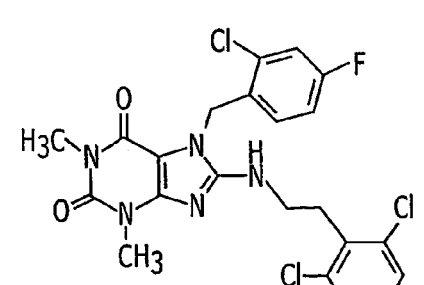 | 511 | 97 |
FIGURE 1I-4     TO FIGURE 1J-4

FROM FIGURE 1I-4
| 703 | 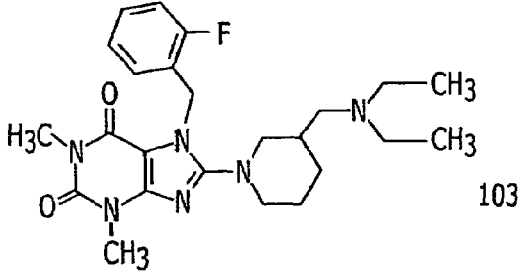 103 | 471 | 97 |
| 704 | 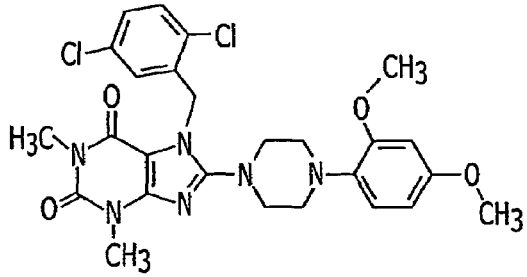 | 559 | 87 |
| 705 | 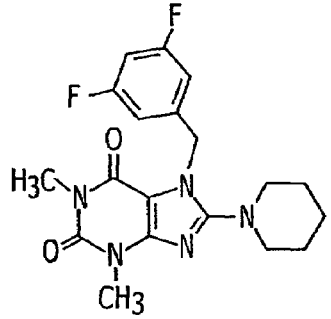 | 389 | 63 |
| 706 | 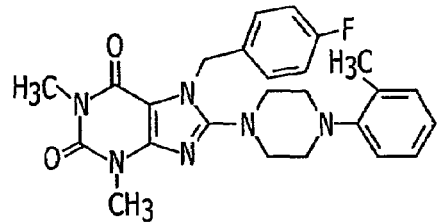 | 463 | 78 |
| 707 | 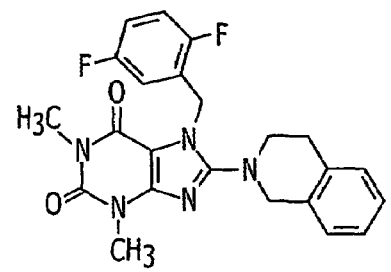 | 437 | 91 |
FIGURE 1J-4    TO FIGURE 1K-4

FROM FIGURE 1J-4
| 708 | 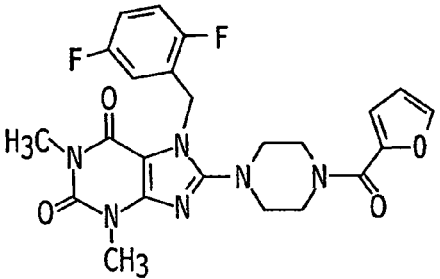 | 484 | 91 |
| 709 | 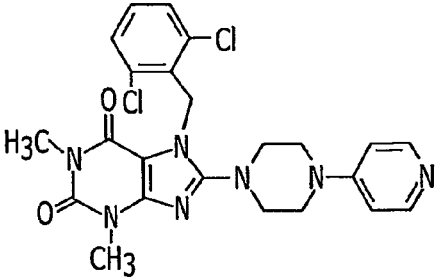 | 500 | 54 |
| 710 | 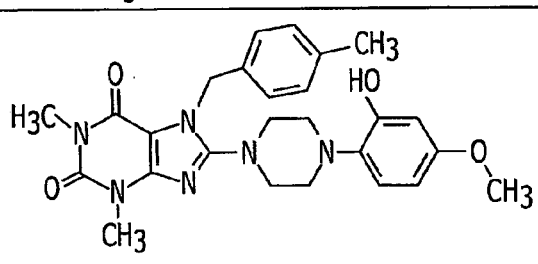 | 505 | 88 |
| 711 | 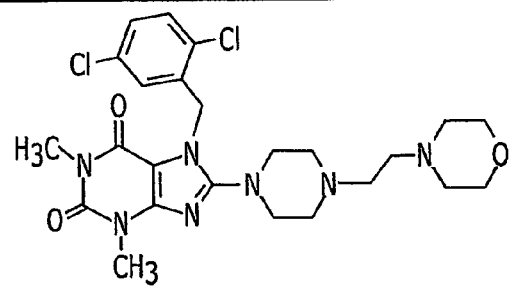 | 536 | 98 |
| 712 | 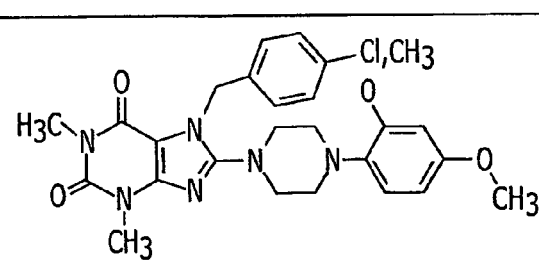 | 525 | 87 |
FIGURE 1K-4    TO FIGURE 1L-4

FROM FIGURE 1K-4

| # | Structure | | |
|---|---|---|---|
| 713 | (xanthine with 7-(2-chloro-4-fluorobenzyl), 1,3-dimethyl, 8-NH-(1-benzylpiperidin-4-yl)) | 511 | 95 |
| 714 | (xanthine with 7-(2-fluorobenzyl), 1,3-dimethyl, 8-NH-(1-benzylpiperidin-4-yl)) | 477 | 90 |
| 715 | (xanthine with 7-(2-methylbenzyl), 1,3-dimethyl, 8-piperidinyl) | 367 | 98 |
| 716 | (xanthine with 7-(3,5-difluorobenzyl), 1,3-dimethyl, 8-(4-(3-(dimethylamino)propyl)piperazin-1-yl)) | 476 | 85 |
| 717 | (xanthine with 7-(2-chloro-4-fluorobenzyl), 1,3-dimethyl, 8-(4-(4-methoxyphenyl)piperazin-1-yl)) | 513 | 100 |

FIGURE 1L-4    TO FIGURE 1M-4

FROM FIGURE 1L-4

| # | Structure | | |
|---|---|---|---|
| 718 | (xanthine with 1,3-dimethyl, 7-(2-chloro-4-fluorobenzyl), 8-thiomorpholinyl) | 424 | 96 |
| 719 | (xanthine with 1,3-dimethyl, 7-(2-chloro-4-fluorobenzyl), 8-piperidinyl) | 406 | 98 |
| 720 | (xanthine with 1,3-dimethyl, 7-(2-chloro-4-fluorobenzyl), 8-NH-(4-phenylbutyl)) | 470 | 98 |
| 721 | (xanthine with 1,3-dimethyl, 7-(2-chloro-4-fluorobenzyl), 8-NH-CH2CH2-(3,5-dimethoxyphenyl)) | 502 | 99 |

FIGURE 1M-4   TO FIGURE 1N-4

| | FROM FIGURE 1M-4 | | |
|---|---|---|---|
| 683 | 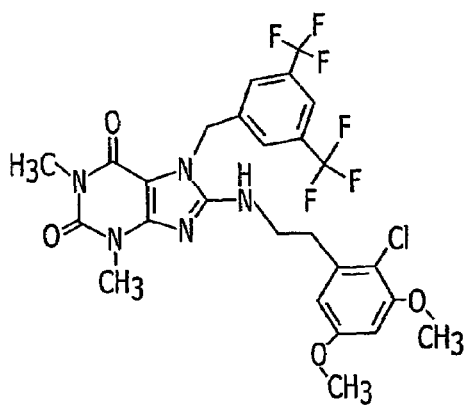 | 586 | 83 |
| 684 | 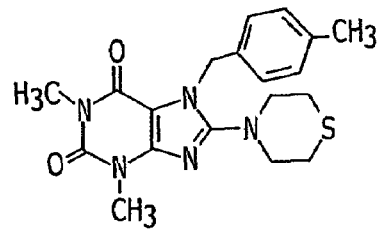 | 385 | 89 |
| 685 | 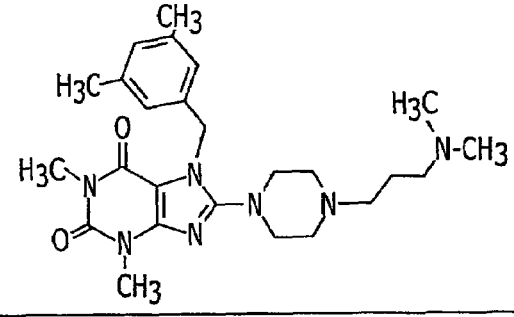 | 468 | 89 |
| 686 | 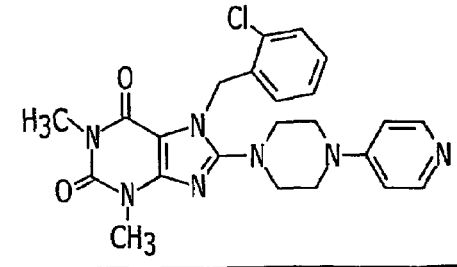 | 466 | 88 |
| | | | |
FIGURE 1N-4     TO FIGURE 1O-4

118/122
FROM FIGURE 1N-4
| 687 | 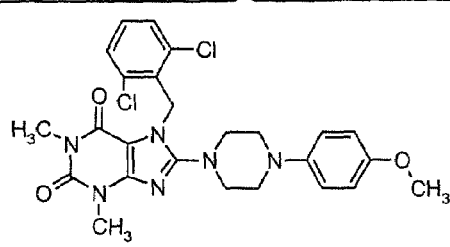 | 529 | 91 |
| 688 | 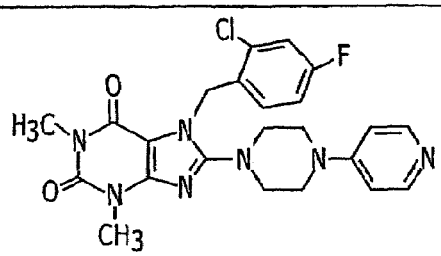 | 484 | 91 |
| 689 | 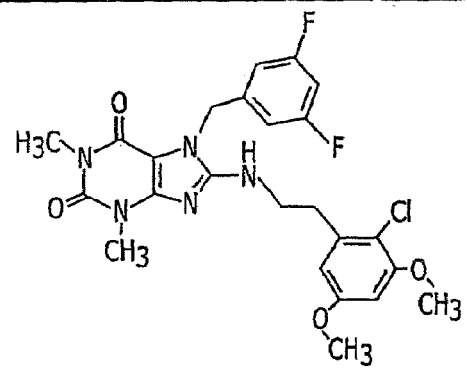 | 485 | 88 |
| 690 | 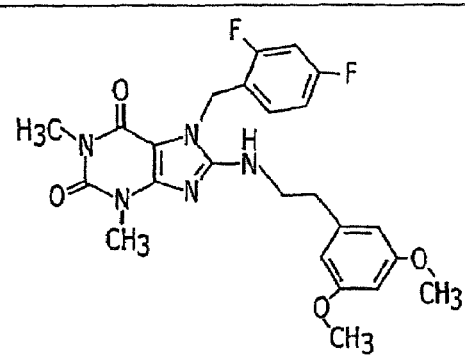 | 485 | 90 |
FIGURE 1O-4     TO FIGURE 1P-4

FROM FIGURE 1O-4
| 691 | 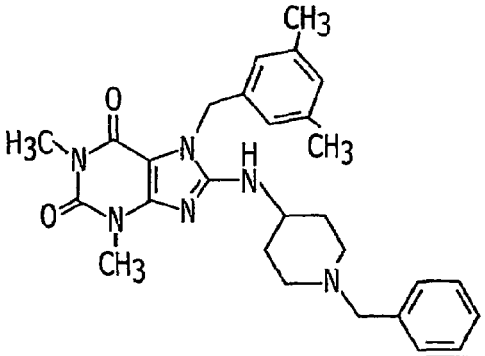 | 487 | 89 |
| 692 | 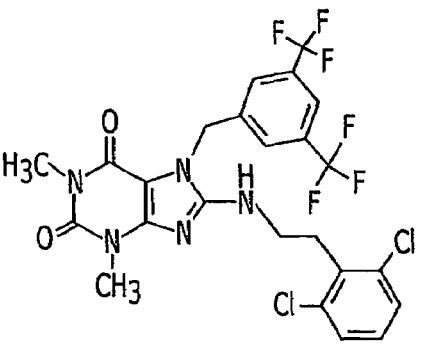 | 594 | 86 |
| 693 | 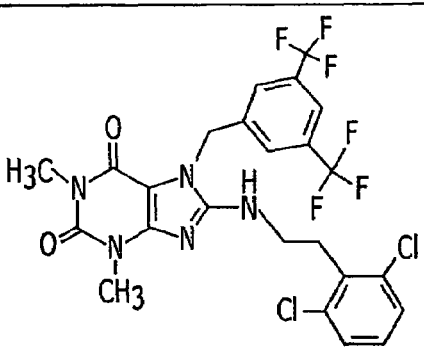 | 385 | 97 |
| 694 | 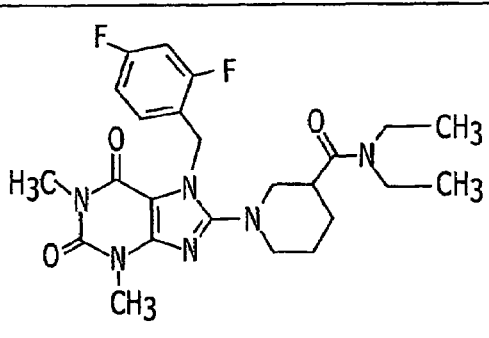 | 489 | 73 |
FIGURE 1P-4    TO FIGURE 1Q-4

FROM FIGURE 1P-4
| 695 | 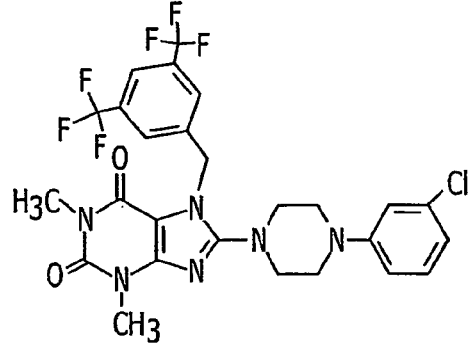 | 601 | 91 |
| --- | --- | --- | --- |
| 696 | 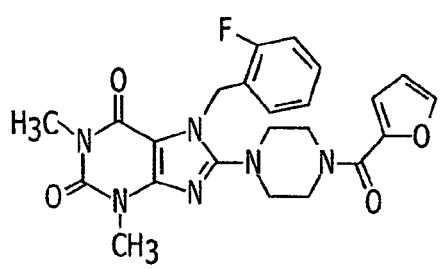 | 466 | 95 |
| 697 | 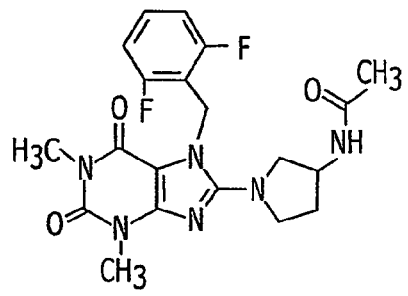 | 432 | 96 |
|  |  |  |  |
FIGURE 1Q-4

| Ex No. | LXRα pEC50 | % control | LXRβ pEC50 | % control | Ex. No. | LXRα pEC50 | % control | LXRβ pEC50 | % control |
|---|---|---|---|---|---|---|---|---|---|
| 4 | 5.9 | 180 | 6.7 | 104 | 89 | 6.3 | 65 | 7.0 | 78 |
| 5 | 6.2 | 104 | 6.8 | 74 | 94 | 6.1 | 88 | 7.2 | 78 |
| 6 | 6.1 | 137 | 6.8 | 90 | 95 | 6.6 | 74 | 7.3 | 69 |
| 7 | 6.3 | 88 | 6.7 | 60 | 98 | 6.1 | 86 | 6.9 | 69 |
| 8 | 5.7 | 102 | 6.2 | 67 | 99 | 6.5 | 84 | 7.1 | 61 |
| 9 | <5.5 | 75 | 6.4 | 140 | 100 | 6.6 | 77 | 7.1 | 56 |
| 10 | 5.7 | 51 | 6.0 | 120 | 103 | 6.5 | 106 | 7.0 | 81 |
| 11 | 5.9 | 46 | 6.3 | 120 | 107 | 6.1 | 78 | 6.6 | 68 |
| 12 | 5.8 | 37 | 6.1 | 91 | 109 | 7.0 | 109 | 7.5 | 77 |
| 13 | <5.5 | 77 | 5.9 | 49 | 111 | 6.2 | 51 | 6.9 | 64 |
| 18 | 5.6 | 43 | 6.5 | 53 | 113 | 6.5 | 44 | 7.3 | 57 |
| 25 | <5.5 | 58 | 6.8 | 38 | 114 | 6.1 | 85 | 7.2 | 78 |
| 26 | 5.6 | 31 | 6.1 | 32 | 125 | 5.5 | 59 | 6.3 | 71 |
| 29 | 6.0 | 34 | 7.4 | 42 | 126 | 5.9 | 87 | 7.2 | 68 |
| 30 | 6.8 | 49 | 7.7 | 44 | 131 | <5.5 | 76 | 5.9 | 68 |
| 31 | 7.0 | 62 | 78.0 | 52 | 132 | <5.5 | 76 | 6.3 | 71 |
| 33 | 6.0 | 90 | 6.6 | 100 | 133 | <5.5 | 59 | 6.1 | 71 |
| 34 | 6.1 | 72 | 6.8 | 124 | 142 | <5.5 | 86 | 6.1 | 62 |
| 38 | 6.3 | 92 | 7.0 | 82 | 143 | <5.5 | 54 | 5.8 | 62 |
| 39 | 5.8 | 61 | 7.6 | 53 | 144 | <5.5 | 204 | 5.9 | 139 |
| 40 | 6.5 | 77 | 7.0 | 91 | 145 | 5.5 | 38 | 6.1 | 75 |
| 41 | 6.0 | 40 | 6.7 | 51 | 146 | <5.5 | 57 | 6.6 | 60 |
| 42 | 6.3 | 52 | 7.0 | 44 | 148 | <5.5 | 107 | 6.5 | 59 |
| 44 | <5.5 | 150 | 6.0 | 133 | 150 | 5.6 | 49 | 5.9 | 55 |
| 45 | <5.5 | 43 | 6.1 | 44 | 155 | <5.5 | 37 | 6.1 | 54 |
| 46 | 5.7 | 40 | 6.2 | 43 | 156 | 5.9 | 39 | 6.5 | 41 |
| 49 | 6.5 | 104 | 6.8 | 77 | 178 | 5.6 | 82 | 6.9 | 79 |

FIGURE 2A

| Ex No. | LXRα pEC50 | % control | LXRβ pEC50 | % control | Ex. No. | LXRα pEC50 | % control | LXRβ pEC50 | % control |
|---|---|---|---|---|---|---|---|---|---|
| 50 | 5.9 | 51 | 5.9 | 59 | 183 | 5.7 | 40 | 6.1 | 54 |
| 51 | <5.5 | 52 | 5.8 | 59 | 201 | <5.5 | 105 | 6.0 | 55 |
| 52 | 6.2 | 88 | 6.7 | 70 | 208 | <5.5 | 81 | 6.2 | 65 |
| 53 | <5.5 | 45 | 6.0 | 46 | 224 | 5.5 | 51 | 6.3 | 47 |
| 54 | 5.5 | 56 | 6.0 | 55 | 228 | 5.8 | 32 | 6.4 | 58 |
| 55 | 5.5 | 45 | 6.0 | 58 | 243 | 7.8 | 46 | 7.6 | 45 |
| 57 | 6.2 | 108 | 6.8 | 66 | 249 | 5.6 | 53 | 7.0 | 50 |
| 58 | 6.0 | 89 | 6.5 | 55 | 250 | <5.5 | 322 | 6.8 | 68 |
| 59 | 6.0 | 92 | 6.7 | 55 | 273 | 7.1 | 61 | 7.1 | 59 |
| 60 | <5.5 | 42 | 6.1 | 35 | 285 | 5.8 | 73 | 6.5 | 84 |
| 61 | <5.5 | 70 | 6.6 | 57 | 288 | 6.4 | 57 | 6.2 | 91 |
| 62 | <5.5 | 44 | 5.6 | 49 | 320 | 7.3 | 62 | 7.3 | 64 |
| 63 | 6.2 | 85 | 6.5 | 82 | 424 | 6.5 | 43 | 6.6 | 50 |
| 65 | <5.5 | 30 | 6.1 | 43 | 430 | 6.1 | 67 | 6.5 | 77 |
| 66 | 5.5 | 89 | 5.5 | 72 | 452 | 5.8 | 75 | 6.3 | 74 |
| 69 | 6.0 | 111 | 6.9 | 79 | 460 | 6.1 | 66 | 6.6 | 70 |
| 71 | <5.5 | 79 | 5.8 | 62 | 496 | 6.4 | 68 | 6.2 | 65 |
| 72 | 5.8 | 84 | 6.6 | 76 | 525 | 6.3 | 53 | 6.2 | 58 |
| 73 | 5.7 | 84 | 6.6 | 74 | 557 | 7.2 | 60 | 7.3 | 54 |
| 74 | 5.8 | 83 | 6.6 | 73 | 575 | 6.2 | 43 | 6.1 | 58 |
| 77 | 6.0 | 86 | 7.0 | 69 | 588 | 7.1 | 37 | 7.0 | 43 |
| 83 | 6.6 | 88 | 6.9 | 56 | 592 | 7.4 | 45 | 7.3 | 51 |
| 87 | 6.3 | 88 | 7.4 | 81 | 672 | 6.3 | 49 | 6.3 | 77 |

FIGURE 2B

SEQUENCE LISTING

<160> NUMBER OF SEQ ID NOS: 5

<210> SEQ ID NO 1
<211> LENGTH: 11
<212> TYPE: PRT
<213> ORGANISM: homo sapien

<400> SEQUENCE: 1

Met Lys Lys Gly His His His His His His Gly
1               5                   10

<210> SEQ ID NO 2
<211> LENGTH: 25
<212> TYPE: PRT
<213> ORGANISM: homo sapien

<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
            20                  25

```
<210> SEQ ID NO 3
<211> LENGTH: 24
<212> TYPE: DNA
<213> ORGANISM: mouse

<400> SEQUENCE: 3
aagggtttct tgctcagat tgtc                                         24

<210> SEQ ID NO 4
<211> LENGTH: 17
<212> TYPE: DNA
<213> ORGANISM: mouse

<400> SEQUENCE: 4
tgccaaaggg tggcaca                                                17

<210> SEQ ID NO 5
<211> LENGTH: 25
<212> TYPE: DNA
<213> ORGANISM: mouse

<400> SEQUENCE: 5
ccagctgtct ttgtttgcat tgccc                                       25
```

PURINE DERIVATIVES AS LIVER X RECEPTOR AGONISTS

This Application is filed pursuant to 35 U.S.C. §371 as a United States National Phase Application of International Application No. PCT/US03/016016, filed 20 May 2003, which claims priority to U.S. patent application Ser. No. 60/389,689, filed Jun. 17, 2002.

BACKGROUND OF THE INVENTION

The present invention relates to Liver X receptors (LXR). More particularly, the present invention relates to compounds useful as agonists for LXR, pharmaceutical formulations comprising such compounds, and therapeutic use of the same.

The orphan nuclear receptors, LXRα and LXRβ (collectively LXR) play a role in the maintenance of cholesterol balance. Peet et al., *Curr. Opin. Genet Dev.* 8:571-575 (1998). LXR is a transcription factor which regulates the expression of Cytochrome P450 7A (CYP7A). CYPP7A catalyses a key step in the conversion of cholesterol to bile acid, which process results in the removal of cholesterol from the liver.

In addition, LXR binds to the ATP Binding Cassette Transporter-1 (ABC1) (also known as ABCA 1) gene and increases expression of the gene to result in increased ABC1 protein. ABC1 is a membrane bound transport protein which is involved in the regulation of cholesterol efflux from extrahepatic cells onto nascent HDL particles. Mutations in the ABC1 gene are responsible for genetic diseases that result in the complete absence or low levels of HDL cholesterol and a concomitant highly increased risk of cardiovascular disease. See Brooks-Wilson et al., *Nat. Genet.* 22:336-345 (1999); Bodzioch et al., *Nat. Genet.* 22: 347-351 (1999); and Rust et al., *Nat. Genet.* 22:352-355 (1999). ABC1 knockout mice homozygous for the mutation in the ABC1 gene have virtually no plasma HDL whereas the heterozygotes produce 50% of the HDL of wild type animals. See, Orso et al., *Nat. Genet.* 24:192-196 (2000) and McNeish et al., *Proc. Natl. Acad. Sci. USA* 97:4245-4250 (2000). ABC1 knockout mice also show increased cholesterol absorption. See, McNeish et al., *Proc. Natl. Acad. Sci. USA* 97:4245-4250 (2000). Increased expression of ABC1 results in increased HDL cholesterol, decreased absorption of cholesterol, and increased removal of excess cholesterol from extrahepatic tissues, including macrophages.

Accordingly compounds which function as LXR agonists would be useful in methods of increasing ABC1 expression, increasing HDL cholesterol and treating LXR mediated diseases and conditions such as cardiovascular disease.

SUMMARY OF THE INVENTION

As a first aspect, the present invention provides a method for the prevention or treatment of an LXR mediated disease or condition in a mammal. The method comprises administering a therapeutically effective amount of a compound of formula (I):

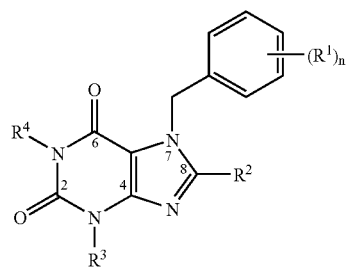

(I)

wherein:

n is 1, 2, 3, 4, 5;

each $R^1$ is the same or different and is independently selected from the group consisting of halo, alkyl, and nitro;

$R^2$ is a substituent selected from the group consisting of formulas i, ii, iii, iv, v, vi and vii:

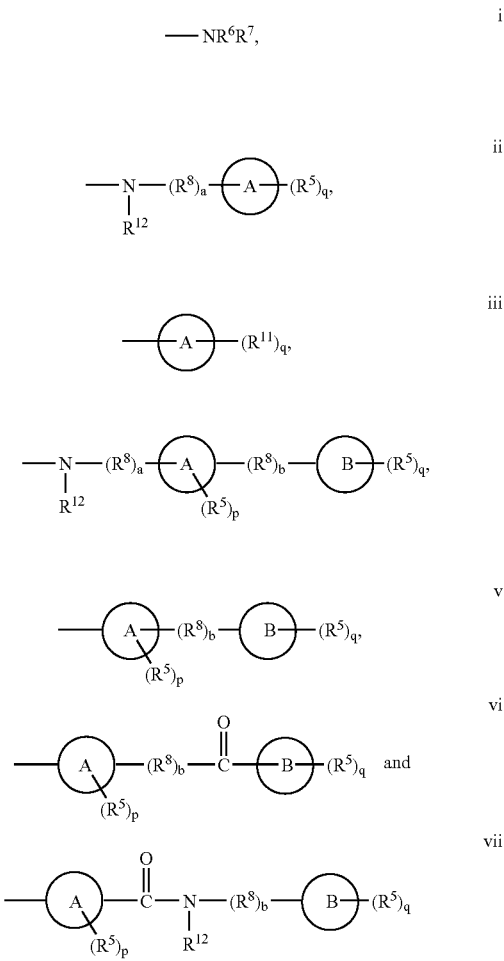

each Ring A and Ring B is the same or different and is independently selected from the group consisting of $C_{3-10}$cycloalkyl, $C_{3-10}$cycloalkenyl, Ay and Het;

Ay is aryl;

Het is a 3-10 membered heterocycle or a 5-10 membered heteroaryl;

a and b are each the same or different and are independently 0 or 1;

p is 0, 1 or 2;

q is 0, 1, 2 or 3;

each $R^5$ is the same or different and is independently selected from the group consisting of halo, alkyl, alkenyl, alkynyl, $-OR^6$, $-OC(O)R^6$, $-OR^8C(O)R^6$, $-S(O)_gR^6$, $-C=O$, $-C(O)R^6$, $-C(O)NR^6R^7$, $-CO_2R^9$, $-NR^6R^7$, $-N(R^6)C(O)R^6$, $-R^8OR^6$, $-R^8NR^6R^7$, $-R^8C(O)R^6$, $-R^8CO_2R^9$, nitro and cyano;

g is 0, 1 or 2;

$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, $-R^8-C_{3-10}$cycloalkyl, $-R^8$-Ay, $-R^8$-Het, $-R^8CO_2R^9$, $-R^8C(O)NR^9R^{10}$, $-R^8OR^9$, $-R^8SR^9$ and $-R^8OAy$;

$R^6$ and $R^7$ are the same or different and are each independently selected from the group consisting of H, alkyl, alkenyl, alkynyl, $-R^8OR^9$, $-R^8SR^9$, $-R^8-NR^9R^{10}$, $-R^8-CN$, $-R^8-CO_2R^9$;

$R^8$ is alkylene or alkenylene;

$R^9$ and $R^{10}$ are each the same or different and are each independently selected from the group consisting of H, alkyl, alkenyl and alkynyl;

each $R^{11}$ is the same or different and is independently selected from the group consisting of halo, alkyl, alkenyl, alkynyl, $-OR^6$, $-OC(O)R^6$, $-OR^8C(O)R^6$, $-S(O)_gR^6$, $-C=O$, $-C(O)R^6$, $-C(O)NR^6R^7$, $-CO_2R^9$, $-C(O)_2R^8Ay$, $-NR^6R^7$, $-N(R^6)C(O)R^6$, $-R^8OR^6$, $-R^8NR^6R^7$, $-R^8C(O)R^6$, $-R^8-C(O)Ay$, $-R^8-C(O)Het$, $-R^8CO_2R^9$, $-R^8C(O)N(R^9)Ay$, $-CH-(Ay)_2$, $-CH-(Het)_2$, nitro and cyano; and $R^{12}$ is selected from the group consisting of H, alkyl, alkenyl, and alkynyl, or a pharmaceutically acceptable salt or solvate thereof. The present invention also provides the use of a compound of formula (I) or a pharmaceutically acceptable salt or solvate thereof, for the preparation of a medicament for the prevention or treatment of an LXR mediated disease or condition in a mammal.

As a second aspect, the present invention also provides a method for increasing reverse cholesterol transport in a mammal. The method comprises administering a therapeutically effective amount of a compound of formula (I) or a pharmaceutically acceptable salt or solvate thereof. The present invention also provides the use of a compound of formula (I) or a pharmaceutically acceptable salt or solvate thereof, for the preparation of a medicament for increasing reverse cholesterol transport in a mammal.

As a third aspect, the present invention provides a method for inhibiting cholesterol absorption in a mammal. The method comprises administering a therapeutically effective amount of a compound of formula (I) or a pharmaceutically acceptable salt or solvate thereof. The present invention also provides the use of a compound of formula (I) or a pharmaceutically acceptable salt or solvate thereof, for the preparation of a medicament for inhibiting cholesterol absorption in a mammal.

As a fourth aspect, the present invention provides a method for increasing HDL-cholesterol in a mammal. The method comprises administering a therapeutically effective amount of a compound of formula (I) or a pharmaceutically acceptable salt or solvate thereof. The present invention also provides the use of a compound of formula (I) or a pharmaceutically acceptable salt or solvate thereof, for the preparation of a medicament for increasing HDL-cholesterol in a mammal.

As a fifth aspect, the present invention provides a method for decreasing LDL-cholesterol in a mammal. The method comprises administering a therapeutically effective amount of a compound of formula (I) or a pharmaceutically acceptable salt or solvate thereof. The present invention also provides the use of a compound of formula (I) or a pharmaceutically acceptable salt or solvate thereof, for the preparation of a medicament for decreasing LDL-cholesterol in a mammal.

As a sixth aspect, the present invention provides a pharmaceutical composition comprising a compound of formula (I) or a pharmaceutically acceptable salt or solvate thereof. In one embodiment, the pharmaceutical composition further comprises a pharamceutically acceptable carrier or diluent.

According to a seventh aspect, the present invention provides a compound of formula (I)

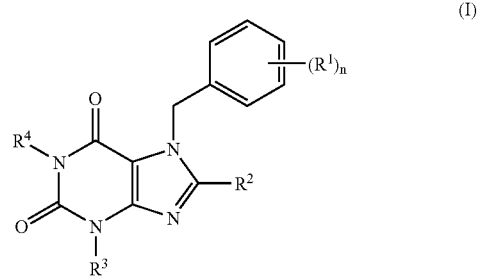

wherein:

n is 1, 2, 3, 4, 5;

each $R^1$ is the same or different and is independently selected from the group consisting of halo, alkyl, and nitro;

$R^2$ is a substituent selected from the group consisting of formulas iv, vi and vii:

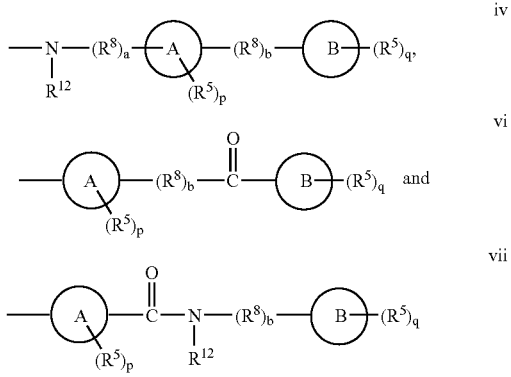

each Ring A and Ring B is the same or different and is independently selected from the group consisting of $C_{3-10}$cycloalkyl, $C_{3-10}$cycloalkenyl, Ay and Het;

Ay is aryl;

Het is a 3-10 membered heterocycle or a 5-10 membered heteroaryl;

a and b are each the same or different and are independently 0 or 1;

p is 0, 1 or 2;

q is 0, 1, 2 or 3;

each $R^5$ is the same or different and is independently selected from the group consisting of halo, alkyl, alkenyl, alkynyl, $-OR^6$, $-OC(O)R^6$, $-OR^8C(O)R^6$, $-S(O)_gR^6$, $-C=O$, $-C(O)R^6$, $-C(O)NR^6R^7$, $-CO_2R^9$, $-NR^6R^7$, $-N(R^6)C(O)R^6$, $-R^8OR^6$, $-R^8NR^6R^7$, $-R^8C(O)R^6$, $-R^8CO_2R^9$, nitro and cyano;

g is 0, 1 or 2;

$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, $-R^8-C_{3-10}$cycloalkyl, $-R^8$-Ay, $-R^8$-Het, $-R^8CO_2R^9$, $-R^8C(O)NR^9R^{10}$, $-R^8OR^9$, $-R^8SR^9$ and $-R^8OAy$;

$R^6$ and $R^7$ are the same or different and are each independently selected from the group consisting of H, alkyl, alkenyl, alkynyl, $-R^8OR^9$, $-R^8SR^9$, $-R^8-NR^9R^{10}$, $-R^8-CN$, $-R^8-CO_2R^9$;

$R^8$ is alkylene or alkenylene;

$R^9$ and $R^{10}$ are each the same or different and are each independently selected from the group consisting of H, alkyl, alkenyl and alkynyl; and $R^{12}$ is selected from the group consisting of H, alkyl, alkenyl, and alkynyl, and pharmaceutically acceptable salts and solvates thereof.

As an eighth aspect, the present invention provides a compound of formula (I-A):

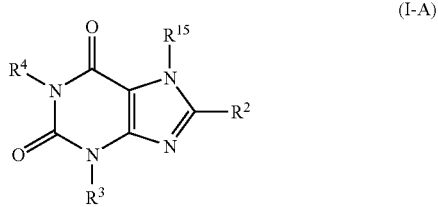

wherein:
$R^{15}$ is selected from the group consisting of

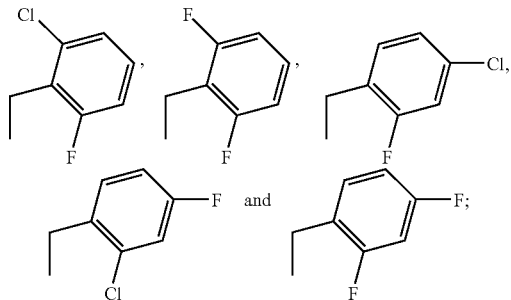

$R^2$ is a substituent selected from the group consisting of formulas i and ii:

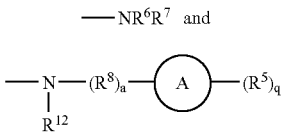

Ring A is selected from the group consisting of $C_{3-10}$cycloalkyl, $C_{3-10}$cycloalkenyl, Ay and Het;

Ay is aryl;

Het is a 3-10 membered heterocycle or a 5-10 membered heteroaryl;

a is 0 or 1;

q is 0, 1, 2 or 3;

each $R^5$ is the same or different and is independently selected from the group consisting of halo, alkyl, alkenyl, alkynyl, —$OR^6$, —$OC(O)R^6$, —$OR^8C(O)R^6$, —$S(O)_gR^6$, —C=O, —$C(O)R^6$, —$C(O)NR^6R^7$, —$CO_2R^9$, —$NR^6R^7$, —$N(R^6)C(O)R^6$, —$R^8OR^6$, —$R^8NR^6R^7$, —$R^8C(O)R^6$, —$R^8CO_2R^9$, nitro and cyano;

g is 0, 1 or 2;

$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, —$R^8$—$C_{3-10}$cycloalkyl, —$R^8$-Ay, —$R^8$-Het, —$R^8CO_2R^9$, —$R^8C(O)NR^9R^{10}$, —$R^8OR^9$, —$R^8SR^9$ and —$R^8OAy$;

wherein $R^3$ and $R^4$ are not both methyl;

$R^6$ and $R^7$ are the same or different and are each independently selected from the group consisting of H, alkyl, alkenyl, alkynyl, —$R^8OR^9$, —$R^8SR^9$, —$R^8$—$NR^9R^{10}$, —$R^8$—CN, —$R^8$—$CO_2R^9$;

$R^8$ is alkylene or alkenylene;

$R^9$ and $R^{10}$ are each the same or different and are each independently selected from the group consisting of H, alkyl, alkenyl and alkynyl; and $R^{12}$ is selected from the group consisting of H, alkyl, alkenyl, and alkynyl, and pharmaceutically acceptable salts and solvates thereof. The present invention also provides a pharmaceutical composition comprising such compound of formula (I-A) and methods of using compounds of formula (I-A) as herein described for compounds of formula (I) generally.

As a ninth aspect, the present invention provides a compound of formula (I-A):

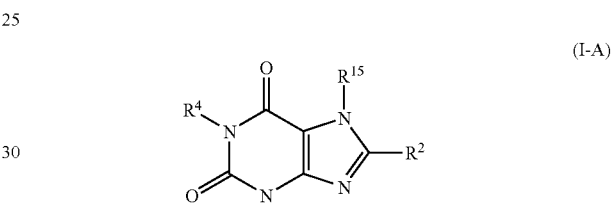

wherein:
$R^{15}$ is selected from the group consisting of

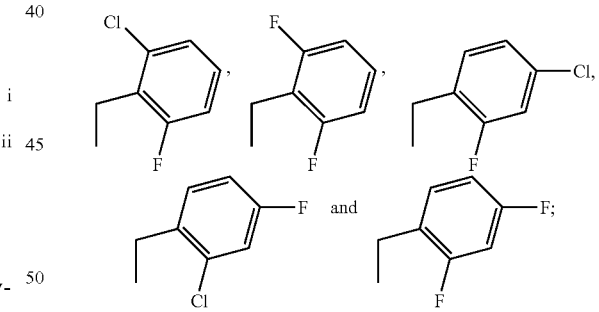

$R^2$ is a substituent selected from the group consisting of:

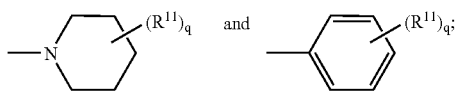

q is 0, 1, 2 or 3;

each $R^{11}$ is the same or different and is independently selected from the group consisting of halo, alkyl, alkenyl, alkynyl, —$OR^6$, —$OC(O)R^6$, —$OR^8C(O)R^6$, —$S(O)_gR^6$, —C=O, —$C(O)R^6$, —$C(O)NR^6R^7$, —$CO_2R^9$, —$C(O)_2R^8Ay$, —$NR^6R^7$, —$N(R^6)C(O)R^6$, —$R^8OR^6$, —R⁸NR⁶R⁷, —R⁸C(O)R⁶, —R⁸—C(O)Ay, —R⁸—C(O)Het, —R⁸CO₂R⁹, —R⁸C(O)N(R⁹)Ay, —CH-(Ay)₂, —CH-(Het)₂, nitro and cyano;

g is 0, 1 or 2;
Ay is aryl;
Het is a 3-10 membered heterocycle or a 5-10 membered heteroaryl;
R³ and R⁴ are the same or different and are each independently selected from the group consisting of H, alkyl, alkenyl, alkynyl, C₃₋₁₀cycloalkyl, C₃₋₁₀cycloalkenyl, Ay, Het, —R⁸—C₃₋₁₀cycloalkyl, —R⁸-Ay, —R⁸-Het, —R⁸CO₂R⁹, —R⁸C(O)NR⁹R¹⁰, —R⁸OR⁹, —R⁸SR⁹ and —R⁸OAy,
wherein when R² is

then R³ and R⁴ are not both methyl;
R⁶ and R⁷ are the same or different and are each independently selected from the group consisting of H, alkyl, alkenyl, alkynyl, —R⁸OR⁹, —R⁸SR⁹, —R⁸—NR⁹R¹⁰, —R⁸—CN, —R⁸—CO₂R⁹;
R⁸ is alkylene or alkenylene; and
R⁹ and R¹⁰ are each the same or different and are each independently selected from the group consisting of H, alkyl, alkenyl and alkynyl;

and pharmaceutically acceptable salts and solvates thereof. The present invention also provides a pharmaceutical composition comprising such compound of formula (I-A) and methods of using compounds of formula (I-A) as herein described for compounds of formula (I) generally.

As a tenth aspect, the present invention provides a compound of formula (I-A):

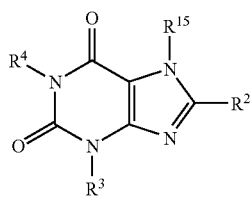

(I-A)

wherein:
R¹⁵ is selected from the group consisting of

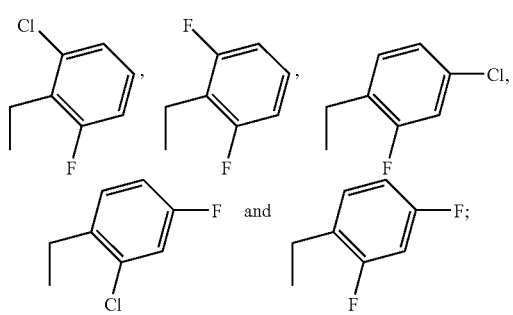

R² is a substituent of formula (v-a):

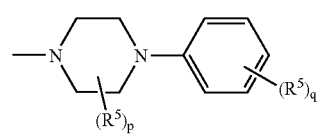

v-a p is 0, 1 or 2;
q is 0, 1, 2 or 3;
each R⁵ is the same or different and is independently selected from the group consisting of halo, alkyl, alkenyl, alkynyl, —OR⁶, —OC(O)R⁶, —OR⁸C(O)R⁶, —S(O)ₘR⁶, —C=O, —C(O)R⁶, —C(O)NR⁶R⁷, —CO₂R⁹, —NR⁶R⁷, —N(R⁶)C(O)R⁶, —R⁸OR⁶, R⁸NR⁶R⁷, —R⁸C(O)R⁶, —R⁸CO₂R⁹, nitro and cyano;
g is 0, 1 or 2;
Ay is aryl;
Het is a 3-10 membered heterocycle or a 5-10 membered heteroaryl;
R³ and R⁴ are the same or different and are each independently selected from the group consisting of H, alkyl, alkenyl, alkynyl, C₃₋₁₀cycloalkyl, C₃₋₁₀cycloalkenyl, Ay, Het, —R⁸—C₃₋₁₀cycloalkyl, —R⁸-Ay, —R⁸-Het, —R⁸CO₂R⁹, —R⁸C(O)NR⁹R¹⁰, —R⁸OR⁹, —R⁸SR⁹ and —R⁸OAy;
R⁶ and R⁷ are the same or different and are each independently selected from the group consisting of H, alkyl, alkenyl, alkynyl, —R⁸OR⁹, —R⁸SR⁹, —R⁸—NR⁹R¹⁰, —R⁸—CN, —R⁸—CO₂R⁹;
R⁸ is alkylene or alkenylene; and
R⁹ and R¹⁰ are each the same or different and are each independently selected from the group consisting of H, alkyl, alkenyl and alkynyl;

and pharmaceutically acceptable salts and solvates thereof. The present invention also provides a pharmaceutical composition comprising such compound of formula (I-A) and methods of using compounds of formula (I-A) as herein described for compounds of formula (I) generally.

As an eleventh aspect, the present invention provides a compound selected from the group consisting of:
7-(2-chloro-6-fluorobenzyl)-1,3-diethyl-8-piperidin-1-yl-3,7-dihydro-1H-purine-2,6-dione;
7-(2-chloro-6-fluorobenzyl)-1-ethyl-3-isopropyl-8-piperidin-1-yl-3,7-dihydro-1H-purine-2,6-dione;
7-(2-chloro-6-fluorobenzyl)-3-ethyl-8-piperidin-1-yl-1-propyl-3,7-dihydro-1H-purine-2,6-dione;
7-(2-chloro-6-fluorobenzyl)-3-isopropyl-8-piperidin-1-yl-1-propyl-3,7-dihydro-1H-purine-2,6-dione;
7-(2-chloro-6-fluorobenzyl)-1-isopropyl-3-methyl-8-piperidin-1-yl-3,7-dihydro-1H-purine-2,6-dione;
7-(2-chloro-6-fluorobenzyl)-1-ethyl-3-(2-methoxyethyl)-8-piperidin-1-yl-3,7-dihydro-1H-purine-2,6-dione;
methyl [7-(2-chloro-6-fluorobenzyl)-1-ethyl-2,6-dioxo-8-piperidin-1-yl-1,2,6,7-tetrahydro-3H-purin-3-yl]acetate;
7-(2-chloro-6-fluorobenzyl)-1-ethyl-3-(2-phenoxyethyl)-8-piperidin-1-yl-3,7-dihydro-1H-purine-2,6-dione;
1-butyl-7-(2-chloro-6-fluorobenzyl)-3-methyl-8-piperidin-1-yl-3,7-dihydro-1H-purine-2,6-dione;
7-(2-chloro-6-fluorobenzyl)-1-(cyclopropylmethyl)-3-isopropyl-8-piperidin-1-yl-3,7-dihydro-1H-purine-2,6-dione;
7-(2-chloro-6-fluorobenzyl)-1,3-diisopropyl-8-piperidin-1-yl-3,7-dihydro-1H-purine-2,6-dione;
7-(2-chloro-6-fluorobenzyl)-1-cyclopropyl-3-isopropyl-8-piperidin-1-yl-3,7-dihydro-1H-purine-2,6-dione;

7-(2-chloro-6-fluorobenzyl)-1-ethyl-3-methyl-8-piperidin-1-yl-3,7-dihydro-1H-purine-2,6-dione;

7-(2-chloro-6-fluorobenzyl)-3-methyl-8-piperidin-1-yl-1-propyl-3,7-dihydro-1H-purine-2,6-dione;

1-benzyl-7-(2-chloro-6-fluorobenzyl)-3-methyl-8-piperidin-1-yl-3,7-dihydro-1H-purine-2,6-dione;

7-(2-chloro-6-fluorobenzyl)-3-ethyl-1-methyl-8-piperidin-1-yl-3,7-dihydro-1H-purine-2,6-dione;

7-(2-chloro-6-fluorobenzyl)-1-methyl-8-piperidin-1-yl-3-propyl-3,7-dihydro-1H-purine-2,6-dione;

7-(2-chloro-6-fluorobenzyl)-3-isopropyl-1-methyl-8-piperidin-1-yl-3,7-dihydro-1H-purine-2,6-dione;

3-benzyl-7-(2-chloro-6-fluorobenzyl)-1-methyl-8-piperidin-1-yl-3,7-dihydro-1H-purine-2,6-dione;

7-(2-chloro-6-fluorobenzyl)-8-(3-chlorophenyl)-3-isopropyl-1-methyl-3,7-dihydro-1H-purine-2,6-dione;

7-(2-chloro-6-fluorobenzyl)-1,3-dimethyl-8-phenyl-3,7-dihydro-1H-purine-2,6-dione;

7-(2-chloro-6-fluorobenzyl)-8-(4-chlorophenyl)-1,3-dimethyl-3,7-dihydro-1H-purine-2,6-dione;

7-(2-chloro-6-fluorobenzyl)-8-(3,5-dichlorophenyl)-1,3-dimethyl-3,7-dihydro-1H-purine-2,6-dione;

7-(2-chloro-6-fluorobenzyl)-1,3-dimethyl-8-(2-naphthyl)-3,7-dihydro-1H-purine-2,6-dione;

7-(2-chloro-6-fluorobenzyl)-8-(3-chlorophenyl)-1,3-dimethyl-3,7-dihydro-1H-purine-2,6-dione;

7-(2-chloro-6-fluorobenzyl)-1,3-dimethyl-8-[3-(trifluoromethyl)phenyl]-3,7-dihydro-1H-purine-2,6-dione;

7-(2-chloro-6-fluorobenzyl)-8-(3-methoxyphenyl)-1,3-dimethyl-3,7-dihydro-1H-purine-2,6-dione;

7-(2-chloro-6-fluorobenzyl)-8-cyclohexyl-1,3-dimethyl-3,7-dihydro-1H-purine-2,6-dione;

7-(2-chloro-6-fluorobenzyl)-8-(3-iodophenyl)-1,3-dimethyl-3,7-dihydro-1H-purine-2,6-dione;

1-[7-(2-chloro-6-fluorobenzyl)-1,3-dimethyl-2,6-dioxo-2,3,6,7-tetrahydro-1H-purin-8-yl]piperidine-3-carboxylic acid;

7-(2-chloro-6-fluorobenzyl)-8-{3-[(4-hydroxypiperidin-1-yl)carbonyl]piperidin-1-yl}-1,3-dimethyl-3,7-dihydro-1H-purine-2,6-dione;

1-[7-(2-chloro-6-fluorobenzyl)-1,3-dimethyl-2,6-dioxo-2,3,6,7-tetrahydro-1H-purin-8-yl]-N-(4-hydroxybutyl)piperidine-3-carboxamide;

7-(2-chloro-6-fluorobenzyl)-1,3-dimethyl-8-{4-[3-(trifluoromethyl)phenyl]piperazin-1-yl}-3,7-dihydro-1H-purine-2,6-dione;

7-(2-chloro-6-fluorobenzyl)-8-[4-(3-methoxyphenyl)piperazin-1-yl]-1,3-dimethyl-3,7-dihydro-1H-purine-2,6-dione;

7-(2-chloro-6-fluorobenzyl)-8-{4-[4-chloro-3-(trifluoromethyl)phenyl]piperazin-1-yl}-1,3-dimethyl-3,7-dihydro-1H-purine-2,6-dione;

and pharmaceutically acceptable salts and solvates thereof. The present invention also provides a pharmaceutical composition comprising such compound and methods of using such compound as herein described for compounds of formula (I) generally.

As additional aspects, the present invention provides a compound of formula (I) or (I-A) as herein before defined, for use in therapy; a compound of formula (I) or (I-A) for use in the prevention or treatment of an LXR mediated disease or condition in a mammal; a compound of formula (I) or (I-A) for use in the prevention or treatment of cardiovascular disease in a mammal; a compound of formula (I) or (I-A) for use in the prevention or treatment of atherosclerosis in a mammal; a compound of formula (I) or (I-A0 for increasing reverse cholesterol transport in a mammal; a compound of formula (I) or (I-A) for inhibiting cholesterol absorption in a mammal; a compound of formula (I) or (I-A) for increasing HDL-cholesterol in a mammal; and a compound of formula (I) or (I-A) for decreasing LDL-cholesterol in a mammal.

Further aspects of the present invention are described in the description of preferred embodiments, examples, and claims which follow.

BRIEF DESCRIPTION OF THE SEVERAL VIEWS OF THE DRAWING(S)

DETAILED DESCRIPTION OF THE PREFERRED EMBODIMENTS

Figure 1Z:
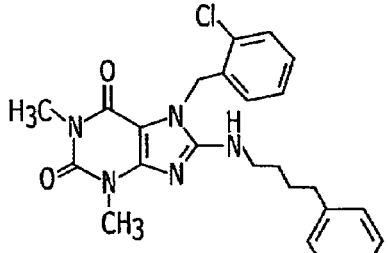
FIG. 1 is a table of compounds according to the present invention. The table also provides physical characterization data including MH+ and HPLC purity.

Herein references to "compounds of formula (I)" shall mean the compounds of formula (I) as described, including subsets of the compounds of formula (I) (e.g., compounds of formula (I-A), together with their pharmaceutically acceptable salts and solvates.

As used herein, the term "alkyl" refers to aliphatic straight or branched saturated hydrocarbon chains containing 1-8 carbon atoms. Examples of "alkyl" groups as used herein include but are not limited to methyl, ethyl, n-propyl, isopropyl, n-butyl, isobutyl, t-butyl, pentyl, hexyl, octyl and the like. The term "alkyl" also refers to halo substituted alkyl, including trihaloalkyl, such as trifluoromethyl and trifluoroethyl among others.

The term "alkylene" refers to an alkyl bridge, i.e., the group -alkyl-, wherein alkyl is as defined above.

As used herein, the term "alkenyl" refers to an aliphatic straight or branched unsaturated hydrocarbon chain containing 2-8 carbon atoms and at least one and up to three carbon-carbon double bonds. Examples of "alkenyl" groups as used herein include but are not limited to ethenyl and propenyl. The term "alkenyl" also refers to halo substituted alkenyl.

The term "alkenylene" refers to an alkenyl bridge, i.e., the group -alkenyl-, wherein alkenyl is as defined above.

As used herein, the term "alkynyl" refers to an aliphatic straight or branched unsaturated hydrocarbon chain containing 2-8 carbon atoms and at least one and up to three carbon-carbon triple bonds. Examples of "alkynyl" groups as used herein include but are not limited to propynyl. The term "alkynyl" also refers to halo substituted alkynyl.

As used herein, the term "cycloalkyl" refers to a non-aromatic monocyclic carbocyclic ring and fused bicyclic carbocyclic rings (including spirocycloalkyl) having the specified number of carbon atoms and no carbon-carbon double bonds. "Cycloalkyl" includes by way of example cyclopropyl, cyclobutyl, cyclopentyl, cyclohexyl, cycloheptyl, cyclooctyl, and bicycloheptane. "Cycloalkyl" also refers to substituted cycloalkyl wherein the ring bears one or more substituents selected from the group consisting of halo, alkyl, alkenyl, —OH, —Oalkyl, —NH$_2$, —NH(alkyl) and —N(alkyl)$_2$. As will be appreciated by those skilled in the art, the number of possible substituents on the cycloalkyl ring will depend upon the size of ring. In one preferred embodiment, the cycloalkyl is a cyclohexyl which may be substituted as described above.

The term "cycloalkenyl" as used herein refers to a non-aromatic monocyclic carbocyclic ring and fused bicyclic carbocyclic rings having the specified number of carbon atoms and at least one and up to three carbon-carbon double bonds.

"Cycloalkenyl" includes by way of example cyclobutenyl, cyclopentenyl, cyclohexenyl and bicyclic cycloalkenyl groups such bicyclo(2.2.1)heptene. "Cycloalkenyl" also refers to substituted cycloalkenyl wherein the ring bears one or more substituents selected from the group consisting of halo, alkyl, alkenyl, —OH, —Oalkyl, —NH$_2$, —NH(alkyl) and —N(alkyl)$_2$. As will be appreciated by those skilled in the art, the number of possible substituents on the cycloalkenyl ring will depend upon the size of ring.

The term "aryl" as used herein refers to aromatic carbocyclic groups selected from the group consisting of phenyl, 1-naphthyl and 2-naphthyl. The term "aryl" also refers to substituted aryl wherein the phenyl or naphthyl ring bears one or more substituents selected from the group consisting of halo, alkyl, alkenyl, —OH, —Oalkyl, —NH$_2$, —NH(alkyl), —N(alkyl)$_2$, nitro and cyano. As will be appreciated by those skilled in the art, the number of possible substituents on the aryl ring will depend upon the size of ring. For example, when the aryl ring is phenyl, the aryl ring may have up to 5 substituents selected from the foregoing list. One skilled in the art will readily be able to determine the maximum number of possible substituents for a 1-naphthyl or 2-naphthyl ring. A particular aryl according to the invention is phenyl, which may be substituted as described above.

The term "heterocycle" refers to a monocyclic saturated or partially unsaturated non-aromatic rings and fused bicyclic non-aromatic carbocyclic rings, having the specified number of members in the ring and being comprised of carbon and 1, 2 or 3 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. The term "heterocycle" also refers to substituted heterocycles wherein the heterocyclic ring bears one or more substituents selected from the group consisting of halo, alkyl, alkenyl, —OH, —Oalkyl, —NH$_2$, —NH(alkyl), —N(alkyl)$_2$, nitro and cyano. As will be appreciated by those skilled in the art, the number of possible substituents on the heterocyclic ring will depend upon the size of ring. There are no restrictions on the positions of the optional substituents in the heterocycles. Thus, the term encompasses rings having a substituent attached to the ring through a heteroatom, particularly through N. One skilled in the art will readily be able to determine the maximum number and locations of possible substituents for any given heterocycle. Particular heterocycles according to the include piperidine and piperizine, either of which may be substituted as described above.

The term "heteroaryl" refers to aromatic monocyclic heterocyclic rings and fused bicyclic rings wherein at least one ring is aromatic, having the specified number of members in the ring, and being comprised of carbon and 1, 2 or 3 heteroatoms selected from N, O and S. Examples of particular heteroaryl groups include, but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. The term "heteroaryl" also refers to substituted heteroaryls wherein the heteroaryl ring bears one or more substituents selected from the group consisting of halo, alkyl, alkenyl, —OH, —Oalkyl, —NH$_2$, —NH(alkyl), —N(alkyl)$_2$, nitro and cyano. As will be appreciated by those skilled in the art, the number of possible substituents on the heteroaryl ring will depend upon the size of ring. There are no restrictions on the positions of the optional substituents in heteroaryls. Thus, the term encompasses rings having a substituent attached to the ring through a heteroatom. One skilled in the art will readily be able to determine the maximum number and locations of possible substituents for any given heteroaryl. A preferred heteroaryl according to the invention is pyridine, which may be substituted as described above.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention relates to compounds of formula (I):

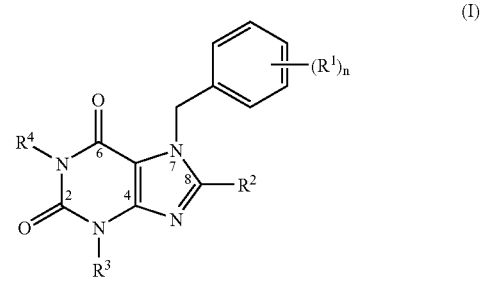

wherein:

n is 1, 2, 3, 4, 5;

each $R^1$ is the same or different and is independently selected from the group consisting of halo, alkyl, and nitro;

$R^2$ is a substituent selected from the group consisting of formulas i, ii, iii, iv, v, vi and vii:

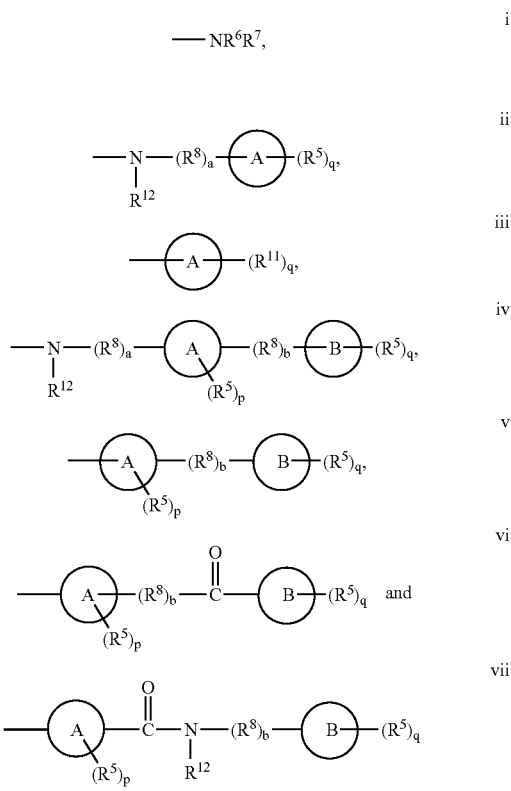

each Ring A and Ring B is the same or different and is independently selected from the group consisting of $C_{3-10}$cycloalkyl, $C_{3-10}$cycloalkenyl, Ay and Het;

Ay is aryl;

Het is a 3-10 membered heterocycle or a 5-10 membered heteroaryl;

a and b are each the same or different and are independently 0 or 1;

p is 0, 1 or 2;

q is 0, 1, 2 or 3;

each $R^5$ is the same or different and is independently selected from the group consisting of halo, alkyl, alkenyl, alkynyl, —$OR^6$, —$OC(O)R^6$, —$OR^8C(O)R^6$, —$S(O)_gR^6$, —C=O, —$C(O)R^6$, —$C(O)NR^6R^7$, —$CO_2R^9$, —$NR^6R^7$, —$N(R^6)C(O)R^6$, —$R^8OR^6$, —$R^8NR^6R^7$ —$R^8C(O)R^6$, —$R^8CO_2R^9$, nitro and cyano;

g is 0, 1 or 2;

$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, —$R^8$—$C_{3-10}$cycloalkyl, —$R^8$-Ay, —$R^8$-Het, —$R^8CO_2R^9$, —$R^8C(O)NR^9R^{10}$, —$R^8OR^9$, —$R^8SR^9$ and —$R^8OAy$;

$R^6$ and $R^7$ are the same or different and are each independently selected from the group consisting of H, alkyl, alkenyl, alkynyl, —$R^8OR^9$, —$R^8SR^9$, —$R^8$—$NR^9R^{10}$, —$R^8$—CN, —$R^8$—$CO_2R^9$;

$R^8$ is alkylene or alkenylene;

$R^9$ and $R^{10}$ are each the same or different and are each independently selected from the group consisting of H, alkyl, alkenyl and alkynyl;

each $R^{11}$ is the same or different and is independently selected from the group consisting of halo, alkyl, alkenyl, alkynyl, —$OR^6$, —$OC(O)R^6$, —$OR^8C(O)R^6$, —$S(O)_gR^6$, —C=O, —$C(O)R^6$, —$C(O)NR^6R^7$, —$CO_2R^9$, —$C(O)_2R^8Ay$, —$NR^6R^7$, —$N(R^6)C(O)R^6$, —$R^8OR^6$, —$R^8NR^6R^7$, —$R^8C(O)R^6$, —$R^8$—C(O)Ay, —$R^8$—C(O)Het, —$R^8CO_2R^9$, —$R^8C(O)N(R^9)Ay$, —CH-(Ay)$_2$, —CH-(Het)$_2$, nitro and cyano; and $R^{12}$ is selected from the group consisting of H, alkyl, alkenyl, and alkynyl, and pharmaceutically acceptable salts or solvates thereof.

In one embodiment, the compounds of formula (I) are defined wherein n is 1 or 2. In one particular embodiment, the compounds of formula (I) are defined wherein n is 1. In another particular embodiment, the compounds of formula (I) are defined wherein n is 2.

$R^1$ may be located in the ortho, meta and/or para position (s). In one embodiment, n is 2 and both $R^1$ groups are in the ortho positions. In another embodiment, n is 2 and one $R^1$ is in the ortho position and the other $R^1$ is in the para position. In one embodiment, each $R^1$ is the same or different and is independently selected from the group consisting of halo and alkyl. In one embodiment, each $R^1$ is the same or different and is halo.

More specifically, in one embodiment, each $R^1$ is the same or different and is independently selected from the group consisting of fluoro, chloro, bromo, iodo, methyl, trihalomethyl, ethyl, trihaloethyl, propyl, isopropyl, butyl, isobutyl, t-butyl and nitro, or any subset thereof. In one particular embodiment, each $R^1$ is the same or different and is independently selected from the group consisting of fluoro, chloro, bromo, iodo, methyl, trifluoromethyl, ethyl and nitro, or any subset thereof. In one particular embodiment, each $R^1$ is the same or different and is independently selected from the group consisting of fluoro and chloro. In particular, one embodiment is defined wherein n is 2, each $R^1$ is ortho and one $R^1$ is fluoro and the other $R^1$ is chloro.

In one embodiment, the variables n and $R^1$ are defined such that the benzyl group in the compound of formula (I) is selected from the group consisting of

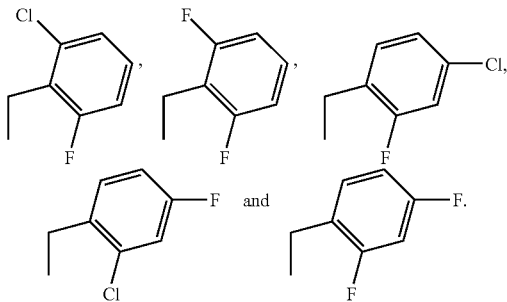

In one embodiment, the compounds of formula (I) are defined wherein R2 is selected from the group consisting of formulas iv, vi and vii:

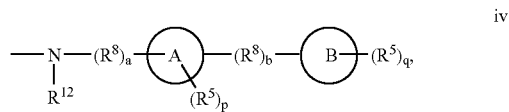

iv

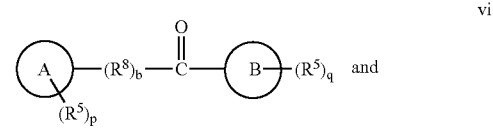

vi and

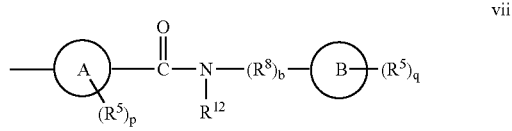

vii or any subset thereof.

In one embodiment, $R^2$ is a substituent of formula (iv) above. In such embodiment, each Ring A and Ring B is the same or different and is independently selected from the group consisting of $C_{3-10}$cycloalkyl, $C_{3-10}$cycloalkenyl, Ay and Het, or any subset thereof; Ay is aryl; and Het is a 3-10 membered heterocycle or a 5-10 membered heteroaryl. In one particular embodiment, $R^2$ is a substituent of formula (iv) and Ring A is a N-containing 3-10 membered heterocycle or a 5-10 membered heteroaryl (i.e., a heterocycle or heteroaryl having at least one N in the ring). In one embodiment $R^2$ is a substituent of formula (iv) or (iv-a) and Ring A is a 5-6 membered heterocycle or heteroaryl; more particularly a N-containing 5-6 membered heterocycle or heteroaryl. In one particular embodiment, $R^2$ is a substituent of formula (iv) or (iv-a) and Ring A is a N-containing 5-6 membered heterocycle.

In another particular embodiment, $R^2$ is a substituent of formula (iv) and Ring B is Ay (aryl). In one embodiment, $R^2$ is a substituent of formula (iv) or (iv-a) and Ring B is phenyl. Thus, in one particular embodiment, $R^2$ is a substituent of formula (iv-a):

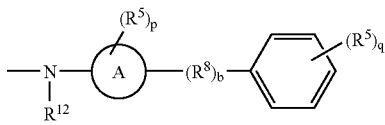

wherein all variables are as defined above in connection with compounds of formula (I).

In one particular embodiment, wherein $R^2$ is a substituent of formula (iv) selected from the group consisting of

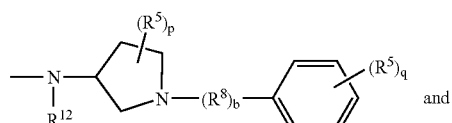

and

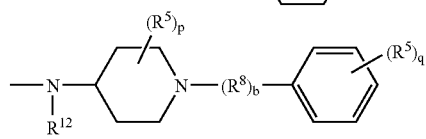

or any subset thereof, wherein all varibles are as defined above in connection with compounds of formula (I).

In one embodiment, when $R^2$ is a substituent of formula (iv) or (iv-a), $R^{12}$ is H or alkyl, or any subset thereof. In one particular embodiment $R^2$ is a substituent of formula (iv) or (iv-a), $R^{12}$ is H or methyl; more particularly H. In one embodiment, $R^{12}$ is methyl. In another embodiment, when $R^2$ is a substituent of formula (iv) or (iv-a), p is 0 or 1. In one particular embodiment, when $R^2$ is a substituent of formula (iv) or (iv-a), p is 0.

In one embodiment, when $R^2$ is a substituent of formula (iv) or (iv-a) and b is 1. In one embodiment wherein b is 1, $R^8$ is alkylene, more particularly $C_{1-3}$ alkylene.

In another embodiment, when $R^2$ is a substituent of formula (iv) or (iv-a), q is 0 or 1. In one particular embodiment, when $R^2$ is a substituent of formula (iv) or (iv-a), q is 1.

In another embodiment, the compounds of formula (I) are defined wherein $R^2$ is a substituent of formula (vi):

vi

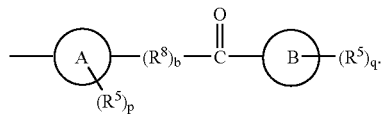

In one embodiment, $R^2$ is a substituent of formula (vi) and Ring A is a Het; more particularly Het bonded to the purine through N. In one embodiment, when $R^2$ is a substituent of formula (vi), Ring A is a 5-6 membered heterocycle bonded to the purine through N. In one particular embodiment, $R^2$ is a substituent of formula (vi-a):

vi-a

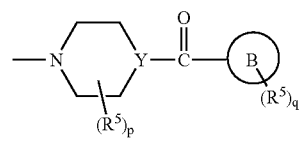

where Y is N or CH and all other variables are as defined in connection with compounds of formula (I).

In one embodiment wherein $R^2$ is a substituent of formula (vi) or (vi-a), Ring B is selected from the group consisting of $C_{3-10}$cycloalkyl, 3-10 membered heterocycle or 5-10 membered heteroaryl, or any subset thereof. In one particular embodiment $R^2$ is a substituent of formula (vi) or (vi-a) and Ring B is selected from the group consisting of $C_{5-6}$cycloalkyl or a 5-6 membered heterocycle or heteroaryl, or any subset thereof. More specifically, in one embodiment, $R^2$ is a substituent of formula (vi) or (vi-a) selected from the group consisting of

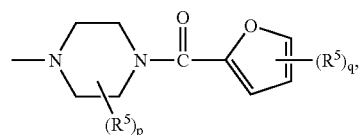

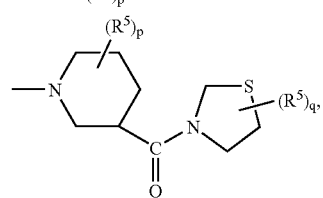

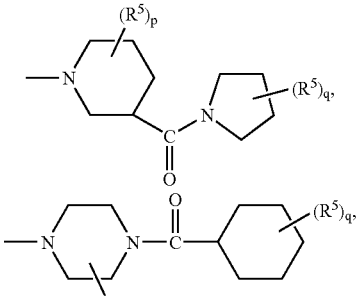

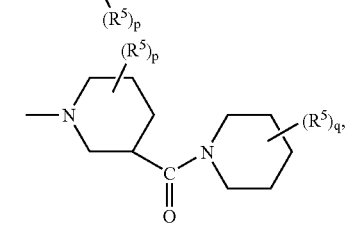

and

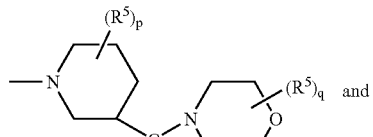

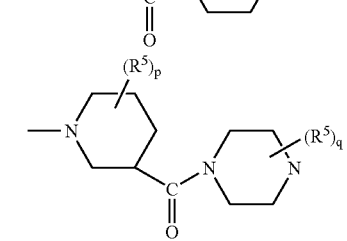

or any subset thereof.

In another embodiment, when $R^2$ is a substituent of formula (vi) or (vi-a), p is 0 or 1. In one particular embodiment, when $R^2$ is a substituent of formula (vi) or (vi-a), p is 0.

In one embodiment, when $R^2$ is a substituent of formula (vi) or (vi-a) and b is 0. In one embodiment wherein b is 1, $R^8$ is alkylene, more particularly C$_{1-3}$alkylene. In another embodiment, when R$^2$ is a substituent of formula (vi) or (vi-a), q is 0, 1 or 2. In one particular embodiment, when R$^2$ is a substituent of formula (vi) or (vi-a), q is 1. In another particular embodiment, when R$^2$ is a substituent of formula (vi) or (vi-a), q is 0.

In another embodiment, the compounds of formula (I) are defined wherein R$^2$ is a sustituent of formula (vii):

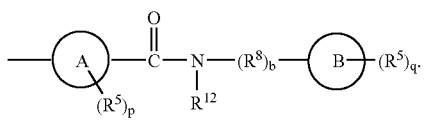

vii

In one embodiment, R$^2$ is a substituent of formula (vii) and Ring A is Het; more particularly Het bonded to the purine through N. In one embodiment, when R$^2$ is a substituent of formula (vii), Ring A is a 5-6 membered heterocycle bonded to the purine through N. In one particular embodiment, R$^2$ is a substituent of formula (vii-a):

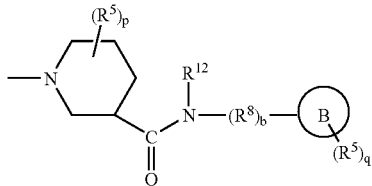

vii-a where all variables are as defined in connection with compounds of formula (I).

In one embodiment wherein R$^2$ is a substituent of formula (vii) or (vii-a), Ring B is selected from the group consisting of C$_{3-10}$cycloalkyl, 3-10 membered heterocycle and 5-10 membered heteroaryl, or any subset thereof. In one particular embodiment R$^2$ is a substituent of formula (vii) or (vii-a) and Ring B is selected from the group consisting of a C$_{3-6}$cycloalkyl and 5-6 membered heterocycle or heteroaryl, or any subset thereof.

More specifically, in one embodiment, R$^2$ is a substituent of formula (vii) or (vii-a) selected from the group consisting of:

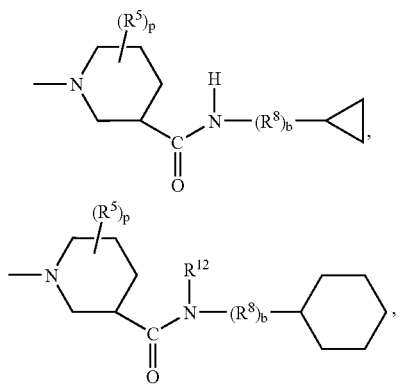

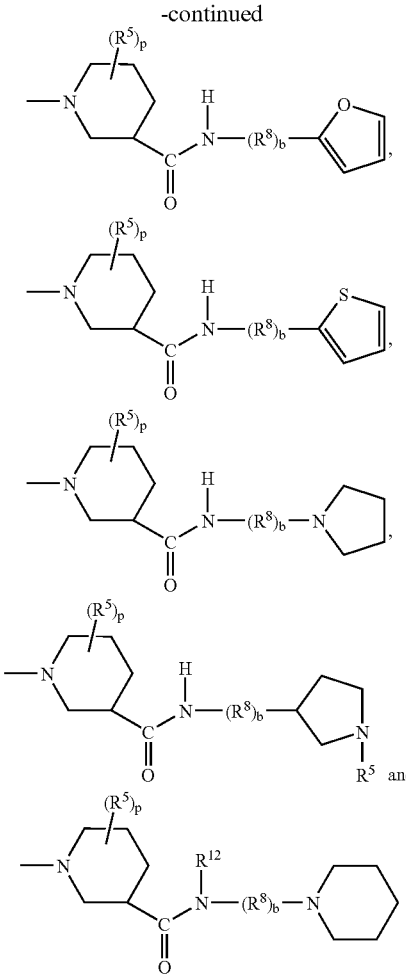

or any subset thereof.

In another embodiment, when R$^2$ is a substituent of formula (vii) or (vii-a), p is 0 or 1. In one particular embodiment, when R$^2$ is a substituent of formula (vii) or (vii-a), p is 0.

In one embodiment, when R$^2$ is a substituent of formula (vii) or (vii-a) and b is 0. In one embodiment wherein b is 1, R$^8$ is alkylene, more particularly C$_{1-3}$ alkylene.

In another embodiment, when R$^2$ is a substituent of formula (vii) or (vii-a), q is 0 or 1. In one particular embodiment, when R$^2$ is a substituent of formula (vii) or (vii-a), q is 1. In another particular embodiment, when R$^2$ is a substituent of formula (vii) or (vii-a), q is 0.

In one embodiment of the present invention wherein the compounds of formula (I) are defined such that R$^2$ is a substituent of formula (iv), (iv-a), (vi), (vi-a), (vii) or (vii-a), and at least one of p and q is not 0, each R$^5$ is the same or different and is independently selected from the group consisting of halo, alkyl, —OR$^6$, —C═O, —C(O)R$^6$, —C(O)NR$^6$R$^7$, —CO$_2$R$^9$, —N(R$^6$)C(O)R$^6$, —R$^8$OR$^6$ and nitro, or any subset thereof. More particular, each R$^5$ is the same or different and is independently selected from the group consisting of halo, alkyl, —OR$^6$, —C(O)NR$^6$R$^7$ and —CO$_2$R$^9$, or any subset thereof.

More specifically, in one embodiment, each R$^5$ is the same or different and is independently selected from the group consisting of halo, alkyl, —OH, —O-alkyl, —C(O)alkyl, —C(O)NH$_2$, —C(O)NH(alkyl), —C(O)N(alkyl)$_2$, —CO$_2$H, —NHC(O)alkyl, —R$^8$Oalkyl, and nitro, or any subset thereof. More particularly, each $R^5$ is the same or different and is independently selected from the group consisting of halo, alkyl, —OH, —O-alkyl, —C(O)NH$_2$, —C(O)NH (alkyl), —C(O)N(alkyl)$_2$ and —CO$_2$H, or any subset thereof.

In one embodiment of the present invention wherein the compounds of formula (I) are defined such that $R^2$ is a substituent of formuls (iv), (iv-a), (vi), (vi-a), (vii) or (vii-a), $R^3$ and $R^4$ are the same or different and are each independently selected from the group consisting of H, alkyl (including halo-substituted alkyl, e.g., trifluoroethyl), $C_{3-10}$cycloalkyl, Ay, $R^8$-Ay, —$R^8$OH, —$R^8$Oalkyl, —$R^8$Salkyl, —$R^8$CO$_2$H, —$R^8$CO$_2$alkyl, $R^8$—O-Ay, —$R^8$C(O)NH$_2$, —$R^8$—$C_{3-10}$cycloalkyl,

or any subset thereof. More particularly, $R^3$ and $R^4$ are the same or different and are each independently selected from the group consisting of alkyl (including halo substituted alkyl, e.g., trifluoroethyl) and $C_{3-5}$cycloalkyl. In one embodiment, $R^3$ and $R^4$ are the same or different and are each independently alkyl, or any subset thereof. More specifically, $R^3$ and $R^4$ are the same or different and are each independently selected from the group consisting of methyl, ethyl, propyl, isopropyl and cyclopropyl, or any subset thereof.

In one embodiment of the present invention, $R^8$ is alkylene, more particularly $C_{1-3}$alkylene.

In one embodiment of the present invention $R^9$ and $R^{10}$ are each the same or different and are selected from the group consisting of H and alkyl, or any subset thereof.

In another embodiment of the present invention, the compounds of formula (I) are defined wherein $R^2$ is a substituent of formula (i) or (ii):

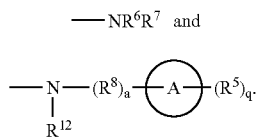

In one particular embodiment, the present invention provides compounds of formula (I-A):

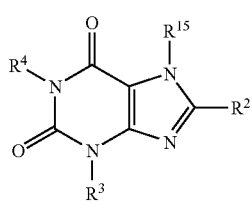

wherein:
$R^{15}$ is selected from the group consisting of

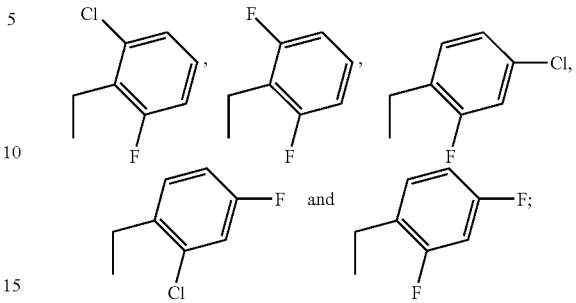

$R^2$ is a substituent selected from the group consisting of formulas i and ii:

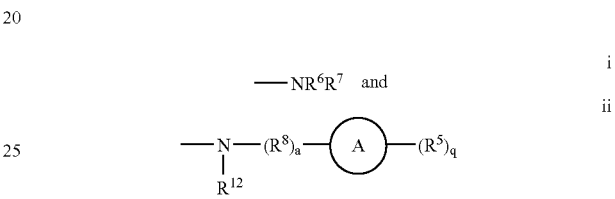

Ring A is selected from the group consisting of $C_{3-10}$cycloalkyl, $C_{3-10}$cycloalkenyl, Ay and Het;
Ay is aryl;
Het is a 3-10 membered heterocycle or a 5-10 membered heteroaryl;
a is 0 or 1;
q is 0, 1, 2 or 3;
each $R^5$ is the same or different and is independently selected from the group consisting of halo, alkyl, alkenyl, alkynyl, —OR$^6$, —OC(O)R$^6$, —OR$^8$C(O)R$^6$, —S(O)$_g$R$^6$, —C=O, —C(O)R$^6$, —C(O)NR$^6$R$^7$, —CO$_2$R$^9$, —NR$^6$R$^7$, —N(R$^6$)C(O)R$^6$, —R$^8$OR$^6$, —R$^8$NR$^6$R$^7$, —R$^8$C(O)R$^6$, —R$^8$CO$_2$R$^9$, nitro and cyano;
g is 0, 1 or 2;
$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, —R$^8$—$C_{3-10}$cycloalkyl, —R$^8$-Ay, —R$^8$-Het, —R$^8$CO$_2$R$^9$, —R$^8$C(O)NR$^9$R$^{10}$, —R$^8$OR$^9$, —R$^8$SR$^9$ and —R$^8$OAy;
$R^6$ and $R^7$ are the same or different and are each independently selected from the group consisting of H, alkyl, alkenyl, alkynyl, —R$^8$OR$^9$, —R$^8$SR$^9$, —R$^8$—NR$^9$R$^{10}$, —R$^8$—CN, —R$^8$—CO$_2$R$^9$;
$R^8$ is alkylene or alkenylene;
$R^9$ and $R^{10}$ are each the same or different and are each independently selected from the group consisting of H, alkyl, alkenyl and alkynyl; and
$R^{12}$ is selected from the group consisting of H, alkyl, alkenyl, and alkynyl, and pharmaceutically acceptable salts and solvates thereof.

In one embodiment, the compounds of formula (I) or (I-A) are defined wherein $R^2$ is a substituent of formula (i). In a particular embodiment, $R^2$ is a substituent of formula (i) and $R^6$ and $R^7$ of formula (i), are the same or different and are each independently selected from the group consisting of H, alkyl, alkenyl, alkynyl, —R$^8$OR$^9$, —R$^8$—CN and —R$^8$—CO$_2$R$^9$, or any subset thereof. More particularly, $R^2$ is a substituent of formula (i) and $R^6$ and $R^7$ of formula (i), are the same or different and are each independently selected from the group consisting of H, alkyl and —$R^8OR^9$, or any subset thereof.

In one embodiment, the compounds of formula (I) or (I-A) are defined wherein $R^2$ is a substituent of formula (ii). In a particular embodiment, $R^2$ is a substituent of formula (ii), and $R^{12}$ is H or alkyl, or any subset thereof.

In another particular embodiment, $R^2$ is a substituent of formula (ii), and a is 1. In one embodiment wherein $R^2$ is a substituent of formula (ii), and a is 1, $R^8$ is alkylene; more particularly $C_{1-3}$alkylene.

In one embodiment the compounds of formula (I) or (I-A) are defined wherein $R^2$ is a substituent of formula (ii), and Ring A is selected from the group consisting of $C_{3-6}$cycloalkyl, phenyl, and 5-6 membered heterocycle or heteroaryl, or any subset thereof; more particularly Ring A is selected from the group consisting of $C_{3-6}$cycloalkyl and phenyl, or any subset thereof. In a particular embodiment, the compounds of formula (I) or (I-A) are defined wherein $R^2$ is a substituent of formula (ii), and Ring A is selected from the group consisting of cyclopropyl, cyclobutyl, cyclopentyl, cyclohexyl, phenyl, dioxolane, furan and piperidine, or any subset thereof. More particular, Ring A in formula (ii) is selected from the group consisting of cyclopropyl, cyclobutyl, cyclopentyl, cyclohexyl and phenyl, or any subset thereof.

In another embodiment, when $R^2$ is a substituent of formula (ii), q is 0 or 1. In one particular embodiment, when $R^2$ is a substituent of formula (ii), q is 1. In another particular embodiment, when $R^2$ is a substituent of formula (ii), q is 0.

In one embodiment of the present invention wherein the compounds of formula (I) are defined such that $R^2$ is a substituent of formula (i) or (ii), and q is 1 or more, each $R^5$ is the same or different and is independently selected from the group consisting of halo, alkyl, —$OR^6$, —C=O, —$C(O)R^6$, —$C(O)NR^6R^7$, —$CO_2R^9$, —$N(R^6)C(O)R^6$, —$R^8OR^6$ and nitro, or any subset thereof. More particular, each $R^5$ is the same or different and is independently selected from the group consisting of halo, alkyl, —$OR^6$, —$C(O)NR^6R^7$ and —$CO_2R^9$, or any subset thereof.

More specifically, in one embodiment, each $R^5$ is the same or different and is independently selected from the group consisting of halo, alkyl, —OH, —O-alkyl, —C(O)alkyl, —$C(O)NH_2$, —C(O)NH(alkyl), —$C(O)N(alkyl)_2$, —$CO_2H$, —NHC(O)alkyl, —$R^8$Oalkyl, and nitro, or any subset thereof. More particularly, each $R^5$ is the same or different and is independently selected from the group consisting of halo, alkyl, —OH, —O-alkyl, —$C(O)NH_2$, —C(O)NH(alkyl), —$C(O)N(alkyl)_2$ and —$CO_2H$, or any subset thereof.

In one embodiment of the present invention wherein the compounds of formula (I) are defined such that $R^2$ is a substituent of formula (i) or (ii), $R^3$ and $R^4$ are the same or different and are each independently selected from the group consisting of H, alkyl (including halo-substituted alkyl such as trifluoroethyl), $C_{3-10}$cycloalkyl, Ay, $R^8$-Ay, —$R^8OH$, —$R^8$Oalkyl, —$R^8$Salkyl, —$R^8CO_2H$, —$R^8CO_2$alkyl, $R^8$—O-Ay, —$R^8C(O)NH_2$, —$R^8$—$C_{3-10}$cycloalkyl,

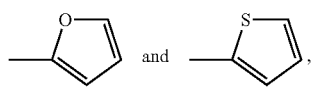 and 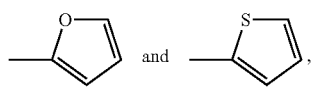, or any subset thereof. More particularly, $R^3$ and $R^4$ are the same or different and are each independently selected from the group consisting of alkyl (including halo substituted alkyl, e.g., trifluoroethyl) and $C_{3-5}$cycloalkyl, or any subset thereof. In one embodiment, $R^3$ and $R^4$ are the same or different and are each independently alkyl. More specifically, $R^3$ and $R^4$ are the same or different and are each independently selected from the group consisting of methyl, ethyl, propyl, isopropyl and cyclopropyl, or any subset thereof. In one embodiment, $R^3$ and $R^4$ are not both methyl.

In one embodiment of the present invention, $R^8$ is alkylene, more particularly $C_{1-3}$alkylene.

In one embodiment of the present invention $R^9$ and $R^{10}$ are each the same or different and are selected from the group consisting of H and alkyl.

In another embodiment of the present invention, the compounds of formula (I) are defined such that $R^2$ is a substituent of formula (iii):

iii

In one embodiment, the compounds of formula (I) are defined wherein $R^2$ is a substituent of formula (iii) and Ring A is selected from the group consisting of $C_{3-10}$cycloalkyl, phenyl, and Het, or any subset thereof; more particularly, Ring A is selected from the group consisting of $C_{3-10}$cycloalkyl, phenyl, and Het bonded to the purine ring through N, or any subset thereof.

More specifically, in one embodiment of the present invention, the compounds of formula (I) are defined wherein $R^2$ is a substituent of formula (iii) and Ring A is selected from the group consisting of

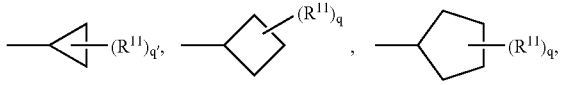

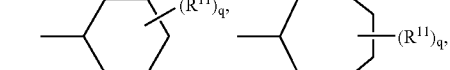

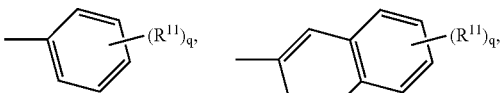

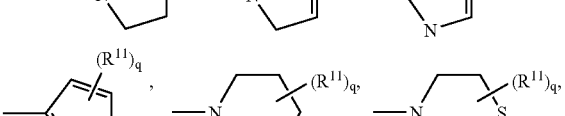

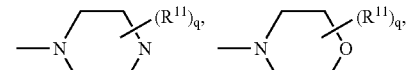

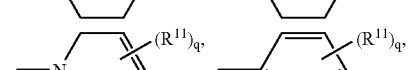

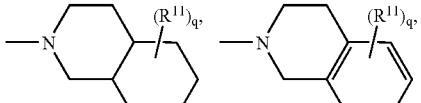

-continued

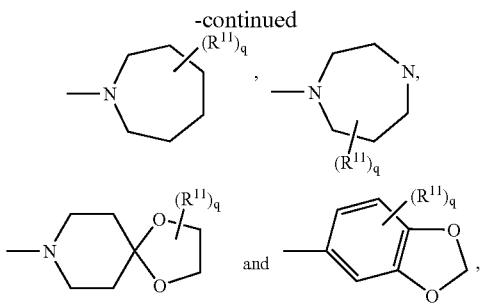

or any subset thereof. In one embodiment, $R^2$ is selected from the group consisting of optionally substituted phenyl and optionally substituted piperidine (i.e.,

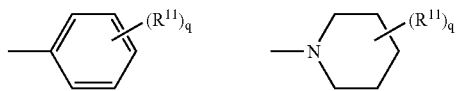

or any subset thereof.

In one particular embodiment, the present invention provides compounds of formula (I-A):

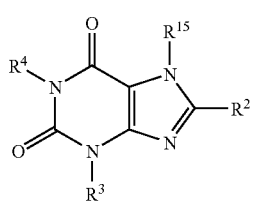
(I-A)

wherein:
$R^{15}$ is selected from the group consisting of

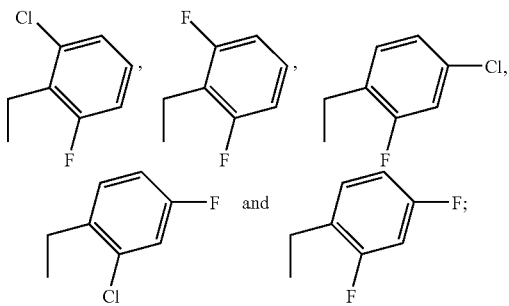

$R^2$ is a substituent selected from the group consisting of:

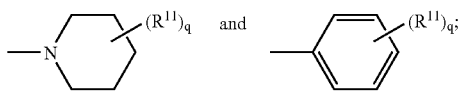

q is 0, 1, 2 or 3;
each $R^{11}$ is the same or different and is independently selected from the group consisting of halo, alkyl, alkenyl, alkynyl, —$OR^6$, —$OC(O)R^6$, —$OR^6C(O)R^6$, —$S(O)_gR^6$, —C=O, —$C(O)R^6$, —$C(O)NR^6R^7$, —$CO_2R^9$, —$C(O)_2R^8Ay$, —$NR^6R^7$, —$N(R^6)C(O)R^6$, —$R^8OR^6$, —$R^8NR^6R^7$, —$R^8C(O)R^6$, —$R^8$—$C(O)Ay$, —$R^8$—$C(O)Het$, —$R^8CO_2R^9$, —$R^8C(O)N(R^9)Ay$, —$CH$-$(Ay)_2$, —$CH$-$(Het)_2$, nitro and cyano;

g is 0, 1 or 2;
Ay is aryl;
Het is a 3-10 membered heterocycle or a 5-10 membered heteroaryl;
$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, —$R^8$—$C_{3-10}$cycloalkyl, —$R^8$-Ay, —$R^8$-Het, —$R^8CO_2R^9$, —$R^8C(O)NR^9R^{10}$, —$R^8OR^9$, —$R^8SR^9$ and —$R^8OAy$,
$R^6$ and $R^7$ are the same or different and are each independently selected from the group consisting of H, alkyl, alkenyl, alkynyl, —$R^8OR^9$, —$R^8SR^9$, —$R^8$—$NR^9R^{10}$, —$R^8$—CN, —$R^8$—$CO_2R^9$;
$R^8$ is alkylene or alkenylene; and
$R^9$ and $R^{10}$ are each the same or different and are each independently selected from the group consisting of H, alkyl, alkenyl and alkynyl;

and pharmaceutically acceptable salts and solvates thereof.

In one embodiment, the compounds of formula (I-A) are defined wherein $R^2$ is optionally substituted piperidinyl, i.e.,

In one embodiment, the compounds of formula (I) wherein $R^2$ is a substituent of formula (iii) or the compounds of formula (I-A) (wherein $R^2$ is optionally substituted piperidinyl or optionally substituted phenyl), q is 0, 1 or 2. In a particular embodiment, q is 0 or 1. In one embodiment q is 1. In one embodiment, q is 0. In one embodiment of the present invention wherein the compounds of formula (I) are defined such that $R^2$ is a substituent of formula (iii) or the compounds of formula (I-A) (wherein $R^2$ is optionally substituted piperidinyl or optionally substituted phenyl), and q is 1 or more, each $R^{11}$ is the same or different and is independently selected from the group consisting of halo, alkyl, —OH, —$OR^6$, —$C(O)R^6$, —$C(O)NR^6R^7$, —$CO_2R^9$, —$C(O)_2R^8Ay$, —$NR^6R^7$, —$N(R^6)C(O)R^6$, —$R^8OR^6$, —$R^8NR^6R^7$, —$R^8CO_2R^9$, $R^8C(O)N(R^9)Ay$ and nitro, or any subset thereof. In particular, in one embodiment of the present invention wherein $R^2$ is a substituent of formula (iii) or the compounds of formula (I-A) (wherein $R^2$ is optionally substituted piperidinyl or optionally substituted phenyl), and $R^{11}$ is —$OR^6$, —$OC(O)R^6$, —$OR^8C(O)R^6$, —$S(O)_gR^6$, —$C(O)R^6$, —$C(O)NR^6R^7$, —$NR^6R^7$, —$N(R^6)C(O)R^6$, —$R^8OR^6$, —$R^8NR^6R^7$ or —$R^8C(O)R^6$; $R^6$ is not —$R^8OR^9$. More particular, each $R^{11}$ is the same or different and is independently selected from the group consisting of halo, alkyl, —$OR^6$, —$C(O)NR^6R^7$ and —$CO_2R^9$, or any subset thereof.

More specifically, in one embodiment of the compounds of formula (I) wherein $R^2$ is a substituent of formula (iii) or the compounds of formula (I-A) (wherein $R^2$ is optionally substituted piperidinyl or optionally substituted phenyl), each $R^{11}$ is the same or different and is independently selected from the group consisting of halo, alkyl, —OH, —Oalkyl, —C(O)alkyl, —$CO_2H$, —$CO_2$alkyl, —$CO_2R^8$-phenyl, —NHC(O)alkyl, —C(O)NHalkyl, —C(O)N(alkyl)$_2$, —C(O)N(H)$R^8$OH, —C(O)N(H)$R^8$Oalkyl, —C(O)N(H) $R^8$CN, —C(O)N(alkyl)$R^8$CN, —C(O)N(alkyl)$R^8NH_2$, —C(O)N(alkyl)R$^8$N(H)alkyl, —C(O)N(alkyl)R$^8$N(alkyl)$_2$, —R$^8$Oalkyl, —R$^8$C(O)N(alkyl)phenyl, —R$^8$CO$_2$alkyl, —R$^8$NH$_2$, —R$^8$N(H)alkyl, —R$^8$N(alkyl)$_2$, —CH(phenyl)$_2$ and nitro, or any subset thereof. More particularly, each R$^{11}$ is the same or different and is independently selected from the group consisting of halo, alkyl, —OH, —O-alkyl, —C(O)alkyl, —C(O)NH$_2$, —C(O)NH(alkyl), —C(O)N(alkyl)$_2$, —CO$_2$H, —NHC(O)alkyl, —R$^8$Oalkyl and nitro, or any subset thereof. In a particular embodiment, each R$^{11}$ is the same or different and is independently selected from the group consisting of halo, alkyl, —OH, —O-alkyl, —C(O)NH$_2$, —C(O)NH(alkyl), —C(O)N(alkyl)$_2$ and —CO$_2$H, or any subset thereof.

In one embodiment of the present invention wherein the compounds of formula (I) wherein R$^2$ is a substituent of formula (iii) or the compounds of formula (I-A) (wherein R$^2$ is optionally substituted piperidinyl or optionally substituted phenyl) are defined such that R$^3$ and R$^4$ are the same or different and are each independently selected from the group consisting of H, alkyl (including halo-substituted alkyl such as trifluoroethyl), C$_{3-10}$cycloalkyl, Ay, R$^8$-Ay, —R$^8$OH, —R$^8$Oalkyl, —R$^8$Salkyl, —R$^8$CO$_2$H, —R$^8$CO$_2$alkyl, R$^8$—O-Ay, —R$^8$C(O)NH$_2$, —R$^8$—C$_{3-10}$cycloalkyl,

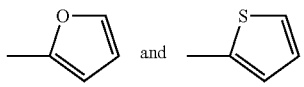 and 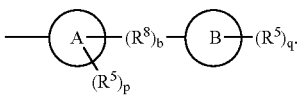

or any subset thereof. More particularly, R$^3$ and R$^4$ are the same or different and are each independently selected from the group consisting of alkyl (including halo substituted alkyl, e.g., trifluoroethyl) and C$_{3-5}$cycloalkyl, or any subset thereof. In one embodiment, R$^3$ and R$^4$ are the same or different and are each independently alkyl. More specifically, R$^3$ and R$^4$ are the same or different and are each independently selected from the group consisting of methyl, ethyl, propyl, isopropyl and cyclopropyl, or any subset thereof. In one embodiment when R$^2$ is optionally substituted piperidine, R$^3$ and R$^4$ are not both methyl. In one embodiment, when R$^2$ is a substituent of formula (iii), R$^3$ and R$^4$ are not both methyl.

In one embodiment of the present invention, R$^8$ is alkylene, more particularly C$_{1-3}$alkylene.

In one embodiment of the present invention R$^9$ and R$^{10}$ are each the same or different and are selected from the group consisting of H and alkyl.

In another embodiment of the present invention, the compounds of formula (I) are defined such that R$^2$ is a substituent of formula (v)

$$—\text{(A)}—(R^8)_b—\text{(B)}—(R^5)_q.$$
$(R^5)_p$ v

In one embodiment, the compounds of formula (I) are defined wherein R$^2$ is a substituent of formula (v) and Ring A is Het; more particularly, Ring A is selected from the group consisting of 5-6 membered heterocycle and heteroaryl, or any subset thereof. In one embodiment, Ring A is a N-containing 3-10 membered heterocycle or 5-10 membered heteroaryl, or any subset thereof; more particularly Ring A is a N-containing 5-6 membered heterocycle or heteroaryl, or any subset thereof. In a particular embodiment Ring A is Het bonded to the purine through N. In a particular embodiment Ring A is 5-6 membered heterocycle or heteroaryl bonded to the purine through N. In one embodiment Ring A is piperazine.

In one embodiment, the compounds of formula (I) are defined wherein R$^2$ is a substituent of formula (v) and Ring B is selected from the group consisting of C$_{3-10}$cycloalkyl, phenyl, 3-10 membered heterocycle and 5-10 membered heteroaryl, or any subset thereof; more particularly C$_{5-6}$cycloalkyl, phenyl, 5-6 membered heterocycle and 5-6 membered heteroaryl. In one embodiment, Ring B is Ay, particularly phenyl.

In one embodiment, the compounds of formula (I) are defined wherein R$^2$ is a substituent of formula (v) selected from the group consisting of

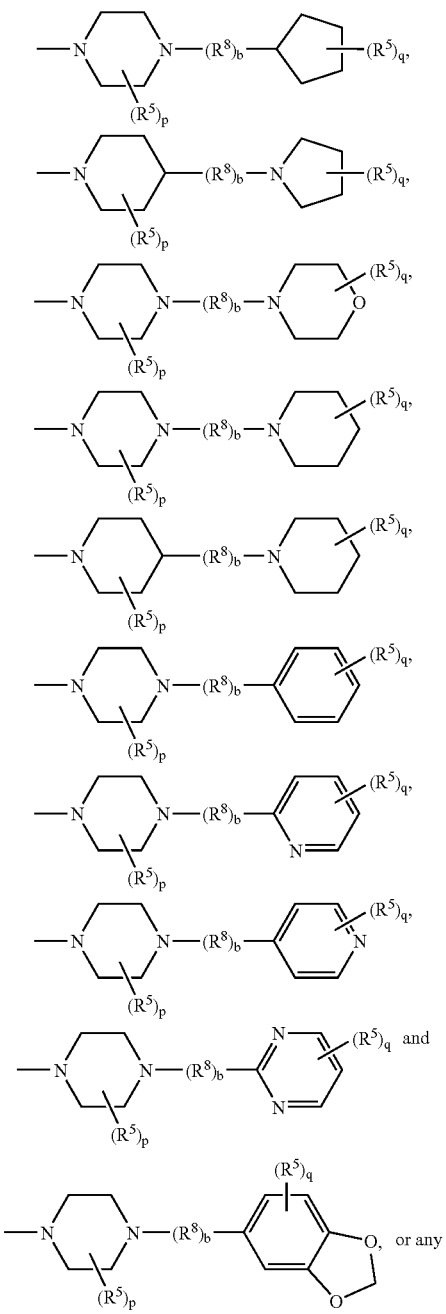

or any subset thereof.

In one particular embodiment, the present invention provides compounds of formula (I-A)

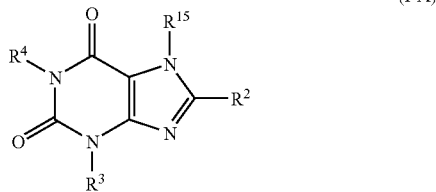

(I-A)

wherein:
R$^{15}$ is selected from the group consisting of

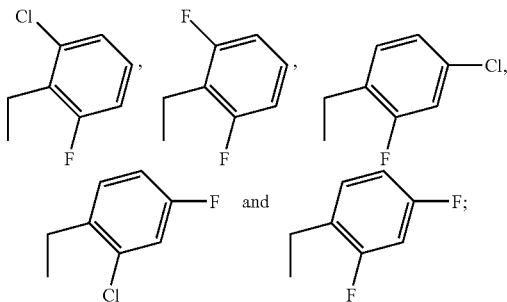

R$^2$ is a substituent of formula (v-a):

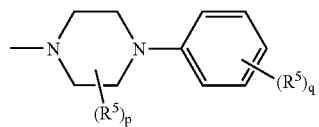

v-a p is 0, 1 or 2;
q is 0, 1, 2 or 3;
each R$^5$ is the same or different and is independently selected from the group consisting of halo, alkyl, alkenyl, alkynyl, —OR$^6$, —OC(O)R$^6$, —OR$^8$C(O)R$^6$, —S(O)$_g$R$^6$, —C=O, —C(O)R$^6$, —C(O)NR$^6$R$^7$, —CO$_2$R$^9$, —NR$^6$R$^7$, —N(R$^6$)C(O)R$^6$, —R$^8$OR$^6$, —R$^8$NR$^6$R$^7$, —R$^8$C(O)R$^6$, —R$^8$CO$_2$R$^9$, nitro and cyano;
g is 0, 1 or 2;
Ay is aryl;
Het is a 3-10 membered heterocycle or a 5-10 membered heteroaryl;
R$^3$ and R$^4$ are the same or different and are each independently selected from the group consisting of H, alkyl, alkenyl, alkynyl, C$_{3-10}$cycloalkyl, C$_{3-10}$cycloalkenyl, Ay, Het, —R$^8$—C$_{3-1}$cycloalkyl, —R$^8$-Ay, —R$^8$-Het, —R$^8$CO$_2$R$^9$, —R$^8$C(O)NR$^9$R$^{10}$, —R$^8$OR$^9$, —R$^8$SR$^9$ and —R$^8$OAy;
R$^6$ and R$^7$ are the same or different and are each independently selected from the group consisting of H, alkyl, alkenyl, alkynyl, —R$^8$OR$^9$, —R$^8$SR$^9$, —R$^8$—NR$^9$R$^{10}$, —R$^8$—CN, —R$^8$—CO$_2$R$^9$;
R$^8$ is alkylene or alkenylene; and
R$^9$ and R$^{10}$ are each the same or different and are each independently selected from the group consisting of H, alkyl, alkenyl and alkynyl;
and pharmaceutically acceptable salts and solvates thereof.

In one embodiment, the compounds of formula (I) wherein R$^2$ is a substituent of formula (v) or the compounds of formula (I-A) (wherein R$^2$ is a substituent of formula (v-a)), p is 0

In one embodiment, the compounds of formula (I) wherein R$^2$ is a substituent of formula (v) or the compounds of formula (I-A) (wherein R$^2$ is a substituent of formula (v-a)), q is 0, 1 or 2. In a particular embodiment, q is 0 or 1. In one embodiment q is 1. In one embodiment, q is 0.

In one embodiment of the present invention wherein the compounds of formula (I) are defined such that R$^2$ is a substituent of formula (v) or the compounds of formula (I-A) (wherein R$^2$ is a substituent of formula (v-a)), and q is 1 or more, each R$^5$ is the same or different and is independently selected from the group consisting of halo, alkyl, —OR$^6$, —C=O, —C(O)R$^6$, —C(O)NR$^6$R$^7$, —CO$_2$R$^9$, —N(R$^6$)C(O)R$^6$, R$^8$OR$^6$ and nitro, or any subset thereof. More particular, each R$^5$ is the same or different and is independently selected from the group consisting of halo, alkyl, —OR$^6$, —C(O)NR$^6$R$^7$ and —CO$_2$R$^9$, or any subset thereof.

More specifically, in one embodiment of the compounds of formula (I) wherein R$^2$ is a substituent of formula (v) or the compounds of formula (I-A) (wherein R$^2$ is a substituent of formula (v-a)), each R$^5$ is the same or different and is independently selected from the group consisting of halo, alkyl, —OH, —O-alkyl, —C(O)alkyl, —C(O)NH$_2$, —C(O)NH(alkyl), —C(O)N(alkyl)$_2$, —CO$_2$H, —NHC(O)alkyl, —R$^8$Oalkyl, and nitro, or any subset thereof. More particularly, each R$^5$ is the same or different and is independently selected from the group consisting of halo, alkyl, —OH, —O-alkyl, —C(O)NH$_2$, —C(O)NH(alkyl), —C(O)N(alkyl)$_2$ and —CO$_2$H, or any subset thereof.

In one embodiment of the present invention wherein the compounds of formula (I) wherein R$^2$ is a substituent of formula (v) or the compounds of formula (I-A) (wherein R$^2$ is a substituent of formula (v-a)) are defined such that R$^3$ and R$^4$ are the same or different and are each independently selected from the group consisting of H, alkyl (including halo-substituted alkyl such as trifluoroethyl), C$_{3-10}$cycloalkyl, Ay, R$^8$-Ay, —R$^8$OH, —R$^8$Oalkyl, —R$^8$Salkyl, —R$^8$CO$_2$H, —R$^8$CO$_2$alkyl, R$^8$—O-Ay, —R$^8$C(O)NH$_2$, —R$^8$—C$_{3-10}$cycloalkyl,

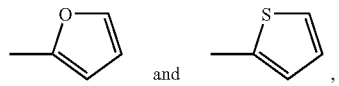

or any subset thereof. More particularly, R$^3$ and R$^4$ are the same or different and are each independently selected from the group consisting of alkyl (including halo substituted alkyl, e.g., trifluoroethyl) and C$_{3-5}$cycloalkyl, or any subset thereof. In one embodiment, R$^3$ and R$^4$ are the same or different and are each independently alkyl. More specifically, R$^3$ and R$^4$ are the same or different and are each independently selected from the group consisting of methyl, ethyl, propyl, isopropyl and cyclopropyl, or any subset thereof.

In one embodiment when R$^2$ is a substituent of formula (v) or (v-a), R$^3$ and R$^4$ are not both methyl.

In one embodiment of the present invention, R$^8$ is alkylene, more particularly C$_{1-3}$alkylene.

In one embodiment of the present invention R$^9$ and R$^{10}$ are each the same or different and are selected from the group consisting of H and alkyl.

Specific examples of particular compounds of the present invention are selected from the group consisting of:
7-(2-chloro-6-fluorobenzyl)-1,3-diethyl-8-piperidin-1-yl-3,7-dihydro-1H-purine-2,6-dione;

7-(2-chloro-6-fluorobenzyl)-1-ethyl-3-isopropyl-8-piperidin-1-yl-3,7-dihydro-1H-purine-2,6-dione;
7-(2-chloro-6-fluorobenzyl)-3-ethyl-8-piperidin-1-yl-1-propyl-3,7-dihydro-1H-purine-2,6-dione;
7-(2-chloro-6-fluorobenzyl)-3-isopropyl-8-piperidin-1-yl-1-propyl-3,7-dihydro-1H-purine-2,6-dione;
7-(2-chloro-6-fluorobenzyl)-1-isopropyl-3-methyl-8-piperidin-1-yl-3,7-dihydro-1H-purine-2,6-dione;
7-(2-chloro-6-fluorobenzyl)-1-ethyl-3-(2-methoxyethyl)-8-piperidin-1-yl-3,7-dihydro-1H-purine-2,6-dione;
methyl [7-(2-chloro-6-fluorobenzyl)-1-ethyl-2,6-dioxo-8-piperidin-1-yl-1,2,6,7-tetrahydro-3H-purin-3-yl]acetate;
7-(2-chloro-6-fluorobenzyl)-1-ethyl-3-(2-phenoxyethyl)-8-piperidin-1-yl-3,7-dihydro-1H-purine-2,6-dione;
1-butyl-7-(2-chloro-6-fluorobenzyl)-3-methyl-8-piperidin-1-yl-3,7-dihydro-1H-purine-2,6-dione;
7-(2-chloro-6-fluorobenzyl)-1-(cyclopropylmethyl)-3-isopropyl-8-piperidin-1-yl-3,7-dihydro-1H-purine-2,6-dione;
7-(2-chloro-6-fluorobenzyl)-1,3-diisopropyl-B-piperidin-1-yl-3,7-dihydro-1H-purine-2,6-dione;
7-(2-chloro-6-fluorobenzyl)-1-cyclopropyl-3-isopropyl-8-piperidin-1-yl-3,7-dihydro-1H-purine-2,6-dione;
7-(2-chloro-6-fluorobenzyl)-1-ethyl-3-methyl-8-piperidin-1-yl-3,7-dihydro-1H-purine-2,6-dione;
7-(2-chloro-6-fluorobenzyl)-3-methyl-8-piperidin-1-yl-1-propyl-3,7-dihydro-1H-purine-2,6-dione;
1-benzyl-7-(2-chloro-6-fluorobenzyl)-3-methyl-8-piperidin-1-yl-3,7-dihydro-1H-purine-2,6-dione;
7-(2-chloro-6-fluorobenzyl)-3-ethyl-1-methyl-8-piperidin-1-yl-3,7-dihydro-1H-purine-2,6-dione;
7-(2-chloro-6-fluorobenzyl)-1-methyl-8-piperidin-1-yl-3-propyl-3,7-dihydro-1H-purine-2,6-dione;
7-(2-chloro-6-fluorobenzyl)-3-isopropyl-1-methyl-8-piperidin-1-yl-3,7-dihydro-1H-purine-2,6-dione;
3-benzyl-7-(2-chloro-6-fluorobenzyl)-1-methyl-8-piperidin-1-yl-3,7-dihydro-1H-purine-2,6-dione;
7-(2-chloro-6-fluorobenzyl)-8-(3-chlorophenyl)-3-isopropyl-1-methyl-3,7-dihydro-1H-purine-2,6-dione;
7-(2-chloro-6-fluorobenzyl)-1,3-dimethyl-8-phenyl-3,7-dihydro-1H-purine-2,6-dione;
7-(2-chloro-6-fluorobenzyl)-8-(4-chlorophenyl)-1,3-dimethyl-3,7-dihydro-1H-purine-2,6-dione;
7-(2-chloro-6-fluorobenzyl)-8-(3,5-dichlorophenyl)-1,3-dimethyl-3,7-dihydro-1H-purine-2,6-dione;
7-(2-chloro-6-fluorobenzyl)-1,3-dimethyl-8-(2-naphthyl)-3,7-dihydro-1H-purine-2,6-dione;
7-(2-chloro-6-fluorobenzyl)-8-(3-chlorophenyl)-1,3-dimethyl-3,7-dihydro-1H-purine-2,6-dione;
7-(2-chloro-6-fluorobenzyl)-1,3-dimethyl-8-[3-(trifluoromethyl)phenyl]-3,7-dihydro-1H-purine-2,6-dione;
7-(2-chloro-6-fluorobenzyl)-8-(3-methoxyphenyl)-1,3-dimethyl-3,7-dihydro-1H-purine-2,6-dione;
7-(2-chloro-6-fluorobenzyl)-8-cyclohexyl-1,3-dimethyl-3,7-dihydro-1H-purine-2,6-dione;
7-(2-chloro-6-fluorobenzyl)-8-(3-iodophenyl)-1,3-dimethyl-3,7-dihydro-1H-purine-2,6-dione;
1-[7-(2-chloro-6-fluorobenzyl)-1,3-dimethyl-2,6-dioxo-2,3,6,7-tetrahydro-1H-purin-8-yl]piperidine-3-carboxylic acid;
7-(2-chloro-6-fluorobenzyl)-8-{3-[(4-hydroxypiperidin-1-yl)carbonyl]piperidin-1-yl}-1,3-dimethyl-3,7-dihydro-1H-purine-2,6-dione;
1-[7-(2-chloro-6-fluorobenzyl)-1,3-dimethyl-2,6-dioxo-2,3,6,7-tetrahydro-1H-purin-8-yl]-N-(4-hydroxybutyl)piperidine-3-carboxamide;
7-(2-chloro-6-fluorobenzyl)-1,3-dimethyl-8-{4-[3-(trifluoromethyl)phenyl]piperazin-1-yl}-3,7-dihydro-1H-purine-2,6-dione;
7-(2-chloro-6-fluorobenzyl)-8-[(3-methoxyphenyl)piperazin-1-yl]-1,3-dimethyl-3,7-dihydro-1H-purine-2,6-dione;
7-(2-chloro-6-fluorobenzyl)-8-{4-[4-chloro-3-(trifluoromethyl)phenyl]piperazin-1-yl}-1,3-dimethyl-3,7-dihydro-1H-purine-2,6-dione;

and pharmaceutically acceptable salts and solvates thereof.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted.

The present invention contemplates and includes all combinations and subsets of the particular groups defined above.

Suitable pharmaceutically acceptable salts according to the present invention will be readily determined by one skilled in the art and will include, for example, acid addition salts prepared from inorganic acids such as hydrochloric, hydrobromic, phosphoric, metaphosphoric, nitric, sulphonic, and sulfuric acids, and organic acids such as acetic, benzenesulphonic, benzoic, citric, ethanesulphonic, fumaric, gluconic, glycollic, isothionic, lactic, lactobionic, maleic, malic, methanesulphonic, succinic, p-toluenesulfonic, salicylic, tartaric, and trifluoroacetic, formic, malonic, naphthalene-2-sulfonic, sulfamic, decanoic, orotic, 1-hydroxy-2-naphthoic, cholic, and pamoic. In one embodiment, the compounds of formula (I) are in the form of the hydrochloride salt.

When used in medicine, the salts of a compound of formula (I) should be pharmaceutically acceptable, but pharmaceutically unacceptable salts may conveniently be used to prepare the corresponding free base or pharmaceutically acceptable salts thereof.

As used herein, the term "solvate" is a crystal form containing the compound of formula (I) or a pharmaceutically acceptable salt thereof and either a stoichiometric or a non-stoichiometric amount of a solvent. Solvents, by way of example, include water, methanol, ethanol, or acetic acid. Hereinafter, reference to a compound of formula (I) is to any physical form of that compound, unless a particular form, salt or solvate thereof is specified.

In one embodiment, the compounds of formula (I) or (I-A) are LXR agonists. As used herein, the term "LXR agonist" refers to compounds which achieve at least 50% activation of LXR relative to 24(S),25-epoxycholesterol, the appropriate positive control in the HTRF assay described below in the example below. More particularly, the compounds of this invention achieve 100% activation of LXR in the HTRF assay. In addition, in one embodiment, the compounds of formula (I) will upregulate expression of ABC1. By upregulating expression of ABC1, is meant that the induction of ABC1 upon treatment of cells with compounds of formula (I) at a concentration less than or equal to 10 micromolar is greater than 2 fold greater than in the absence of compounds of formula (I) in the assay described in the Examples below. Thus the compounds of formula (I) are also useful in methods for upregulating expression of ABC1.

The compounds of formula (I) are useful in therapy in mammals, particularly humans. In particular, the compounds of formula (I) is useful prevention or treatment of an LXR mediated disease or condition in a mammal, particularly a human. The compounds of formula (I) are also useful in the prevention or treatment of cardiovascular disease in a mammal, particularly a human. The compounds of formula (I) are useful in the prevention or treatment of atherosclerosis in a mammal, particularly a human.

The compounds of formula (I) are also useful for the treatment and/or prophylaxis of a disease or condition characterised by neuron degeneration, inflammation in the CNS, injury or impaired plasticity. The invention also provides a method for the promotion of growth and/or repair of neurons in diseases or conditions characterised by neuron degeneration, inflammation in the CNS, injury or impaired plasticity which method comprises the administration of an effective, non-toxic and pharmaceutically acceptable amount of a compound of formula (I). Particular diseases or conditions are characterised by neuron degeneration and inflammation, and thus benefiting from the growth and/or repair of neurons including stroke, Alzheimer's disease, fronto-temporal dementias (tauopathies), peripheral neuropathy, Parkinson's disease, dementia with Lewy bodies, Huntington's disease, amyotrophic lateral sclerosis and multiple sclerosis. Diseases or conditions characterised by neuron degeneration and/or impaired plasticity include psychiatric disorders such as schizophrenia and depression. Particular diseases or conditions characterised by neuronal injury include those conditions associated with brain and/or spinal cord injury, including trauma.

The compounds of formula (I) are useful for the prevention and treatment of inflammatory conditions mediated by LXR. Inflammatory conditions include those of the lungs, joints, eyes, bowel, skin and periodontal tissue; particularly those inflammatory conditions mediated by LXR. Conditions of the lung include asthma, adult respiratory distress syndrome, chronic obstructive pulmonary disease, pneumonia bronchitis and cystic fibrosis (which may additionally or alternatively involve the bowel or other tissue(s)). Conditions of the joint include rheumatoid arthritis, rheumatoid spondylitis, osteoarthritis, gouty arthritis and other arthritic conditions. Inflammatory eye conditions include uveitis (including iritis) and conjunctivitis. Inflammatory bowel conditions include Crohn's disease, ulcerative colitis and distal proctitis. Other conditions of the gastro intestinal tract include periodontal disease, esophagitis, NSAID—induced gastrointestinal damage, chemotherapy-induced mucositis, AIDS related diarrhoea and infectious diarrhoea. Skin diseases include those associated with cell proliferation, such as psoriasis, eczema and dermatitis (whether or not of allergic origin). Inflammatory conditions of the periodontal tissue include periodontal disease.

The compounds of formula (I) are useful for increasing reverse cholesterol transport in a mammal, particularly a human. The compounds of formula (I) are useful for inhibiting cholesterol absorption in a mammal, particularly a human. The compounds of formula (I) are useful for increasing HDL-cholesterol in a mammal, particularly a human. The compounds of formula (I) are useful for decreasing LDL-cholesterol in a mammal, particularly a human.

The present invention provides a method for the treatment or prevention of an LXR mediated disease or condition in a mammal, particularly a human. LXR mediated diseases or conditions include but are not limited to cardiovascular disease including atherosclerosis, arteriosclerosis, hypercholesteremia, and hyperlipidemia. In particular, the compounds of formula (I) are useful in the treatment and prevention of cardiovascular disease including artherosclerosis and hypercholesteremia. Certain diseases or conditions characterised by neuron degeneration, inflammation in the CNS, injury or impaired plasticity, including Alzheimer's disease are also believed to be mediated through LXR and as such, the present invention provides a method for the treatment or prevention of such diseases or conditions. In addition, inflammatory conditions are also believed to be mediated by LXR and as such the present invention provides a method for the treatment or prevention of inflammatory conditions, particularly inflammatory conditions mediated by LXR. The present invention also provides the use of a compound of formula (I) for the preparation of a medicament for the treatment or prevention of an LXR mediated disease or condition. The present invention also provides a method for increasing reverse cholesterol transport in a mammal, particularly a human. The present invention also provides the use of a compound of formula (I) for the preparation of a medicament for increasing reverse cholesterol transport in a mammal, particularly a human. Lipoprotein metabolism is a dynamic process comprised of production of triglyceride rich particles from the liver (as VLDL), modification of these lipoprotein particles within the plasma (VLDL to IDL to LDL) and clearance of the particles from the plasma, again by the liver. This process provides the transport of triglycerides and free cholesterol to cells of the body. Reverse cholesterol transport is the proposed mechanism by which peripheral cholesterol is returned to the liver from extra-hepatic tissue. The process is carried out by HDL cholesterol. The combination of lipoprotein production (VLDL, HDL) from the liver, modification of particles (all) within the plasma and subsequent clearance back to the liver, accounts for the steady state cholesterol concentration of the plasma. Without wishing to be bound by any particular theory, it is currently believed that the compounds of formula (I) increase reverse cholesterol transport by raising the plasma level of HDL cholesterol and/or by increasing cholesterol efflux from the arteries.

The present invention provides a method for inhibiting cholesterol absorption in a mammal, particularly a human. The present invention also provides the use of a compound of formula (I) for the preparation of a medicament for inhibiting cholesterol absorption in a mammal, particularly a human.

The present invention provides a method for increasing HDL-cholesterol in a mammal, particularly a human. The present invention also provides the use of a compound of formula (I) for the preparation of a medicament for inhibiting cholesterol absorption in a mammal, particularly a human.

The present invention also provides a method for decreasing LDL-cholesterol in a mammal, particularly a human. The present invention also provides the use of a compound of formula (I) for the preparation of a medicament for inhibiting cholesterol absorption in a mammal, particularly a human.

All of the methods of the present invention comprise the step of administering a therapeutically effective amount of the compound of formula (I) or a pharmaceutically acceptable salt or solvate thereof. As used herein, the term "therapeutically effective amount" refers to an amount of the compound of formula (I) which is sufficient to achieve the stated effect. Accordingly, a therapeutically effective amount of a compound of formula (I) used in the method for the prevention or treatment of LXR mediated diseases or conditions will be an amount sufficient to prevent or treat the LXR mediated disease or condition. Similarly, a therapeutically effective amount of a compound of formula (I) for use in the method of increasing reverse cholesterol transport will be an amount sufficient to increase reverse cholesterol transport.

The amount of a compound of formula (I) or pharmaceutically acceptable salt or solvate thereof, which is required to achieve the desired biological effect will depend on a number of factors such as the use for which it is intended, the means of administration, and the recipient, and will be ultimately at the discretion of the attendant physician or veterinarian. In general, a typical daily dose for the prevention or treatment of an LXR mediated disease or condition in a human, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including upregulating expression of ABC1, increasing reverse cholesterol transport, inhibiting cholesterol absorption, increasing HDL-cholesterol and decreasing LDL-cholesterol.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers or diluents. The carrier(s) and/or diluent(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers and/or diluents.

Pharmaceutical formulations may be presented in unit dose form containing a predetermined amount of active ingredient per unit dose. Such a unit may contain a therapeutically effective dose of the compound of formula (I) or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

A compound of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

A compound of formula (I) may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6):318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient. Pharmaceutical compositions adapted for administration by inhalation include fine particle dusts or mists, which may be generated by means of various types of metered, dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. Thus, the present invention also encompasses pharmaceutical compositions further comprising one or more therapeutic agents. In one embodiment, the pharmaceutical compositions further comprise one or more lipid altering compounds. Examples of suitable lipid altering compound include other LXR agonsts (such as derivatives of CDCA); MHG-CoA reductase inhibitors such as statins (atorvastatin, fluvastatin, pravastatin, lovastatin, cerivastatin, and nisvastatin); squalene epoxidase inhibitors, squalene synthetase inhibitors, bile acid trasport inhibitors (BATi), human peroxisome proliferator activated receptor (PPAR) gamma agonists such as rosiglitazone, troglitazone, and pioglitazone and thiazolidinediones; PPAR alpha agonists such as clofibrate, fenogibrate and gemfibronzil; PPAR dual alpha/gamma agonists; cyclooxygenase-2 (COX-2) inhibitors such as rofecoxib and celecoxib; thrombin inhibitors; acyl-coenzyme A; cholesterol acyltransferase (ACAT) inhibitors including selective ACAT inhibitors; microsomal trilyceride transfer protein (MTP) inhibitors; probucol, niacin; cholester absorption inhibitors; bile acid sequestrants; LDL receptor inducers; platelet aggregation inhibitors such as flycoprotein IIb/IIIa fibrinogen receptor antagonists and aspirin; vitamin B6 and pharmaceutically acceptable salts thereof; vitamine B12; folic acid or a pharmaceutically acceptable salt or ester thereof; antioxidant viramins such as C and E and beta carotene; beta blockers; angiotensin II antagonists such as losartan; antiotensin converting enzyme inhibitors such as enalapril and captopril; calcium channel blockers such as nifedipine and diltiazam; endothelian antagonists; agents other than LXR ligands that enhance ABC1 gene expression; and bisphosphonate compounds such as alendronate sodium.

The methods and uses employing these combinations may comprise the administration of the compound of formula (I) and the other therapeutic agent either sequentially in any order or simultaneously in separate or combined pharmaceutical compositions. When combined in the same composition it will be appreciated that the two compounds must be stable and compatible with each other and the other components of the composition and may be formulated for administration. When formulated separately they may be provided in any convenient formulation, in such a manner as are known for such compounds in the art.

When a compound of formula (I) is used in combination with another therapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are in the within the expertise and discretion of the attendent clinician.

Compounds of the invention can be made according to any suitable method of organic chemistry. According to one method, compounds of formula (I) are prepared using the process depicted in Scheme 1:

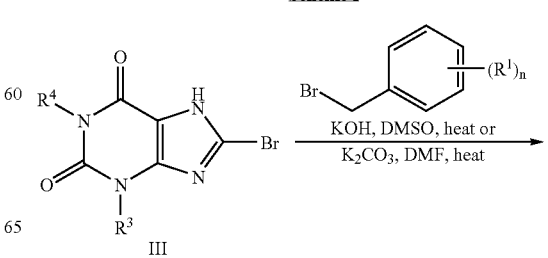

-continued

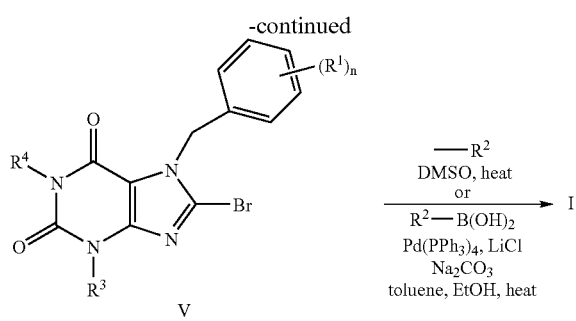

wherein all variables are as defined above in connection with the description of compounds of formula (I).

In general, the process comprises the steps of:
a) alkylating a compound of formula (III) with a substituted benzyl bromide of formula (IV) to prepare a compound of formula (V); and
b) either
   1) reacting the compound of formula (V) with an amine of formula —$R^2$; or
   2) reacting the compound of formula (V) with a boronic acid of formula $R_2$—$B(OH)_2$ in the presence of a palladium catalyst, to prepare a compound of formula (I).

Compounds of formula (IV) are commercially available or can be prepared using conventional techniques known to those skilled in the art.

The compounds of formula (III) are also commercially available. In addition, a compound of formula (III) may be prepared by brominating a compound with formula (II) to prepare a compound of formula (III).

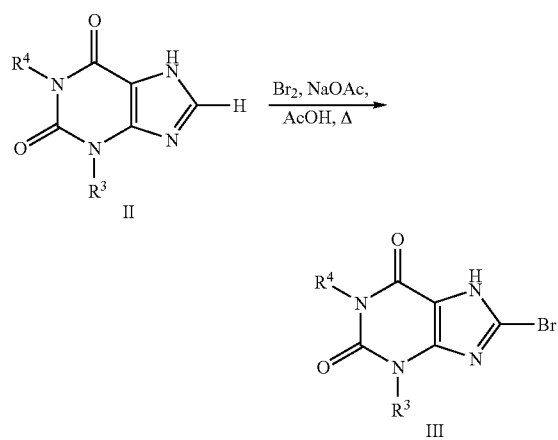

The bromination reaction may be carried out using any suitable brominating agent such as bromine. The reaction may be carried out in the presence of sodium acetate or acetic anhydride under heat.

The alkylation reaction of the compound of formula (III) with the compound of formula (IV) is typically carried out in an inert solvent. A suitable solvent for this reaction is dimethylsulfoxide (DMSO). A base, such as potassium hydroxide or sodium hydroxide may be employed. The reaction may be heated.

Alternatively, the reaction may be carried out using a base such as potassium carbonate in a solvent such as dimethylformamide, with heating. In the embodiment wherein $R^3$ and/or $R^4$ are H, the compound of formula (V) may be reacted with an alkyl halide of formula $R^3$—X and/or $R^4$—X, where X is halo, to prepare a compound of formula (V) wherein $R^3$ and $R^4$ are other than H, if desired.

The reaction of the compound of formula (V) with the nucleophile of formula —$R^2$ can be carried out in any suitable inert solvent, including, for example dimethylsulfoxide. The reaction may be carried out with heating.

The reaction of the cmopound of formula (V) with a boronic acid of formula $R^2$—$B(OH)_2$ in the presence of a palldium catalyst is typically carried out in a suitable solvent, such as, for example toluene and ethanol, with heating. A base may also be employed. A suitable base is sodium carbonate. Lithium chloride may be added if desired.

In an analogous process, the compounds of formula (I) may be prepared using the process depicted in Scheme 2

Scheme 2

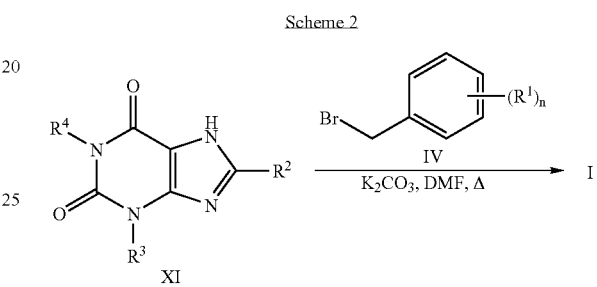

wherein all variables are as defined in connection with the description of compounds of formula (I).

In general, the process comprises the step of reacting a compound of formula (XI) with a benzyl bromide of formula (IV) to produce a compound of formula (I). The process is carried out in the same manner as for the reaction of a compound of formula (III) with the benzyl bromide of formula (IV).

The compounds of formula (XI) are commercially available or can be prepared using conventional means. In addition, certain compounds of formula (XI) wherein $R^2$ is other than cycloalkyl, may be prepared by reacting a compound of formula (III) with 1) a nucleophile of formula —$R^2$ wherein $R^2$ is other than cycloalkyl (suitable nucloephiles include an amine or substituted amine); or 2) a boronic acid of formula $R_2$—$B(OH)_2$ in the presence of a palladium catalyst These reactions can be carried out in a manner analogous to that described above for the reaction of a compound of formula (V) to prepare a compound of formula (I).

As will be apparent to one skilled in the art based upon a comparison of the processes depicted in Schemes 1 and 2 above, the order in which the steps of the foregoing reactions are carried out is not critical to the invention and the steps of these reactions may be carried out in any suitable order according to the knowledge in the art.

Alternatively, a compound of formula (I) may be prepared by the process depicted in Scheme 3 below.

Scheme 3

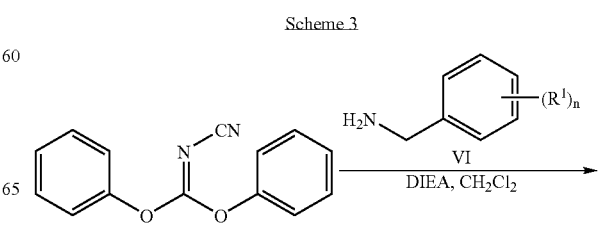

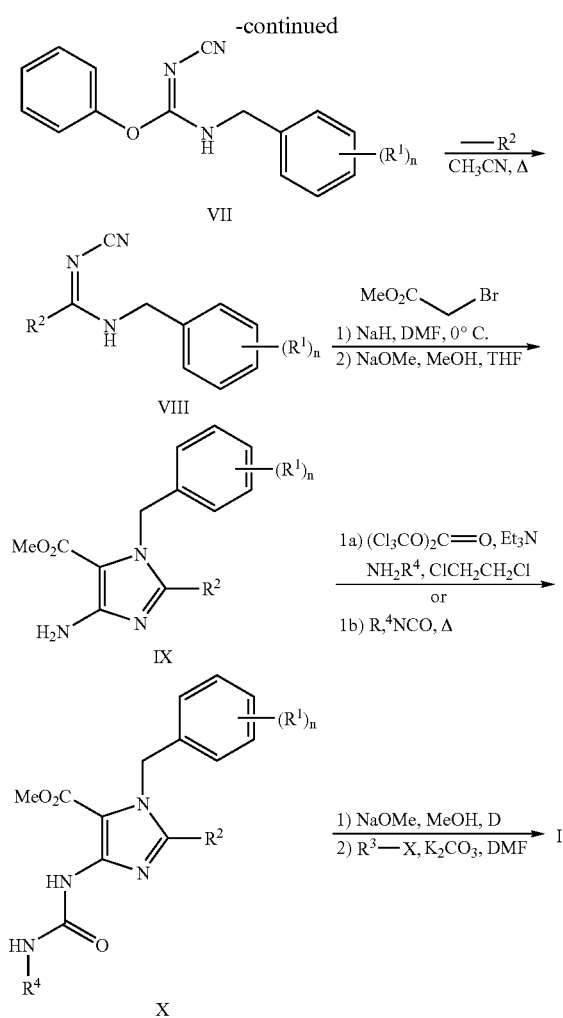

The reaction of the compound of formula (VII) with the amine of formula —R² to prepare a compound of formula (VIII) is typically carried out in a suitable solvent such as acetonitrile, under heating.

The alkylation reaction of the compound of formula (VIII) with methyl bromoacetate is carried out in a suitable solvent such as dimethylformamide or tetrahydroformamide at reduced temperature of about 0° C. in the presence of sodium hydride. Th base is typcially sodium methoxide and the reaction with the base may be carried out in methanol and tetrahydrofuran.

The compound of formula (IX) may be reacted with either an isocyanate of formula R⁴NCO or triphosgene and an amine of formula NH₂—R⁴ to prepare a compound of formula (X). The process involving reaction with the isocyanate may be carried out with heating. The reaction with triphosgene and the amine is typically carried out in a suitable solvent such as, for example 1,2-dichloroethane. Triethylamine may be employed as a base.

The compound of formula (X) may be cyclized with a base such as sodium methoxide in a suitable solvent such as methanol, with heating. The cyclization reaction results in a compound of formula (I) wherein $R^3$ is H.

Optionally, the compound of formula (I) so prepared may be alkylated with an alkyl halide of formula $R^3$—X, wherein X is halo, to prepare a compound of formula (I) wherein $R^3$ is other than H. The alkylating reaction may be carried out in a suitable solvent such as dimethylformamide in the presence of a base such as potassium carbonate.

As will be apparent to those skilled in the art, a compound of formula (I) may be converted to a different compound of formula (I) using conventional techniques. As an example, a compound of formula (I-A), prepared using any of the foregoing processes, may be converted to a compound of formula (I-B), which may in turn be converted to a compound of formula (I-C) using the process depicted in Scheme 4 below.

wherein all variables are as defined in connection with compounds of formula (I) above.

In general, the process comprises the steps of:

a) reacting diphenyl cyanoimidocarbonate with an amine of formula (VI) to prepare a compound of formula (VII);

b) reacting the compound of formula (VII) with an amine of formula —R² to prepare a compound of formula (VIII);

c) alkylating the compound of formula (VII) with methyl bromoacetate in the presence of base to prepare a compound of formula (IX);

d) reacting a compound of formula (IX) with an isocyanate or, with triphosgene and an amine of formula NH₂—R⁴ to prepare a compound of formula (X);

e) cyclizating a compound of formula (X) with base to prepare a compound of formula (I) wherein $R^3$ is H; and f) optionally alkylating the compound of formula (I) with an alkyl halide of formula $R^3$—X, wherein X is halo, to prepare a compound of formula (I) wherein $R^3$ is other than H.

Step a) of reacting the diphenyl cyanoimidocarbonate with an amine of formula (VI) is typically carried out in a suitable solvent such as methylene chloride, in the presence of N,N-diisopropylethylamine (DIEA). The diphenyl cyanoimidocar-bonate is commercially available or may be prepared using conventional techniques. The amines of formula (VI) are commercially available or may be prepared using conventional techniques.

Scheme 4

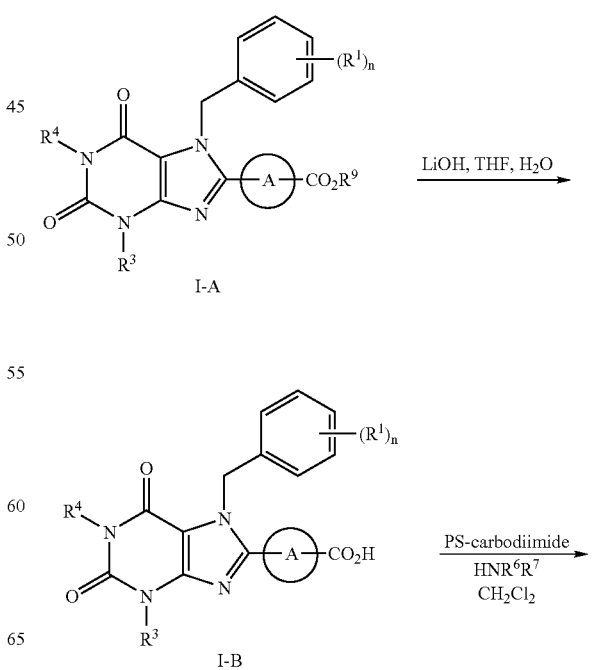

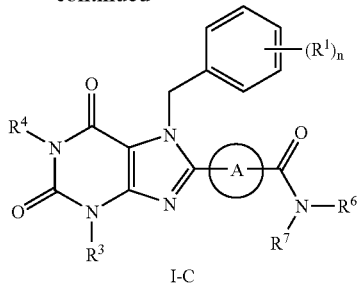

wherein $R^9$ in the compound of formula (I-A) is not H and all other variables are as defined above in connection with the description of compounds of formula (I).

In general, the process comprises the steps of:
a) saponifing a compound of formula (I-A) to produce a compound with formula (I-B); and
b) reacting the compound of formula (I-B) with an amine of formula H—$NR^6R^7$ and polymer-supported carbodiimide to prepare a compound of formula (I-C).

The saponification reaction may be carried out using lithium hydroxide in a suitable solvent such as tetrahydrofuran, with heating.

The reaction of the compound of formula (I-B) with the amine and carbodiimide can be carried out in a suitable solvent such as methylene chloride.

Other general conversion techniques are known in the art for derivatizing an organic compound. Such techniques may be applied to the compounds of formula (I) for the purposes of converting a compound of formula (I) to a different compound of formula (I), and as such they are contemplated by the present invention.

The following examples are intended for illustration only and are not intended to limit the scope of the invention in any way, the present invention being defined by the claims.

In the examples, the following terms have the designated meaning: "pRSETa" is a known expression vector available from Invitrogen; "IPTG" means isopropyl β-D- thiogalactopyranoside; "$PO_4$" means phosphate; "PBS" means phosphate buffered saline; "TBS" means tris-buffered saline; EDTA means ethylenediamine tetraacetic acid; "DTT" means dithiothreitol; "FAF-BSA" means fatty-acid free bovine serum albumin; "SRC-1" means steroid receptor coactivator 1; "CS" means charcoal stripped; 'nM' means nanomolar; "μM" means micromolar; "mM" means millimolar; "pM" means picomolar; "mmol" means millimoles; "g" means grams; "ng" means nanograms; "mg/ml" means milligram per milliliter; "μL" means microliters; and "mL" means milliliter.

EXAMPLE 1

N-(2-chloro-6-fluorobenzyl)-N'-cyanopiperidine-1-carboximidamide

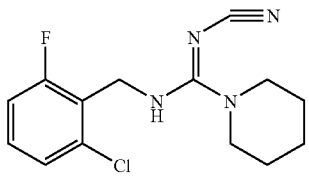

A solution of diphenylcyanocarboimidate (10 g, 42 mmol) in 168 mL $CH_2Cl_2$ was treated with 2-chloro-6-fluorobenzylamine (6.7 g, 42 mmol) and diisopropylethylamine (7.3 mL, 42 mmol). The reaction mixture was stirred at room temperature for 24 hr. The solvent was removed by reduced pressure and the remaining white solid was diluted with $CH_2Cl_2$ and $H_2O$ and extracted 3× with $CH_2Cl_2$. The organic layers were combined and the solvent removed by reduced pressure yielding a crude white solid. This intermediate (12.8 g, 42 mmol) was dissolved in 80 mL acetonitrile and treated with piperidine (6.2 mL, 63 mmol). The reaction was heated to reflux for 24 hr. The reaction mixture was cooled and the solvent removed by reduced pressure. The crude product was triturated with ether and collected by filtration to yield a white solid (10 g, 82% yield): $^1$H NMR (CDCl$_3$, 400 MHz) 7.28-7.23 (m, 1H), 7.22-7.18 (m, 1H), 7.04-6.98 (m, 1H), 4.94-4.85 (m, 1H), 4.68-4.63 (m, 2H), 3.45-3.39 (m, 4H), 1.65-1.57 (m, 6H); MS (ESP+) m/e 295 (MH$^+$); Analytical CHN.

EXAMPLE 2

Methyl 4-amino-1-(2-chloro-6-fluorobenzyl)-2-piperidin-1-yl-1H-imidazole-5-carboxylate

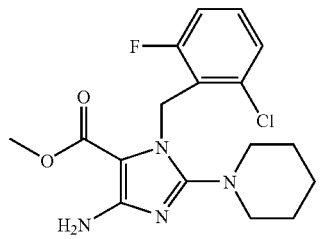

A solution of N-(2-chloro-6-fluorobenzyl)-N'-cyanopiperidine-1-carboximidamide (8.35 g, 28.3 mmol) in 142 mL DMF was cooled to 0° C. and treated in portions with NaH (1.25 g, 31.2 mmol). The reaction mixture was stirred for 30 min at 0° C. and then methylbromoacetate (2.95 mL, 31.2 mmol) was added dropwise. The reaction was slowly brought to room temperature and stirred for 15 hr. The reaction was quenched with 20 mL saturated aqueous $NH_4Cl$ and extracted with 50% EtOAc:hexanes. The organic layers were combined and the solvent was removed by reduced pressure. The crude product was filtered through a large silica plug and rinsed with 50% EtOAc:hexanes to yield 8.83 g (85% yield) of a yellow oil. This oil (8.83 g, 24.1 mmol) was dissolved in 241 mL THF, treated with 0.5 M NaOMe in MeOH (4.8 mL, 2.41 mmol), and stirred for 4 hr. The reaction mixture was filtered through a large silica plug and rinsed with 100% EtOAc. The solvent was removed by reduced pressure affording the title compound (7.92 g, 90% yield) as a light yellow solid:): $^1$H NMR (CDCl$_3$, 400 MHz) 7.17-7.06 (m, 2H), 6.92-6.86 (m, 1H), 5.23 (s, 2H), 5.14-4.97 (m, 2H), 3.61 (s, 3H), 3.14-3.05 (m, 4H), 1.68-1.48 (m, 6H); MS (ESP+) m/e 367 (MH$^+$); TLC (EtOAc:hexanes/1:1) $R_f$=0.34.

EXAMPLE 3

7-(2-chloro-6-fluorobenzyl)-3-methyl-1-phenyl-8-piperidin-1-yl-3,7-dihydro-1H-purine-2,6-dione

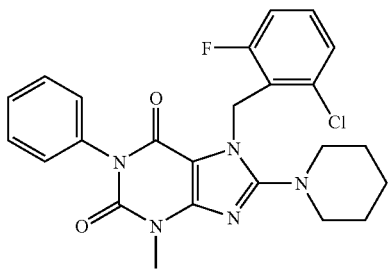

In a sealed tube, a solution of methyl 4-amino-1-(2-chloro-6-fluorobenzyl)-2-piperidin-1-yl-1H-imidazole-5-carboxylate (150 mg, 0.41 mmol) in xylenes (3.5 mL) was treated with phenyl isocyanate (98 □L, 0.90 mmol). The reaction was heated to 140° C. for 3 hr. cooled to room temperature, and concentrated in vacuo. The crude product was purified by flash chromatography (silica gel cartridge, Biotage, 32-63 □m, 60 Å) with 33% EtOAc:hexanes as the eluent to afford 160 mg (80% yield) of the urea intermediate. The urea (150 mg, 0.31 mmol) was dissolved in MeOH (3.1 mL) and treated with 0.5 M NaOMe in MeOH (1.36 mL, 0.68 mmol). The reaction was heated to 80° C. and stirred for 1 hr. The crude product was filtered through a plug of silica and rinsed with 100% EtOAc to yield the cyclized intermediate (83 mg, 59% yield). A solution of this intermediate (20 mg, 0.044 mmol) and $K_2CO_3$ (61 mg, 0.44 mmol) in 880 µL DMF was treated with methyl iodide (14 mL, 0.22 mmol). The reaction was stirred at room temperature for 24 hr. filtered through a silica plug, and rinsed with EtOAc. After removal of the solvent under reduced pressure, the crude product was purified by preparative thin layer chromatography (silica gel, 1 mm plate, EM Science 20×20 cm silica gel 60 $F_{264}$) eluting with EtOAc:hexane (1:1) to give 16 mg (76% yield) of the title compound as a white solid: $^1$H NMR (CDCl$_3$, 400 MHz) 7.45-7.39 (m, 2H), 7.38-7.32 (m, 1H), 7.22-7.11 (m, 4H), 6.96-6.90 (m, 1H), 5.56 (s, 2H), 3.54 (s, 3H), 3.14-3.01 (m, 4H), 1.52-1.46 (m, 6H); MS (ESP+) m/e 468 (MH$^+$); TLC (EtOAc:hexanes/1:1) $R_f$=0.15.

EXAMPLE 4

7-(2-chloro-6-fluorobenzyl)-1,3-diethyl-8-piperidin-1-yl-3,7-dihydro-1H-purine-2,6-dione

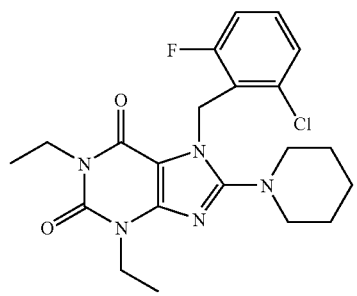

The title compound was prepared according to the procedure of Example 3 to give 24 mg (73% yield) of a pale yellow solid: $^1$H NMR (CDCl$_3$, 400 MHz) 7.21-7.14 (m, 1H), 7.13-7.09 (m, 1H), 6.97-6.90 (m, 1H), 5.53 (s, 2H), 4.08 (q, 2H, J=7.1 Hz), 3.96 (q, 2H, J=7.1 Hz), 3.07-3.01 (m, 4H), 1.52-1.46 (m, 6H), 1.29 (t, 3H, J=7.1 Hz), 1.13 (t, 3H, J=7.1 Hz); MS (ESP+) m/e 434 (MH$^+$).

EXAMPLE 5

7-(2-chloro-6-fluorobenzyl)-1-ethyl-3-isopropyl-8-piperidin-1-yl-3,7-dihydro-1H-purine-2,6-dione

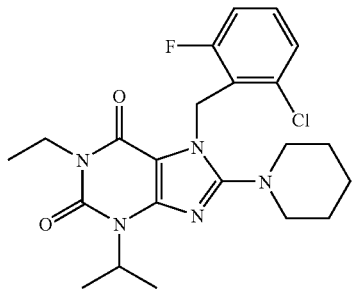

The title compound was prepared according to the procedure of Example 3 to give 23 mg (70% yield) of a pale pink solid: $^1$H NMR (CDCl$_3$, 400 MHz) 7.20-7.13 (m, 1H), 7.13-7.09 (m, 1H), 6.96-6.90 (m, 1H), 5.53 (s, 2H), 5.15-5.04 (m, 1H), 3.95 (q, 2H, J=7.1 Hz), 3.07-2.99 (m, 4H), 1.53 (d, 6H, J=7.0 Hz), 1.51-1.46 (m, 6H), 1.13 (t, 3H, J=7.1 Hz); MS (ESP+) m/e 448 (MH$^+$).

EXAMPLE 6

7-(2-chloro-6-fluorobenzyl)-3-ethyl-8-piperidin-1-yl-1-propyl-3,7-dihydro-1H-purine-2,6-dione

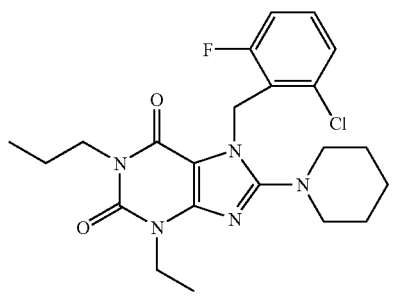

The title compound was prepared according to the procedure of Example 3 to give 19 mg (80% yield) of a yellow oil: $^1$H NMR (CDCl$_3$, 400 MHz) 7.20-7.13 (m, 1H), 7.13-7.09 (m, 1H), 6.96-6.90 (m, 1H), 5.53 (s, 2H), 4.07 (q, 2H, J=7.1 Hz), 3.89-3.83 (m, 2H), 3.08-3.00 (m, 4H), 1.62-1.52 (m, 2H), 1.52-1.46 (m; 6H), 1.28 (t, 3H, J=7.1 Hz), 0.83 (t, 3H, J=7.4 Hz); MS (ESP+) m/e 448 (MH$^+$).

EXAMPLE 7

7-(2-chloro-6-fluorobenzyl)-3-isopropyl-8-piperidin-1-yl-1-propyl-3,7-dihydro-1H-purine-2,6-dione

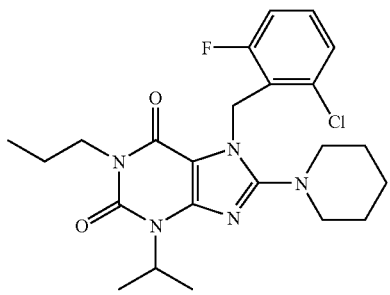

The title compound was prepared according to the procedure of Example 3 to give 21 mg (86% yield) of a white solid: $^1$H NMR (CDCl$_3$, 400 MHz) 7.20-7.13 (m, 1H), 7.13-7.09 (m, 1H), 6.96-6.90 (m, 1H), 5.53 (s, 2H), 5.14-5.05 (m, 1H), 3.88-3.81 (m, 2H), 3.06-3.01 (m, 4H), 1.62-1.55 (m, 2H), 1.52 (d, 6H, J=6.9 Hz), 1.50-1.46 (m, 6H), 0.84 (t, 3H, J=7.6 Hz); MS (ESP+) m/e 462 (MH$^+$).

EXAMPLE 8

7-(2-chloro-6-fluorobenzyl)-1-isopropyl-3-methyl-8-piperidin-1-yl-3,7-dihydro-1H-purine-2,6-dione

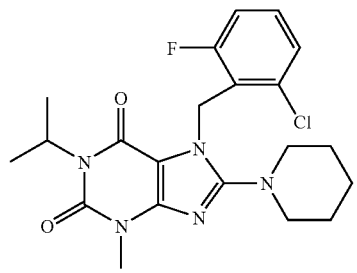

The title compound was prepared according to the procedure of Example 3 to give 11 mg (46% yield) of a pink solid: $^1$H NMR (CDCl$_3$, 400 MHz) 7.22-7.14 (m, 1H), 7.14-7.10 (m, 1H), 6.96-6.90 (m, 1H), 5.54 (s, 2H), 5.23-5.13 (m, 1H), 3.46 (s, 3H), 3.07-2.98 (m, 4H), 1.52-1.45 (m, 6H), 1.40 (d, 6H, J=6.9); MS (ESP+) m/e 434 (MH$^+$).

EXAMPLE 9

7-(2-chloro-6-fluorobenzyl)-1-ethyl-3-(2-methoxy-ethyl)-8-piperidin-1-yl-3,7-dihydro-1H-purine-2,6-dione

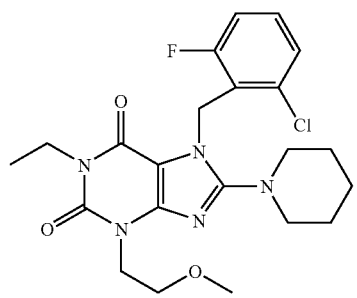

The title compound was prepared according to the procedure of Example 3 to give 20 mg (88% yield) of a clear oil: $^1$H NMR (CDCl$_3$, 400 MHz) 7.21-7.14 (m, 1H), 7.13-7.10 (m, 1H), 6.96-6.91 (m, 1H), 5.52 (s, 2H), 4.23 (t, 2H, J=6.0 Hz), 3.95 (q, 2H, J=7.1 Hz), 3.70 (t, 2H, J=6.0 Hz), 3.35 (s, 3H), 3.07-3.00 (m, 4H), 1.52-1.45 (m, 6H), 1.13 (t, 3H, J=7.1 Hz); MS (ESP+) m/e 464 (MH$^+$); TLC (EtOAc:hexanes/1:1) R$_f$=0.45.

EXAMPLE 10

Methyl [7-(2-chloro-6-fluorobenzyl)-1-ethyl-2,6-dioxo-8-piperidin-1-yl-1,2,6,7-tetrahydro-3H-purin-3-yl]acetate

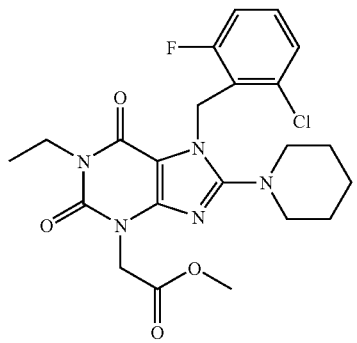

The title compound was prepared according to the procedure of Example 3 to give 20 mg (84% yield) of a clear oil: $^1$H NMR (CDCl$_3$, 400 MHz) 7.21-7.15 (m, 1H), 7.14-7.10 (m, 1H), 6.97-6.91 (m, 1H), 5.52 (s, 2H), 4.75 (s, 2H), 3.96 (q, 2H, J=7.1 Hz), 3.74 (s, 3H), 3.04-3.00 (m, 4H), 1.51-1.45 (m, 6H), 1.13 (t, 3H, J=7.1 Hz); MS (ESP+) m/e 478 (MH$^+$); TLC (EtOAc:hexanes/1:1) R$_f$=0.48.

EXAMPLE 11

7-(2-chloro-6-fluorobenzyl)-1-ethyl-3-(2-phenoxy-ethyl)-8-piperidin-1-yl-3,7-dihydro-1H-purine-2,6-dione

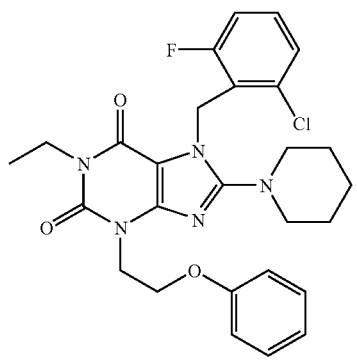

The title compound was prepared according to the procedure of Example 3 to give 23 mg (89% yield) of a pale pink solid: $^1$H NMR (CDCl$_3$, 400 MHz) 7.26-7.15 (m, 3H), 7.14-7.10 (m, 1H), 6.98-6.93 (m, 1H), 6.93-6.87 (m, 3H), 5.52 (s, 2H), 4.43 (t, 2H, J=6.1 Hz), 4.30 (t, 2H, J=6.1 Hz), 3.96 (q, 2H, J=7.1 Hz), 3.07-2.99 (m, 4H), 1.55-1.45 (m, 6H), 1.14 (t, 3H, J=7.1 Hz); MS (ESP+) m/e 527 (MH$^+$); TLC (EtOAc:hexanes/1:1) R$_f$=0.61.

EXAMPLE 12

7-(2-chloro-6-fluorobenzyl)-1-ethyl-3-(2-hydroxyethyl)-8-piperidin-1-yl-3,7-dihydro-1H-purine-2,6-dione

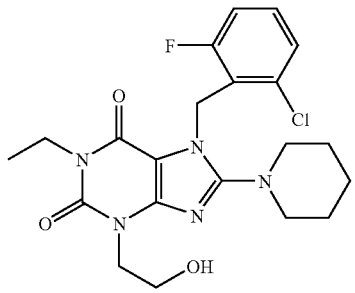

The title compound was prepared according to the procedure of Example 3 to give 22 mg (99% yield) of a clear oil: $^1$H NMR (CDCl$_3$, 400 MHz) 7.22-7.16 (m, 1H), 7.14-7.11 (m, 1H), 6.98-6.92 (m, 1H), 5.53 (s, 2H), 4.32-4.28 (m, 2H), 3.96 (q, 2H, J=7.1 Hz), 3.92-3.88 (m, 2H), 3.08-3.02 (m, 4H), 1.51-1.46 (m, 6H), 1.13 (t, 3H, J=7.1 Hz); MS (ESP+) m/e 450 (MH$^+$); TLC (EtOAc:hexanes/1:1) R$_f$=0.18.

EXAMPLE 13

7-(2-chloro-6-fluorobenzyl)-3-cyclopentyl-1-ethyl-8-piperidin-1-yl-3,7-dihydro-1H-purine-2,6-dione

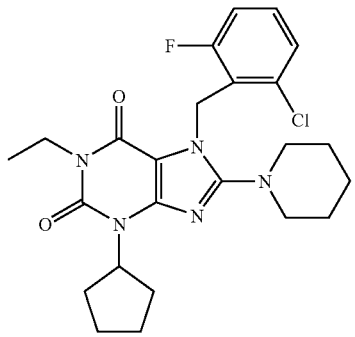

The title compound was prepared according to the procedure of Example 3 to give 11 mg (49% yield) of a clear oil: $^1$H NMR (CDCl$_3$, 400 MHz) 7.21-7.14 (m, 1H), 7.13-7.10 (m, 1H), 6.97-6.91 (m, 1H), 5.54 (s, 2H), 5.28-5.17 (m, 1H), 3.96 (q, 2H, J=7.1 Hz), 3.08-2.99 (m, 4H), 2.28-2.16 (m, 2H), 2.04-1.84 (m, 4H), 1.63-1.54 (m, 2H), 1.52-1.45 (m, 6H), 1.14 (t, 3H, J=7.1 Hz); MS (ESP+) m/e 474 (MH$^+$); TLC (EtOAc:hexanes/1:1) R$_f$=0.68.

EXAMPLE 14

2-[7-(2-chloro-6-fluorobenzyl)-1-ethyl-2,6-dioxo-8-piperidin-1-yl-1,2,6,7-tetrahydro-3H-purin-3-yl]acetamide

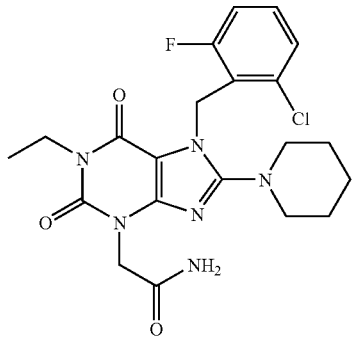

The title compound was prepared according to the procedure of Example 3 to give 17 mg (72% yield) of a white solid: $^1$H NMR (CDCl$_3$, 400 MHz) 7.22-7.15 (m, 1H), 7.14-7.09 (m, 1H), 6.98-6.90 (m, 1H), 6.11 (s, 1H), 5.79 (s, 1H), 5.51 (s, 2H), 4.68 (s, 2H), 3.95 (q, 2H, J=7.1 Hz), 3.09-2.99 (m, 4H), 1.52-1.43 (m, 6H), 1.13 (t, 3H, J=7.1 Hz); MS (ESP+) m/e 463 (MH$^+$); TLC (MeOH:CH$_2$Cl$_2$/1:1) R$_f$=0.45.

EXAMPLE 15 tert-Butyl [7-(2-chloro-6-fluorobenzyl)-1-ethyl-2,6-dioxo-8-piperidin-1-yl-1,2,6,7-tetrahydro-3H-purin-3-yl]acetate

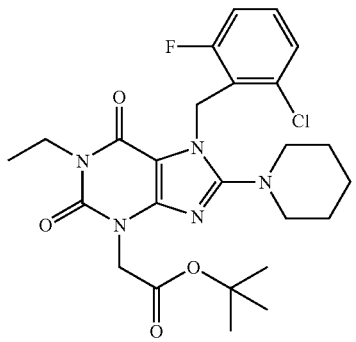

The title compound was prepared according to the procedure of Example 3 to give 29 mg (86% yield) of a pale yellow oil: $^1$H NMR (CDCl$_3$, 400 MHz) 7.20-7.14 (m, 1H), 7.13-7.09 (m, 1H), 6.96-6.90 (m, 1H), 5.52 (s, 2H), 4.63 (s, 2H), 3.96 (q, 2H, J=7.1 Hz), 3.06-2.96 (m, 4H), 1.51-1.45 (m, 6H), 1.42 (s, 9H), 1.13 (t, 3H, J=7.1 Hz); MS (ESP+) m/e 520 (MH$^+$); TLC (EtOAc:hexanes/1:1) R$_f$=0.73.

EXAMPLE 16

7-(2-chloro-6-fluorobenzyl)-3-isopropyl-1-(3-methoxypropyl)-8-piperidin-1-yl-3,7-dihydro-1H-purine-2,6-dione

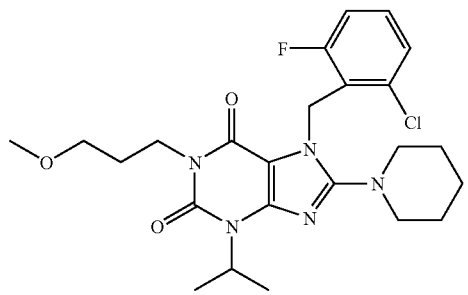

A solution of methyl 4-amino-1-(2-chloro-6-fluorobenzyl)-2-piperidin-1-yl-1H-imidazole-5-carboxylate (50 mg, 0.14 mmol) in dichloroethane (1.75 mL) was cooled to 0° C. and treated with triphosgene (33 mg, 0.11 mmol). The reaction was stirred for 10 min and triethylamine (41 μL, 0.29 mmol) was pipetted in. After an additional 10 min, 3-methoxypropylamine (69 μL, 0.68 mmol) was added and the reaction was heated to 85° C. for 15 hr. The reaction was cooled to room temperature, filtered through a silica plug, rinsed with EtOAc, and concentrated in vacuo. The crude product was purified by preparative thin layer chromatography (silica gel, 1 mm plate, EM Science 20×20 cm silica gel 60 $F_{264}$) eluting with 30% EtOAc:$CH_2Cl_2$ to give 30 mg (44% yield) of the intermediate urea. The urea (30 mg, 0.06 mmol) was dissolved in MeOH (0.6 mL) and treated with 0.5 M NaOMe in MeOH (0.26 mL, 0.13 mmol). The reaction was heated to 70° C. and stirred for 15 hr. The crude product was filtered through a plug of silica and rinsed with 100% EtOAc to yield the cyclized intermediate. A solution of this intermediate (28 mg, 0.06 mmol) and $K_2CO_3$ (83 mg, 0.60 mmol) in 600 μL DMF was treated with isopropyl iodide (29 μL, 0.30 mmol). The reaction was stirred at room temperature for 24 hr. filtered through a silica plug, and rinsed with EtOAc. After removal of the solvent under reduced pressure, the crude product was purified by preparative thin layer chromatography (silica gel, 1 mm plate, EM Science 20×20 cm silica gel 60 $F_{264}$) eluting with EtOAc:hexane (1:1) to give 23 mg (78% yield) of the title compound as a clear oil: $^1$H NMR (CDCl$_3$, 400 MHz) 7.20-7.14 (m, 1H), 7.13-7.09 (m, 1H), 6.96-6.90 (m, 1H), 5.54 (s, 2H), 5.13-5.05 (m, 1H), 3.98 (t, 2H, J=7.1 Hz), 3.35 (t, 2H, J=6.6 Hz), 3.26 (s, 3H), 3.05-3.00 (m, 4H), 1.88-1.80 (m, 2H), 1.53 (d, 6H, J=6.9 Hz), 1.50-1.45 (m, 6H); MS (ESP+) m/e 492 (MH$^+$); TLC (EtOAc:hexanes/1:1) R$_f$=0.60.

EXAMPLE 17
Methyl 3-[7-(2-chloro-6-fluorobenzyl)-3-isopropyl-2,6-dioxo-8-piperidin-1-yl-2,3,6,7-tetrahydro-1H-purin-1-yl]propanoate

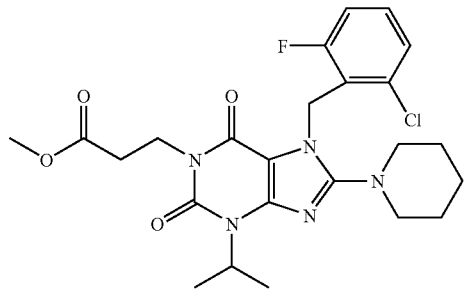

The title compound was prepared according to the procedure of Example 16 to give 3 mg (14% yield) of a pale yellow oil: $^1$H NMR (CDCl$_3$, 400 MHz) 7.23-7.17 (m, 1H), 7.16-7.12 (m, 1H), 6.99-6.93 (m, 1H), 5.54 (s, 2H), 5.15-5.06 (m, 1H), 4.22 (t, 2H, J=7.7 Hz), 3.64 (s, 3H), 3.09-3.03 (m, 4H), 2.60 (t, 2H, J=7.7 Hz), 1.57-1.54 (m, 6H), 1.54-1.49 (m, 6H); MS (ESP+) m/e 506 (MH$^+$); TLC (EtOAc:hexanes/1:1) R$_f$=0.61.

EXAMPLE 18

1-Butyl-7-(2-chloro-6-fluorobenzyl)-3-methyl-8-piperidin-1-yl-3,7-dihydro-1H-purine-2,6-dione

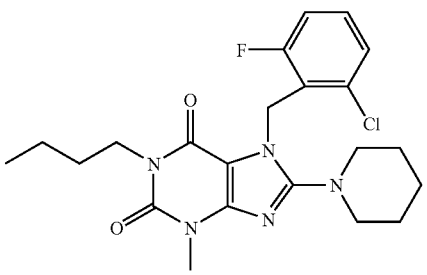

The title compound was prepared according to the procedure of Example 16 to give 17 mg (65% yield) of a pale yellow oil: $^1$H NMR (CDCl$_3$, 400 MHz) 7.21-7.14 (m, 1H), 7.13-7.09 (m, 1H), 6.96-6.90 (m, 1H), 5.54 (s, 2H), 3.93-3.87 (m, 2H), 3.49 (s, 3H), 3.07-3.02 (m, 4H), 1.54-1.44 (m, 8H), 1.19-1.31 (m, 2H), 0.86 (t, 3H, J=7.2 Hz); MS (ESP+) m/e 448 (MH$^+$); TLC (EtOAc:hexanes/1:1) R$_f$=0.72.

EXAMPLE 19

1-Butyl-7-(2-chloro-6-fluorobenzyl)-3-isopropyl-8-piperidin-1-yl-3,7-dihydro-1H-purine-2,6-dione

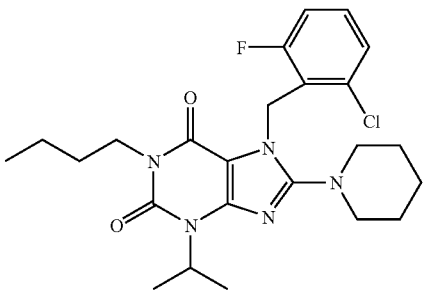

The title compound was prepared according to the procedure of Example 16 to give 14 mg (54% yield) of a pale yellow oil: $^1$H NMR (CDCl$_3$, 400 MHz) 7.21-7.14 (m, 1H), 7.13-7.10 (m, 1H), 6.97-6.90 (m, 1H), 5.55 (s, 2H), 5.15-5.06 (m, 1H), 3.93-3.84 (m, 2H), 3.08-3.00 (m, 4H), 1.56-1.44 (m, 8H), 1.33-1.21 (m, 2H), 0.87 (t, 3H, J=7.2 Hz); MS (ESP+) m/e 476 (MH$^+$); TLC (EtOAc:hexanes/1:1) R$_f$=0.88.

EXAMPLE 20 tert-butyl [7-(2-chloro-6-fluorobenzyl)-3-isopropyl-2,6-dioxo-8-piperidin-1-yl-2,3,6,7-tetrahydro-1H-purin-1-yl]acetate

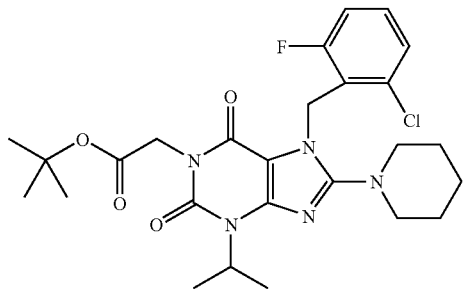

The title compound was prepared according to the procedure of Example 16 to give 10 mg (28% yield) of a clear oil: $^1$H NMR (CDCl$_3$, 400 MHz) 7.20-7.14 (m, 1H), 7.13-7.10 (m, 1H), 6.96-6.90 (m, 1H), 5.54 (s, 2H), 5.13-5.05 (m, 1H), 4.54 (s, 2H), 3.06-3.01 (m, 4H), 1.53 (d, 6 h, J=7.1 Hz), 1.50-1.46 (m, 6H), 1.40 (s, 9H); MS (ESP+) m/e 535 (MH$^+$); TLC (EtOAc:hexanes/1:1) R$_f$=0.66.

EXAMPLE 21

7-(2-Chloro-6-fluorobenzyl)-3-isopropyl-1-(2-methoxyethyl)-8-piperidin-1-yl-3,7-dihydro-1H-purine-2,6-dione

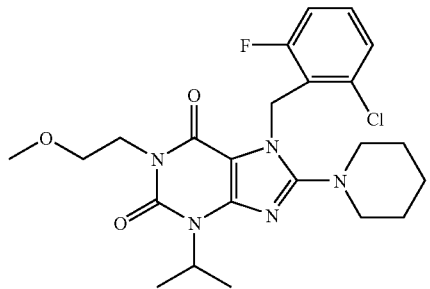

The title compound was prepared according to the procedure of Example 16 to give 22 mg (56% yield) of a white solid: $^1$H NMR (CDCl$_3$, 400 MHz) 7.21-7.14 (m, 1H), 7.13-7.10 (m, 1H), 6.96-6.90 (m, 1H), 5.55 (s, 2H), 5.16-5.04 (m, 1H), 4.14 (t, 2H, J=6.0 Hz), 3.55 (t, 2H, J=6.0 Hz), 3.30 (s, 3H), 3.05-2.97 (m, 4H), 1.53 (d, 6H, J=6.9 Hz), 1.51-1.44 (m, 6H); MS (ESP+) m/e 479 (MH$^+$); TLC (EtOAc:hexanes/1:1) R$_f$=0.64.

EXAMPLE 22

7-(2-Chloro-6-fluorobenzyl)-1-cyclopentyl-3-isopropyl-8-piperidin-1-yl-3,7-dihydro-1H-purine-2,6-dione

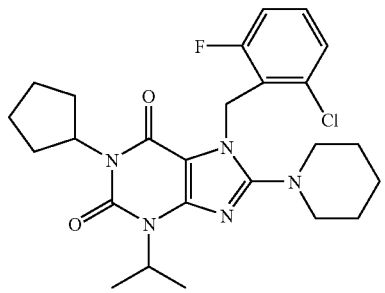

The title compound was prepared according to the procedure of Example 16 to give 17 mg (51% yield) of a yellow solid: $^1$H NMR (CDCl$_3$, 400 MHz) 7.21-7.14 (m, 1H), 7.14-7.10 (m, 1H), 6.96-6.90 (m, 1H), 5.56 (s, 2H), 5.37-5.26 (m, 1H), 5.14-5.05 (m, 1H), 3.06-2.97 (m, 4H), 2.13-2.03 (m, 2H), 1.96-1.86 (m, 2H), 1.79-1.69 (m, 2H), 1.57-1.55 (m, 2H), 1.53 (d, 6H, J=6.9 Hz), 1.49-1.43 (m, 6H); MS (ESP+) m/e 488 (MH$^+$); TLC (EtOAc:hexanes/1:1) R$_f$=0.85.

EXAMPLE 23

7-(2-Chloro-6-fluorobenzyl)-1-(2-furyl)-3-isopropyl-8-piperidin-1-yl-3,7-dihydro-1H-purine-2,6-dione

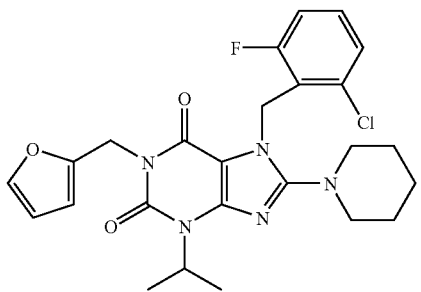

The title compound was prepared according to the procedure of Example 16 to give 9 mg (20% yield) of a white solid: $^1$H NMR (CDCl$_3$, 400 MHz) 7.29-7.26 (m, 1H), 7.21-7.15 (m, 1H), 7.14-7.10 (m, 1H), 6.98-6.91 (m, 1H), 6.25-6.22 (m, 2H), 5.58 (s, 2H), 5.15-5.07 (m, 3H), 3.05-2.99 (m, 4H), 1.53 (d, 6H, J=6.9 Hz), 1.49-1.43 (m, 6H); MS (ESP+) m/e 500 (MH$^+$); TLC (EtOAc:hexanes/1:1) R$_f$=0.81.

EXAMPLE 24

7-(2-Chloro-6-fluorobenzyl)-3-isopropyl-8-piperidin-1-yl-1-thien-2-yl-3,7-dihydro-1H-purine-2,6-dione

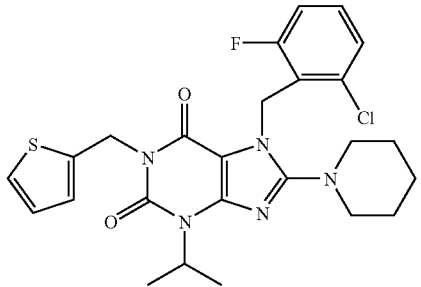

The title compound was prepared according to the procedure of Example 16 to give 27 mg (66% yield) of a white solid: $^1$H NMR (CDCl$_3$, 400 MHz) 7.22-7.15 (m, 1H), 7.14-7.08 (m, 3H), 6.98-6.91 (m, 1H), 6.88-6.84 (m, 1H), 5.57 (s, 2H), 5.25 (s, 2H), 5.14-5.06 (m, 1H), 3.04-2.98 (m, 4H), 1.52 (d, 6H, J=6.9 Hz), 1.49-1.43 (m, 6H); MS (ESP+) m/e 516 (MH$^+$); TLC (EtOAc:hexanes/1:1) R$_f$=0.74.

EXAMPLE 25

7-(2-Chloro-6-fluorobenzyl)-3-isopropyl-8-piperidin-1-yl-1-(2,2,2-trifluoroethyl)-3,7-dihydro-1H-purine-2,6-dione

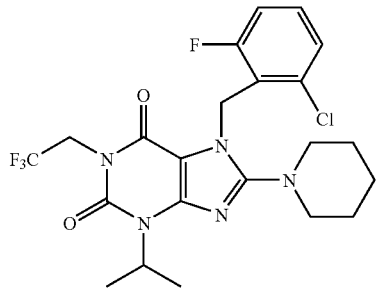

The title compound was prepared according to the procedure of Example 16 to give 27 mg (67% yield) of a white solid: $^1$H NMR (CDCl$_3$, 400 MHz) 7.22-7.15 (m, 1H), 7.13-7.10 (m, 1H), 6.97-6.91 (m, 1H), 5.50 (s, 2H), 5.15-5.06 (m, 1H), 4.61 (q, 2H, J=8.6 Hz), 3.13-3.05 (m, 4H), 1.57-1.48 (m, 12H); MS (ESP+) m/e 502 (MH$^+$); TLC (EtOAc:hexanes/1:1) R$_f$=0.74.

EXAMPLE 26

7-(2-Chloro-6-fluorobenzyl)-1-isobutyl-3-isopropyl-8-piperidin-1-yl-3,7-dihydro-1H-purine-2,6-dione

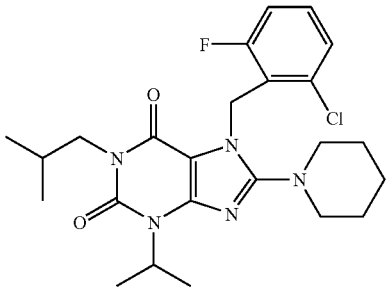

The title compound was prepared according to the procedure of Example 16 to give 24 mg (56% yield) of a clear oil: $^1$H NMR (CDCl$_3$, 400 MHz) 7.19-7.12 (m, 1H), 7.12-7.07 (m, 1H), 6.96-6.89 (m, 1H), 5.52 (s, 2H), 5.14-5.04 (m, 1H), 3.73 (d, 2H, J=7.4 Hz), 3.09-3.00 (m, 4H), 2.10-1.96 (m, 1H), 1.57-1.44 (m, 12H), 0.79 (d, 6H, J=6.7 Hz); MS (ESP+) m/e 476 (MH$^+$) R$_f$=0.88.

EXAMPLE 27

7-(2-Chloro-6-fluorobenzyl)-1-isopentyl-3-isopropyl-8-piperidin-1-yl-3,7-dihydro-1H-purine-2,6-dione

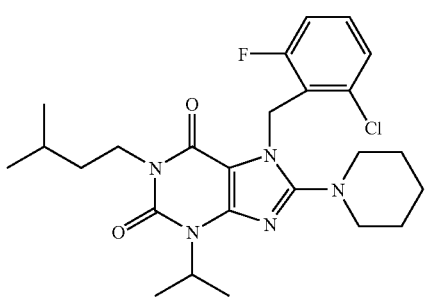

The title compound was prepared according to the procedure of Example 16 to give 30 mg (55% yield) of a yellow oil: $^1$H NMR (CDCl$_3$, 400 MHz) 7.20-7.13 (m, 1H), 7.13-7.09 (m, 1H), 6.97-6.89 (m, 1H), 5.57 (s, 2H), 5.15-5.05 (m, 1H), 3.96-3.84 (m, 2H), 3.05-2.97 (m, 4H), 1.60-1.55 (m, 1H), 1.53 (d, 6H, J=6.9 Hz), 1.48-1.40 (m, 8H), 0.90 (d, 6H, J=6.5 Hz); MS (ESP+) m/e 490 (MH$^+$); TLC (EtOAc:hexanes/1:1) R$_f$=0.91.

EXAMPLE 28

7-(2-Chloro-6-fluorobenzyl)-3-isopropyl-1-[3-(methylthio)propyl]-8-piperidin-1-yl-3,7-dihydro-1H-purine-2,6-dione

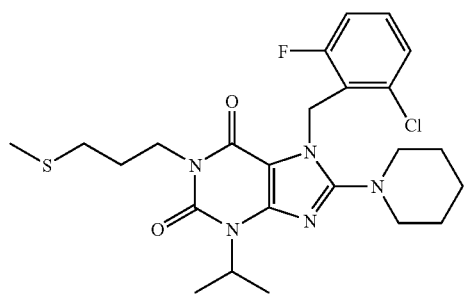

The title compound was prepared according to the procedure of Example 16 to give 24 mg (70% yield) of a clear oil: $^1$H NMR (CDCl$_3$, 400 MHz) 7.21-7.14 (m, 1H), 7.14-7.09 (m, 1H), 6.97-6.91 (m, 1H), 5.53 (s, 2H), 5.13-5.05 (m, 1H), 3.98 (t, 2H, J=7.1 Hz), 3.08-3.01 (m, 4H), 2.45-2.38 (m, 2H), 1.90-1.81 (m, 2H), 1.53 (d, 6H, J=6.9 Hz), 1.51-1.47 (m, 6H); MS (ESP+) m/e 508 (MH$^+$); TLC (EtOAc:hexanes/1:1) R$_f$=0.76.

EXAMPLE 29

7-(2-Chloro-6-fluorobenzyl)-1-(cyclopropylmethyl)-3-isopropyl-8-piperidin-1-yl-3,7-dihydro-1H-purine-2,6-dione

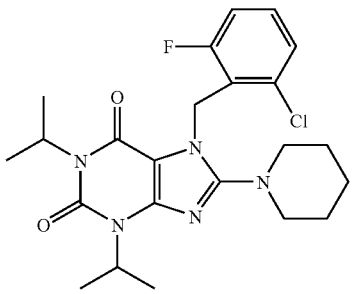

The title compound was prepared according to the procedure of Example 16 to give 19 mg (65% yield) of a white solid: $^1$H NMR (CDCl$_3$, 400 MHz) 7.21-7.13 (m, 1H), 7.13-7.09 (m, 1H), 6.97-6.90 (m, 1H), 5.53 (s, 2H), 5.15-5.06 (m, 1H), 3.79 (d, 2H, J=7.3 Hz), 3.08-2.99 (m, 4H), 1.54 (d, 6H, J=6.9 Hz), 1.52-1.46 (m, 6H), 1.23-1.14 (m, 1H), 0.38-0.26 (m, 4H); MS (ESP+) m/e 474 (MH$^+$); TLC (EtOAc:hexanes/1:1) R$_f$=0.84.

EXAMPLE 30

7-(2-Chloro-6-fluorobenzyl)-1,3-diisopropyl-8-piperidin-1-yl-3,7-dihydro-1H-purine-2,6-dione

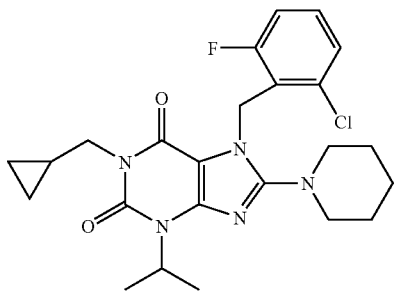

The title compound was prepared according to the procedure of Example 16 to give 18 mg (49% yield) of a pale yellow oil: $^1$H NMR (CDCl$_3$, 400 MHz) 7.21-7.13 (m, 1H), 7.13-7.09 (m, 1H), 6.97-6.89 (m, 1H), 5.54 (s, 2H), 5.22-5.13 (m, 1H), 5.13-5.03 (m, 1H), 3.05-2.98 (m, 4H), 1.52 (d, 6H, J=6.9 Hz), 1.50-1.44 (m, 6H), 1.40 (d, 6H, J=6.9 Hz); MS (ESP+) m/e 462 (MH$^+$); TLC (EtOAc:hexanes/1:1) R$_f$=0.88.

EXAMPLE 31

7-(2-Chloro-6-fluorobenzyl)-1-cyclopropyl-3-isopropyl-8-piperidin-1-yl-3,7-dihydro-1H-purine-2,6-dione

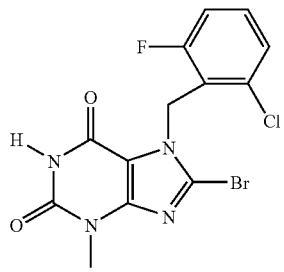

The title compound was prepared according to the procedure of Example 16 to give 5 mg (20% yield) of a yellow oil: $^1$H NMR (CDCl$_3$, 400 MHz) 7.21-7.14 (m, 1H), 7.13-7.09 (m, 1H), 6.97-6.90 (m, 1H), 5.53 (s, 2H), 5.11-5.02 (m, 1H), 3.06-2.99 (m, 4H), 2.61-2.54 (m, 1H), 1.52 (d, 6H, J=6.9 Hz), 1.50-1.46 (m, 6H), 1.10-1.04 (m, 2H), 0.67-0.61 (m, 2H); MS (ESP+) m/e 460 (MH$^+$); TLC (EtOAc:hexanes/1:1) R$_f$=0.64.

EXAMPLE 32

8-Bromo-7-(2-chloro-6-fluorobenzyl)-3-methyl-3,7-dihydro-1H-purine-2,6-dione

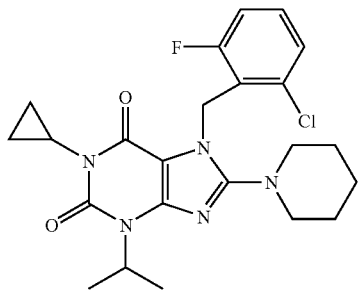

A solution of 3-methyl-8-bromoxanthine (1.5 g, 6.1 mmol, Klein, J. P. PCT Int. Appl. WO 0061583, 2000) and K$_2$CO$_3$ (0.84 g, 6.1 mmol) in 6 mL DMF was treated with 2-chloro-6-fluorobenzyl bromide. The reaction mixture was heated to 60° C. for 2 hr, cooled, and poured onto ice water. The solid precipitate was filtered and dried to yield 1.8 g (76% yield) of a white solid: $^1$H NMR (DMSO, 400 MHz) 7.43-7.36 (m, 1H), 7.34-7.30 (m, 1H), 7.22-7.15 (m, 1H), 5.67 (s, 2H), 3.29 (s, 3H); MS (AP+) m/e 389 (MH$^+$).

EXAMPLE 33

7-(2-chloro-6-fluorobenzyl)-1-ethyl-3-methyl-8-piperidin-1-yl-3,7-dihydro-1H-purine-2,6-dione

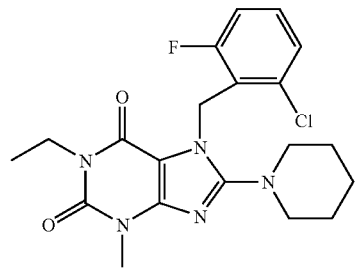

A solution of 8-bromo-7-(2-chloro-6-fluorobenzyl)-3-methyl-3,7-dihydro-1H-purine-2,6-dione (200 mg, 0.52 mmol) and K$_2$CO$_3$ (357 mg, 2.6 mmol) in 4 mL DMF was treated with iodoethane (412 µL, 5.2 mmol). The reaction was heated to 50° C. for 48 hr. The reaction mixture was cooled, diluted with H$_2$O, and extracted 3× with 50% EtOAc:hexanes. The organic layers were combined and the solvent removed under reduced pressure (116 mg, 54% yield). The crude product (52 mg, 0.13 mmol) was dissolved in 200 µL DMSO and treated with piperidine (37 µL, 0.38 mmol). The reaction mixture was heated to 100° C. for 15 hr. The reaction mixture was cooled, diluted with H$_2$O, and extracted 3× with 50% EtOAc:hexanes. The organic layers were combined, dried with Mg$_2$SO$_4$, and evaporated under reduced pressure. The crude product was purified by preparative thin layer chromatography (silica gel, 1 mm plate, EM Science 20×20 cm silica gel 60 F$_{264}$) eluting with EtOAc:hexane (1:1) to give 31 mg (56% yield) of the title compound as a white solid: $^1$H NMR (CDCl$_3$, 400 MHz) 7.21-7.14 (m, 1H), 7.13-7.09 (m, 1H), 6.96-6.90 (m, 1H), 5.53 (s, 2H), 3.96 (q, 2H, J=7.0 Hz), 3.49 (s, 3H), 3.09-3.00 (m, 4H), 1.54-1.46 (m, 6H), 1.13 (t, 3H, J=7.0 Hz); MS (ESP+) m/e 420 (MH+).

EXAMPLE 34

7-(2-Chloro-6-fluorobenzyl)-3-methyl-8-piperidin-1-yl-1-propyl-3,7-dihydro-1H-purine-2,6-dione

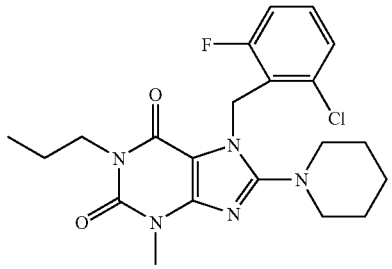

The title compound was prepared according to the procedure of Example 33 to give 22 mg (51% yield) of a pale yellow solid: $^1$H NMR (CDCl$_3$, 400 MHz) 7.21-7.14 (m, 1H), 7.13-7.09 (m, 1H), 6.96-6.90 (m, 1H), 5.53 (s, 2H), 3.90-3.83 (m, 2H), 3.49 (s, 3H), 3.07-3.02 (m, 4H), 1.62-1.53 (m, 2H), 1.52-1.46 (m, 6H), 0.83 (t, 3H, J=7.5 Hz); MS (ESP+) m/e 434 (MH+); TLC (EtOAc:CH$_2$Cl$_2$/1:9) R$_f$=0.29.

EXAMPLE 35

1-Benzyl-7-(2-chloro-6-fluorobenzyl)-3-methyl-8-piperidin-1-yl-3,7-dihydro-1H-purine-2,6-dione

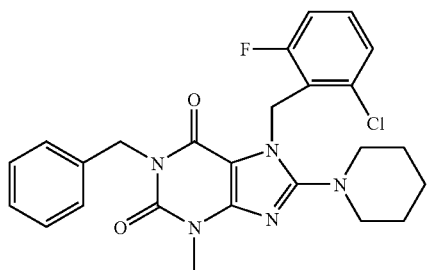

The title compound was prepared according to the procedure of Example 33 to give 125 mg (74% yield) of a white solid: $^1$H NMR (CDCl$_3$, 400 MHz) 7.32-7.28 (m, 2H), 7.24-7.14 (m, 4H), 7.14-7.10 (m, 1H), 6.98-6.91 (m, 1H), 5.55 (s, 2H), 5.09 (s, 2H), 3.47 (s, 3H), 3.09-3.03 (m, 4H), 1.53-1.46 (m, 6H); MS (ESP+) m/e 482 (MH+); TLC (EtOAc:CH$_2$Cl$_2$/1:9) R$_f$=0.36.

EXAMPLE 36

7-(2-Chloro-6-fluorobenzyl)-1-(3-methoxybenzyl)-3-methyl-8-piperidin-1-yl-3,7-dihydro-1H-purine-2,6-dione

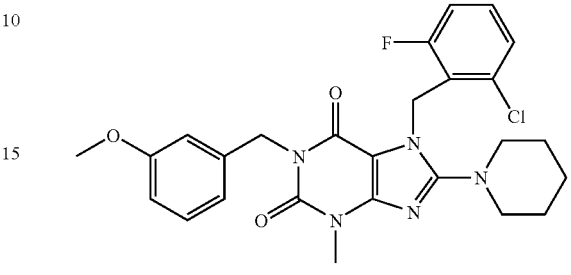

The title compound was prepared according to the procedure of Example 33 to give 13 mg (29% yield) of a yellow oil: $^1$H NMR (CDCl$_3$, 400 MHz) 7.25-7.09 (m, 3H), 6.98-6.85 (m, 3H), 6.75-6.70 (m, 1H), 5.56 (s, 2H), 5.08 (s, 2H), 3.74 (s, 3H), 3.48 (s, 3H), 3.10-3.02 (m, 4H), 1.53-1.46 (m, 6H); MS (ESP+) m/e 513 (MH+); TLC (EtOAc:CH$_2$Cl$_2$/1:9) R$_f$=0.28.

EXAMPLE 37

8-Bromo-7-(2-chloro-6-fluorobenzyl)-1-methyl-3,7-dihydro-1H-purine-2,6-dione

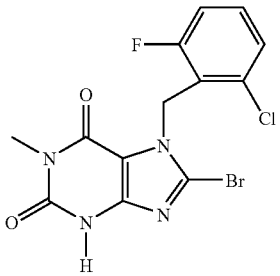

A solution of 1-methylxanthine (1 g, 6 mmol) and sodium acetate (591 mg, 7.2 mmol) in 30 mL acetic acid was treated with bromine (371 µL, 7.2 mmol). The reaction mixture was heated to 50° C. for 15 hr. An additional 246 mg sodium acetate and 155 µL bromine was added and the reaction was heated at 50° C. for another 15 hr. The reaction was cooled and the solids collected by filtration, rinsed with chloroform, and dried under reduced pressure to yield a white solid (1.0 g, 68% yield). A solution of the solid (1.0 g, 4.1 mmol) in 30 mL DMF was heated at 80° C. for 30 min. The reaction mixture was cooled and treated with Na$_2$CO$_3$ (435 mg, 4.1 mmol) and 2-chloro-6fluorobenzyl bromide (1.0 g, 4.5 mmol) and stirred at room temperature for 15 hr. Upon addition of H$_2$O, the resulting precipitate was collected by filtration and then triturated with EtOAc. The remaining solids were collected by filtration, rinsed with EtOAc, and dried under reduced pressure to yield 0.69 g (43% yield) of a white solid: $^1$H NMR (DMSO, 400 MHz) 12.06 (s, 1H), 7.42-7.35 (m, 1H), 7.34-7.30 (m, 1H), 7.21-7.14 (m, 1H), 5.67 (s, 2H), 3.09 (s, 3H); MS (ESP+) m/e 389 (MH+).

EXAMPLE 38

7-(2-Chloro-6-fluorobenzyl)-3-ethyl-1-methyl-8-piperidin-1-yl-3,7-dihydro-1H-purine-2,6-dione

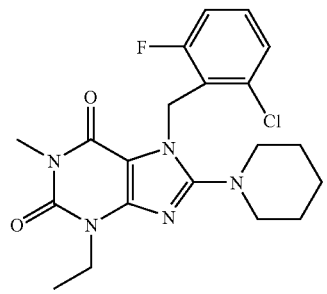

A solution of 8-bromo-7-(2-chloro-6-fluorobenzyl)-1-methyl-3,7-dihydro-1H-purine-2,6-dione (200 mg, 0.52 mmol) and K₂CO₃ (86 mg, 0.62 mmol) in 5.2 mL DMF was treated with iodoethane (412 µL, 5.2 mmol). The reaction was stirred at room temperature for 15 hr. The reaction mixture was diluted with H₂O, and extracted 3× with 50% EtOAc:hexanes. The organic layers were combined and the solvent removed under reduced pressure (50 mg, 23% yield). The crude product (50 mg, 0.12 mmol) was dissolved in 200 µL DMSO and treated with piperidine (36 µL, 0.36 mmol). The reaction mixture was heated to 100° C. for 15 hr. The reaction mixture was cooled, diluted with H₂O, and extracted 3× with 50% EtOAc:hexanes. The organic layers were combined and evaporated under reduced pressure. The crude product was purified by preparative thin layer chromatography (silica gel, 1 mm plate, EM Science 20×20 cm silica gel 60 F₂₆₄) eluting with EtOAc:hexane (2:3) to give 27 mg (54% yield) of the title compound as a white solid: ¹H NMR (CDCl₃, 400 MHz) 7.22-7.15 (m, 1H), 7.15-7.11 (m, 1H), 6.98-6.91 (m, 1H), 5.55 (s, 2H), 4.10 (q, 2H, J=7.1 Hz), 3.30 (s, 3H), 3.08-3.01 (m, 4H), 1.53-1.47 (m, 6H), 1.30 (t, 3H, J=7.1 Hz); MS (ESP+) m/e 420 (MH+); TLC (EtOAc:hexanes/1:2) R$_f$=0.24.

EXAMPLE 39

7-(2-Chloro-6-fluorobenzyl)-1-methyl-8-piperidin-1-yl-3-propyl-3,7-dihydro-1H-purine-2,6-dione

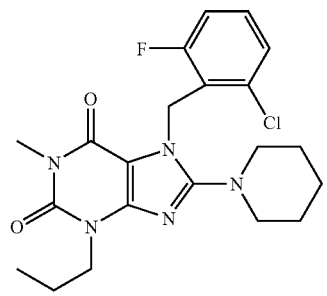

The title compound was prepared according to the procedure of Example 38 to give 22 mg (11% yield) of a clear oil: ¹H NMR (CDCl₃, 400 MHz) 7.21-7.14 (m, 1H), 7.13-7.10 (m, 1H), 6.97-6.90 (m, 1H), 5.53 (s, 2H), 4.02-3.96 (m, 2H), 3.28 (s, 3H), 3.06-3.01 (m, 4H), 1.80-1.69 (m, 2H), 1.51-1.46 (m, 6H), 0.91 (t, 3H, J=7.6 Hz); MS (ESP+) m/e 434 (MH+); TLC (EtOAc:hexanes/1:2) R$_f$=0.35.

EXAMPLE 40

7-(2-chloro-6-fluorobenzyl)-3-isopropyl-1-methyl-8-piperidin-1-yl-3,7-dihydro-1H-purine-2,6-dione

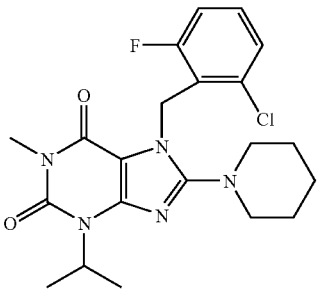

The title compound was prepared according to the procedure of Example 38 to give 22 mg (11% yield) of a white solid: ¹H NMR (CDCl₃, 400 MHz) 7.21-7.14 (m, 1H), 7.14-7.10 (m, 1H), 6.96-6.90 (m, 1H), 5.55 (s, 2H), 5.17-5.05 (m, 1H), 3.27 (s, 3H), 3.06-3.01 (m, 4H), 1.53 (d, 6H, J=6.9), 1.50-1.46 (m, 6H); MS (ESP+) m/e 434 (MH+); TLC (EtOAc:hexanes/1:2) R$_f$=0.39.

EXAMPLE 41

3-Benzyl-7-(2-chloro-6-fluorobenzyl)-1-methyl-8-piperidin-1-yl-3,7-dihydro-1H-purine-2,6-dione

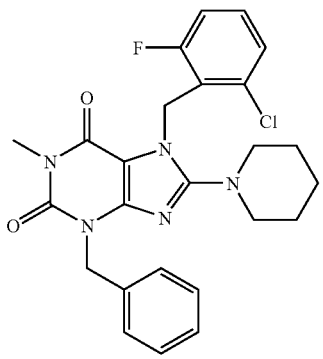

The title compound was prepared according to the procedure of Example 38 to give 11 mg (24% yield) of a clear oil: ¹H NMR (CDCl₃, 400 MHz) 7.51-7.46 (m, 2H), 7.31-7.10 (m, 5H), 6.97-6.91 (m, 1H), 5.53 (s, 2H), 5.20 (s, 2H), 3.27 (s, 3H), 3.11-3.05 (m, 4H), 1.54-1.46 (m, 6H); MS (ESP+) m/e 482 (MH+); TLC (EtOAc:hexanes/1:2) R$_f$=0.27.

EXAMPLE 42

7-(2-Chloro-6-fluorobenzyl)-8-(3-chlorophenyl)-3-isopropyl-1-methyl-3,7-dihydro-1H-purine-2,6-dione

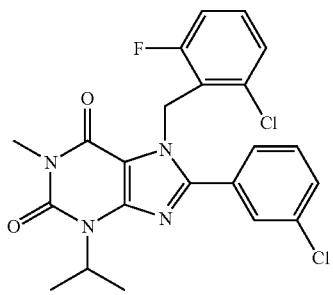

A solution of 8-bromo-7-(2-chloro-6-fluorobenzyl)-1-methyl-3,7-dihydro-1H-purine-2,6-dione (67 mg, 0.17 mmol) and $K_2CO_3$ (239 mg, 1.7 mmol) in 1.7 mL DMF was treated with isopropyl iodide (85 μL, 0.86 mmol). The reaction was stirred at room temperature for 15 hr. The reaction mixture was filtered through a silica plug and rinsed with EtOAc. The solvent was removed under reduced pressure and the crude product was purified by preparative thin layer chromatography (silica gel, 1 mm plate, EM Science 20×20 cm silica gel 60 $F_{264}$) eluting with EtOAc:hexane (1:3) to give 46 mg (63% yield) of 8-bromo-7-(2-chloro-6-fluorobenzyl)-3-isopropyl-1-methyl-3,7-dihydro-1H-purine-2,6-dione. A solution of this intermediate (45 mg, 0.11 mmol) in 110 μL aqueous sodium carbonate (2 M), 270 μL toluene, and 45 μL ethanol was treated with 3-chlorophenylboronic acid (18 mg, 0.12 mmol), tetrakis(triphenylphosphine)palladium(0) (3.6 mg, 0.0032 mmol), and lithium chloride (catalytic). The reaction mixture was heated to 100° C. in a sealed vial and stirred overnight. The reaction mixture was cooled, filtered through a silica plug, and rinsed with 50% EtOAc:hexanes. The solvent was removed under reduced pressure and the crude product was purified by preparative thin layer chromatography (silica gel, 1 mm plate, EM Science 20×20 cm silica gel 60 h64) eluting with ether:hexane (1:1) to give 38 mg (77% yield) of the title compound as a white solid: $^1$H NMR ($CDCl_3$, 400 MHz) 7.41-7.37 (m, 1H), 7.37-7.22 (m, 3H), 7.13-7.06 (m, 1H), 7.05-7.00 (m, 1H), 6.82-6.74 (m, 1H), 5.86 (s, 2H), 5.25-5.13 (m, 1H), 3.35 (s, 3H), 1.58 (d, 6H, J=7); MS (ESP+) m/e 461 (MH$^+$); TLC (ether:hexanes/1:1) $R_f$=0.37.

EXAMPLE 43

8-Bromo-7-(2-chloro-6-fluorobenzyl)-1,3-dimethyl-3,7-dihydro-1H-purine-2,6-dione

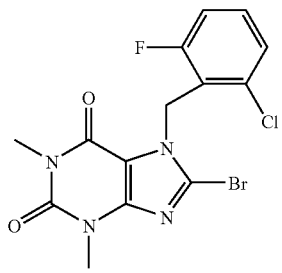

A solution of 8-bromotheophylline (10 g, 39 mmol) in 30 mL water was treated with potassium carbonate (2.6 g, 48 mmol). The reaction mixture was refluxed until dissolved. Ethanol (30 mL) was added to the hot reaction mixture and the resulting potassium salt was filtered, washed with acetone, and dried in a 100° C. vacuum oven. A solution of 2-chloro-6-fluorobenzyl bromide (5.3 g, 24 mmol) in 10 mL DMSO was treated with the solid potassium salt The reaction mixture was heated to 100° C. for 1 hour and cooled. Upon addition of 5 mL water, the mixture was collected by filtration and dried in a vacuum oven to yield a white solid (6.0 g, 89% yield): $^1$H NMR ($CDCl_3$, 300 MHz) 7.37-7.21 (m, 2H), 7.07-6.96 (m, 1H), 5.87 (s, 2H), 3.60 (s, 3H), 3.42 (s, 3H); MS (ESP+) m/e 402 (MH$^+$).

EXAMPLE 44

7-(2-Chloro-6-fluorobenzyl)-1,3-dimethyl-8-phenyl-3,7-dihydro-1H-purine-2,6-dione

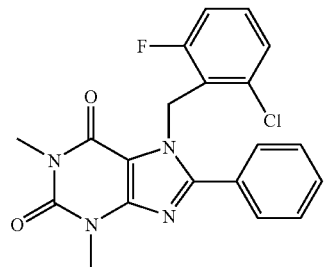

A solution of 8-bromo-7-(2-chloro-6-fluorobenzyl)-1,3-dimethyl-3,7-dihydro-1H-purine-2,6-dione (100 mg, 0.25 mmol) in 260 μL aqueous sodium carbonate (2 M), 650 μL toluene, and 110 μL ethanol was treated with commercially available phenylboronic acid (34 mg, 0.27 mmol), tetrakis(triphenylphosphine)-palladium(0) (9 mg, 0.0075 mmol), and lithium chloride (catalytic). The reaction mixture was heated to 100° C. in a sealed vial and stirred overnight The reaction mixture was cooled and separated between water and ether. The aqueous layer was extracted with ether (3×) and the combined organics were dried with magnesium sulfate, filtered, and concentrated in vacuo. The crude product was purified by flash chromatography (silica gel cartridge, Biotage, 32-63 μm, 60 Å) with 50% EtOAc:hexanes as the eluent to afford 71 mg (71% yield) of the title compound as a white solid: $^1$H NMR ($CDCl_3$, 300 MHz) 7.61-7.36 (m, 5H), 7.19-7.04 (m, 2H), 6.88-6.76 (m, 1H), 5.89 (s, 2H), 3.67 (s, 3H), 3.43 (s, 3H); MS (ESP+) m/e 400 (MH$^+$); TLC (EtOAc:hexanes/1:1) $R_f$=0.45.

EXAMPLE 45

7-(2-chloro-6-fluorobenzyl)-8-(4-chlorophenyl)-1,3-dimethyl-3,7-dihydro-1H-purine-2,6-dione

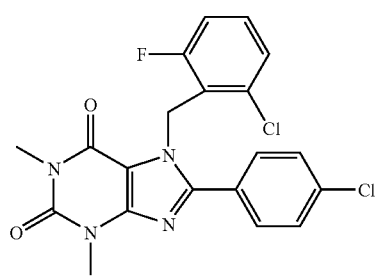

The title compound was prepared according to the procedure of Example 44 to give 56 mg (52% yield) of a white solid: $^1$H NMR (CDCl$_3$, 300 MHz) 7.48-7.36 (m, 4H), 7.21-7.07 (m, 2H), 6.90-6.79 (m, 1H), 5.89 (s, 2H), 3.66 (s, 3H), 3.44 (s, 3H); MS (AP+) m/e 433 (MH$^+$).

EXAMPLE 46

7-(2-Chloro-6-fluorobenzyl)-8-(4-isopropylphenyl)-1,3-dimethyl-3,7-dihydro-1H-purine-2,6-dione

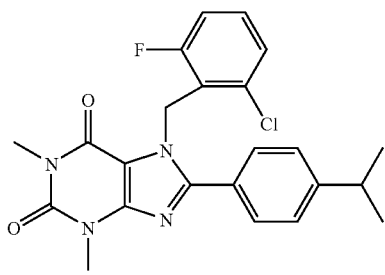

The title compound was prepared according to the procedure of Example 44 to give 74 mg (67% yield) of a white solid: $^1$H NMR (CDCl$_3$, 400 MHz) 7.38-7.33 (d, 2H, J=8.2 Hz), 7.24-7.18 (d, 2H, J=8.2 Hz), 7.11-6.99 (m, 2H), 6.79-6.72 (m, 1H), 5.80 (s, 2H), 3.60 (s, 3H), 3.36 (s, 3H), 3.01-2.89 (m, 1H), 1.20 (d, 6H, J=6.9 Hz); MS (AP+) m/e 441 (MH$^+$).

EXAMPLE 47

7-(2-Chloro-6-fluorobenzyl)-1,3-dimethyl-8-pyridin-3-yl-3,7-dihydro-1H-purine-2,6-dione

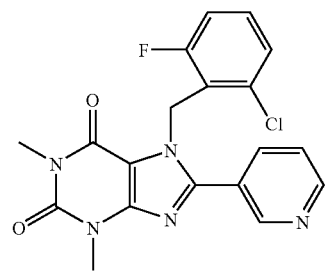

The title compound was prepared according to the procedure of Example 44 to give 12 mg (6% yield) of a white solid: $^1$H NMR (CDCl$_3$, 400 MHz) 8.72-8.59 (m, 2H), 7.80-7.72 (m, 1H), 7.34-7.27 (m, 1H), 7.15-7.07 (m, 1H), 7.07-7.02 (m, 1H), 6.84-6.74 (m, 1H), 5.88 (s, 2H), 3.61 (s, 3H), 3.40 (s, 3H); MS (ESP+) m/e 400 (MH$^+$).

EXAMPLE 48

7-(2-Chloro-6-fluorobenzyl)-8-(3-furyl)-1,3-dimethyl-3,7-dihydro-1H-purine-2,6-dione

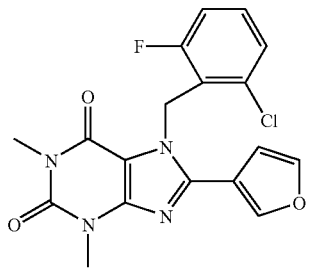

The title compound was prepared according to the procedure of Example 44 to give 24 mg (12% yield) of a pale yellow solid: $^1$H NMR (CDCl$_3$, 400 MHz) 7.73-7.69 (m, 1H), 7.46-7.43 (m, 1H), 7.20-7.15 (m, 2H), 6.92-6.85 (m, 1H), 6.66-6.63 (m, 1H), 5.86 (s, 2H), 3.60 (s, 3H), 3.36 (s, 3H); MS (ESP+) m/e 389 (MH$^+$); TLC (EtOAc:hexanes/1:1) R$_f$=0.39.

EXAMPLE 49

7-(2-Chloro-6-fluorobenzyl)-8-(3,5-dichlorophenyl)-1,3-dimethyl-3,7-dihydro-1H-purine-2,6-dione

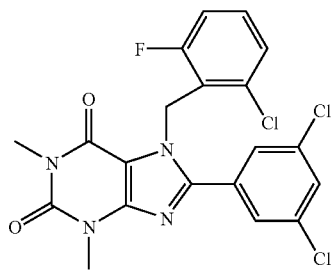

The title compound was prepared according to the procedure of Example 44 to give 20 mg (34% yield) of a white solid: $^1$H NMR (CDCl$_3$, 400 MHz) 7.40-7.36 (m, 1H), 7.30-7.26 (m, 2H), 7.19-7.12 (m, 1H), 7.10-7.06 (m, 1H), 6.87-6.81 (m, 1H), 5.91 (s, 2H), 3.61 (s, 3H), 3.42 (s, 3H); MS (ESP+) m/e 468 (MH$^+$).

EXAMPLE 50

7-(2-Chloro-6-fluorobenzyl)-1,3-dimethyl-8-(3-methylphenyl)-3,7-dihydro-1H-purine-2,6-dione

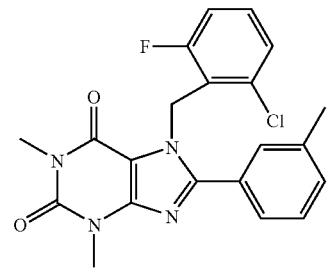

The title compound was prepared according to the procedure of Example 44 to give 73 mg (71% yield) of a white solid: $^1$H NMR (CDCl$_3$, 400 MHz) 7.31-7.19 (m, 4H), 7.13-7.06 (m, 1H), 7.06-7.02 (m, 1H), 6.82-6.75 (m, 1H), 5.85 (s, 2H), 3.63 (s, 3H), 3.40 (s, 3H), 2.33 (s, 3H); MS (ESP+) m/e 413 (MH$^+$); TLC (EtOAc:hexanes/2:1) R$_f$=0.66.

EXAMPLE 51

8-(3-Acetyl phenyl)-7-(2-chloro-6-fluorobenzyl)-1,3-dimethyl-3,7-dihydro-1H-purine-2,6-dione

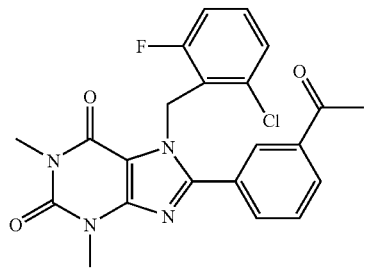

The title compound was prepared according to the procedure of Example 44 to give 18 mg (15% yield) of a white solid: $^1$H NMR (CDCl$_3$, 400 MHz) 8.01-7.96 (m, 2H), 7.66-7.61 (m, 1H), 7.51-7.45 (m, 1H), 7.12-6.99 (m, 2H), 6.80-6.73 (m, 1H), 5.88 (s, 2H), 3.63 (s, 3H), 3.41 (s, 3H), 2.56 (s, 3H); MS (ESP+) m/e 441 (MH$^+$); TLC (EtOAc:hexanes/2:1) R$_f$=0.55.

EXAMPLE 52

7-(2-Chloro-6-fluorobenzyl)-1,3-dimethyl-8-(2-naphthyl)-3,7-dihydro-1H-purine-2,6-dione

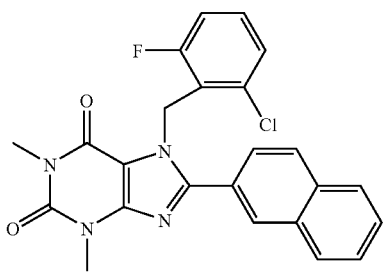

The title compound was prepared according to the procedure of Example 44 to give 64 mg (57% yield) of a white solid: $^1$H NMR (CDCl$_3$, 400 MHz) 8.01-7.94 (m, 1H), 7.86-7.80 (m, 3H), 7.59-7.49 (m, 3H), 7.10-6.96 (m, 2H), 6.74-6.65 (m, 1H). 5.94 (s, 2H), 3.66 (s, 3H), 3.41 (s, 3H); MS (ESP+) m/e 449 (MH$^+$); TLC (EtOAc:hexanes/2:1) R$_f$=0.61.

EXAMPLE 53

7-(2-Chloro-6-fluorobenzyl)-1,3-dimethyl-8-(3-nitrophenyl)-3,7-dihydro-1H-purine-2,6-dione

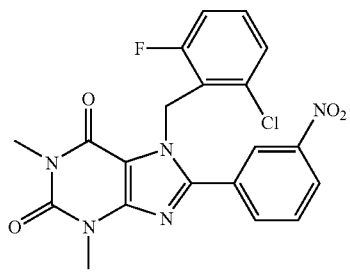

The title compound was prepared according to the procedure of Example 44 to give 40 mg (36% yield) of a pale yellow solid: $^1$H NMR (CDCl$_3$, 400 MHz) 8.31-8.21 (m, 2H), 7.82-7.75 (m, 1H), 7.60-7.53 (m, 1H), 7.15-7.00 (m, 2H), 6.82-6.73 (m, 1H), 5.93 (s, 2H), 3.62 (s, 3H), 3.42 (s, 3H); MS (ESP+) m/e 444 (MH$^+$); TLC (EtOAc:hexanes/2:1) R$_f$=0.55.

EXAMPLE 54

8-(1,3-Benzodioxol-5-yl)-7-(2-chloro-6-fluorobenzyl)-1,3-dimethyl-3,7-dihydro-1H-purine-2,6-dione

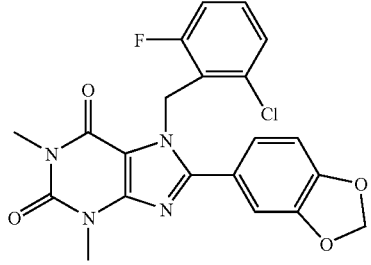

The title compound was prepared according to the procedure of Example 44 to give 10 mg (8% yield) of a pale yellow solid: $^1$H NMR (CDCl$_3$, 400 MHz) 7.17-7.05 (m, 2H), 6.99-6.91 (m, 2H), 6.87-6.77 (m, 2H), 5.99 (s, 2H), 5.83 (s, 2H), 3.61 (s, 3H), 3.38 (s, 3H); MS (ESP+) m/e 443 (MH$^+$); TLC (EtOAc:hexanes/2:1) R$_f$=0.63.

EXAMPLE 55

8-(3-Aminophenyl)-7-(2-chloro-6-fluorobenzyl)-1,3-dimethyl-3,7-dihydro-1H-purine-2,6-dione

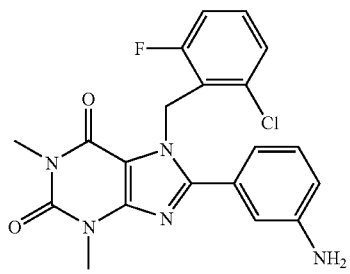

The title compound was prepared according to the procedure of Example 44 to give 530 mg (51% yield) of a pale yellow solid: ¹H NMR (CDCl₃, 400 MHz) 7.15-7.02 (m, 3H), 6.84-6.77 (m, 2H), 6.75-6.73 (m, 1H), 6.71-6.66 (m, 1H), 5.83 (s, 2H), 3.72 (s, 2H), 3.61 (s, 3H), 3.37 (s, 3H); MS (ESP+) m/e 414 (MH⁺); TLC (EtOAc:hexanes/2:1) R_f=0.22.

EXAMPLE 56 tert-Butyl 2-[7-(2-chloro-6-fluorobenzyl)-1,3-dimethyl-2,6-dioxo-2,3,6,7-tetrahydro-1H-purin-8-yl]-1H-pyrrole-1-carboxylate

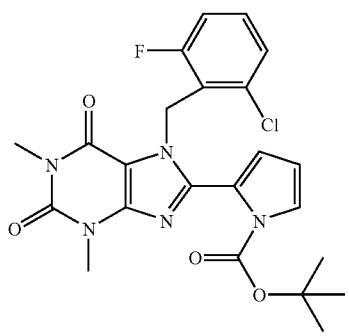

The title compound was prepared according to the procedure of Example 44 to give 19 mg (16% yield) of a white solid: ¹H NMR (CDCl₃, 400 MHz) 7.26-7.23 (m, 1H), 7.12-7.05 (m, 1H), 7.04-7.00 (m, 1H), 6.81-6.74 (m, 1H), 6.04-6.01 (m, 1H), 6.01-5.98 (m, 1H), 5.80 (s, 2H), 3.60 (s, 3H), 3.44 (s, 3H), 1.44 (s, 9H); MS (ESP+) m/e 488 (MH⁺); TLC (EtOAc:hexanes/2:1) R_f=0.75.

EXAMPLE 57

7-(2-Chloro-6-fluorobenzyl)-8-(3-chlorophenyl)-1,3-dimethyl-3,7-dihydro-1H-purine-2,6-dione

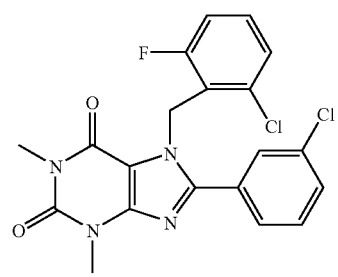

The title compound was prepared according to the procedure of Example 44 (8 mg, 7% yield): ¹H NMR (CDCl₃, 400 MHz) 7.40-7.35 (m, 2H), 7.31-7.26 (m, 2H), 7.14-7.07 (m, 1H), 7.05-7.02 (m, 1H), 6.82-6.75 (m, 1H), 5.86 (s, 2H), 3.60 (s, 3H), 3.39 (s, 3H); MS (ESP+) m/e 433 (MH⁺); TLC (EtOAc:hexanes/1:1) R_f=0.71.

EXAMPLE 58

7-(2-chloro-6-fluorobenzyl)-1,3-dimethyl-8-[3-(trifluoromethyl)phenyl]-3,7-dihydro-1H-purine-2,6-dione

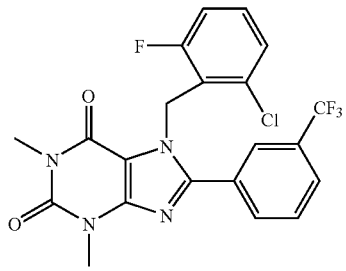

The title compound was prepared according to the procedure of Example 44 (53 mg, 45% yield): ¹H NMR (CDCl₃, 400 MHz) 7.65-7.58 (m, 3H), 7.51-7.45 (m, 1H), 7.10-7.03 (m, 1H), 7.01-6.97 (m, 1H), 6.76-6.70 (m, 1H), 5.87 (s, 2H), 3.60 (s, 3H), 3.39 (s, 3H); MS (ESP+) m/e 467 (MH⁺); TLC (EtOAc:hexanes/1:1) R_f=0.69.

EXAMPLE 59

7-(2-Chloro-6-fluorobenzyl)-8-(3-methoxyphenyl)-1,3-dimethyl-3,7-dihydro-1H-purine-2,6-dione

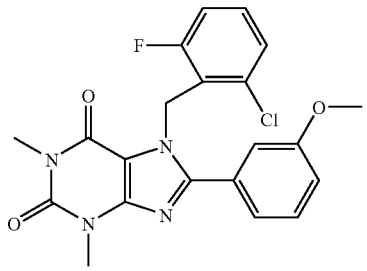

The title compound was prepared according to the procedure of Example 44 (13 mg, 12% yield): ¹H NMR (CDCl₃, 400 MHz) 7.29-7.24 (m, 1H), 7.13-6.98 (m, 3H), 6.96-6.91 (m, 2H), 6.81-6.75 (m, 1H), 5.82 (s, 2H), 3.75 (s, 3H), 3.61 (s, 3H), 3.37 (s, 3H); MS (ESP+) m/e 429 (MH⁺); TLC (EtOAc:hexanes/1:1) R_f=0.51.

EXAMPLE 60

7-(2-Chloro-6-fluorobenzyl)-8-cyclopentyl-1,3-dimethyl-3,7-dihydro-1H-purine-2,6-dione

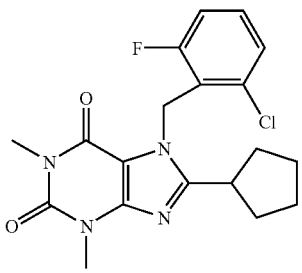

A solution of 8-cyclopentyl-1,3-dimethylxanthine (100 mg, 0.40 mmol) and $K_2CO_3$ (80 mg, 0.58 mmol) was treated with 2-chloro-6-fluorobenzyl bromide (142 mg, 0.64 mmol) dissolved in 400 µL DMF. The reaction mixture was sealed and heated to 60° C. for 24 hrs. The reaction mixture was cooled and purified by preparative thin layer chromatography (silica gel, 1 mm plate, EM Science 20×20 cm silica gel 60 $F_{264}$) eluting with EtOAc:hexane (1:1) to give 23 mg (14% yield) of the title compound as a white solid: $^1$H NMR (CDCl$_3$, 400 MHz) 7.29-7.11 (m, 2H), 7.01-6.85 (m, 1H), 5.86 (s, 2H), 3.54 (s, 3H), 3.38 (s, 3H); 3.02-2.81 (m, 1H), 1.83-1.43 (m, 8H); MS (ESP+) m/e 391 (MH$^+$); TLC(EtOAc:hexanes/1:1) $R_f$=0.58.

EXAMPLE 61

7-(2-Chloro-6-fluorobenzyl)-8-cyclohexyl-1,3-dimethyl-3,7-dihydro-1H-purine-2,6-dione

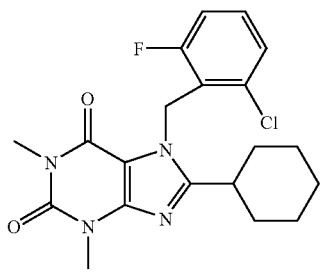

A solution of 5,6-diamino-1,3-dimethyluracil hydrate (1 g, 5.9 mmol) and 2,3-dichloro-5,6-dicyanoquinone (1.34 g, 5.9 mmol) in 15 mL acetonitrile was treated with cyclohexane carboxaldehyde (0.71 mL, 5.9 mmol). The reaction mixture was stirred at room temperature for 15 hrs and then treated with 0.5 M NaOH (24 mL) and stirred an additional 48 hrs. The precipitate was filtered and dried (345 mg, 22% yield). A solution of the precipitate (200 mg, 0.76 mmol) and $K_2CO_3$ (105 mg, 0.76 mmol) was treated with 2-chloro-6-fluorobenzyl bromide (187 mg, 0.84 mmol) dissolved in 1 mL DMF. The reaction mixture was heated in a sealed vial to 60° C. for 24 hrs. An additional 28 mg $K_2CO_3$ and 51 mg 2-chloro-6-fluorobenzyl bromide was added to the reaction and the reaction mixture was heated in a sealed vial to 60° C. for another 24 hrs. The reaction mixture was cooled and, upon addition of water, the resulting precipitate was collected by filtration. The crude product was purified by flash chromatography (silica gel cartridge, Biotage, 32-63 □m, 60 Å) with 33% EtOAc:hexanes as the eluent to afford 134 mg (44% yield) of the title compound as a tan solid: $^1$H NMR (CDCl$_3$, 400 MHz) 7.30-7.20 (m, 2H), 7.01-6.94 (m, 1H), 5.90 (s, 2H), 3.60 (s, 3H), 3.40 (s, 3H), 2.64-2.53 (m, 1H), 1.79-1.53 (m, 5H), 1.42-1.05 (m, 5H); MS (ESP+) m/e 405 (MH$^+$); TLC (EtOAc:hexanes/1:1) $R_f$=0.59.

EXAMPLE 62

7-(2-Chloro-6-fluorobenzyl)-8-(3-hydroxyphenyl)-1,3-dimethyl-3,7-dihydro-1H-purine-2,6-dione

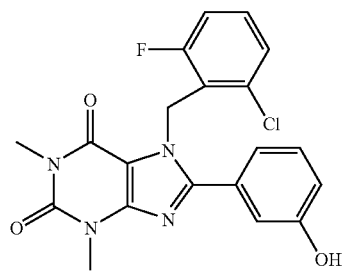

A solution of 8-(3-aminophenyl)-7-(2-chloro-6-fluorobenzyl)-1,3-dimethyl-3,7-dihydro-1H-purine-2,6-dione (88 mg, 0.21 mmol) in 310 µL water was treated with concentrated HCl and then sodium nitrite (19 mg, 0.23 mmol) dissolved in ~300 µL water. The reaction mixture was stirred at 0° C. for 30 min and then heated to 100° C. for 15 min. The reaction mixture was cooled, dried under reduced pressure, and purified by preparative thin layer chromatography (silica gel, 1 mm plate, EM Science 20×20 cm silica gel 60 $F_{264}$) eluting with EtOAc:hexane (2:1) to give 37 mg (43% yield) of the title compound as a pale orange solid: $^1$H NMR (CDCl$_3$, 400 MHz) 7.22-7.16 (m, 1H), 7.12-7.01 (m, 2H), 6.96-6.91 (m, 2H), 6.86-6.81 (m, 1H), 6.80-6.74 (m, 1H), 5.82 (s, 2H), 3.60 (s, 3H), 3.37 (s, 3H); MS (ESP+) m/e 415 (MH$^+$); TLC (EtOAc:hexanes/2:1) $R_f$=0.41.

EXAMPLE 63

7-(2-Chloro-6-fluorobenzyl)-8-(3-iodophenyl)-1,3-dimethyl-3,7-dihydro-1H-purine-2,6-dione

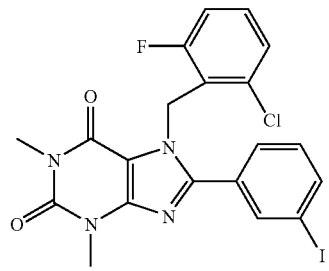

A solution of 8-(3-aminophenyl)-7-(2-chloro-6-fluorobenzyl)-1,3-dimethyl-3.7-dihydro-1H-purine-2,6-dione (100 mg, 0.24 mmol) in 600 µL 1 N HCl was cooled to 0° C. and slowly treated with sodium nitrite (27 mg, 0.32 mmol) dissolved in ~700 µL water. The reaction mixture was stirred at 0° C.-5° C. for 30 min and then KI (100 mg, 0.60 mmol) was added in small portions. The reaction mixture was then heated to 80° C. for 1 hr. cooled, and extracted with EtOAc. The EtOAc layers were combined, dried over $Na_2SO_4$, and dried under reduced pressure. The crude product was purified by preparative thin layer chromatography (silica gel, 1 mm plate, EM Science 20×20 cm silica gel 60 $F_{264}$) eluting with EtOAc:hexane (1:1) to give 40 mg (32% yield) of the title compound as an off-white solid: $^1$H NMR (CDCl$_3$, 400 MHz) 7.74-7.67 (m, 2H), 7.40-7.36 (m, 1H), 7.15-7.02 (m, 3H), 6.82-6.75 (m, 1H), 5.85 (s, 2H), 3.60 (s, 3H), 3.39 (s, 3H); MS (ESP+) m/e 525 (MH+); TLC (EtOAc:hexanes/1:1) R$_f$=0.54.

EXAMPLE 64

N-{3-[7-(2-Chloro-6-fluorobenzyl)-1,3-dimethyl-2,6-dioxo-2,3,6,7-tetrahydro-1H-purin-8-yl]phenyl}acetamide

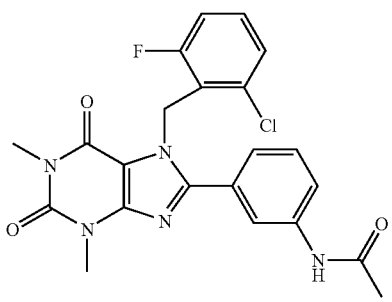

A solution of 8-(3-aminophenyl)-7-(2-chloro-6-fluorobenzyl)-1,3-dimethyl-3,7-dihydro-1H-purine-2,6-dione (25 mg, 0.06 mmol) in 255 μL CH$_2$Cl$_2$ was treated with acetic anhydride (6.6 μL, 0.07 mmol). The reaction was stirred for 1.5 hr and then blown dry under nitrogen. The crude product was purified by preparative thin layer chromatography (silica gel, 1 mm plate, EM Science 20×20 cm silica gel 60 F$_{264}$) eluting with EtOAc:hexane (3:1) to give 4 mg (15% yield) of the title compound as a clear oil: $^1$H NMR (CDCl$_3$, 400 MHz) 7.67-7.61 (m, 2H), 7.36-7.26 (m, 2H), 7.21-7.15 (m, 1H), 7.13-7.01 (m, 2H), 6.84-6.75 (m, 1H), 5.86 (s, 2H), 3.62 (s, 3H), 3.38 (s, 3H), 2.97 (s, 3H); MS (ESP+) m/e 456 (MH+); TLC (EtOAc:hexanes/3:1) R$_f$=0.11.

EXAMPLE 65

N-{3-[7-(2-chloro-6-fluorobenzyl)-1,3-dimethyl-2,6-dioxo-2,3,6,7-tetrahydro-1H-purin-8-yl]phenyl}-2,2,2-trifluoroacetamide

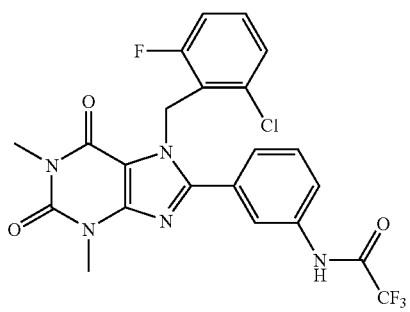

A solution of 8-(3-aminophenyl)-7-(2-chloro-6-fluorobenzyl)-1,3-dimethyl-3,7-dihydro-1H-purine-2,6-dione (20 mg, 0.05 mmol) in 213 μL CH$_2$Cl$_2$ was treated with trifluoroacetic anhydride (7.8 μL, 0.06 mmol). The reaction was stirred for 1.5 hr and then blown dry under nitrogen. The crude product was purified by preparative thin layer chromatography (silica gel, 1 mm plate, EM Science 20×20 cm silica gel 60 F$_{264}$) eluting with EtOAc:hexane (2:1) to give 18 mg (72% yield) of the title compound as a white solid: $^1$H NMR (CDCl$_3$, 400 MHz) 8.16 (s, 1H), 7.74-7.65 (m, 2H), 7.41 (t, 1H, J=8.1 Hz), 7.35-7.30 (m, 1H), 7.14-7.01 (m, 2H), 6.83-6.75 (m, 1H), 5.88 (s, 2H), 3.62 (s, 3H), 3.39 (s, 3H), 2.97 (s, 3H); MS (ESP+) m/e 510 (MH+); TLC (EtOAc:hexanes/3:1) R$_f$=0.68.

EXAMPLE 66

[7-(2-Chloro-6-fluorobenzyl)-1-ethyl-2,6-dioxo-8-piperidin-1-yl-1,2,6,7-tetrahydro-3H-purin-3-yl]acetic acid

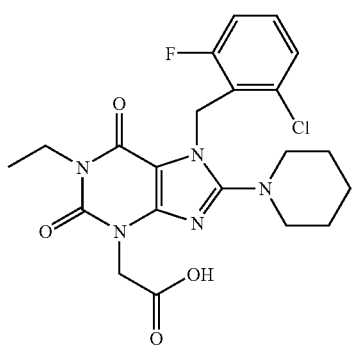

A solution of tert-butyl [7-(2-chloro-6-fluorobenzyl)-1-ethyl-2,6-dioxo-8-piperidin-1-yl-1,2,6,7-tetrahydro-3H-purin-3-yl]acetate (24 mg, 0.046 mmol) in 230 μL CH$_2$Cl$_2$ was treated with 230 μL TFA. The reaction was stirred at room temperature for 1 hr and then the solvent was removed by reduced pressure. The crude product was filtered through a silica plug and rinsed with 20% MeOH/EtOAc. The solvent was removed affording the title compound (19 mg, 90% yield) as a white solid: $^1$H NMR (CDCl$_3$, 400 MHz) 7.22-7.16 (m, 1H), 7.14-7.10 (m, 1H), 6.98-6.91 (m, 1H), 5.51 (s, 2H), 4.80 (s, 2H), 3.95 (q, 2H, J=7.0 Hz), 3.11-3.01 (m, 4H), 1.54-1.41 (m, 6H), 1.12 (t, 3H, J=7.0 Hz); MS (ESP+) m/e 464 (MH+).

EXAMPLE 67

3-[7-(2-Chloro-6-fluorobenzyl)-3-isopropyl-2,6-dioxo-8-piperidin-1-yl-2,3,6,7-tetrahydro-1H-purin-1-yl]propanoic acid

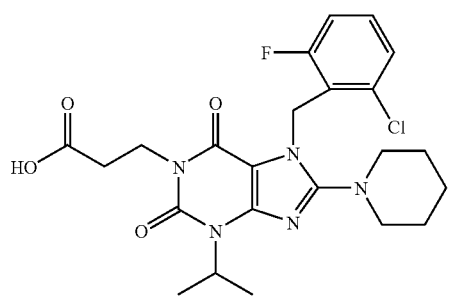

A solution of methyl 3-[7-(2-chloro-6-fluorobenzyl)-3-isopropyl-2,6-dioxo-8-piperidin-1-yl-2,3,6,7-tetrahydro-1H-purin-1-yl]propanoate (9 mg, 0.018 mmol) in 150 μTHF and 50 μL H$_2$O was treated with 18 μL 1 N LiOH. The reaction mixture was stirred at room temperature overnight and then treated with 18 μL 1 N acetic acid. The product was extracted into EtOAc and then the solvent was removed by reduced pressure. The crude product was purified by preparative thin layer chromatography (silica gel, 1 mm plate, EM Science 20×20 cm silica gel 60 F$_{264}$) eluting with 100% EtOAc to give 3 mg (13% yield) of the title compound as a clear oil: $^1$H NMR (CDCl$_3$, 400 MHz) 7.23-7.17 (m, 1H), 7.15-7.12 (m, 1H), 6.99-6.94 (m, 1H), 5.52 (s, 2H), 5.16-5.07 (m, 1H), 4.21 (t, 2H, J=6.9 Hz), 3.14-3.04 (m, 4H), 2.66 (t, 2H, J=6.9 Hz), 1.56-1.51 (m, 12H); MS (ESP+) m/e 492 (MH$^+$); TLC (EtOAc:hexanes/1:1) R$_f$=0.61.

EXAMPLE 69

Ethyl 1-[7-(2-chloro-6-fluorobenzyl)-1,3-dimethyl-2,6-dioxo-2,3,6,7-tetrahydro-1H-purin-8-yl]piperidine-3-carboxylate

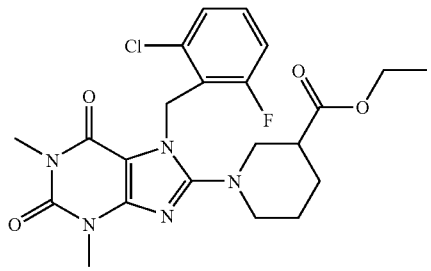

A solution of 8-bromo-7-(2-chloro-6-fluorobenzyl)-1,3-dimethyl-3,7-dihydro-1H-purine-2,6-dione (6.0 g, 0.015 mol) in 30 mL of DMSO was treated with (+/−)-ethyl piperidine-3-carboxylate (11.7 g, 0.075 mol) and heated at 100° C. for 15 h. The reaction was cooled to room temperature and treated with H$_2$O and CH$_2$Cl$_2$. The layers were separated, and the aqueous layer was extracted with CH$_2$Cl$_2$ (2×). The combined organic layers were washed with H$_2$O, dried over Na$_2$SO$_4$, filtered, and concentrated in vacuo. The crude product was purified by flash chromatography (silica gel, Merck 20×20 cm silica gel 60 F$_{254}$) eluting with 7:3/hexanes:EtOAc to give 6.33 g (88% yield) of the title compound: $^1$H NMR (CDCl$_3$, 400 MHz) δ 7.20 (dt, 2H, J=8.1, 5.7), 7.14 (t, 1H, J=7.6), 6.98-6.90 (m, 1H), 5.57 (AB quartet, 2H, J=15.7, 5.7), 4.18-4.00 (m, 2H), 3.51 (s, 3H), 3.42 (dd, 1H, J=12.6, 4.0), 3.30 (s, 3H), 3.18 (br d, 1H), 3.06 (dd, 1H, J=12.4, 10.0), 2.91-2.83 (m, 1H), 2.52-2.41 (m, 1H), 2.03-1.92 (m, 1H), 1.75-1.66 (m, 1H), 1.63-1.40 (m, 2H), 1.21 (t, 3H, J=7.1); LRMS (ESI) m/z 478 (M+H$^+$); TLC (hexanes:EtOAc/7:3) R$_f$=0.20.

EXAMPLE 70

1-[7-(2-Chloro-6-fluorobenzyl)-1,3-dimethyl-2,6-dioxo-2,3,6,7-tetrahydro-1H-purin-8-yl]piperidine-3-carboxylic acid

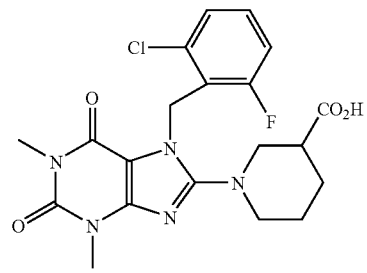

A solution of ethyl 1-[7-(2-chloro-6-fluorobenzyl)-1,3-dimethyl-2,6-dioxo-2,3,6,7-tetrahydro-1H-purin-8-yl]piperidine-3-carboxylate (5.0 g, 10.5 mmol) in 75 mL THF and 25 mL H$_2$O at room temperature was treated with solid LiOH (1.8 g, 43.9 mmol). After stirring overnight the THF was removed under reduced pressure, and the residue was diluted with H$_2$O. The aqueous layer was acidified to pH 4, and the aqueous layer was extracted with CH$_2$Cl$_2$. The combined extracts were concentrated under reduced pressure to give 4.9 g (>99% yield) of the title compound: $^1$H NMR (CDCl$_3$, 400 MHz) δ7.18 (dt, 2H, J=8.1, 5.7), 7.14 (t, 1H, J=7.6), 6.98-6.90 (m, 1H), 5.57 (AB quartet, 2H, J=15.7, 5.7), 3.51 (s, 3H), 3.42 (dd, 1H, J=12.6, 4.0), 3.30 (s, 3H), 3.20-3.05 (m, 2 H), 2.94-2.83 (m, 1H), 2.59-2.47 (m, 1H), 2.03-1.93 (m, 1H), 1.75-1.40 (m, 3H); LRMS (ESI) m/z 450 (M+H$^+$); TLC (hexanes:EtOAc/1:1) R$_f$=0.10.

EXAMPLE 71

1-[7-(2-Chloro-6-fluorobenzyl)-1,3-dimethyl-2,6-dioxo-2,3,6,7-tetrahydro-1H-purin-8-yl]-N-(2-hydroxyethyl)piperidine-3-carboxamide

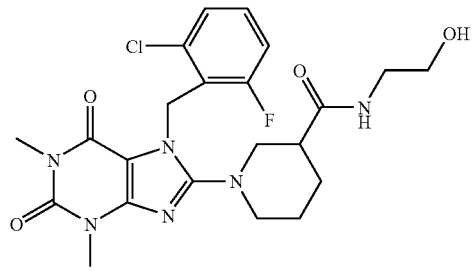

A solution of 1-[7-(2-chloro-6-fluorobenzyl)-1,3-dimethyl-2,6-dioxo-2,3,6,7-tetrahydro-1H-purin-8-yl]piperidine-3-carboxylic acid (30 mg, 0.066 mmol) in 1.0 mL of CH$_2$Cl$_2$ at room temperature was treated with polystyrene-carbodiimide (1.15 mmol/g, 104 mg, 0.12 mmol) and stirred for 30 min. The reaction mixture was treated with 2-aminoethanol (0.004 mL, 0.066 mmol), allowed to rotate overnight, filtered, and concentrated in vacuo. The crude product was purified by preparative TLC chromatography eluting with 5:5:1/hexanes:EtOAc:MeOH to give 11 mg (33% yield) of the title compound: $^1$H NMR (CDCl$_3$, 400 MHz) δ 7.26-7.14 (m, 2H), 7.00-6.93 (m, 1H), 6.17 (br s), 5.58 (d, 2H, J=1.5), 3.70 (t, 2H, J=5.1), 3.51 (s, 3H), 3.47-3.36 (m, 3H), 3.31 (s, 3H), 3.23 (br d, 1H, J=12.3), 3.12 (dd, 1H, J=12.8, 10.3), 2.97-2.88 (m, 1H), 2.42-2.32 (m, 1H), 1.94-1.86 (m, 1H), 1.82-1.45 (m, 4H); LRMS (ESI) m/z 493 (M+H⁺); TLC (hexanes:EtOAc:MeOH/5:5:1) R$_f$=0.12.

EXAMPLES 72-143

(Table 1) Were Prepared as in Example 71

TABLE 1

| Ex # | Structure | MH⁺ | HPLC purity | t$_r$ |
|---|---|---|---|---|
| 72 | 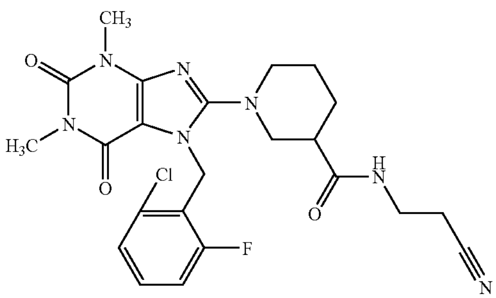 | 502 | 100 | 3.8 |
| 73 | 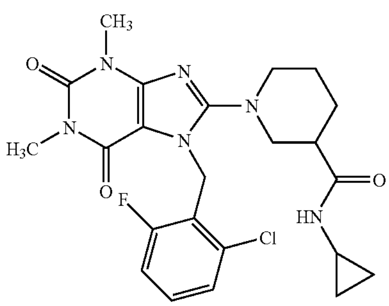 | 489 | 97 | 3.9 |
| 74 | 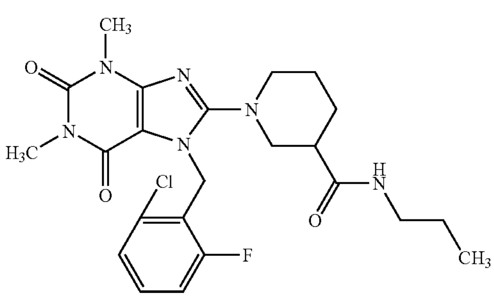 | 491 | 79 | 4.0 |
| 75 | 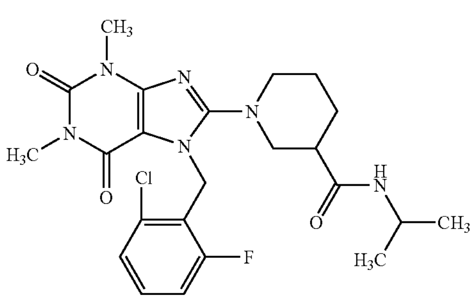 | 491 | 60 | 4.1 |

TABLE 1-continued

| Ex # | Structure | MH+ | HPLC purity | $t_r$ |
|---|---|---|---|---|
| 76 | 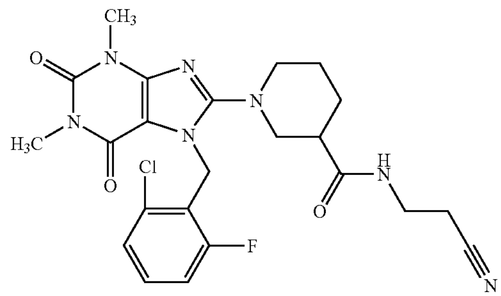 | 502 | 90 | 3.7 |
| 77 | 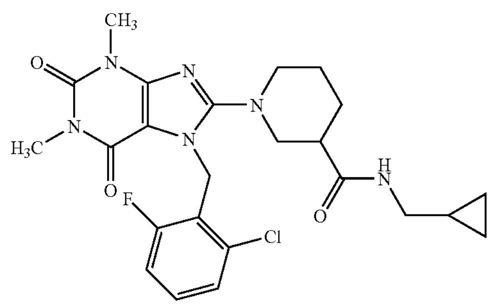 | 503 | 100 | 4.1 |
| 78 | 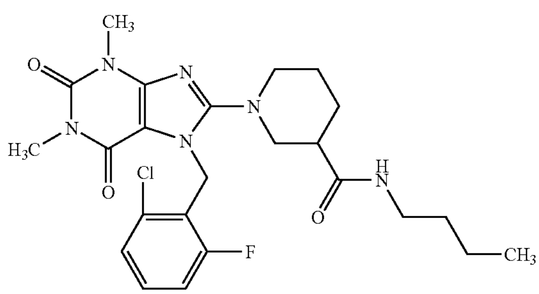 | 505 | 100 | 4.2 |
| 79 | 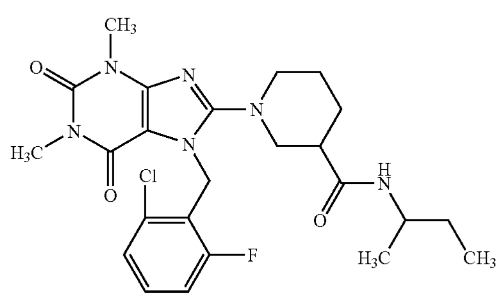 | 505 | 80 | 4.1 |
| 80 | 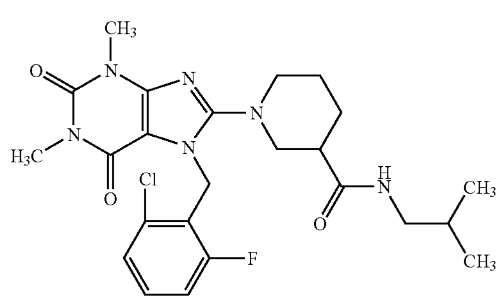 | 505 | 98 | 4.2 |

TABLE 1-continued

| Ex # | Structure | MH+ | HPLC purity | t_r |
|---|---|---|---|---|
| 81 | 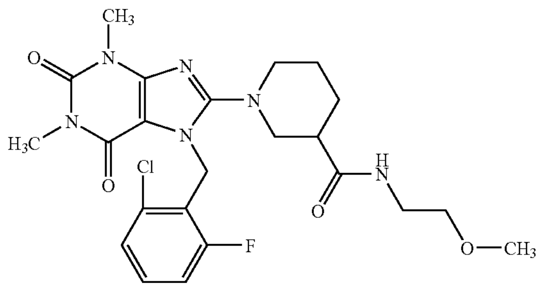 | 507 | 100 | 3.9 |
| 82 | 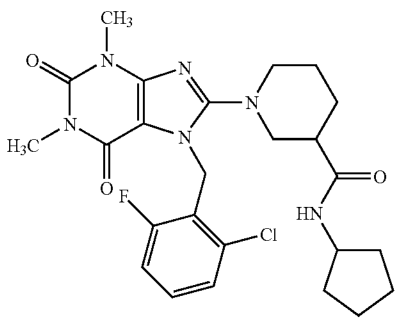 | 517 | 98 | 4.2 |
| 83 | 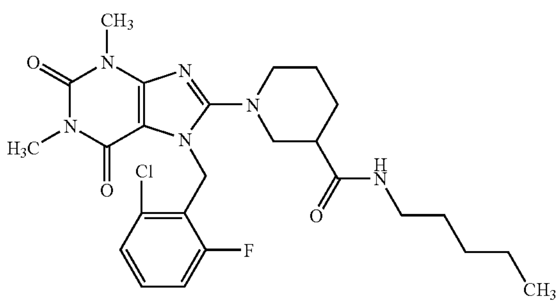 | 519 | 100 | 4.3 |
| 84 | 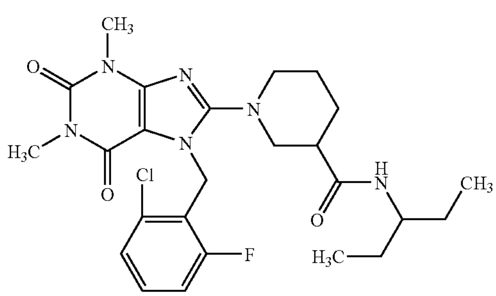 | 519 | 100 | 4.3 |
| 85 | 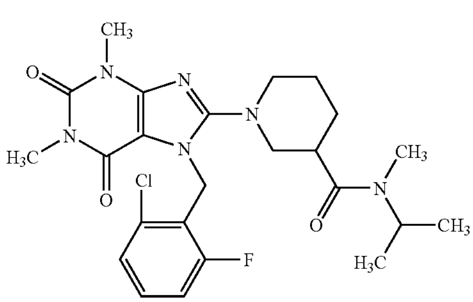 | 505 | 40 | 4.2 |

TABLE 1-continued

| Ex # | Structure | MH+ | HPLC purity | $t_r$ |
|---|---|---|---|---|
| 86 | 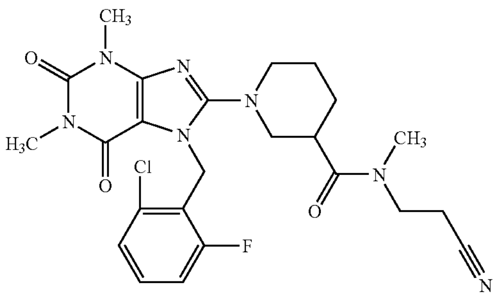 | 516 | 100 | 3.8 |
| 87 | 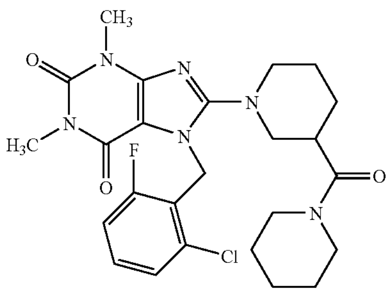 | 517 | 100 | 4.3 |
| 88 | 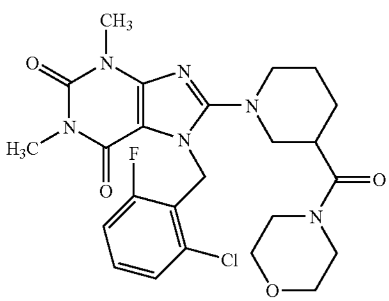 | 519 | 100 | 3.9 |
| 89 | 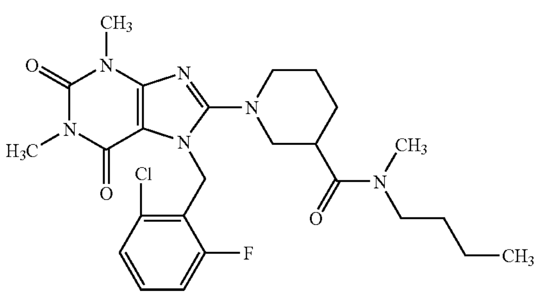 | 519 | 100 | 4.4 |
| 90 | 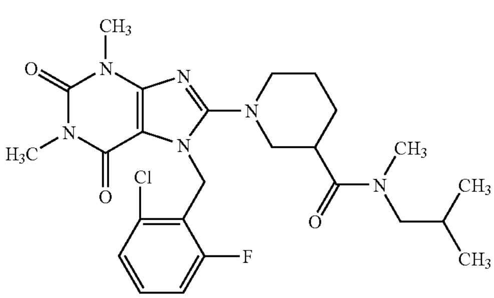 | 519 | 70 | 4.4 |

TABLE 1-continued

| Ex # | Structure | MH+ | HPLC purity | $t_r$ |
|---|---|---|---|---|
| 91 | 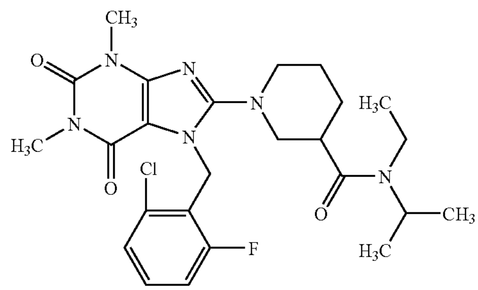 | 519 | 40 | 4.4 |
| 92 | 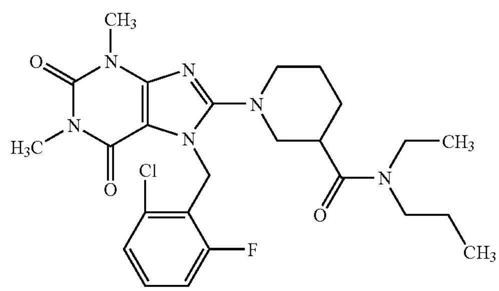 | 519 | 72 | 4.3 |
| 93 | 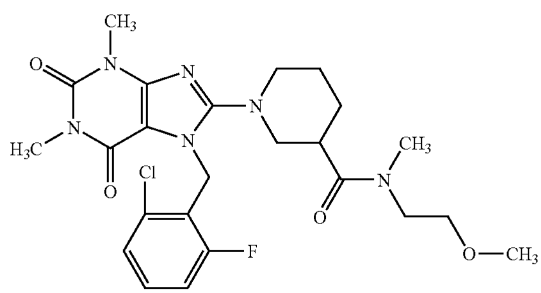 | 521 | 100 | 4.0 |
| 94 | 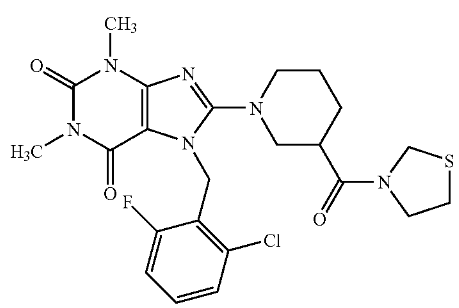 | 521 | 80 | 4.1 |
| 95 | 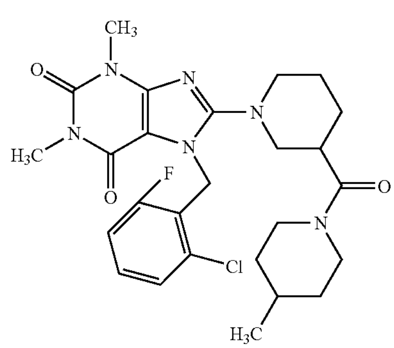 | 531 | 100 | 4.4 |

TABLE 1-continued

| Ex # | Structure | MH+ | HPLC purity | t_r |
|---|---|---|---|---|
| 96 | 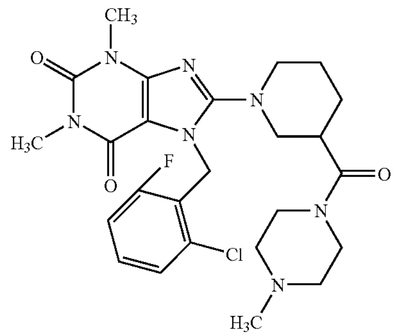 | 532 | 100 | 2.8 |
| 97 | 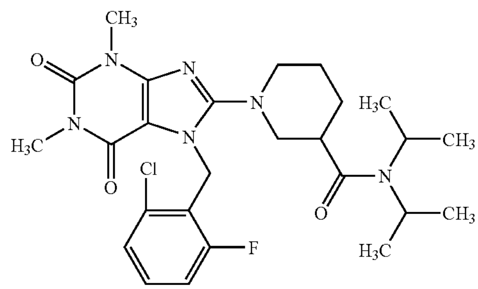 | 533 | 68 | 5.5 |
| 98 | 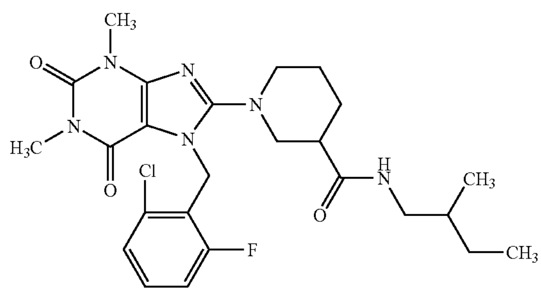 | 519 | 100 | 4.3 |
| 99 | 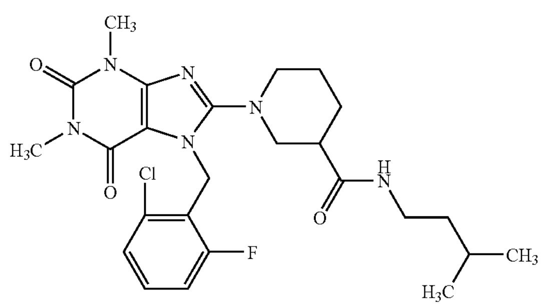 | 519 | 100 | 4.4 |
| 100 | 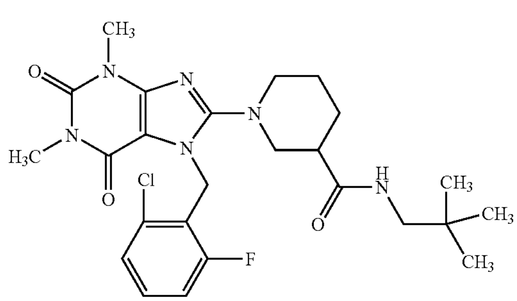 | 519 | 100 | 4.3 |

TABLE 1-continued

| Ex # | Structure | MH+ | HPLC purity | $t_r$ |
|---|---|---|---|---|
| 101 | 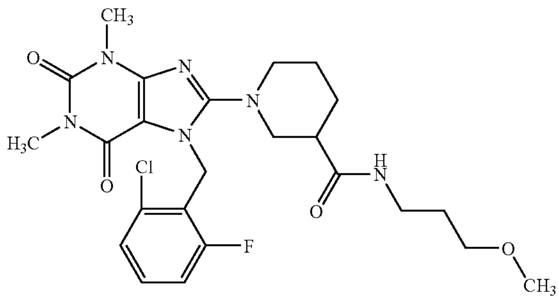 | 521 | 90 | 3.9 |
| 102 | 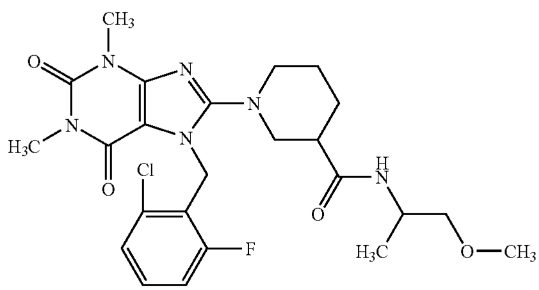 | 521 | 100 | 4.0 |
| 103 | 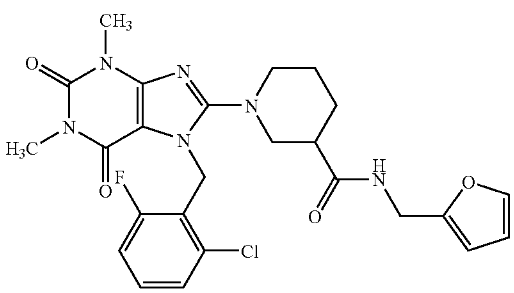 | 529 | 100 | 4.0 |
| 104 | 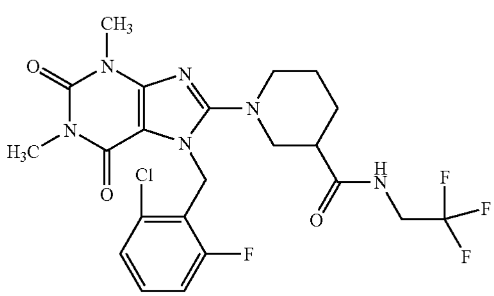 | 531 | 2 | 4.1 |
| 105 | 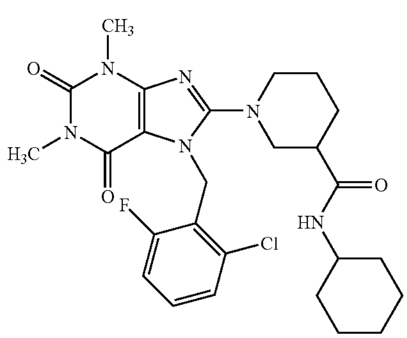 | 531 | 100 | 4.4 |

TABLE 1-continued

| Ex # | Structure | MH+ | HPLC purity | $t_r$ |
|---|---|---|---|---|
| 106 | 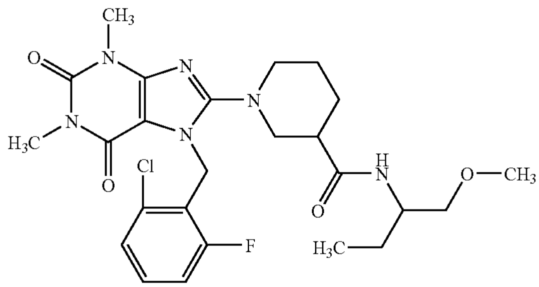 | 535 | 100 | 4.1 |
| 107 | 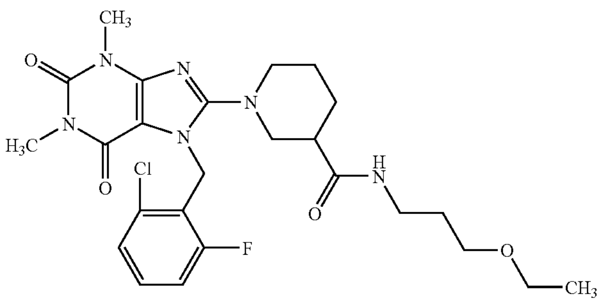 | 535 | 100 | 4.1 |
| 108 | 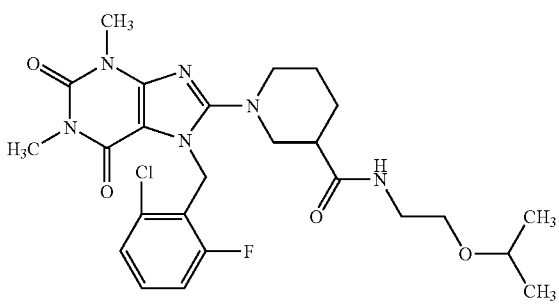 | 535 | 100 | 4.1 |
| 109 | 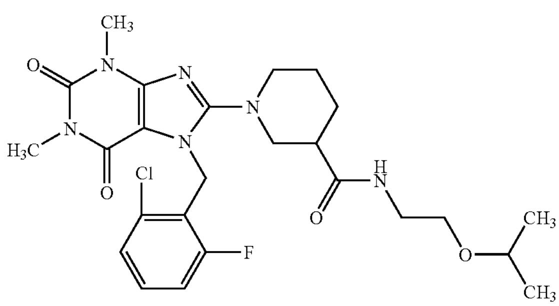 | 545 | 100 | 4.1 |
| 110 | 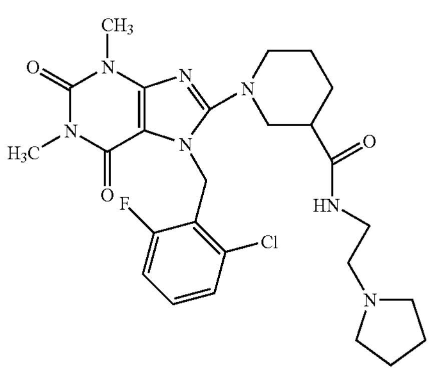 | 546 | 80 | 2.9 |

TABLE 1-continued

| Ex # | Structure | MH+ | HPLC purity | $t_r$ |
|---|---|---|---|---|
| 111 | 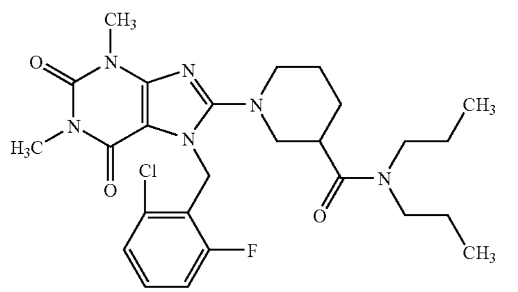 | 533 | 99 | 4.5 |
| 112 | 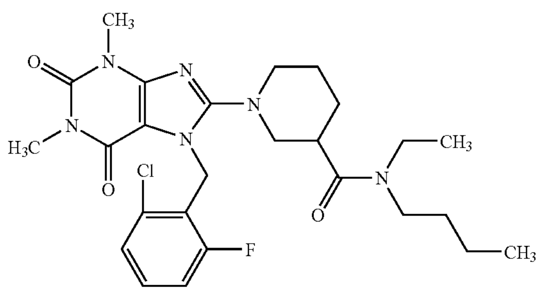 | 533 | 40 | 4.5 |
| 113 | 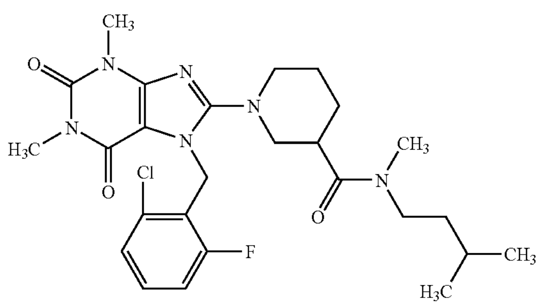 | 533 | 93 | 4.5 |
| 114 | 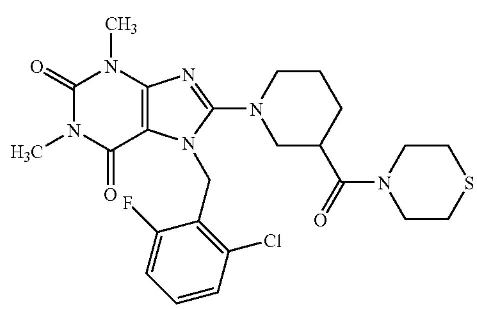 | 535 | 100 | 4.2 |
| 115 | 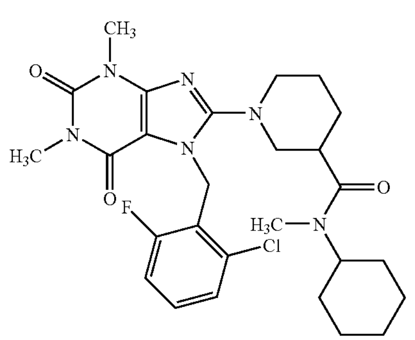 | 545 | 100 | 4.5 |

TABLE 1-continued

| Ex # | Structure | MH+ | HPLC purity | $t_r$ |
|---|---|---|---|---|
| 116 | 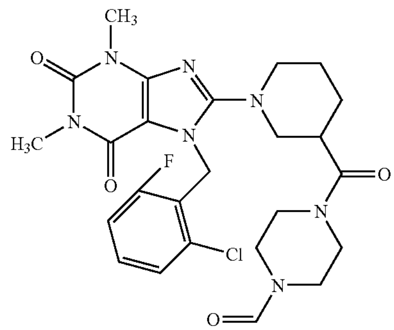 | 546 | 83 | 3.7 |
| 117 | 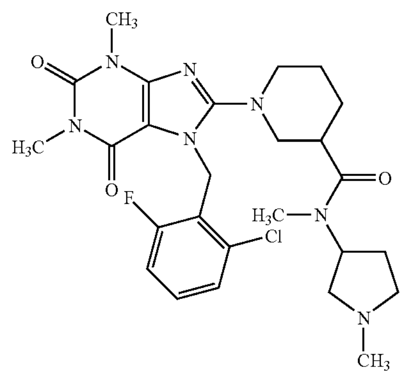 | 546 | 100 | 2.9 |
| 118 | 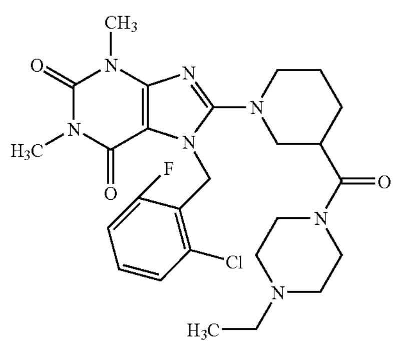 | 546 | 100 | 2.8 |
| 119 | 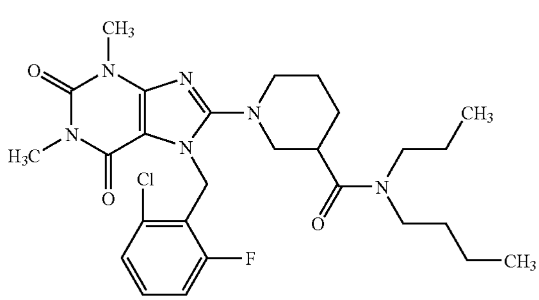 | 547 | 100 | 4.6 |

TABLE 1-continued

| Ex # | Structure | MH+ | HPLC purity | t_r |
|---|---|---|---|---|
| 120 | 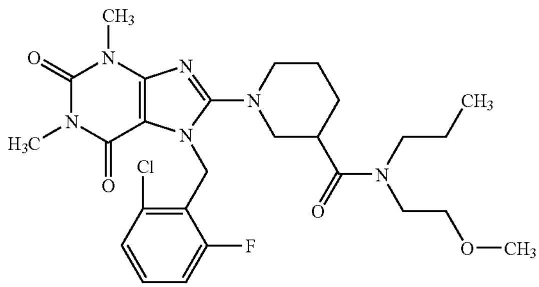 | 549 | 97 | 4.3 |
| 121 | 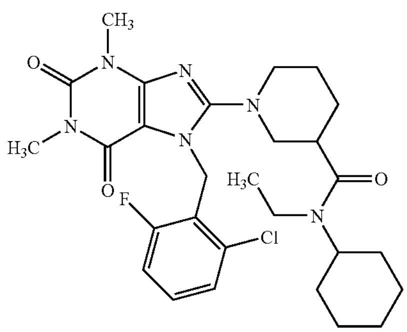 | 559 | 93 | 4.6 |
| 122 | 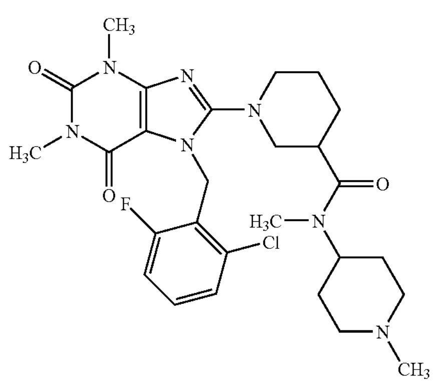 | 560 | 90 | 2.9 |
| 123 | 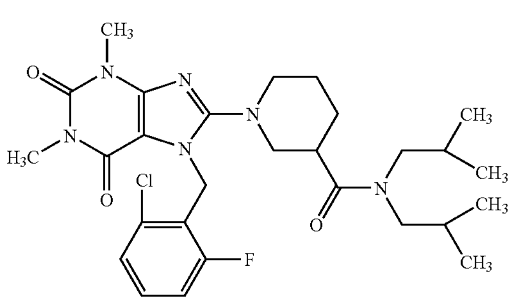 | 561 | 100 | 4.7 |

TABLE 1-continued

| Ex # | Structure | MH+ | HPLC purity | $t_r$ |
|---|---|---|---|---|
| 124 | 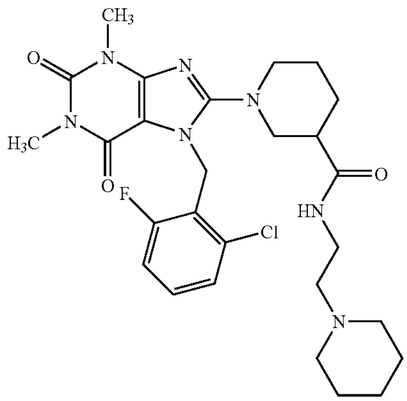 | 560 | 80 | 3.0 |
| 125 | 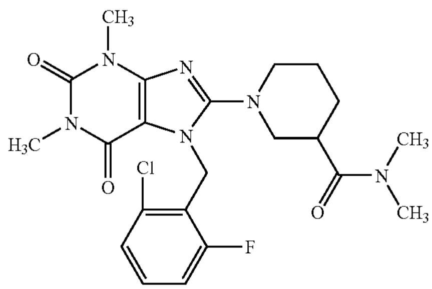 | 477 | 100 | 3.9 |
| 126 | 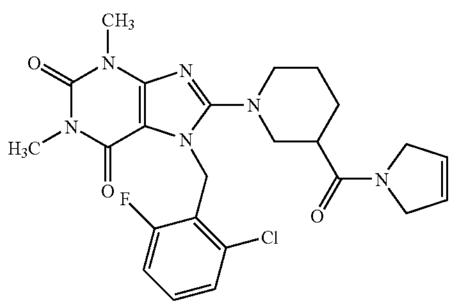 | 501 | 100 | 5.2 |
| 127 | 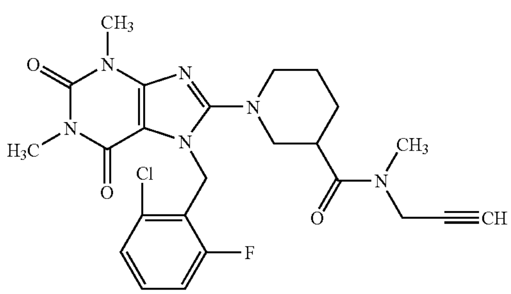 | 501 | 50 | 5.2 |
| 128 | 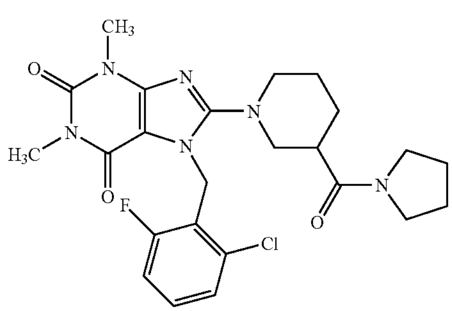 | 503 | 80 | 4.1 |

TABLE 1-continued

| Ex # | Structure | MH+ | HPLC purity | t_r |
|---|---|---|---|---|
| 129 | 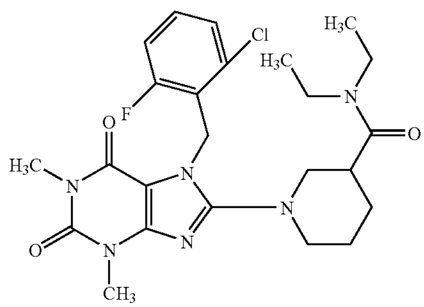 | 505 | 98 | 4.2 |
| 130 | 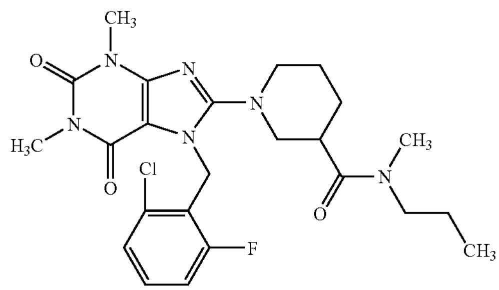 | 505 | 0 | 4.2 |
| 131 | 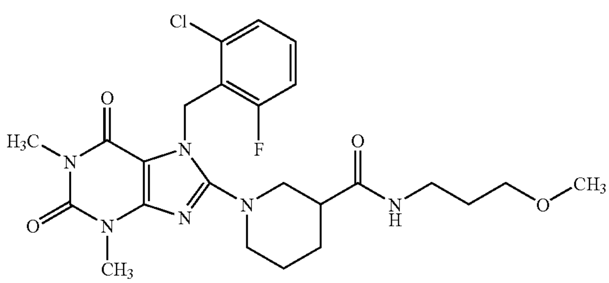 | 521 | 100 | 3.9 |
| 132 | 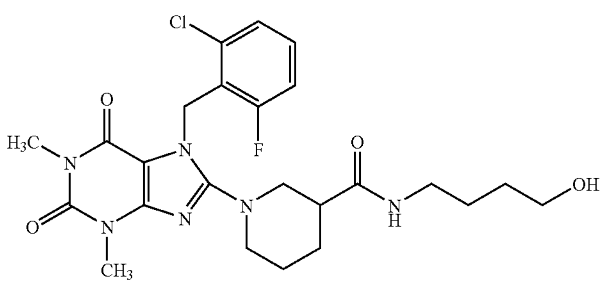 | 521 | 97 | 3.7 |
| 133 | 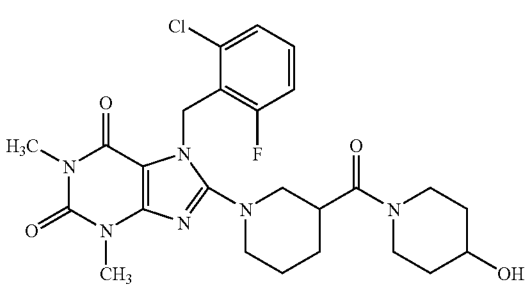 | 533 | 100 | 3.8 |

TABLE 1-continued

| Ex # | Structure | MH+ | HPLC purity | t_r |
|---|---|---|---|---|
| 134 | 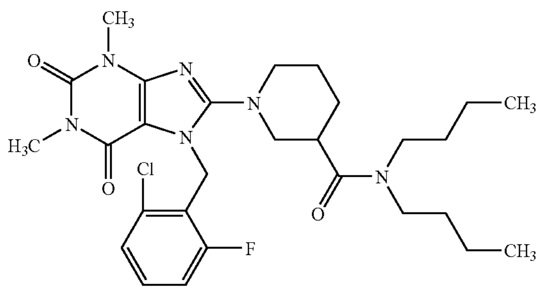 | 561 | 100 | 4.7 |
| 135 | 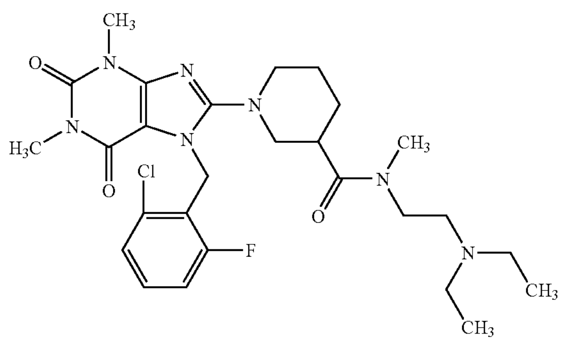 | 562 | 89 | 2.9 |
| 136 | 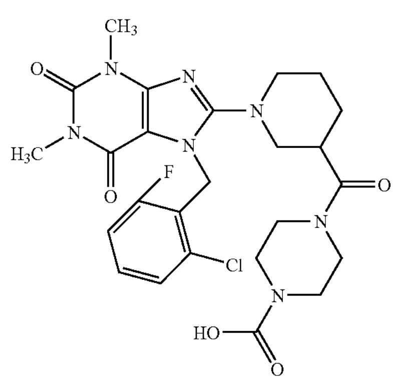 | 562 | 100 | 3.7 |
| 137 | 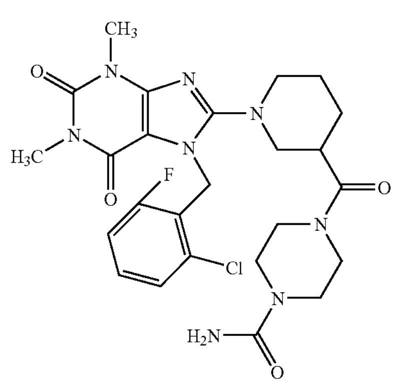 | 560 | 100 | 3.7 |

TABLE 1-continued

| Ex # | Structure | MH+ | HPLC purity | t_r |
|---|---|---|---|---|
| 138 | 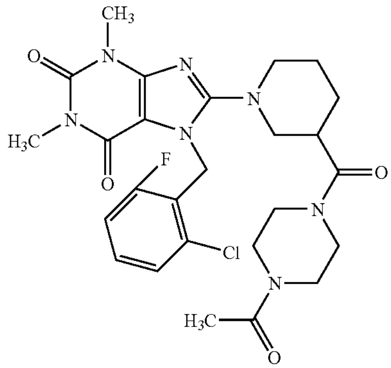 | 560 | 100 | 3.7 |
| 139 | 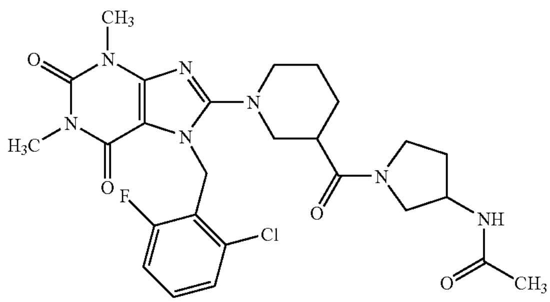 | 560 | 100 | 3.7 |
| 140 | 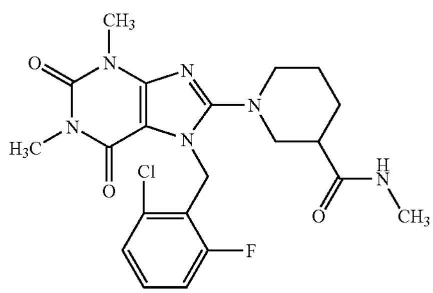 | 463 | 100 | 3.8 |
| 141 | 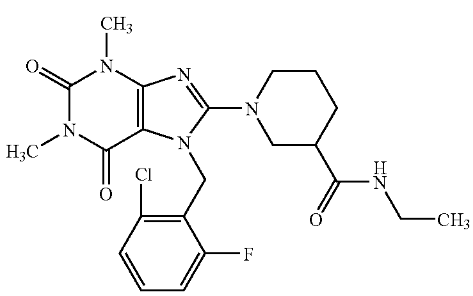 | 477 | 100 | 3.9 |
| 142 | 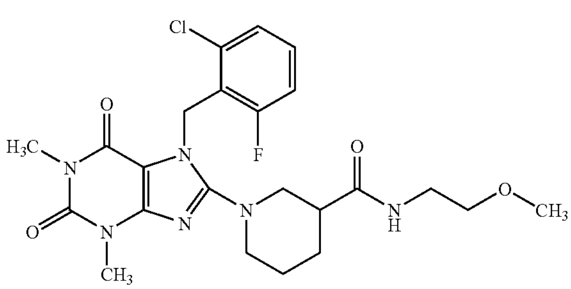 | 507 | 100 | 3.9 |

TABLE 1-continued

| Ex # | Structure | MH+ | HPLC purity | t$_r$ |
|---|---|---|---|---|
| 143 | 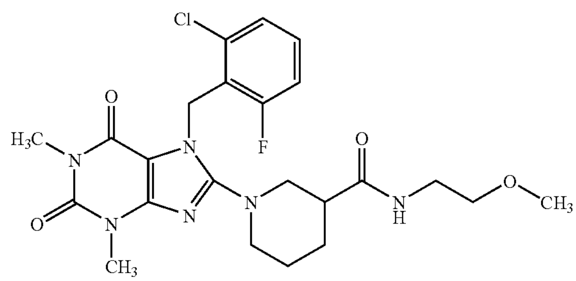 | 507 | 100 | 3.7 |

EXAMPLE 144

7-(2-Chloro-6-fluorobenzyl)-1,3-dimethyl-8-pyrrolidin-1-yl-3,7-dihydro-1H-purine-2,6-dione

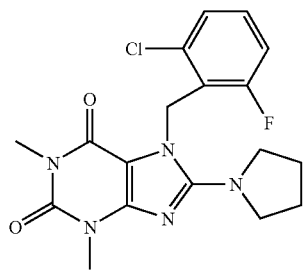

A solution of 8-bromo-7-(2-chloro-6-fluorobenzyl)-1,3-dimethyl-3,7-dihydro-1H-purine-2,6-dione (50 mg, 0.12 mmol) in 300 μL DMSO was treated with pyrrolidine (55 μL, 0.55 mmol) and heated at 130° C. for 15 h. The reaction was cooled to 25° C. and treated with 1 mL H$_2$O. After centrifugation for 1 h the liquid was decanted, and the process was repeated. The reaction was treated with 1 mL toluene and concentrated under reduced pressure. The residue was treated with 2 mL CH$_2$Cl$_2$ followed by isocyanate scavenger resin (500 mg, 0.58 mmol, 1.16 mmol/g). The reaction was filtered after agitating for 30 min, and the filtrate was concentrated under reduced pressure to give 48 mg (>99% yield) of the title compound: $^1$H NMR (CDCl$_3$, 300 MHz) 7.27-7.18 (m, 2H), 7.02-6.91 (m, 1H), 5.73 (s, 2H), 3.59-3.48 (m, 7H), 3.35 (s, 3H), 1.98-1.87 (m, 4H); MS (ESP+) m/e 392 (MH$^+$); TLC (EtOAc:hexanes/1:1) R$_f$=0.24.

EXAMPLES 145-721

Figure 1:
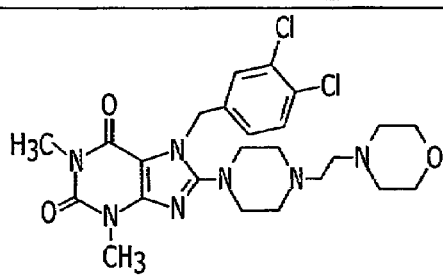
Figure 1A:
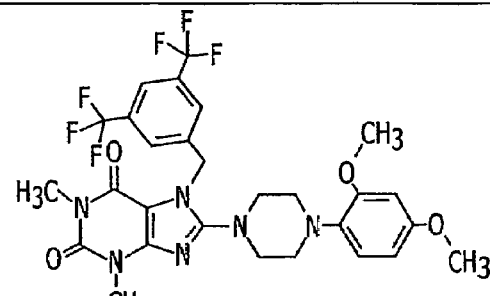
Figure 2:
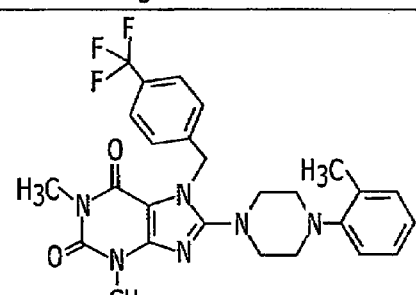
FIGS. 2A and 2B are tables reporting the biological activity of certain exemplified compounds. The table reports the LXRα data in pEC50 and as a percent of the control and LXRβ data in pEC50 and as a percent of control.
Figure 1I:
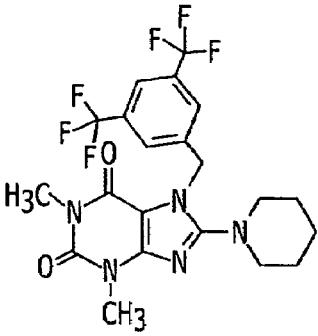
Figure 1:
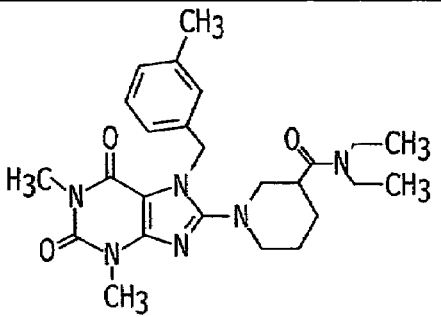
Figure 2:
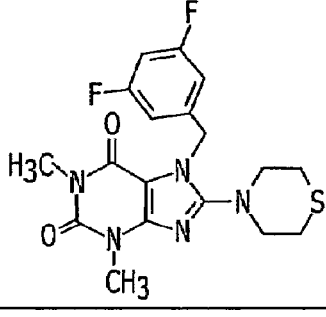
Figure 1J:
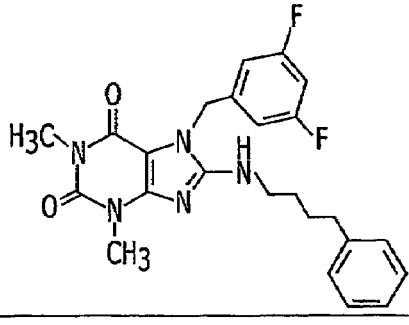
Figure 1M:
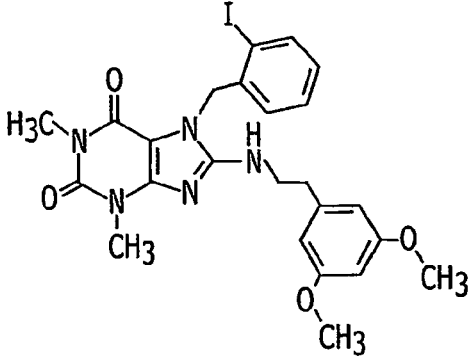
Figure 1:
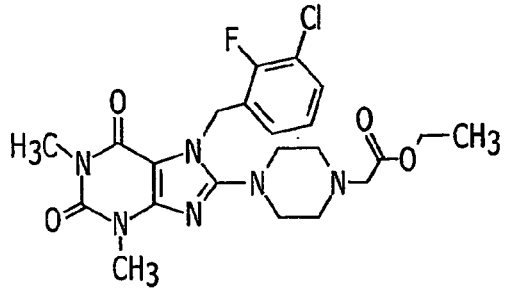
Figure 2:
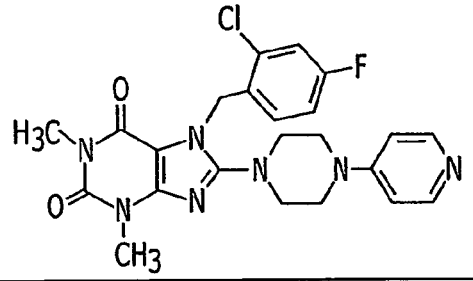
Figure 1N:
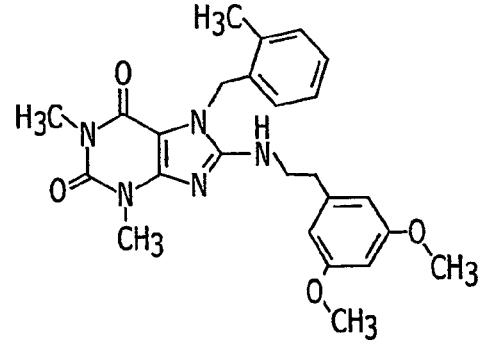
Figure 1N:
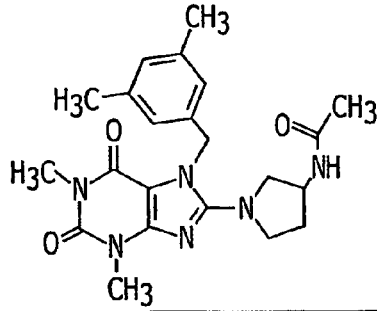
Figure 1:
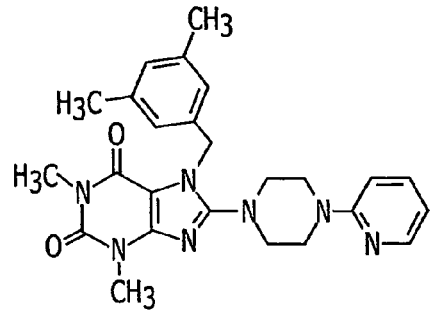
Figure 2:
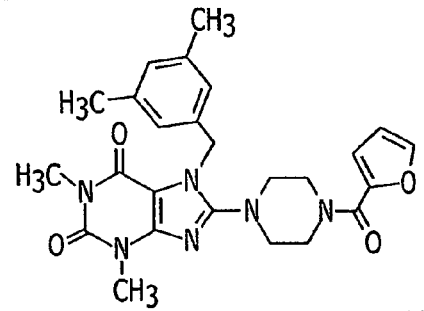
Figure 1O:
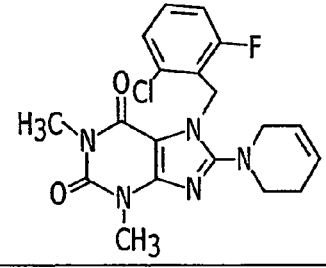
Figure 1Y:
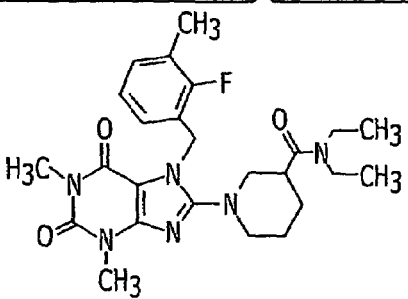
Figure 1:
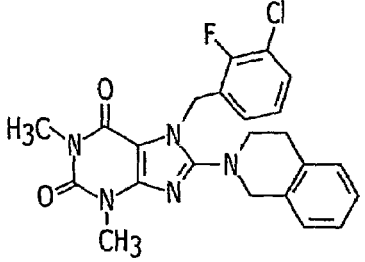
Figure 2:
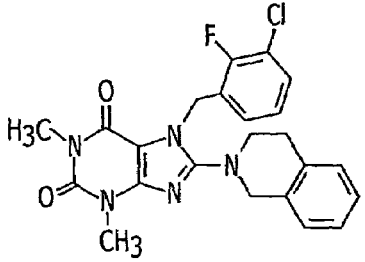
Figure 1Z:
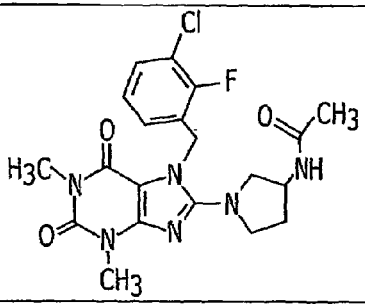
Figure 1A:
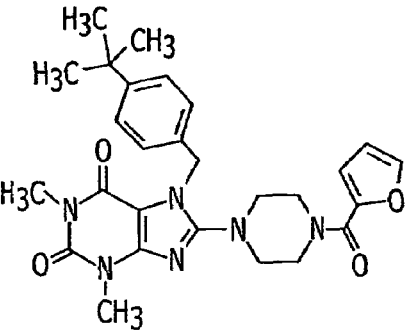
Figure 1:
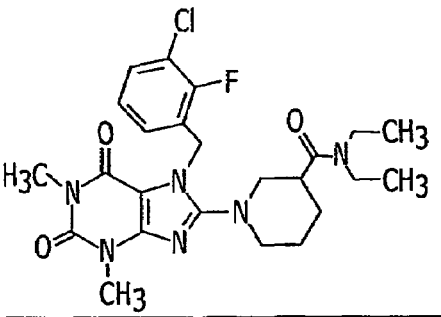
Figure 2:
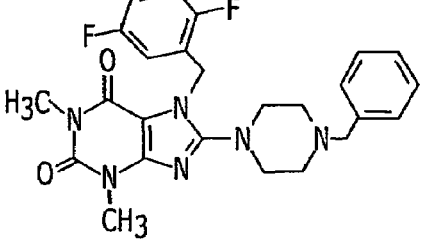
Figure 3:
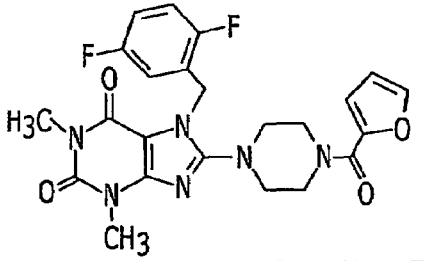
Figure 1B:
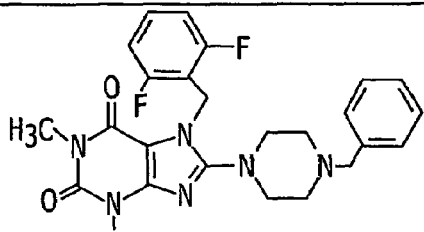
Figure 1B:
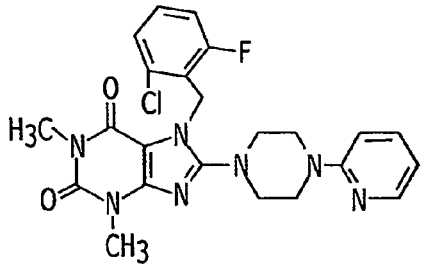
Figure 1:
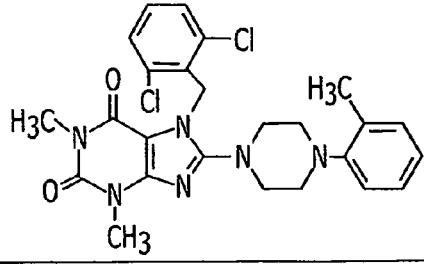
Figure 2:
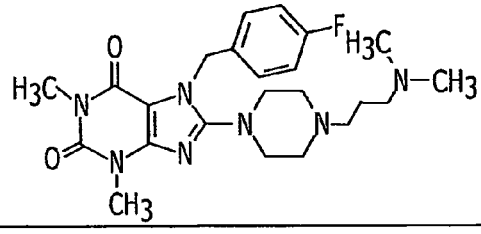
Figure 3:
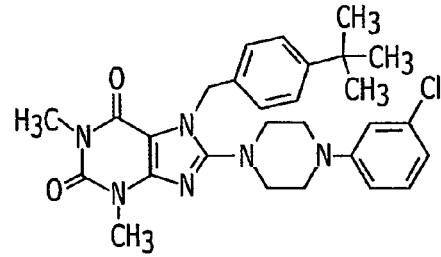
Figure 1C:
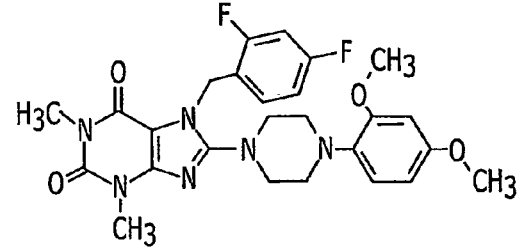
Figure 1C:
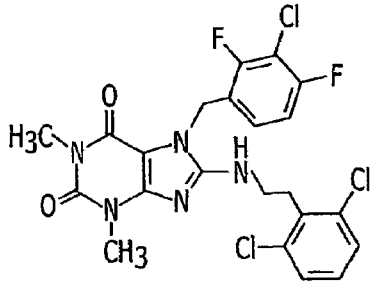
Figure 1:
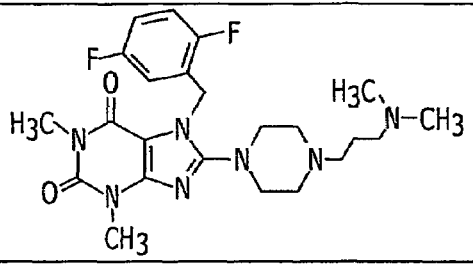
Figure 2:
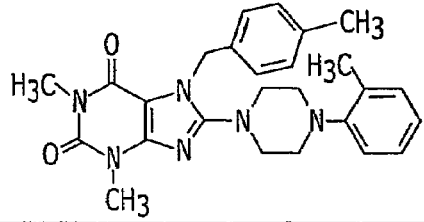
Figure 3:
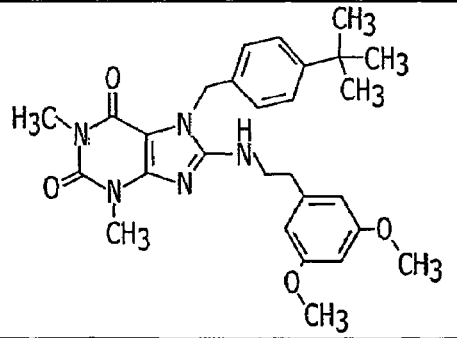
Figure 1D:
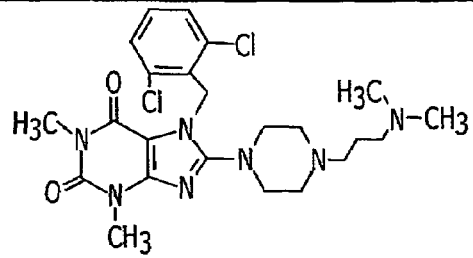
Figure 1F:
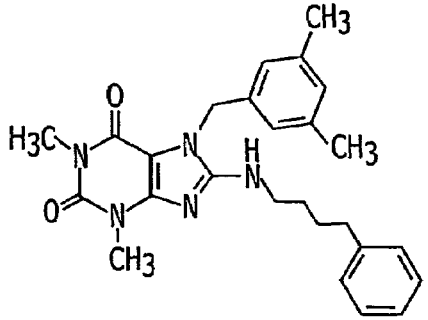
Figure 1:
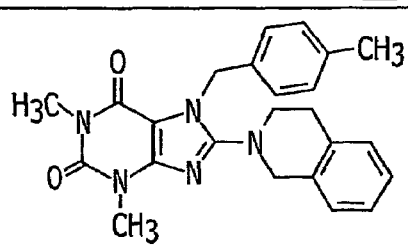
Figure 2:
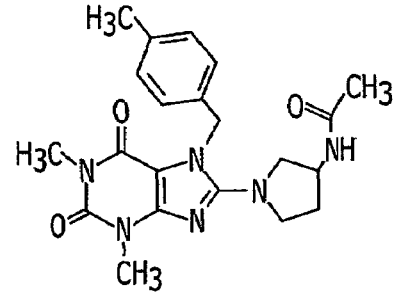
Figure 3:
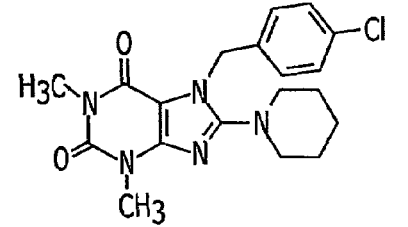
Figure 1G:
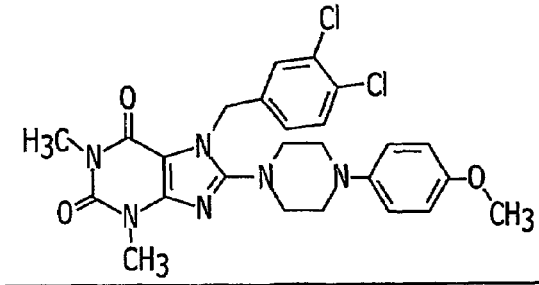
Figure 1G:
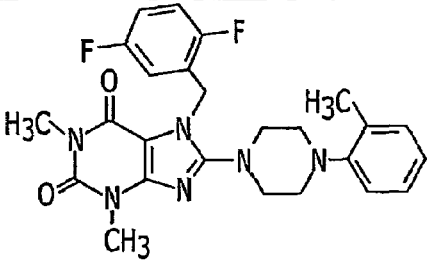
Figure 1:
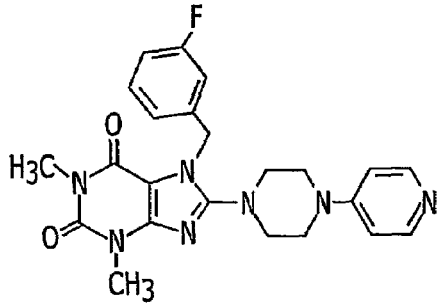
Figure 2:
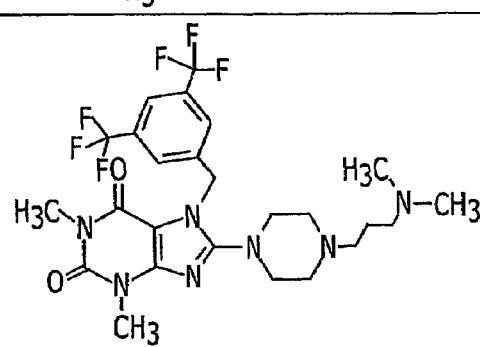
Figure 3:
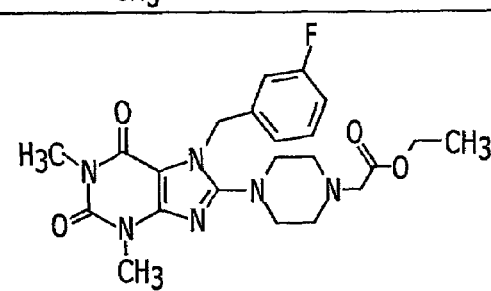
Figure 1H:
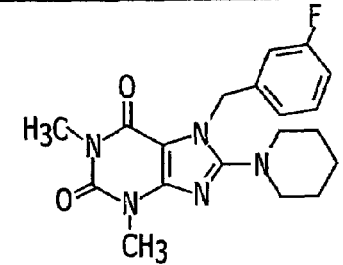
Figure 1I:
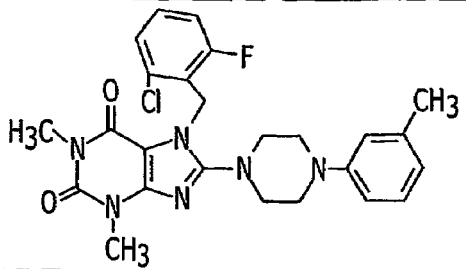
Figure 1:
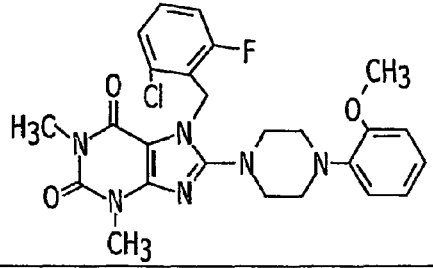
Figure 2:
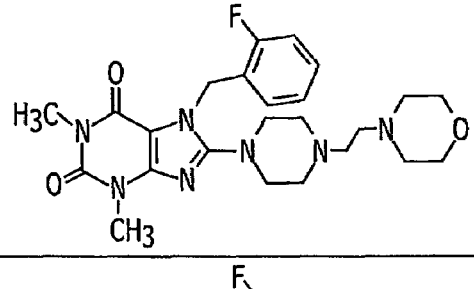
Figure 3:
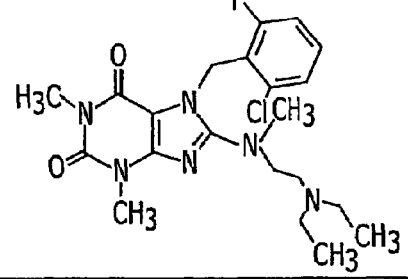
Figure 1J:
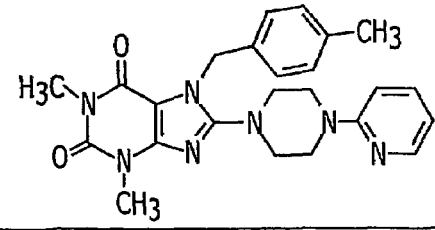
Figure 1L:
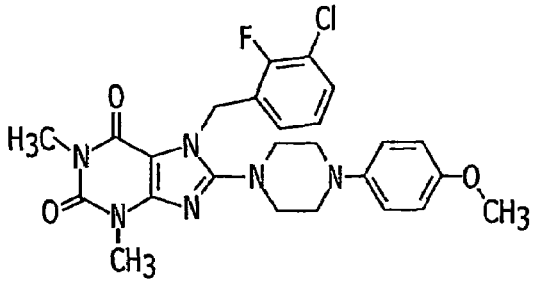
Figure 1:
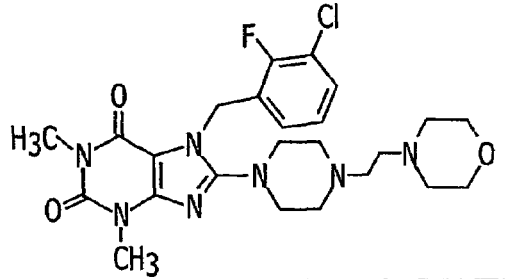
Figure 2:
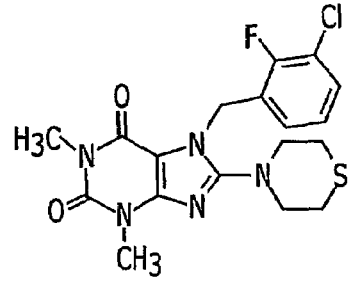
Figure 3:
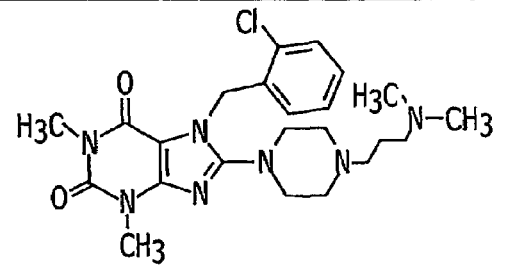
Figure 1M:
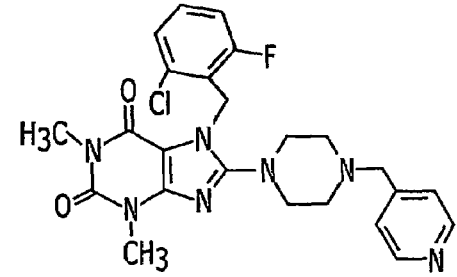
Figure 1M:
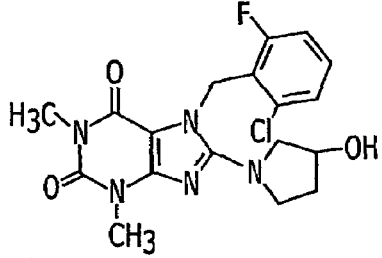
Figure 1:
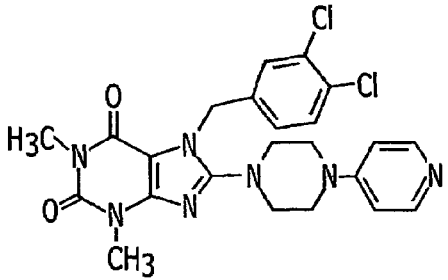
Figure 2:
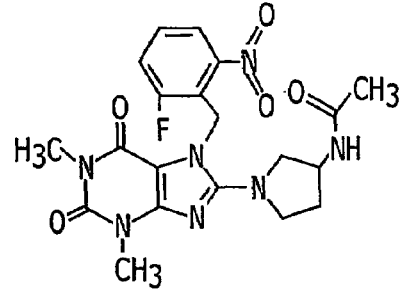
Figure 3:
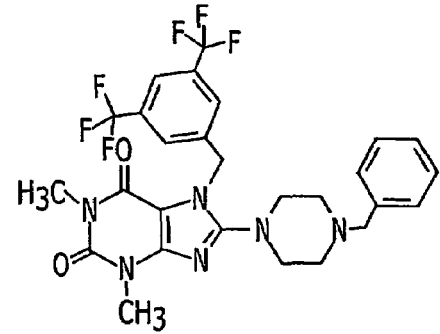
Figure 1N:
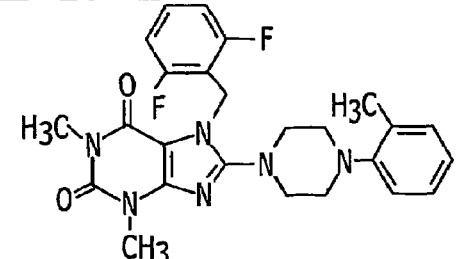
Figure 1P:
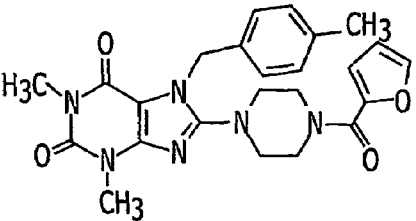
Figure 1:
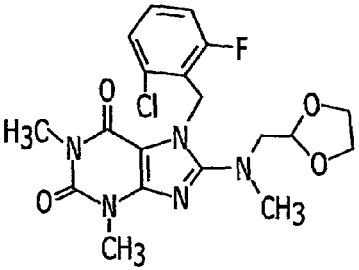
Figure 2:
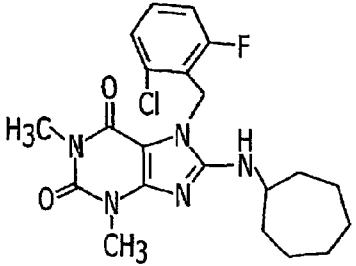
Figure 3:
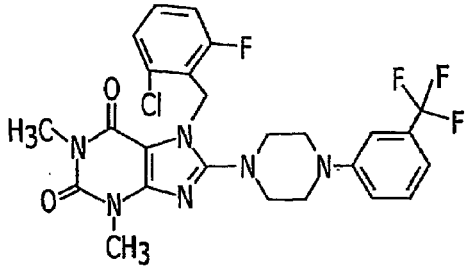
Figure 1Q:
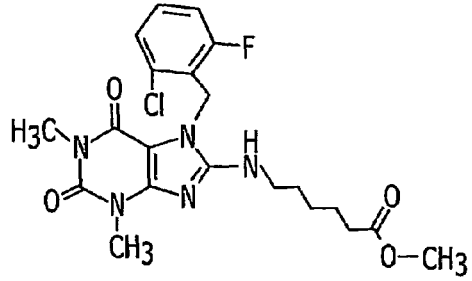
Figure 1Q:
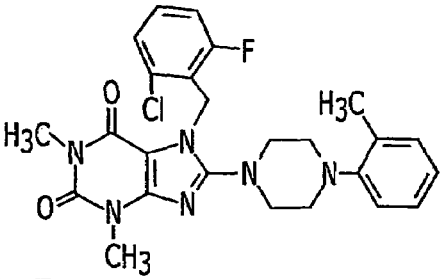
Figure 1:
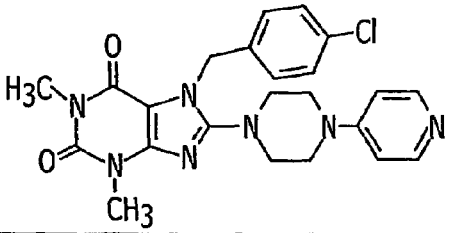
Figure 2:
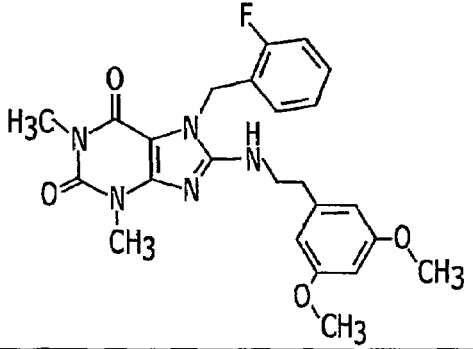
Figure 3:
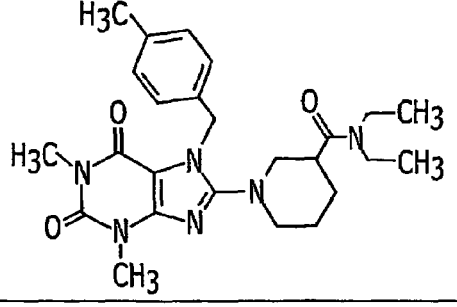
Figure 1R:
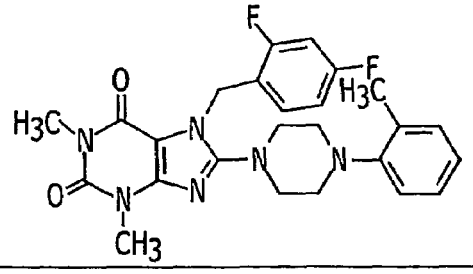
Figure 1R:
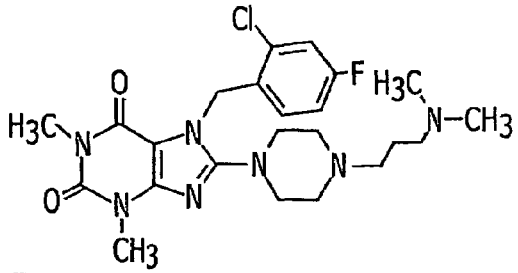
Figure 1:
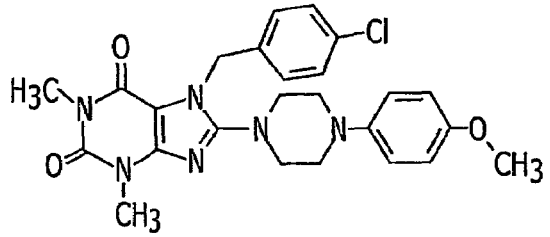
Figure 2:
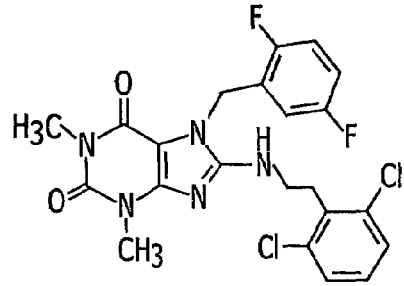
Figure 3:
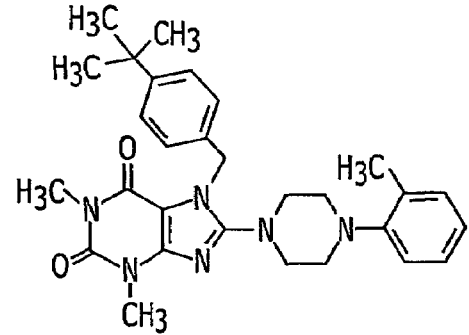
Figure 1S:
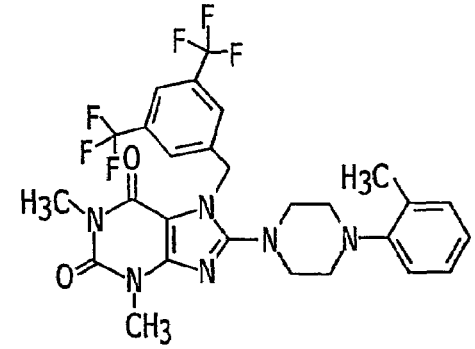
Figure 1T:
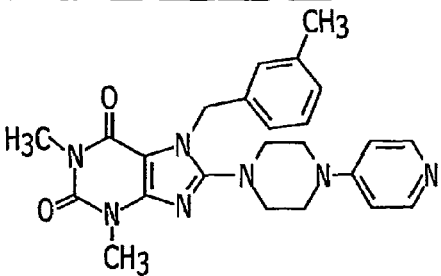
Figure 1:
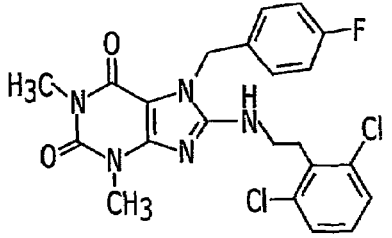
Figure 2:
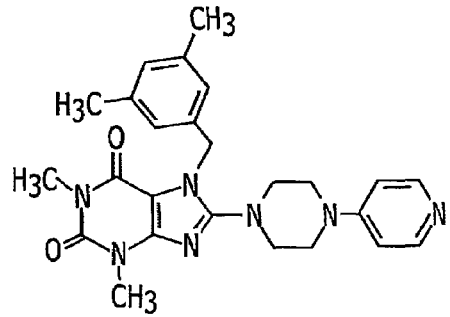
Figure 3:
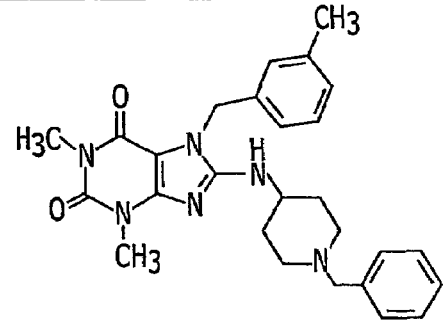
Figure 1U:
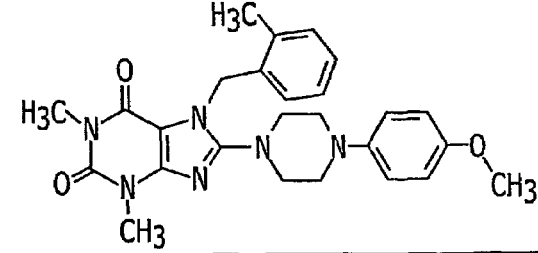
Figure 1U:
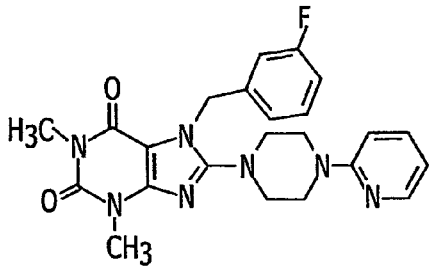
Figure 1:
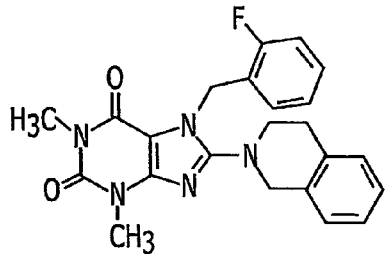
Figure 2:
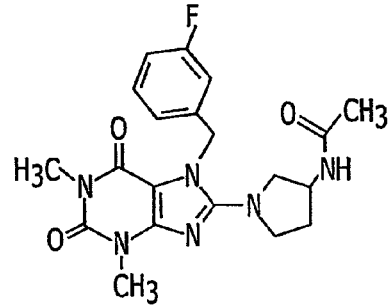
Figure 3:
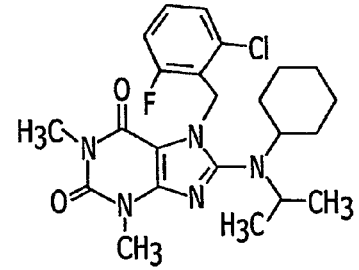
Figure 1V:
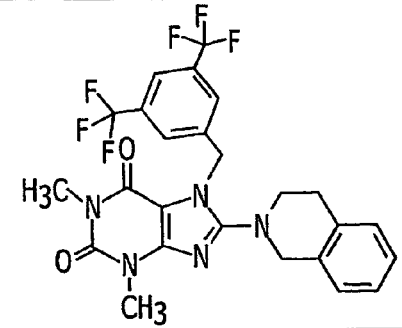
Figure 1V:
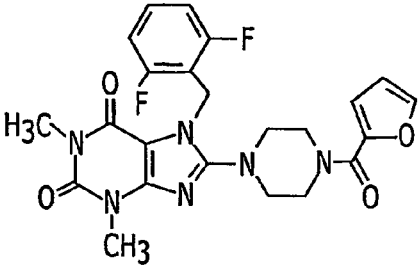
Figure 1:
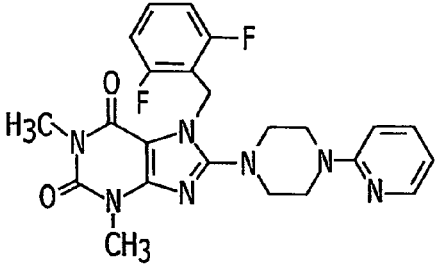
Figure 2:
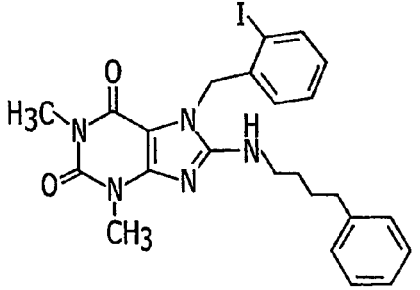
Figure 3:
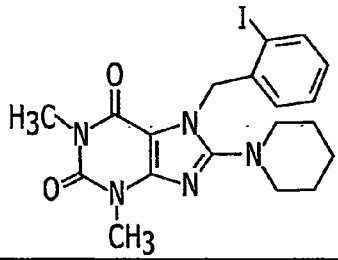
Figure 1W:
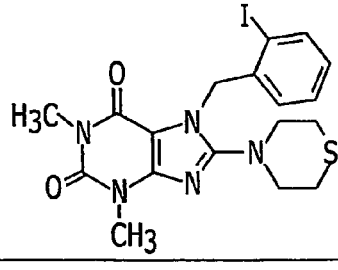
Figure 1W:
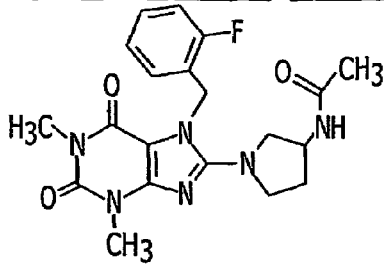
Figure 1:
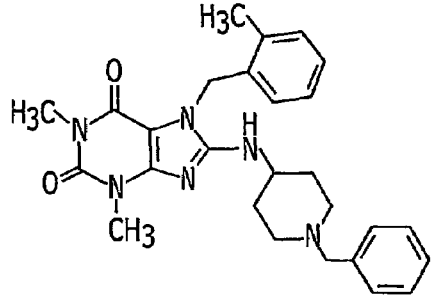
Figure 2:
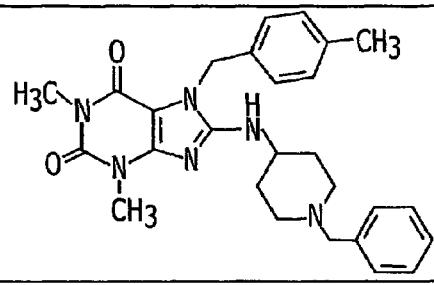
Figure 3:
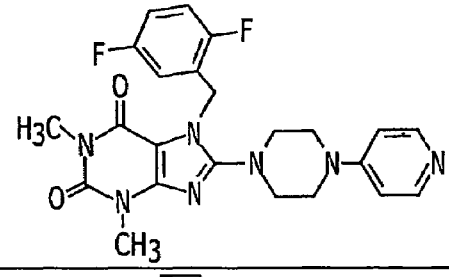
Figure 1X:
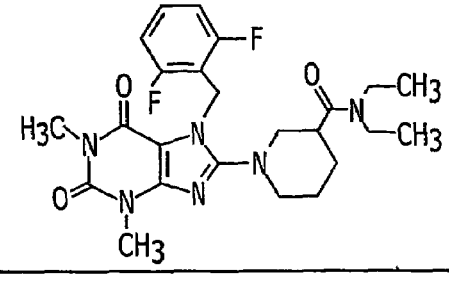
Figure 1X:
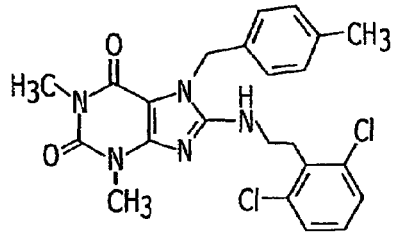
Figure 1:
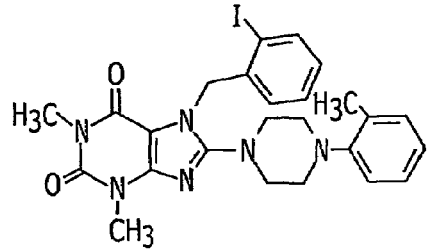
Figure 2:
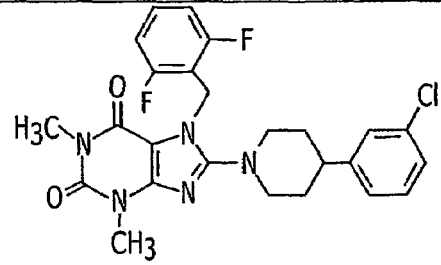
Figure 3:
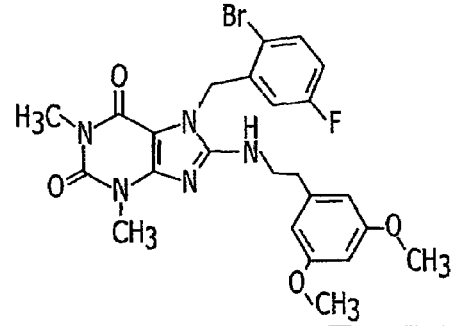
Figure 1Y:
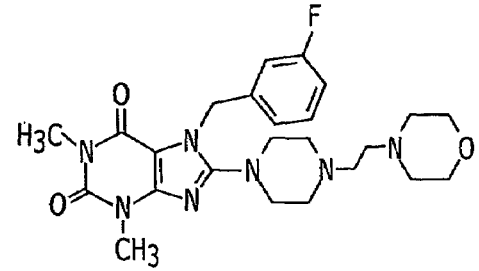
Figure 1Y:
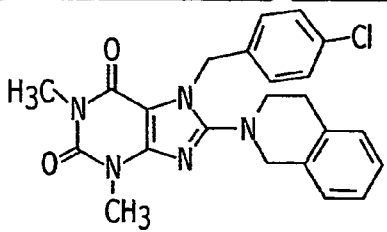
Figure 1:
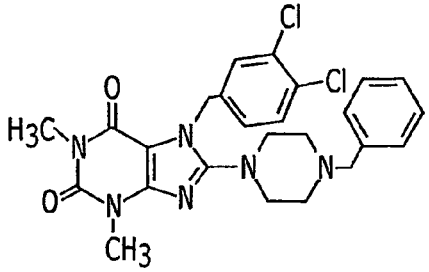
Figure 2:
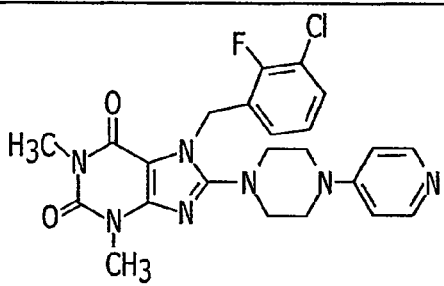
Figure 3:
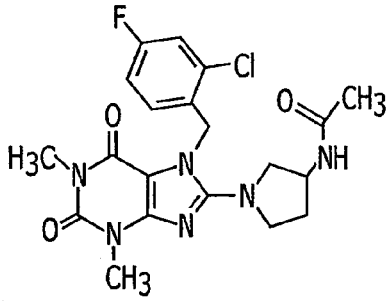
Figure 1Z:
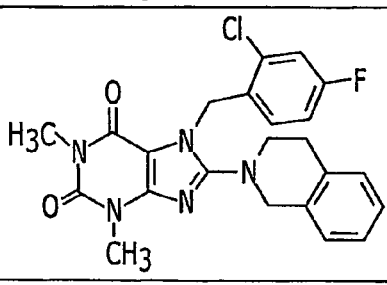

(FIG. 1) Were Prepared According to the Method Described in Example 144

Physical characterizing data is provided for each in MH+ and HPLC purity.

EXAMPLE 722

Assay for LXRβ Activity

A modified polyhistidine tag (MKKGHHHHHHG) (SEQ ID No. 1) was fused in frame to the human LXRβ ligand binding domain (amino acids 185-461 of Genbank accession number U07132) and subcloned into the expression vector pRSETa (Invitrogen) under the control of an IPTG inducible T7 promoter. The human LXRβ ligand binding domain was expressed in E. coli strain BL21 (DE3). Ten-liter fermentation batches were grown in Rich PO$_4$ media with 0.1 mg/mL Ampicillin at 25° C. for 12 hours, cooled to 9° C. and held at that temperature for 36 hours to a density of OD600=14. At this cell density, 0.25 mM IPTG was added and induction proceeded for 24 hours at 9° C., to a final OD600=16. Cells were harvested by centrifugation (20 minutes, 3500 g, 4° C.), and concentrated cell slurries were stored in PBS at −80° C.

Typically 25-50 g of cell paste is resuspended in 250-500 mL TBS, pH 8.0 (25 mM Tris, 150 mM NaCl). Cells are lysed by passing 3 times through an APV Rannie MINI-lab homogenizer, and cell debris is removed by centrifugation (30 minutes, 20,000 g, 4° C.). The cleared supernatant is filtered through coarse pre-filters, and TBS, pH 8.0, containing 500 mM imidazole is added to obtain a final imidazole concentration of 50 mM. This lysate is loaded onto a column (XK-26, 10 cm) packed with Sepharose [Ni++ charged] Chelation resin (available from Pharmacia) and pre-equilibrated with TBS pH 8.0/50 mM imidazole. After washing to baseline absorbance with equilibration buffer, the column is washed with approximately one column volume of TBS pH −8.0 containing 95 mM imidazole. LXRβLBD(185-461) is eluted with a gradient from 50 to 500 mM imidazole. Column peak fractions are pooled immediately and diluted 5 fold with 25 mM Tris pH 8.0, containing 5% 1,2-propanediol, 0.5 mM EDTA and 5 mM DTT. The diluted protein sample is then loaded onto a column (XK-16, 10 cm) packed with Poros HQ resin (anion exchange). After washing to baseline absorbance with the dilution buffer the protein is eluted with a gradient from 50-500 mM NaCl. Peak fractions are pooled and concentrated using Centri-prep 10K (Amicon) filter devices and subjected to size exclusion, using a column (XK-26, 90 cm) packed with Superdex-75 resin (Pharmacia) pre-equilibrated with TBS, pH 8.0, containing 5% 1,2-propanediol, 0.5 mM EDTA and 5 mM DTT.

LXRβ protein was diluted to approximately 10 microM in PBS and five-fold molar excess of NHS-LC-Biotin (Pierce) was added in a minimal volume of PBS. This solution was incubated with gentle mixing for 30 minutes at ambient room temperature. The biotinylation modification reaction was stopped by the addition of 2000× molar excess of Tris-HCl, pH 8. The modified LXRβ protein was dialyzed against 4 buffer changes, each of at least 50 volumes, PBS containing 5 mM DTT, 2 mM EDTA and 2% sucrose. The biotinylated LXRβ protein was subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from one to nine.

The biotinylated protein was incubated for 20-25 minutes at a concentration of 25 nM in assay buffer (50 mM KCl, 50 mM Tris-pH8, 0.1 mg/ml FAF-BSA, 10 mM DTT) with equimolar amounts of streptavidin-AlloPhycoCyanin (APC, Molecular Probes). At the same time, the biotinylated peptide comprising amino acids 675-699 of SRC-1 (CPSSHSS-LTERHKILHRLLQEGSPS-CONH2) (SEQ ID No. 2) at a concentration of 20 nM was incubated in assay buffer with a ½ molar amount of streptavidin-labelled Europium (Wallac) for 20-25 minutes. After the initial incubations are completed, a 10 molar excess (250 nM) of cold biotin was added to each of the solutions to block the unattached streptavidin reagents. After 20 min at room temp, the solutions were mixed yielding a concentration of 10 nM for the dye-labelled LXRβ protein and SRC-1 peptide. Representative data is shown in Tables 2A and 2B. Percentage control is relative to 24(S),25-epoxycholesterol.

In this assay 1 µM 24(S),25-epoxycholesterol gave a reading of 20000 fluorescence units over a background reading of 10000 fluorescence units.

EXAMPLE 723

Assay for LXRα Activity

The assay for LXRα was run according to the procedures of Example 1, above using his-tagged LXRα ligand binding domain (amino acids 183-447 of Genbank accession number U22662, with the 14$^{th}$ amino acid corrected to A from R). Representative data is shown in Tables 2A and 2B. Percentage control is relative to 24(S),25-epoxycholesterol.

In this assay 1 µM 24(S),25-epoxycholesterol gave a reading of 20000 fluorescence units over a background reading of 10000 fluorescence units.

EXAMPLE 724

Assay for ABC1 Expression in Macrophages

RAW 264.7 cells, obtained from ATCC, were grown in Dulbecco's Modified Eagle Media (DMEM, GIBCO) supplemented with 10% fetal bovine serum (FBS, Irvine Scientific), 2 mM glutamine (Irvine Scientific), 100 U penicillin/ml and 100 mg streptomycin/ml (Irvine Scientific). Cells were passaged routinely at 3-4 day intervals at a plating density of 1:3.

To assess the effects of test compounds on ABC1 expression, the cells were passaged into CS media (DMEM/F12 media without phenol red supplemented with 10% charcoal/dextran-treated FBS, 2 mM glutamine, 100 U penicillin/ml and 100 mg streptomycin/ml and 100 mM mevalonic acid lactone). Two days later, the media was replaced with fresh CS media containing 10 µM of the test compound. After 24 hours, the media was removed and replaced with fresh CS media containing fresh drug. After 24 more hours, the media was aspirated and the cells lysed in Trizol reagent (GIBCO). RNA was then extracted according to manufacturer's instructions. The RNA was quantitated following RNAse-free DNAse treatment by using the Ribogreen System (Molecular Probes), and then diluted to 10 ng/microL.

ABC1 expression was determined by quantitative PCR. TaqMan reactions were performed using the standard conditions on the ABI7700; 5.5 mM MgCl2, 1× TaqMan Buffer A, 300 microM each dNTP, 20 U RNAse inhibitor, 12.5 U MuLV RT; ase, 300 nM of each primer, 200 nM TaqMan probe, 1.25 U AmpliTaq Gold, and 50 ng RNA in a 50 uL volume. The reaction conditions were 48° C. for 30 minutes, 95° C. for 10 minutes, and 40 cycles of 94° C. for 15 seconds/60° C. for 1 minute. The sequence of the primers and probe for mouse ABC1 (X75926) were: forward primer: AAGGGTTTCTTTGCTCAGATTGTC (SEQ ID No. 3); reverse primer: TGCCAAAGGGTGGCACA (SEQ ID No. 4); probe oligo: CCAGCTGTCTTTGTTTGCATTGCCC (SEQ ID No. 5). Results were analyzed on the ABI7700 using Sequence Detector v1.6 software provided with the machine. ABC1 expression was calculated as fold induction in test compound-treated cells relative to vehicle-treated cells.

That which is claimed is:

1. A compound of formula (I):

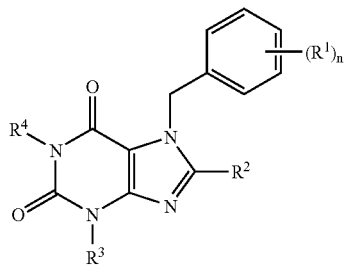

wherein:

n is 1, 2, 3, 4, 5;

each $R^1$ is the same or different and is independently selected from the group consisting of halo, alkyl, and nitro;

$R^2$ is a substituent selected from the group consisting of formulas vi and vii:

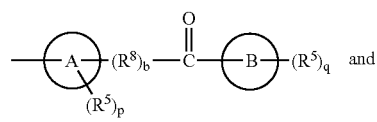

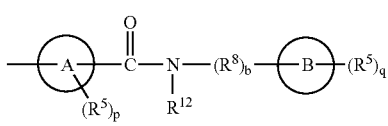

each Ring A and Ring B is the same or different and is independently selected from the group consisting of $C_{3-10}$cycloalkyl, $C_{3-10}$cycloalkenyl, Ay and Het;

Ay is aryl;

Het is a 3-10 membered heterocycle or a 5-10 membered heteroaryl;

a and b are each the same or different and are independently 0 or 1;

p is 0, 1 or 2;

q is 0, 1, 2 or 3;

each $R^5$ is the same or different and is independently selected from the group consisting of halo, alkyl, alkenyl, alkynyl, —$OR^6$, —$OC(O)R^6$, —$OR^8C(O)R^6$, —$S(O)_gR^6$, —C=O, —$C(O)R^6$, —$C(O)NR^6R^7$, —$CO_2R^9$, —$NR^6R^7$, —$N(R^6)C(O)R^6$, —$R^8OR^6$, —$R^8NR^6R^7$, —$R^8C(O)R^6$, —$R^8CO_2R^9$, nitro and cyano;

g is 0, 1 or 2;

$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, —$R^8$—$C_{3-10}$cycloalkyl, —$R^8$-Ay, —$R^8$-Het, —$R^8CO_2R^9$, —$R^8C(O)NR^9R^{10}$, —$R^8OR^9$, —$R^8SR^9$ and —$R^8OAy$;

$R^6$ and $R^7$ are the same or different and are each independently selected from the group consisting of H, alkyl, alkenyl, alkynyl, —$R^8OR^9$, —$R^8SR^9$, —$R^8$—$NR^9R^{10}$, —$R^8$—CN, —$R^8$—$CO_2R^9$;

$R^8$ is alkylene or alkenylene;

$R^9$ and $R^{10}$ are each the same or different and are each independently selected from the group consisting of H, alkyl, alkenyl and alkynyl; and $R^{12}$ is selected from the group consisting of H, alkyl, alkenyl, and alkynyl, or a pharmaceutically acceptable salt thereof.

2. The compound according to claim 1, wherein n is 1 or 2.

3. The compound according to claim 1, wherein each $R^1$ is the same or different and is independently selected from the group consisting of halo and alkyl.

4. The compound according to claim 1, wherein each $R^1$ is the same or different and is halo.

5. The compound according to claim 1, wherein $R^2$ is a substituent of formula (vi-a):

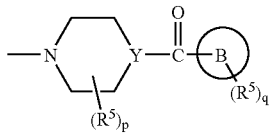

where Y is N or CH.

6. The compound according to claim 1, wherein $R^2$ is a substituent of formula (vii-a):

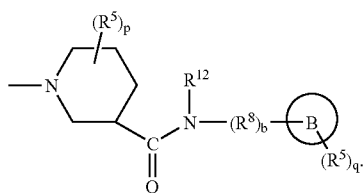

7. A compound of formula (I-A):

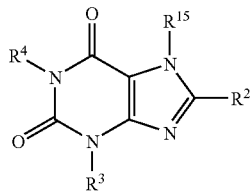

wherein:

$R^{15}$ is selected from the group consisting of

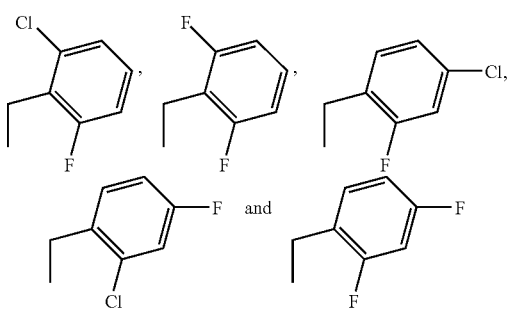

$R^2$ is a substituent selected from the group consisting of:

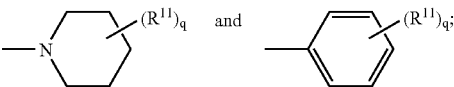

q is 0, 1, 2 or 3;

each $R^{11}$ is the same or different and is independently selected from the group consisting of halo, alkyl, alkenyl, alkynyl, —$OR^6$, —$OC(O)R^6$, —$OR^8C(O)R^6$, —$S(O_gR^6$, —C=O, —$C(O)R^6$, —$C(O)NR^6R^7$, —$CO_2R^9$, —$C(O)_2R^8Ay$, —$NR^6R^7$, —$N(R^6)C(O)R^6$, —$R^8OR^6$, —$R^8NR^6R^7$, —$R^8C(O)R^6$, —$R^8$—$C(O)Ay$, —$R^8$—$C(O)Het$, —$R^8CO_2R^9$, —$R^8C(O)N(R^9)Ay$, —$CH-(Ay)_2$, —$CH-(Het)_2$, nitro and cyano;

g is 0, 1 or 2;

Ay is aryl;

Het is a 3-10 membered heterocycle or a 5-10 membered heteroaryl;

$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, —$R^8$—$C_{3-10}$ cycloalkyl, —$R^8$-Ay, —$R^8$-Het, —$R^8CO_2R^9$, —$R^8C(O)NR^9R^{10}$, —$R^8OR^9$, —$R^8SR^9$ and —$R^8OAy$, wherein when $R^2$ is

then $R^3$ and $R^4$ are not both methyl;

$R^6$ and $R^7$ are the same or different and are each independently selected from the group consisting of H, alkyl, alkenyl, alkynyl, —$R^8OR^9$, —$R^8SR^9$, —$R^8$—$NR^9R^{10}$, —$R^8$—CN, —$R^8$—$CO_2R^9$;

$R^8$ is alkylene or alkenylene; and $R^9$ and $R^{10}$ are each the same or different and are each independently selected from the group consisting of H, alkyl, alkenyl and alkynyl;

or a pharmaceutically acceptable salt thereof.

8. The compound according to claim 7 wherein $R^2$ is

9. The compound according to claim 7, wherein q is 0, 1 or 2.

10. The compound according to claim 7, wherein each $R^{11}$ is the same or different and is independently selected from the group consisting of halo, alkyl, —OH, —$OR^6$, —$C(O)R^6$, —$C(O)NR^6R^7$, —$CO_2R^9$, —$C(O)_2R^8Ay$, —$NR^6R^7$, —$N(R^6)C(O)R^6$, —$R^8OR^6$, —$R^8NR^6R^7$, —$R^8CO_2R^9$, $R^8C(O)N(R^9)Ay$ and nitro.

11. The compound according to claim 7, wherein $R^3$ and $R^4$ are the same or different and are each independently selected from the group consisting of H, alkyl (trifluoroethyl), $C_{3-10}$cycloalkyl, Ay, $R^8$-Ay, —$R^8OH$, —$R^8Oalkyl$, —$R^8Salkyl$, —$R^8CO_2H$, —$R^8CO_2alkyl$, $R^8$-O-Ay, —$R^8C(O)NH_2$, —$R^8$-cycloalkyl

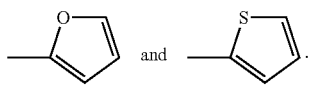

12. A compound of formula (I-A):

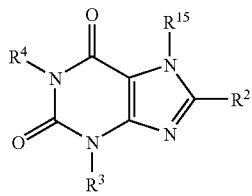

wherein:

$R^{15}$ is selected from the group consisting of

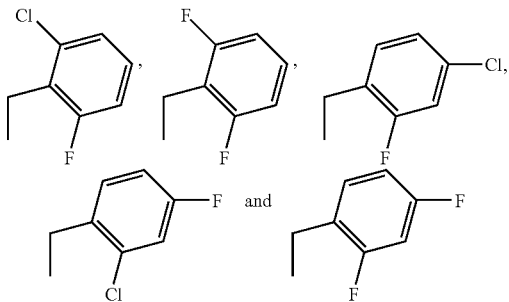

$R^2$ is a substituent of formula (v-a):

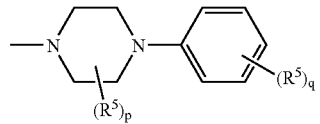

p is 0, 1 or 2;
q is 0, 1, 2 or 3;
each $R^5$ is the same or different and is independently selected from the group consisting of halo, alkyl, alkenyl, alkynyl, —$OR^6$, —$OC(O)R^6$, —$OR^8C(O)R^6$, —$S(O)_gR^6$, —C=0, —$C(O)R^6$, —$C(O)NR^6R^7$, —$CO_2R^9$, —$NR^6R^7$, —$N(R^6)C(O)R^6$, —$R^8OR^6$, —$R^8NR^6R^7$, —$R^8C(O)R^6$, —$R^{8CO}{}_2R^9$, nitro and cyano;
g is 0, 1 or 2;
Ay is aryl;
Het is a 3-10 membered heterocycle or a 5-10 membered heteroaryl;
$R^3$ and $R^4$ are the same or different and are each independently selected from the group consisting of H, alkyl, alkenyl, alkynyl, $C_{3-10}$cycloalkyl, $C_{3-10}$cycloalkenyl, Ay, Het, —$R^8$—$C_{3-10}$cycloalkyl, —$R^8$-Ay, —$R^8$-Het, —$R^8CO_2R^9$, —$R^8C(O)NR^9R^{10}$, —$R^8OR^9$, —$R^8SR^9$ and —$R^8OAy$;
$R^6$ and $R^7$ are the same or different and are each independently selected from the group consisting of H, alkyl, alkenyl, alkynyl, —$R^8OR^9$, —$R^8SR^9$, —$R^8$—$NR^9R^{10}$, —$R^8$—CN, —$R^8$—$CO_2R^9$;
$R^8$ is alkylene or alkenylene; and
$R^9$ and $R^{10}$ are each the same or different and are each independently selected from the group consisting of H, alkyl, alkenyl and alkynyl;
or a pharmaceutically acceptable salt thereof.

13. The compound according to claim 12, wherein p is 0.

14. The compound according to claim 12, wherein q is 0, 1 or 2.

15. The compound according to claim 12, wherein each $R^5$ is the same or different and is independently selected from the group consisting of halo, alkyl, —$OR^6$, —C=O, —$C(O)R^6$, —$C(O)NR^6R^7$, —$CO_2R^9$, —$N(R^6)C(O)R^6$, —$R^8OR^6$ and nitro.

16. The compound according to claim 12, wherein $R^3$ and $R^4$ are the same or different and are each independently selected from the group consisting of H, alkyl (trifluoroethyl), $C_{3-10}$cycloalkyl, Ay, $R^8$-Ay, —$R^8$OH, —$R^8$Oalkyl, —$R^8$Salkyl, —$R^8CO_2H$, —$R^8CO_2$alkyl, $R^8$—O-Ay, —$R^8$C(O)NH_2$, —$R^8$—$C_{3-10}$cycloalkyl,

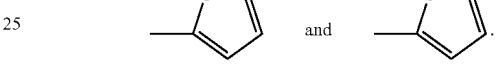

17. A compound selected from the group consisting of:
7-(2-chloro-6-fluorobenzyl)-1,3-diethyl-8-piperidin-1-yl-3,7-dihydro-1H-purine-2,6-dione;
7-(2-chloro-6-fluorobenzyl)-1-ethyl-3-isopropyl-8-piperidin-1-yl-3,7-dihydro-1H-purine-2,6-dione;
7-(2-chloro-6-fluorobenzyl)-3-ethyl-8-piperidin-1-yl-1-propyl-3,7-dihydro-1H-purine-2,6-dione;
7-(2-chloro-6-fluorobenzyl)-3-isopropyl-8-piperidin-1-yl-1-propyl-3,7-dihydro-1H-purine-2,6-dione;
7-(2-chloro-6-fluorobenzyl)-1-isopropyl-3-methyl-8-piperidin-1-yl-3,7-dihydro-1H-purine-2,6-dione;
7-(2-chloro-6-fluorobenzyl)-1-ethyl-3-(2-methoxyethyl)-8-piperidin-1-yl-3,7-dihydro-1H-purine-2,6-dione;
methyl[7-(2-chloro-6-fluorobenzyl)-1-ethyl-2,6-dioxo-8-piperidin-1-yl-1,2,6,7-tetrahydro-3H-purin-3-yl]acetate;
7-(2-chloro-6-fluorobenzyl)-1-ethyl-3-(2-phenoxyethyl)-8-piperidin-1-yl-3,7-dihydro-1H-purine-2,6-dione;
1-butyl-7-(2-chloro-6-fluorobenzyl)-3-methyl-8-piperidin-1-yl-3,7-dihydro-1H-purine-2,6-dione;
7-(2-chloro-6-fluorobenzyl)-1-(cyolopropylmethyl)-3-isopropyl-8-piperidin-1-yl-3,7-dihydro-1H-purine-2,6-dione;
7-(2-chloro-6-fluorobenzyl)-1,3-diisopropyl-8-piperidin-1-yl-3,7-dihydro-1H-purine-2,6-dione;
7-(2-chloro-6-fluorobenzyl)-1-cyclopropyl-3-isopropyl-8-piperidin-1-yl-3,7-dihydro-1H-purine-2,6-dione;
7-(2-chloro-6-fluorobenzyl)-1-ethyl-3-methyl-8-piperidin-1-yl-3,7-dihydro-1H-purine-2,6-dione;
7-(2-chloro-6-fluorobenzyl)-3-methyl-8-piperidin-1-yl-1-propyl-3,7-dihydro-1H-purine-2,6-dione;
1-benzyl-7-(2-chloro-6-fluorobenzyl)-3-methyl-8-piperidin-1-yl-3,7-dihydro-1H-purine-2,6-dione;
7-(2-chloro-6-fluorobenzyl)-3-ethyl-1-methyl-8-piperidin-1-yl-3,7-dihydro-1H-purine-2,6-dione;
7-(2-chloro-6-fluorobenzyl)-1-methyl-8-piperidin-1-yl-3-propyl-3,7-dihydro-1H-purine-2,6-dione;
7-(2-chloro-6-fluorobenzyl)-3-isopropyl-1-methyl-8-piperidin-1-yl-3,7-dihydro-1H-purine-2,6-dione;

3-benzyl-7-(2-chloro-6-fluorobenzyl)-1-methyl-8-piperidin-1-yl-3,7-dihydro-1H-purine-2,6-dione;

7-(2-chloro-6-fluorobenzyl)-8-(3-chlorophenyl)-3-isopropyl-1-methyl-3,7-dihydro-1H-purine-2,6-dione;

7-(2-chloro-6-fluorobenzyl)-1, 3-dimethyl-8-phenyl-3,7-dihydro-1H-purine-2,6-dione;

7-(2-chloro-6-fluorobenzyl)-8-(4-chlorophenyl)-1,3-dimethyl-3,7-dihydro-1H-purine-2,6-dione;

7-(2-chloro-6-fluorobenzyl)-8-(3,5-dichlorophenyl)-1,3-dimethyl-3,7-dihydro-1H-purine-2,6-dione;

7-(2-chloro-6-fluorobenzyl)-1,3-dimethyl-8-(2-naphthyl)-3,7-dihydro-1H-purine-2,6-dione;

7-(2-chloro-6-fluorobenzyl)-8-(3-chlorophenyl)-1,3-dimethyl-3,7-dihydro-1H-purine-2,6-dione;

7-(2-chloro-6-fluorobenzyl)-1,3-dimethyl-8-[3-(trifluoromethyl)phenyl]-3,7-dihydro-1H-purine-2,6-dione;

7-(2-chloro-6-fluorobenzyl)-8-(3-methoxyphenyl)-1,3-dimethyl-3,7-dihydro-1H-purine-2,6-dione;

7-(2-chloro-6-fluorobenzyl)-8-cyclohexyl-1,3-dimethyl-3,7-dihydro-1H-purine-2,6-dione;

7-(2-chloro-6-fluorobenzyl)-8-(3-iodophenyl)-1,3-dimethyl-3,7-dihydro-1H-purine-2,6-dione;

1-[7-(2-chloro-6-fluorobenzyl)-1,3-dimethyl-2,6-dioxo-2,3,6,7-tetrahydro-1H-purin-8-yl]piperidine-3-carboxylic acid;

7-(2-chloro-6-fluorobenzyl)-8-{3-[(4-hydroxypiperidin-1-yl)carbonyl]piperidin-1-yl}-1,3-dimethyl-3,7-dihydro-1H-purine-2,6-dione;

1-[7-(2-chloro-6-fluorobenzyl)-1,3-dimethyl-2,6-dioxo-2,3,6,7-tetrahydro-1H-purin-8-yl]-N-(4-hydroxybutyl)piperidine-3-carboxamide;

7-(2-chloro-6-fluorobenzyl)-1,3-dimethyl-8-{4-[3-(trifluoromethyl)phenyl]piperazin-1-yl}-3,7-dihydro-1H-purine-2,6-dione;

7-(2-chloro-6-fluorobenzyl)-8-[4-(3-methoxyphenyl)piperazin-1-yl]-1,3-dimethyl-3,7-dihydro-1H-purine-2,6-dione;

7-(2-chloro-6-fluorobenzyl)-8-{4-[4-chloro-3-(trifluoromethyl)phenyl]piperazin-1-yl}-1,3-dimethyl-3,7-dihydro-1H-purine-2,6-dione;

and pharmaceutically acceptable salts thereof.

18. A pharmaceutical composition comprising a compound according to claim 1.

19. The pharmaceutical composition according to claim 18 further comprising a pharmaceutically acceptable carrier or diluent.

* * * * *